US009963689B2

(12) United States Patent
Doudna et al.

(10) Patent No.: US 9,963,689 B2
(45) Date of Patent: May 8, 2018

(54) CAS9 CRYSTALS AND METHODS OF USE THEREOF

(71) Applicant: The Regents of the University of California, Oakland, CA (US)

(72) Inventors: Jennifer A. Doudna, Oakland, CA (US); Samuel H. Sternberg, Oakland, CA (US); Martin Jinek, Oakland, CA (US); Fuguo Jiang, Oakland, CA (US); Emine Kaya, Oakland, CA (US); David W. Taylor, Jr., Oakland, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days. days.

(21) Appl. No.: 15/108,545

(22) PCT Filed: Dec. 29, 2014

(86) PCT No.: PCT/US2014/072590
§ 371 (c)(1),
(2) Date: Jun. 27, 2016

(87) PCT Pub. No.: WO2015/103153
PCT Pub. Date: Jul. 9, 2015

(65) Prior Publication Data
US 2016/0319262 A1 Nov. 3, 2016

Related U.S. Application Data

(60) Provisional application No. 61/922,556, filed on Dec. 31, 2013.

(51) Int. Cl.
*C12N 9/22* (2006.01)
*C12N 15/10* (2006.01)
*G06F 19/16* (2011.01)

(52) U.S. Cl.
CPC ........... *C12N 9/22* (2013.01); *C12N 15/1031* (2013.01); *C12Y 301/00* (2013.01); *G06F 19/16* (2013.01); *C07K 2299/00* (2013.01)

(58) Field of Classification Search
None
See application file for complete search history.

(56) References Cited

U.S. PATENT DOCUMENTS

| 8,260,596 B2 | 9/2012 | Kobilka et al. |
| 2011/0217739 A1 | 9/2011 | Terns et al. |
| 2012/0028287 A1 | 2/2012 | Chen et al. |
| 2014/0179006 A1 | 6/2014 | Zhang |

FOREIGN PATENT DOCUMENTS

| WO | WO 2013/126794 A1 | 8/2013 |
| WO | WO 2013/142578 A1 | 9/2013 |
| WO | WO 2013/176772 A1 | 11/2013 |

OTHER PUBLICATIONS

McPherson, A. Current Approaches to Macromolecular Crystallization. European Journal of Biochemistry. 1990. vol. 189, pp. 1-23.*
Kundrot, C.E. Which Strategy for a Protein Crystallization Project? Cellular Molecular Life Science. 2004. vol. 61, pp. 525-536.*
Benevenuti et al., Crystallization of Soluble Proteins in Vapor Diffusion for X-ray Crystallography, Nature Protocols, published on-line Jun. 28, 2007, 2(7):1633-1651.*
Cudney R. Protein Crystallization and Dumb Luck. The Rigaku Journal. 1999. vol. 16, No. 1, pp. 1-7.*
Drenth, "Principles of Protein X-Ray Crystallography", 2nd Edition, 1999 Springer-Verlag New York Inc., Chapter 1, p. 1-21.*
Moon et al., "A synergistic approach to protein crystallization: Combination of a fixed-arm carrier with surface entropy reduction", Protein Science, 2010, 19:901-913.*
McPherson & Gavira, "Introduction to protein crystallization", Acta Crystallographica Section F Structural Biology Communications, 2014, F70, pp. 2-20.*
Koo, et al.; "Crystal Structure of *Streptococcus pyogenes* Csn2 Reveals Calcium-Dependent Conformational Changes in Its Tertiary and Quaternary Structure"; PLoS One; vol. 7, No. 3, e33401 (Mar. 30, 2012).
Makarova, et al.; "Evolution and Classification of the CRISPR-Cas Systems"; Nat. Rev. Microbiol.; vol. 9, No. 6, pp. 467-477 (Jun. 2011).
Mali, et al.; "Cas9 as a Versatile Tool for Engineering Biology"; Nat. Methods; vol. 10, No. 10, pp. 957-963 (Oct. 2013).
Nishimasu, et al.; "Crystal Structure of Cas9 in Complex With Guide RNA and Target DNA"; Cell; vol. 156, No. 5, pp. 935-949 (Feb. 27, 2014).
Osawa, et al.; "Crystallization and Preliminary X-Ray Diffraction Analysis of the Cmr2-Cmr3 Subcomplex in the CRISPR-Cas RNA-Silencing Effector Complex"; Acta Crystallogr Sect F Struct Biol Cryst Commun.; vol. 69, No. 5, pp. 585-587 (May 1, 2013).
International Search Report and Written Opinion of PCT Application No. PCT/US2014/072590, dated Apr. 22, 2015.
Barrangou et al., "CRISPR Provides Acquired Resistance Against Viruses in Prokaryotes" Science 315, 1709-1712 (2007).
Berger, S. J. Gamblin, S. C. Harrison, J. C. Wang, "Structure and mechanism of DNA topoisomerase II" Nature 379, 225-232 (1996).
Bikard et al., "Programmable repression and activation of bacterial gene expression using an engineered CRISPR-Cas system" Nucleic Acids Res 41, 7429-7437 (2013).

(Continued)

*Primary Examiner* — Suzanne M Noakes
(74) *Attorney, Agent, or Firm* — Bozicevic Field & Francis, LLP; Paula A. Borden

(57) ABSTRACT

The present disclosure provides atomic structures of Cas9 with and without polynucleotides bound thereto. Also provided is a computer-readable medium comprising atomic coordinates for Cas9 polypeptides in both an unbound configuration and a configuration wherein the Cas9 polypeptide is bound to one or more polynucleotides. The present disclosure provides crystals comprising Cas9 polypeptides; and compositions comprising the crystals. The present disclosure provides methods for the engineering of Cas9 polypeptides wherein Cas9 activity has been altered, ablated, or preserved and amended with additional activities.

6 Claims, 58 Drawing Sheets

(56) References Cited

OTHER PUBLICATIONS

Brouns et al., "Small CRISPR RNAs Guide Antiviral Defense in Prokaryotes" Science 321, 960-964 (2008).
Chylinski, A. Le Rhun, E. Charpentier, "The tracrRNA and Cas9 families of type II CRISPR-Cas immunity systems." RNA Biology 10, 726-737 (2013).
Esvelt et al., "Orthogonal Cas9 proteins for RNA-guided gene regulation and editing" Nat Methods; vol. 10, No. 11, pp. 1116-1121 (Nov. 2013).
Garneau et al., "The CRISPR/Cas bacterial immune system cleaves bacteriophage and plasmid DNA" Nature 468, 67-71 (2010).
Gasiunas, R. Barrangou, P. Horvath, V. Siksnys, "Cas9-crRNA ribonucleoprotein complex mediates specific DNA cleavage for adaptive immunity in bacteria." Proc Natl Acad Sci US A 109, E2579-86 (2012).
Gilbert et al., "CRISPR-Mediated Modular RNA-Guided Regulation of Transcription in Eukaryotes" Cell 154, 442-451 (2013).
Hou et al., "Efficient genome engineering in human pluripotent stem cells using Cas9 from Neisseria meningitidis" Proc Natl Acad Sci USA; vol. 110, No. 39, pp. 15644-15649 (Sep. 24, 2013).
Jinek et al., "A Programmable Dual-RNA—Guided DNA Endonuclease in Adaptive Bacterial Immunity" Science 337, 816-821 (2012).
Makarova, L. Aravind, Y. I. Wolf, E. V. Koonin, "Unification of Cas protein families and a simple scenario for the origin and evolution of CRISPR-Cas systems" Biol Direct 6, 38 (2011).
Mali et al., "CAS9 transcriptional activators for target specificity screening and paired nickases for cooperative genome engineering" Nat Biotechnol; vol. 31, No. 9, pp. 833-838 (Sep. 2013).
Qi et al., "Repurposing CRISPR as an RNA-Guided Platform for Sequence-Specific Control of Gene Expression" Cell 152, 1173-1183 (2013).
Sampson, S. D. Saroj, A. C. Llewellyn, Y.-L. Tzeng, D. S. Weiss, "A CRISPR/Cas system mediates bacterial innate immune evasion and virulence" Nature; vol. 497, No. 7448, pp. 254-257 (May 9, 2013).
Sapranauskas et al., "The *Streptococcus thermophilus* CRISPR/Cas system provides immunity in *Escherichia coli*" Nucleic Acids Res 39, 9275-9282 (2011).
Shen, M. Landthaler, D. A. Shub, B. L. Stoddard, "DNA binding and cleavage by the HNH homing endonuclease I-Hmul." J Mol Biol 342, 43-56 (2004).
Wiedenheft et al., "Structural basis for DNase activity of a conserved protein implicated in CRISPR-mediated genome defense"; Structure; vol. 17, pp. 904-912 (Jun. 10, 2009).
Wiedenheft, S. H. Sternberg, J. A. Doudna, "RNA-guided genetic silencing systems in bacteria and archaea" Nature 482, 331-338 (2012).
Zhang et al., "Processing-independent CRISPR RNAs limit natural transformation in Neisseria meningitidis." Mol Cell 50, 488-503 (2013).
Jinek, et al.; "Structures of Cas9 Endonucleases Reveal RNA-Mediated Conformational Activation"; Science; vol. 343, No. 6176, pp. 1-28 (Mar. 14, 2014).

\* cited by examiner

1. S. pyogenes
2. S. thermophilus
3. L. innocua
4. S. agalactiae
5. S. mutans
6. E. faecium 1. S. pyogenes
2. S. thermophilus
3. L. innocua
4. S. agalactiae
5. S. mutans
6. E. faecium 1. S. pyogenes
2. S. thermophilus
3. L. innocua
4. S. agalactiae
5. S. mutans
6. E. faecium 1. S. pyogenes
2. S. thermophilus
3. L. innocua
4. S. agalactiae
5. S. mutans
6. E. faecium 1. S. pyogenes
2. S. thermophilus
3. L. innocua
4. S. agalactiae
5. S. mutans
6. E. faecium 1. S. pyogenes
2. S. thermophilus
3. L. innocua
4. S. agalactiae
5. S. mutans
6. E. faecium 1. S. pyogenes
2. S. thermophilus
3. L. innocua
4. S. agalactiae
5. S. mutans
6. E. faecium

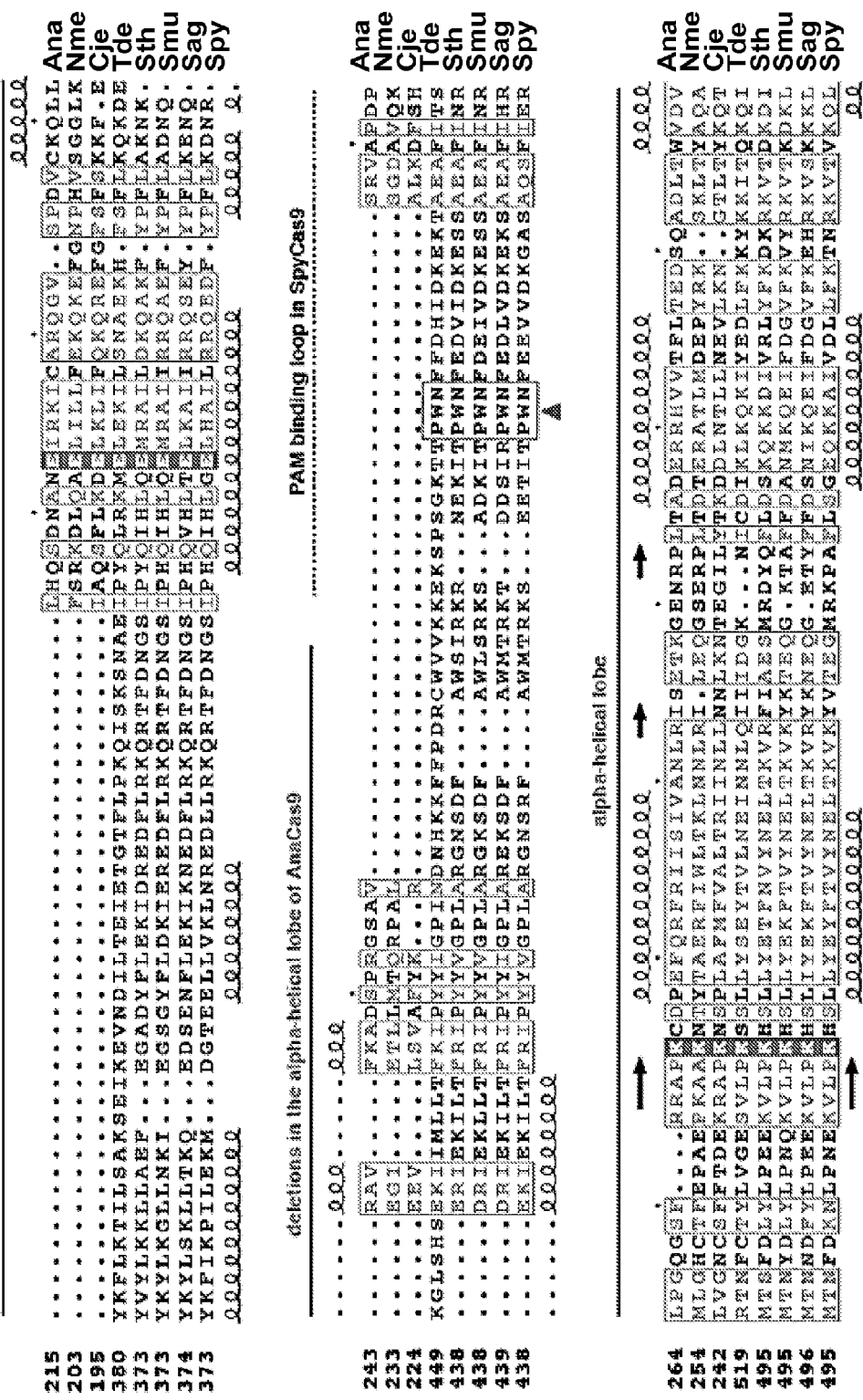

Overall superposition
(rmsd 9.1 Å over 654Cα)

HNH-RuvC-Topo
(rmsd 3.31Å over 175 Cα)

alpha-helical lobe
252$^{Ana}$-468$^{Ana}$ vs 502$^{Spy}$-713$^{Spy}$
showing as cartoon
(rmsd 3.63Å over 149 Cα)

(1) = targeting crRNA
(2) = non-targeting crRNA

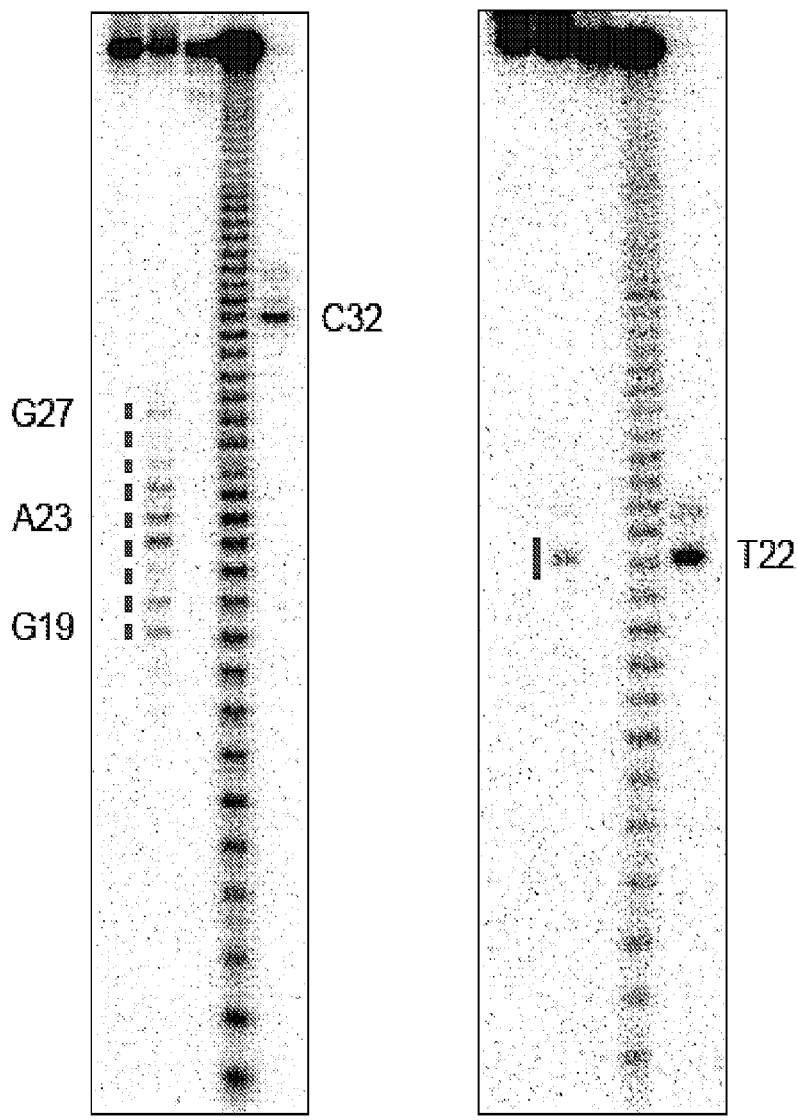
FIGURE 29B Nuclease P1
(1) = targeting crRNA
(2) = non-targeting crRNA

FIGURE 31

| Dataset | Native | Mn soak | SeMet | tungstate soak | Co soak | Er(III) acetate | thimerosal soak |
|---|---|---|---|---|---|---|---|
| X-ray source | SLS PXI | SLS PXIII | ALS 8.2.2 | SLS PXI | SLS PXIII | ALS 8.2.2 | SLS PXIII |
| Space group | P2₁2₁2 | P2₁2₁2 | P2₁2₁2 | P2₁2₁2 | P2₁2₁2 | P2₁2₁2 | P2₁2₁2 |
| Cell dimensions |  |  |  |  |  |  |  |
| $a, b, c$ (Å) | 159.8, 209.5, 91.3 | 159.8, 209.3, 91.0 | 158.9, 201.1, 89.7 | 160.0, 209.5, 90.5 | 161.3, 210.2, 91.0 | 159.5, 209.2, 90.9 | 159.5, 209.1, 90.5 |
| $\alpha, \beta, \gamma$ (°) | 90.0, 90.0, 90.0 | 90.0, 90.0, 90.0 | 90.0, 90.0, 90.0 | 90.0, 90.0, 90.0 | 90.0, 90.0, 90.0 | 90.0, 90.0, 90.0 | 90.0, 90.0, 90.0 |
| Wavelength (Å) | 1.00000 | 1.00000 | 0.979168 | 1.2143 | 1.58855 | 1.475661 | 1.003992 |
| Resolution (Å)* | 127.01–2.62 (2.69–2.62) | 47/48–3.10 (3.18–3.10) | 87.64–4.20 (4.31–4.20) | 49.77–3.50 (4.00–3.50) | 47.9–3.60 (3.69–3.60) | 87.45–3.30 (3.39–3.30) | 47.39–3.59 (3.69–3.59) |
| $R_{sym}$ (%)* | 4.7 (63.8) | 9.6 (194.8) | 15.2 (71.4) | 12.2 (87.0) | 9.6 (76.3) | 6.7 (39.7) | 10.4 (79.8) |
| I/σI* | 13.02 (1.94) | 19.1 (2.3) | 6.7 (2.9) | 17.3 (4.1) | 14.2 (3.0) | 10.4 (2.1) | 10.4 (2.5) |
| Completeness (%)* | 98.2 (98.5) | 100.0 (100.0) | 99.9 (99.8) | 99.9 (99.9) | 100.0 (100.0) | 98.4 (99.4) | 99.4 (92.8) |
| Redundancy* | 2.3 (2.3) | 7.1 (7.3) | 6.0 (6.0) | 14.0 (14.1) | 7.1 (7.0) | 2.1 (2.1) | 7.0 (5.9) |
| Refinement |  |  |  |  |  |  |  |
| Resolution (Å) | 47.52–2.62 | 47.53–3.09 |  |  |  |  |  |
| No. reflections | 92408 | 56200 |  |  |  |  |  |
| $R_{work}/R_{free}$ | 0.245 / 0.290 | 0.258 / 0.280 |  |  |  |  |  |
| No. atoms |  |  |  |  |  |  |  |
| Protein | 16399 | 16399 |  |  |  |  |  |
| Ion | 27 | 13 |  |  |  |  |  |
| Water | 208 | 30 |  |  |  |  |  |
| B-factors |  |  |  |  |  |  |  |
| Mean | 58.9 | 82.3 |  |  |  |  |  |
| Protein | 58.8 | 82.2 |  |  |  |  |  |
| Ion | 61.7 | 79.1 |  |  |  |  |  |
| Water | 45.2 | 91.8 |  |  |  |  |  |
| R.m.s. deviations |  |  |  |  |  |  |  |
| Bond lengths (Å) | 0.007 | 0.003 |  |  |  |  |  |
| Bond angles (°) | 1.07 | 0.75 |  |  |  |  |  |
| Ramachandran plot |  |  |  |  |  |  |  |
| % favoured | 96.2 | 97.6 |  |  |  |  |  |
| % allowed | 3.8 | 2.4 |  |  |  |  |  |
| % outliers | 0.0 | 0.0 |  |  |  |  |  |
| Molprobity |  |  |  |  |  |  |  |
| Clashscore | 10.3 | 8.2 |  |  |  |  |  |

* Values in parentheses denote highest resolution shell

FIGURE 32

| Dataset | SeMet | Native | Mn soak |
|---|---|---|---|
| X-ray source | ALS 8.3.1 | ALS 8.3.1 | ALS 8.2.2 |
| Space group | P1 2,1 | P1 2,1 | P1 2,1 |
| Cell dimensions | | | |
|   a, b, c (Å) | 74.58, 133.09, 80.17 | 75.415, 133.025, 80.69 | 74.61, 132.56, 80.04 |
|   $\alpha, \beta, \gamma$ (°) | 90.00, 95.79, 90.00 | 90, 96.22, 90 | 90, 95.38, 90 |
| Wavelength (Å) | 0.978 | 1.116 | 1.000 |
| Resolution (Å)* | 79.76-3.19 (3.37-3.19) | 80.2-2.2 (2.32-2.2) | 79.69-2.80 (2.95-2.80) |
| $R_{merge}$ (%)* | 0.124(0.428) | 0.096(0.795) | 0.090(0.628) |
| $R_{pim}$* | 0.05(0.176) | 0.029 (0.322) | 0.05(0.358) |
| $I/\sigma I$* | 11.9(4.6) | 14.89 (2.24) | 10.86 (2.27) |
| Completeness (%)* | 99.9(99.7) | 98.0 (86.8) | 99.98 (100.00) |
| Redundancy* | 7.9(7.8) | 8.6(5.8) | 4.0(4.0) |
| Refinement | | | |
| Resolution (Å) | | 68.0-2.2 | 68.3-2.8 (2.9-2.8) |
| No. reflections | | 78398 | 38217 |
| $R_{work}/R_{free}$ | | 0.1867/0.2281 | 0.1941/0.2310 |
| No. atoms | | | |
|   Protein | | 7693 | 6888 |
|   Nucleic Acid | | | |
|   Ligands | | 24 | 27 |
|   Water | | 348 | 4 |
| B-factors | | | |
|   mean | | 57.9 | 67.3 |
|   Protein | | 58.6 | 67.3 |
|   Ion | | 52.2 | 64.9 |
|   Water | | 42.01 | 42.7 |
| R.m.s. deviations | | | |
|   Bond lengths (Å) | | 0.009 | 0.005 |
|   Bond angles (°) | | 1.22 | 0.84 |
| Ramachandran plot | | | |
|   % favoured | | 94.00 | 95.00 |
|   % allowed | | 5.80 | 4.77 |
|   % outliers | | 0.20 | 0.23 |
| Molprobity | | | |
|   Clashscore | | 9.8 | 6.2 |

* Values in parentheses denote highest resolution shell

† $R_{pim}$ = precision-indicating (multiplicity-weighted) $R_{merge}$

CAS9 CRYSTALS AND METHODS OF USE THEREOF

CROSS-REFERENCE

This application claims the benefit of U.S. Provisional Patent Application No. 61/922,556, filed Dec. 31, 2013, which application is incorporated herein by reference in its entirety.

INCORPORATION BY REFERENCE OF SEQUENCE LISTING PROVIDED AS A TEXT FILE

A Sequence Listing is provided herewith as a text file, "BERK-231WO SEQLIST_ST25.txt" created on Dec. 23, 2014 and having a size of 188 KB. The contents of the text file are incorporated by reference herein in their entirety.

TABLES PROVIDED IN ELECTRONIC FORM

This application includes Table 1. Table 1 is a text file named "BERK-231PRV Table 1—Atomic coordinates SpyCas9_apo" created on Dec. 30, 2013. The size of the "BERK-231PRV Table 1—Atomic coordinates SpyCas9_apo" text file is 2,465 KB. The information contained in Table 1 is hereby incorporated by reference in this application.

INTRODUCTION

Bacteria and archaea use RNA-guided adaptive immune systems encoded by CRISPR (Clustered Regularly Interspaced Short Palindromic Repeats)-Cas (CRISPR-associated) genomic loci to recognize and destroy invasive DNA. Upon viral infection or plasmid transformation, short fragments of foreign DNA are integrated into the CRISPR array within the host chromosome. Enzymatic processing of CRISPR transcripts produces mature CRISPR RNAs (crRNAs) that direct Cas protein-mediated targeting of DNA bearing complementary sequences (protospacers). While Type I and III CRISPR-Cas systems rely on large, multi-protein complexes for crRNA-guided DNA targeting, Type II systems employ a single enzyme, Cas9. Cas9 is a dual RNA-guided endonuclease that requires both a mature crRNA and a trans-activating crRNA (tracrRNA) for target DNA recognition and cleavage. The two nuclease active sites in Cas9 act together to generate blunt double-stranded breaks (DSBs). Both a seed sequence and conserved protospacer adjacent motif (PAM) sequence are crucial for efficient target binding and cleavage by Cas9.

Cas9 proteins are abundant across the bacterial kingdom, but they vary widely in both sequence and size. All known Cas9 enzymes contain an HNH domain that cleaves the DNA strand complementary to the guide RNA sequence (target strand), and RuvC nuclease motifs required for cleaving the non-complementary strand (non-target strand). In addition, Cas9 enzymes contain a highly conserved arginine-rich (Arg-rich) region that has been suggested to mediate nucleic acid binding. Based on CRISPR-Cas locus architecture and protein sequence phylogeny, Cas9 genes have been classified into three subfamilies: Type II-A, II-B, and II-C. The Type II-A and -C subfamilies represent most known Cas9 genes, encoding proteins of ~1400 or ~1100 amino acids in length, respectively.

The ability to program Cas9 for DNA cleavage at sites defined by guide RNAs has led to its adoption as a robust and versatile platform for genome engineering. When directed to target loci in eukaryotes by either a natural dual crRNA:tracrRNA guide or a chimeric single-guide RNA, Cas9 generates site-specific DSBs that are repaired either by non-homologous end joining (NHEJ) or homologous recombination (HR).

Despite these ongoing successes, there is a need in the art for understanding the structural basis for guide RNA recognition and DNA targeting by Cas9.

SUMMARY

The present disclosure provides atomic structures of Cas9 with and without polynucleotides bound thereto. Also provided is a computer-readable medium comprising atomic coordinates for Cas9 polypeptides in both an unbound configuration and a configuration wherein the Cas9 polypeptide is bound to one or more polynucleotides. The computer readable medium may further contain programming for displaying a molecular model of a Cas9 polypeptide and for identifying an amino acid residue that binds to a polynucleotide or an amino acid residue that, when substituted with a different amino acid, alters Cas9 function, e.g., polynucleotide binding. The present disclosure also provides crystals comprising Cas9 polypeptides and compositions comprising the crystals.

The present disclosure also provides methods for the engineering of Cas9 polypeptides wherein Cas9 activity has been altered, ablated, or preserved and amended with additional activities. In general terms, methods comprise using the atomic coordinates to computationally identify a site for amino acid residue substitution, insertion, or deletion to alter a function or chemical property of a Cas9 polypeptide. A method is also provided that comprises computationally identifying candidates sites within the Cas9 polypeptide for the insertion of heterologous sequences using the Cas9 atomic structures provided herein. Also provided are methods of engineering chimeric Cas9 polypeptides through the replacement of Cas9 domains with orthologous Cas9 domains or the insertion of heterologous protein domains. Such altered or chimeric Cas9 polypeptides have utility for controlling site-specific gene regulation as well as engineering or editing of prokaryotic and eukaryotic genomes and epigenomes.

(GI 15675041; SEQ ID NO:1), *Streptococcus thermophilus* LMD-9 (GI 116628213; SEQ ID NO:2), *Listeria innocua* Clip 11262 (GI 16801805; SEQ ID NO:3), *Streptococcus agalactiae* A909 (GI 76788458; SEQ ID NO:4), *Streptococcus mutans* UA159 (GI 24379809; SEQ ID NO:5), and *Enterococcus faecium* 1,231,408 (GI 257893735; SEQ ID NO:6) were aligned using MAFFT.

Figure 6:
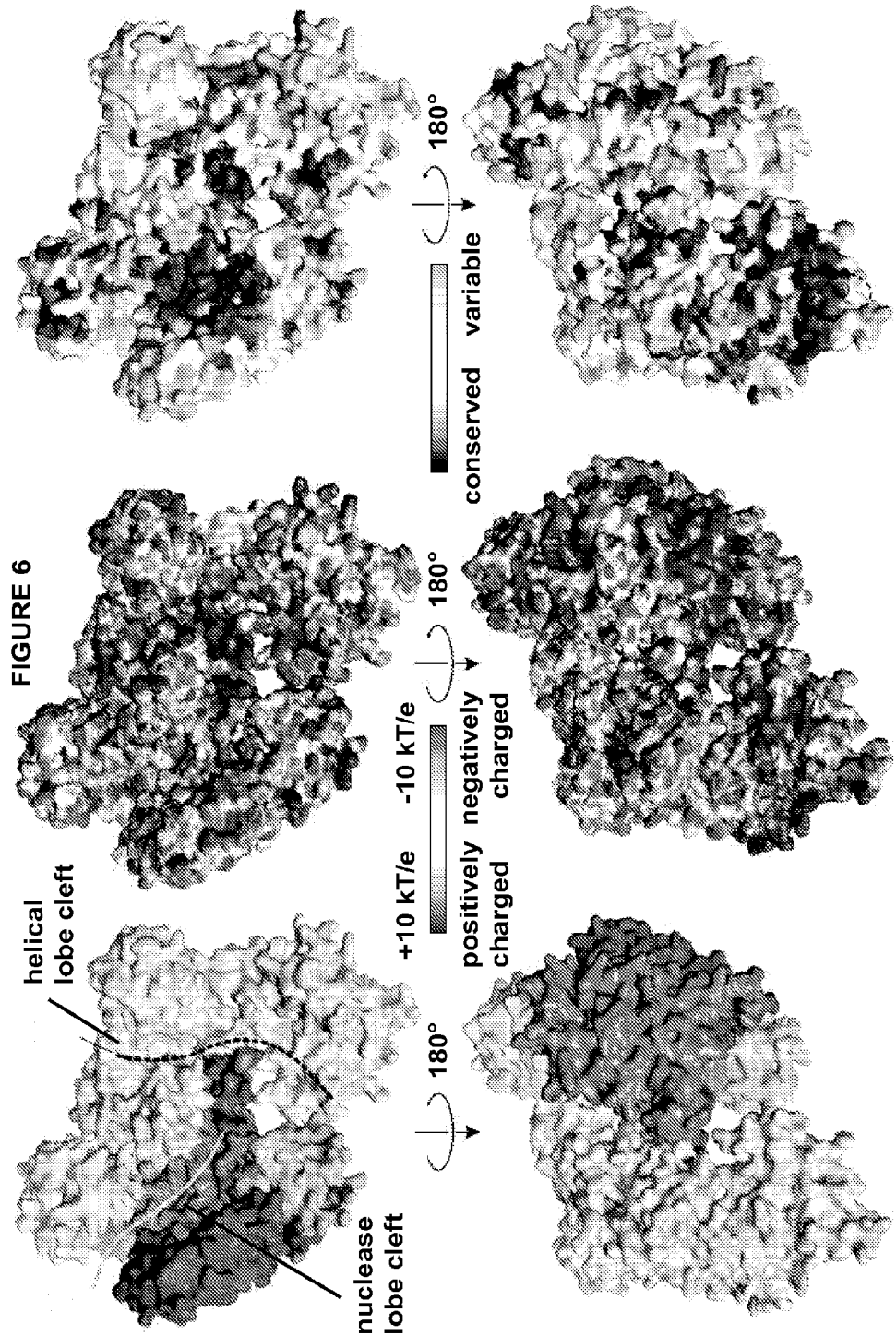

FIG. 6 provides surface representations of the SpyCas9 architecture, electrostatic surface potential, and evolutionary amino acid conservation.

Figure 7:
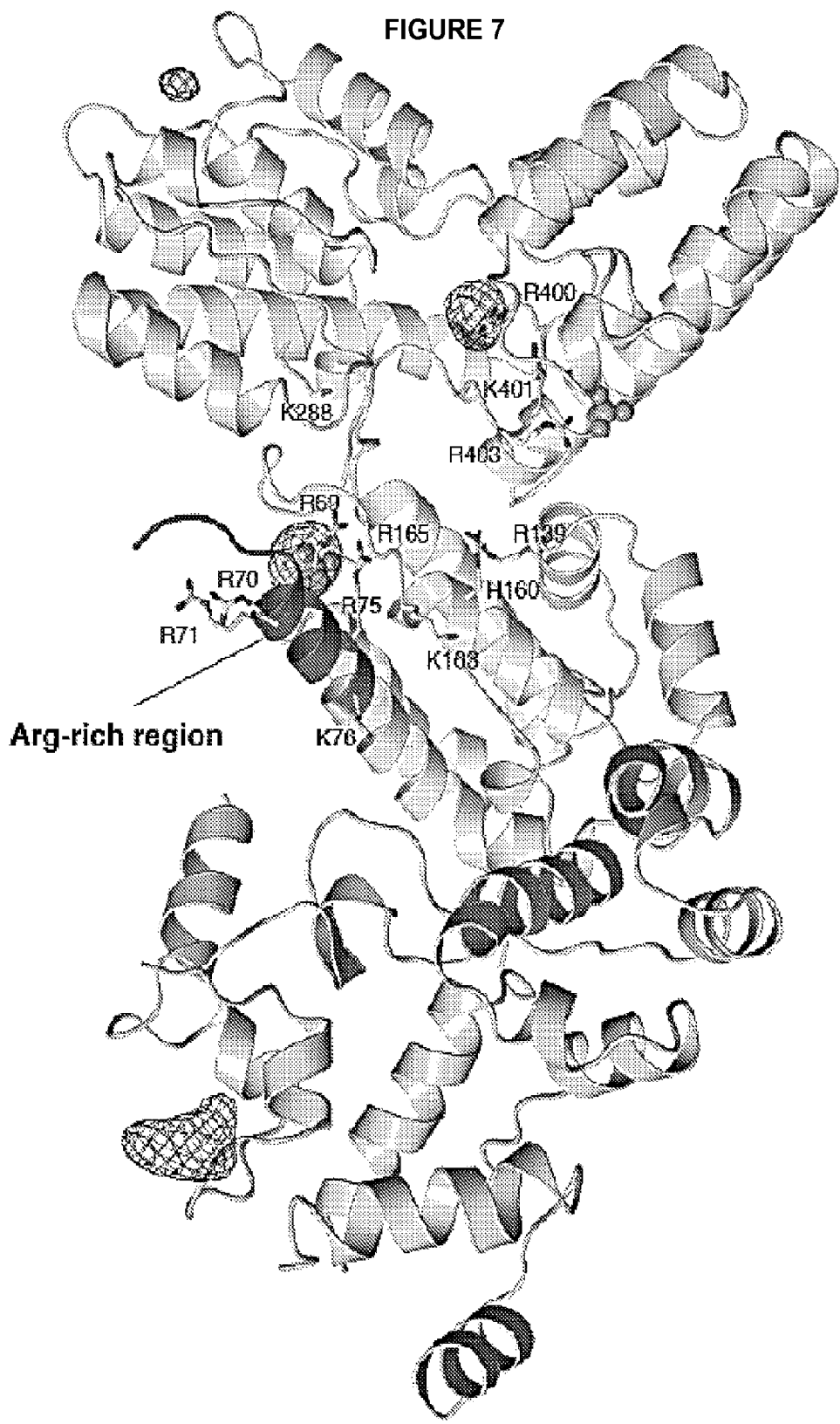

FIG. 7 provides a close-up view of the helical lobe of SpyCas9 including the Arg-rich region and identifying conserved amino acid residues in ball-and-stick format.

Figure 8:
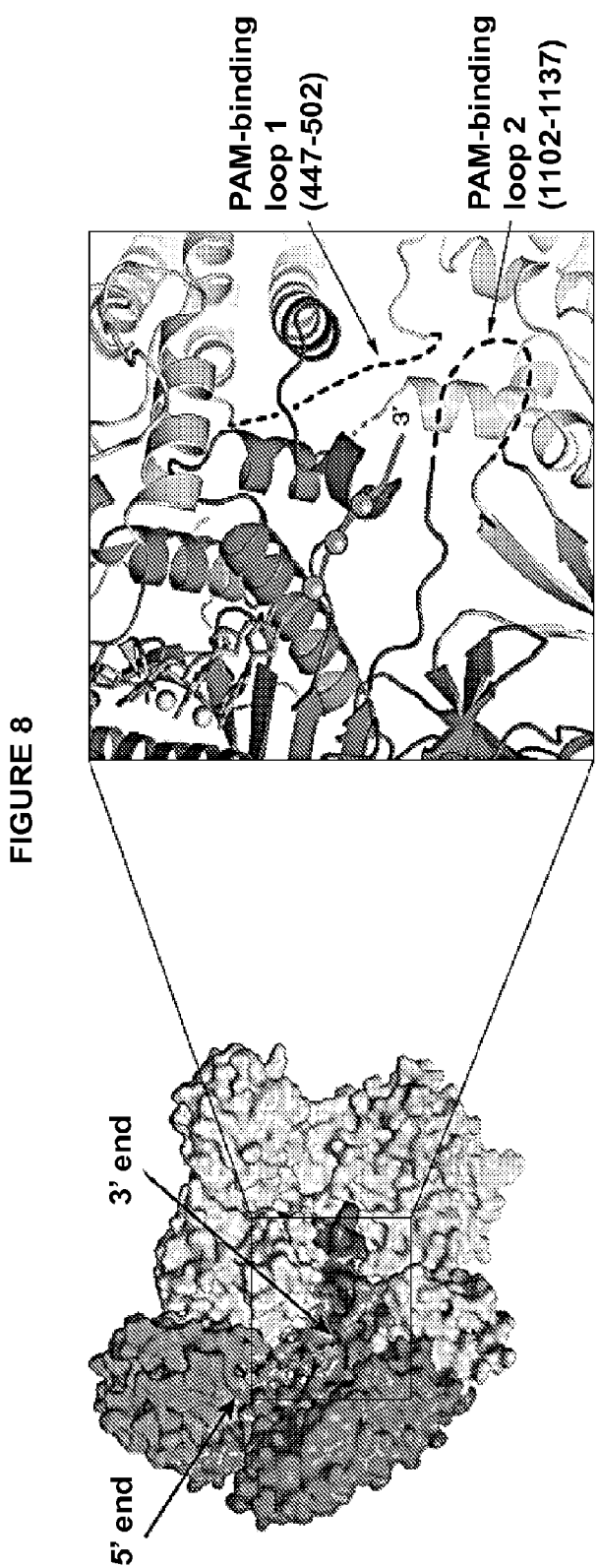

FIG. 8 provides a Model of non-complementary DNA strand bound to the RuvC domain based on a superposition with the DNA-bound complex of *Thermus thermophilus* RuvC Holliday junction resolvase (PDB entry 4LD0) and a zoomed-in view of the modeled DNA binding site showing the modeled non-target DNA strand (stick format) and the predicted path of the downstream (3') sequence containing the PAM.

Figure 9:
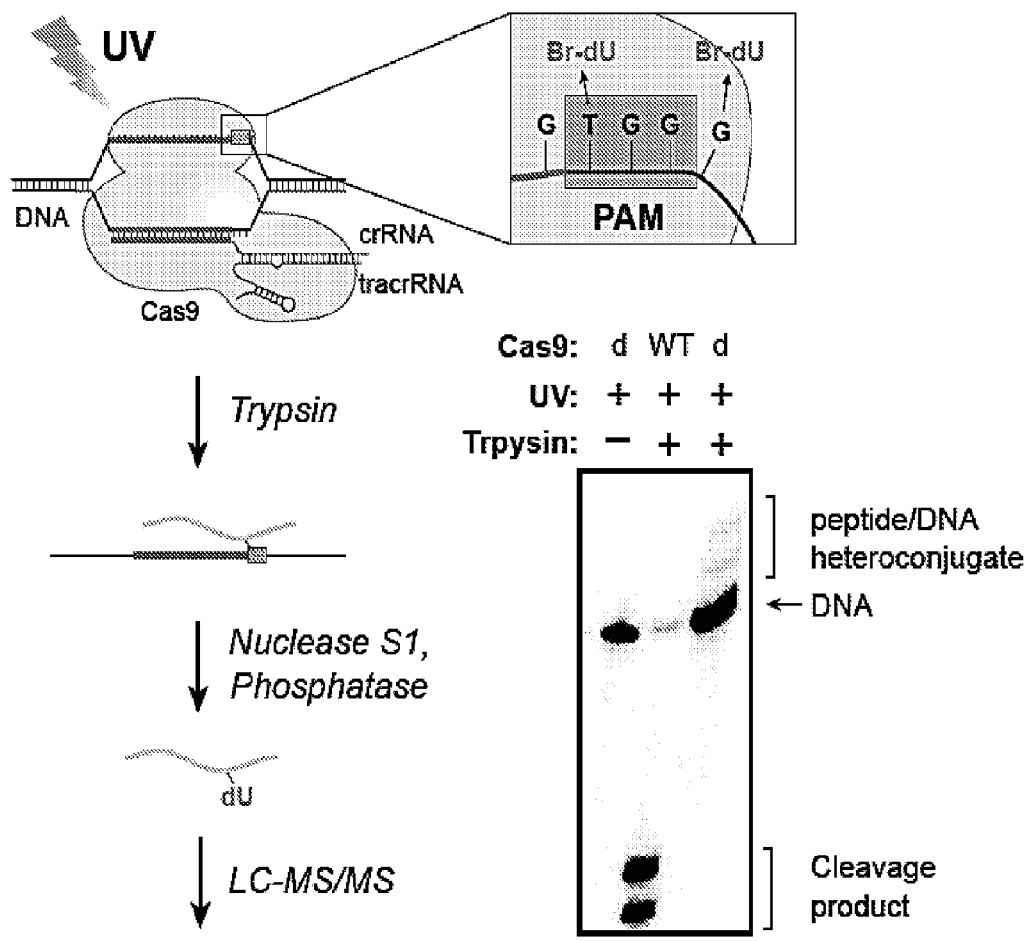

FIG. 9 provides a cartoon showing the design and workflow of crosslinking experiments with DNA substrates containing 5-bromodeoxyuridine (Br-dU) nucleotides for LC-MS/MS analysis. The denaturing polyacrylamide gel demonstrates the generation of covalent peptide-DNA adducts with Br-dU and catalytically inactive SpyCas9 following UV irradiation and trypsin digestion.

Figure 10:
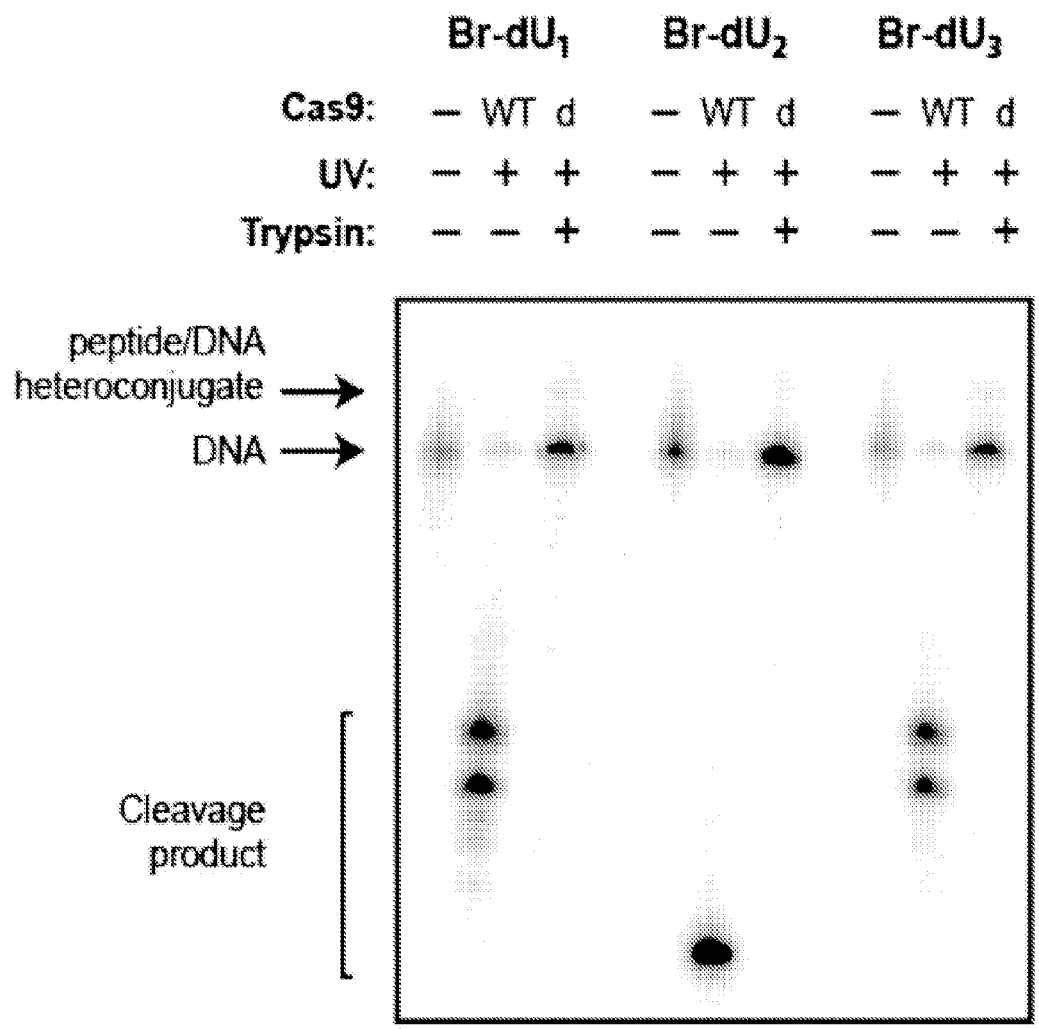
Figure 11A:
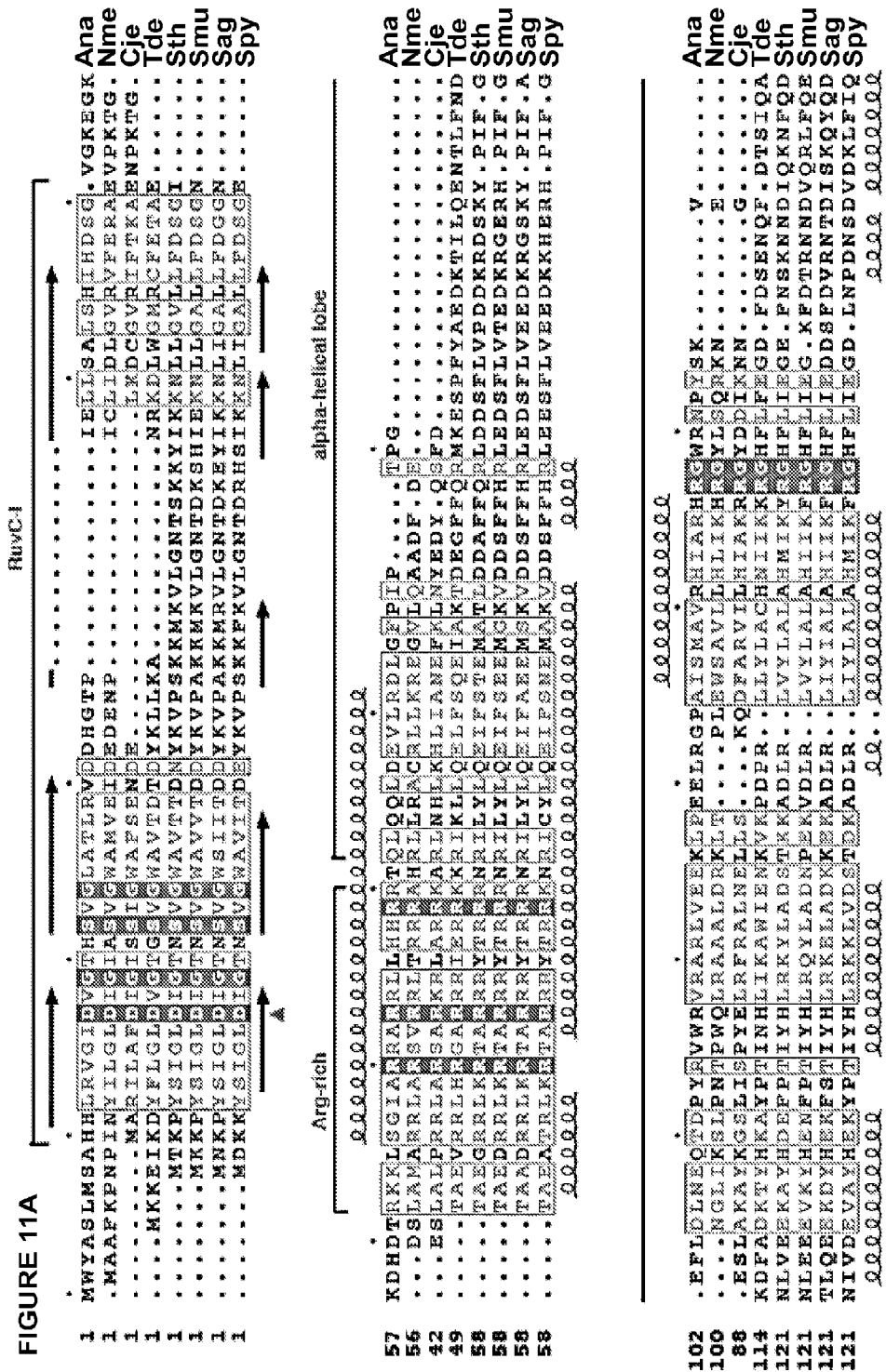
Figure 11B:
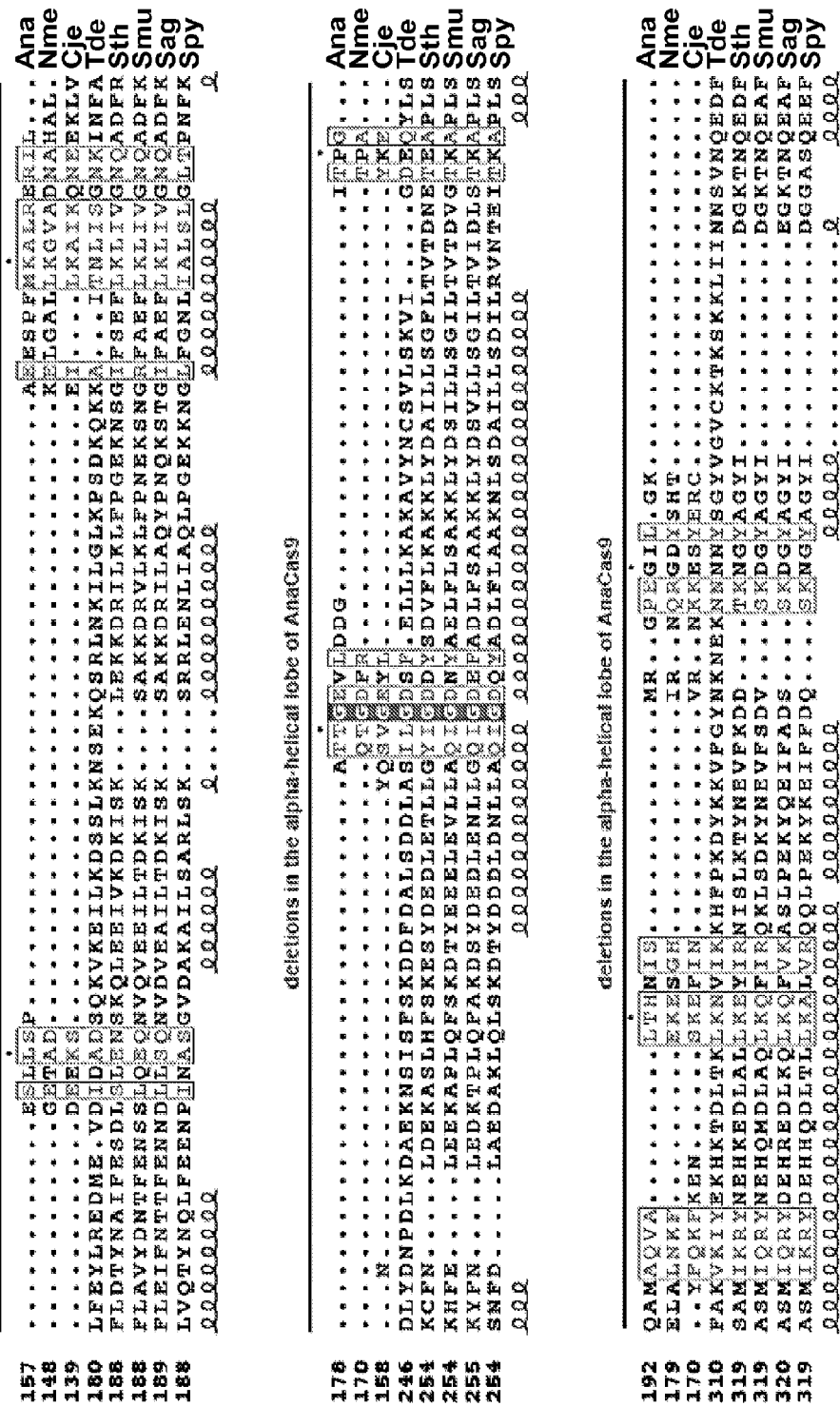
Figure 11D:
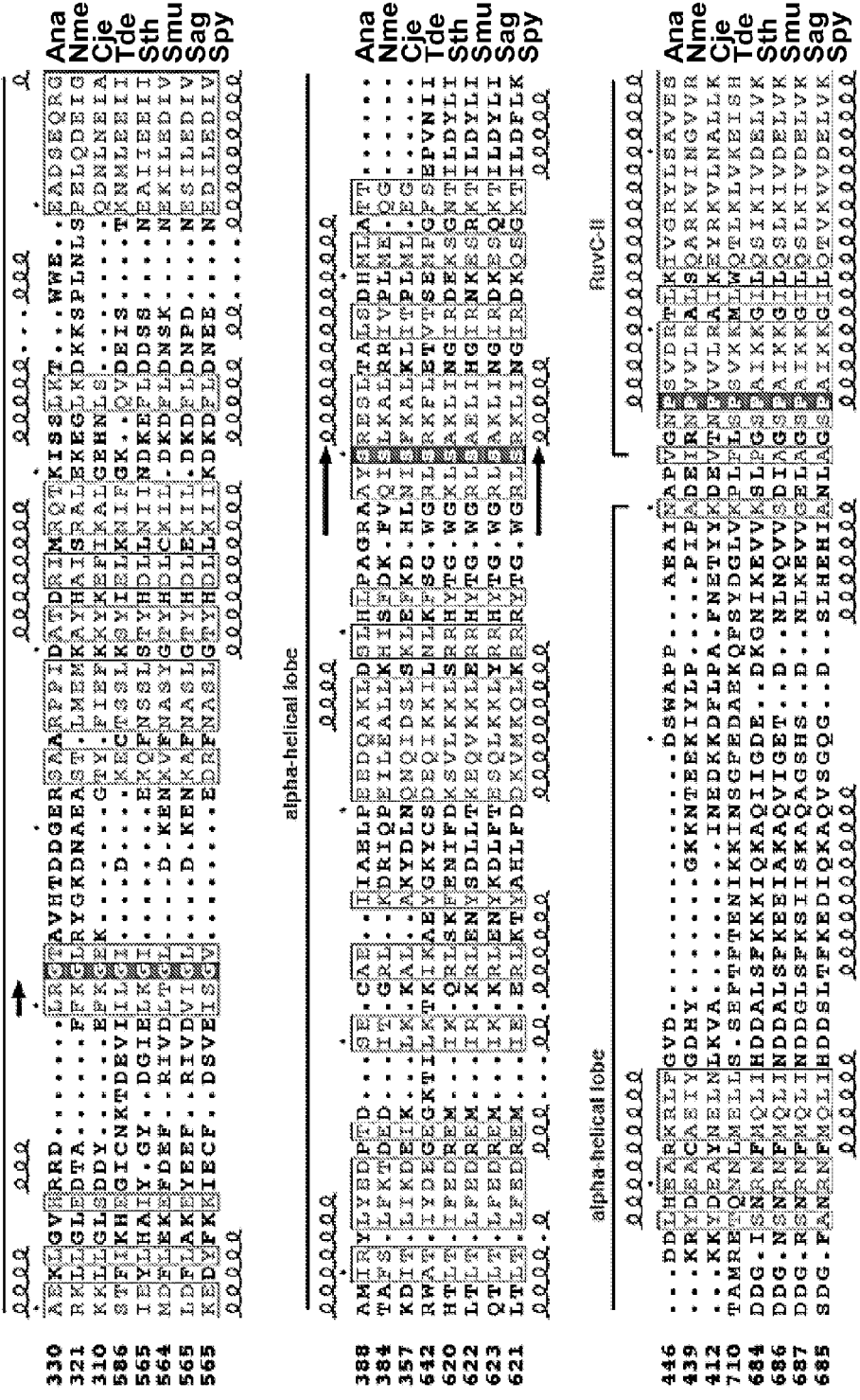
Figure 11E:
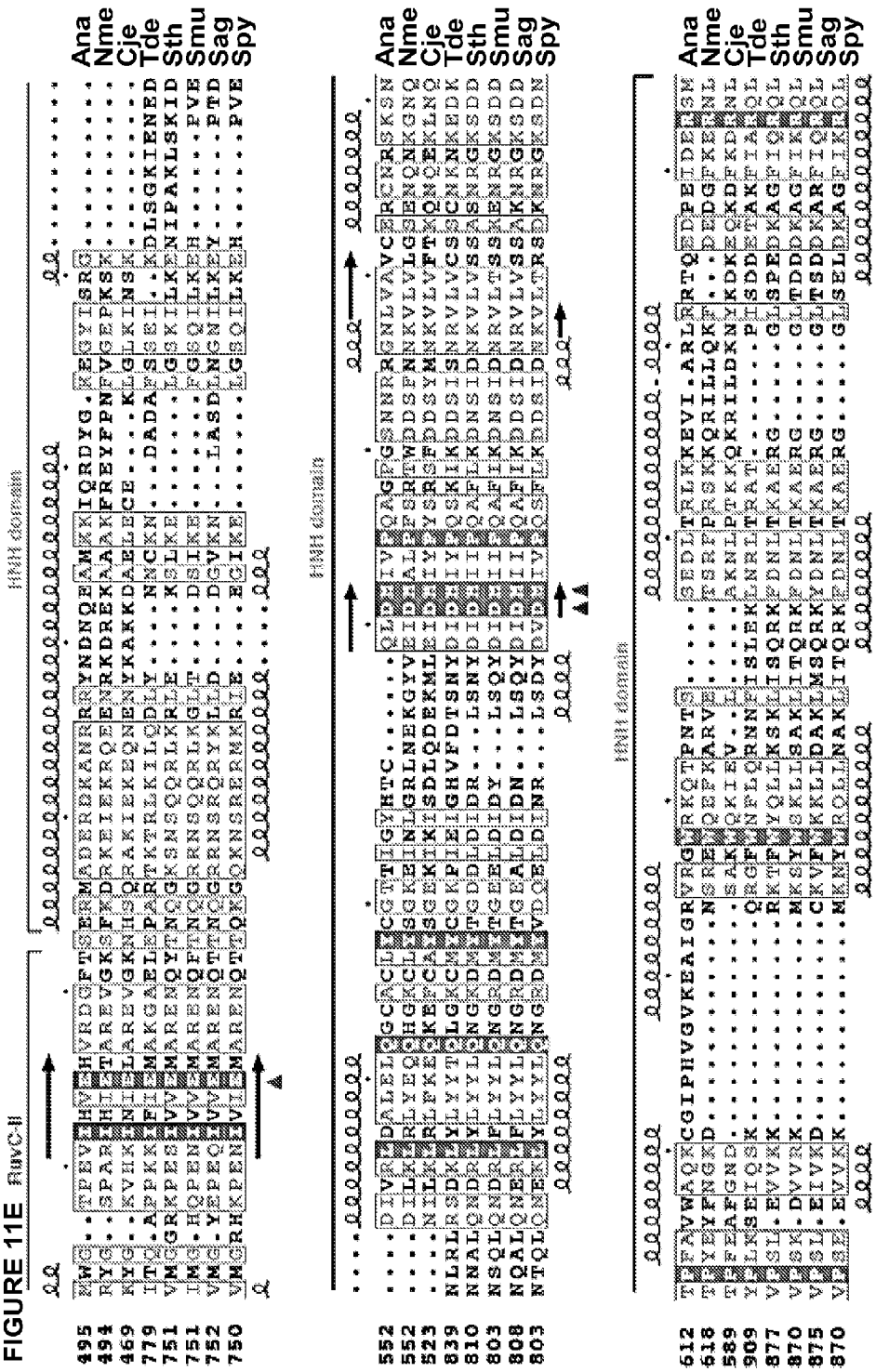
Figure 11F:
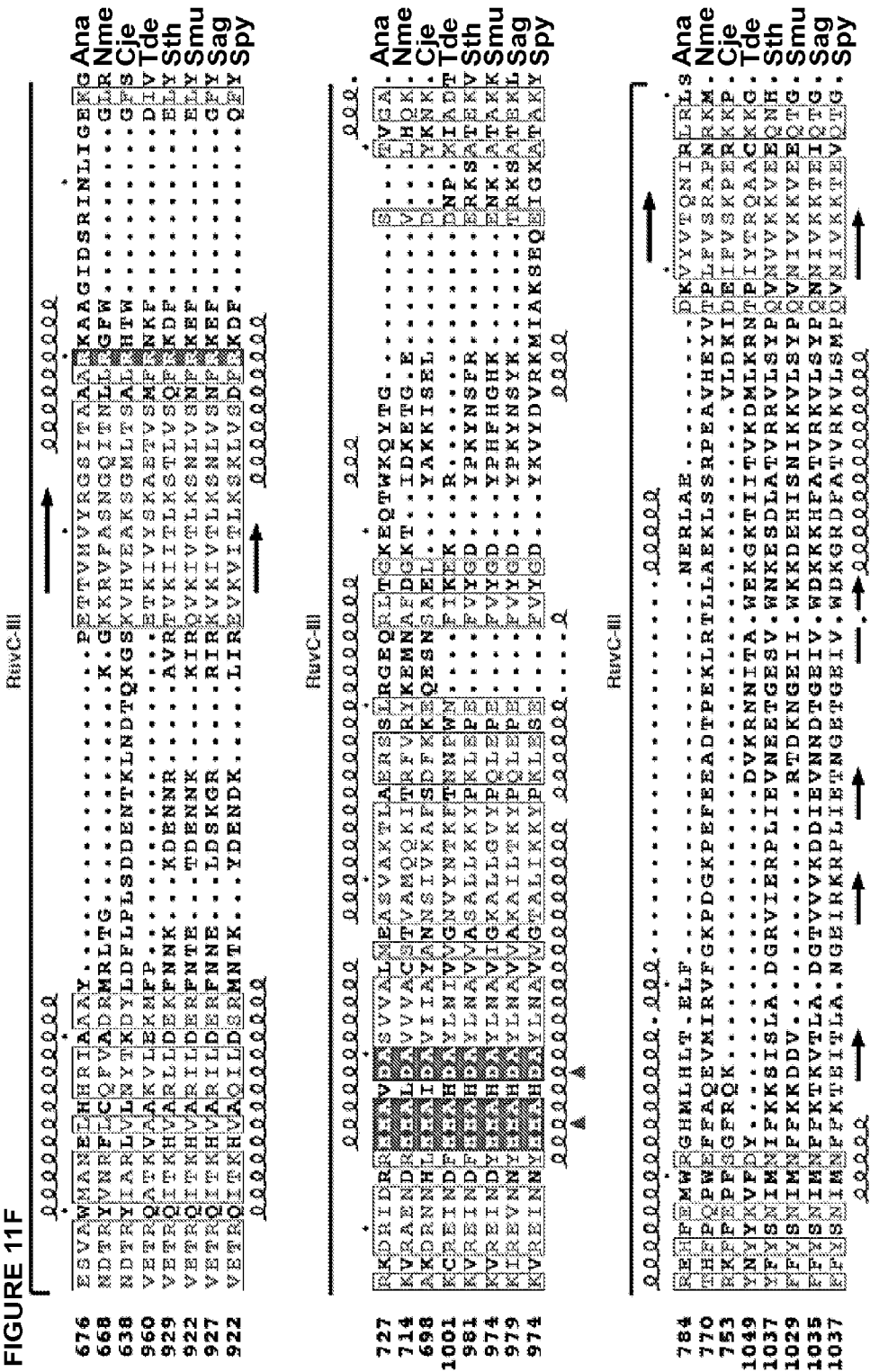
Figure 11G:
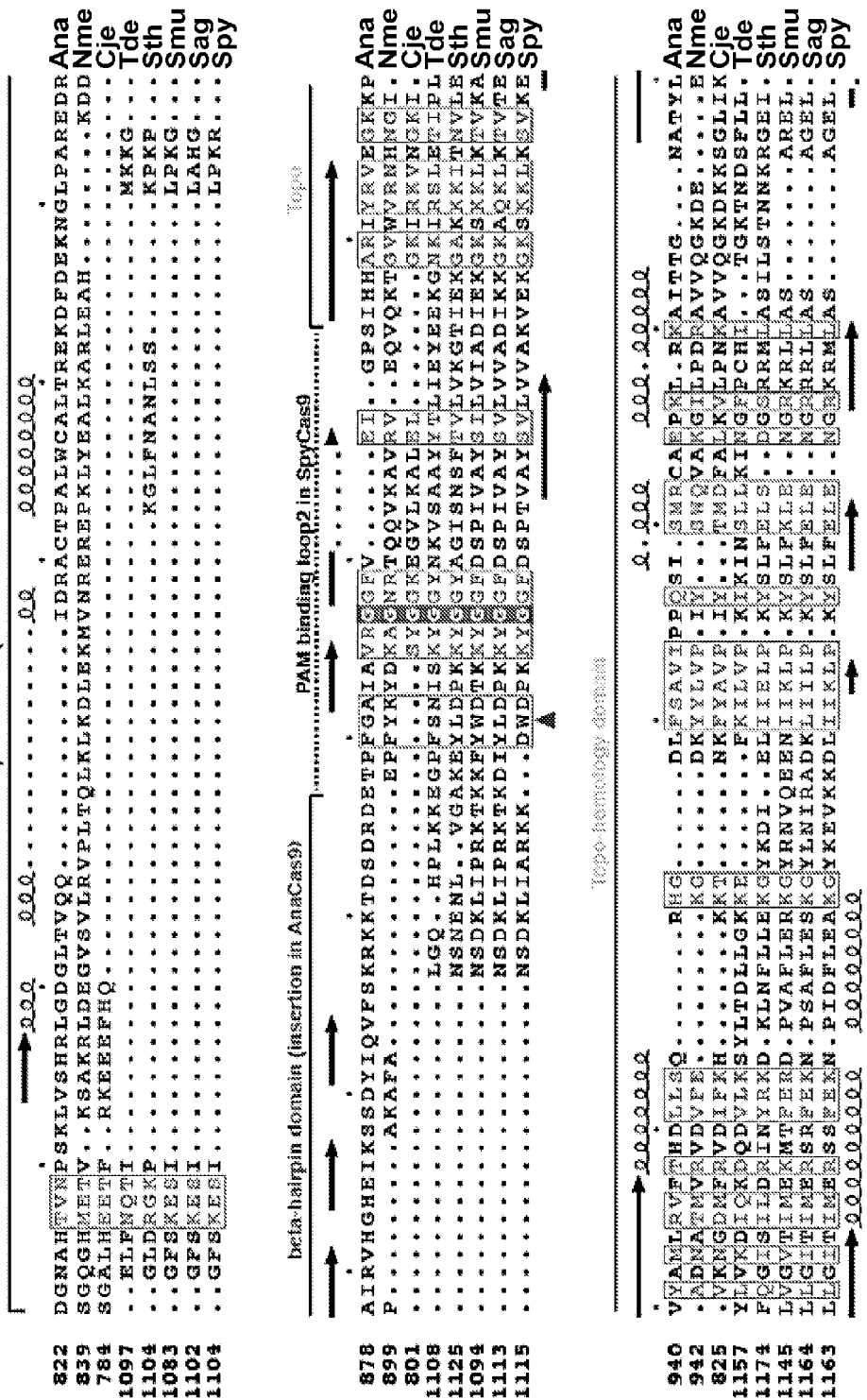
Figure 11H:
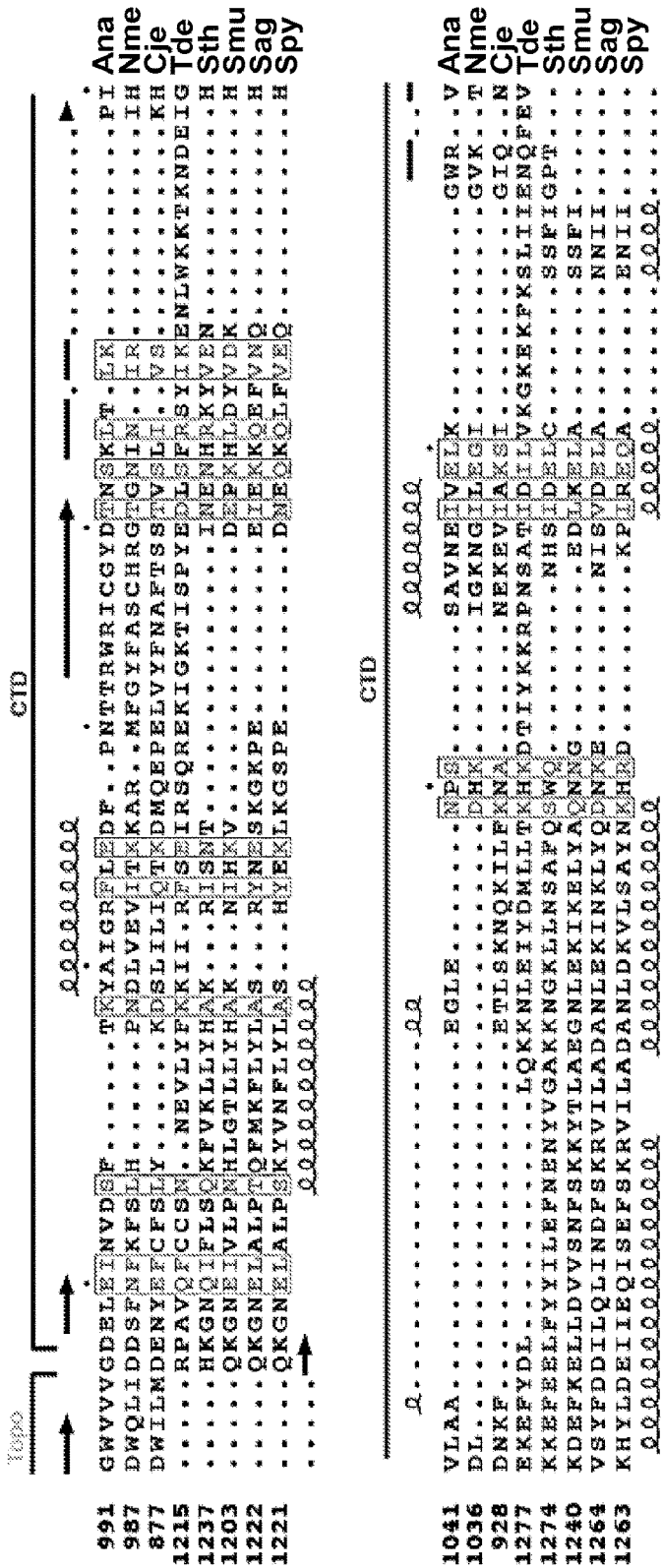
Figure 11I:
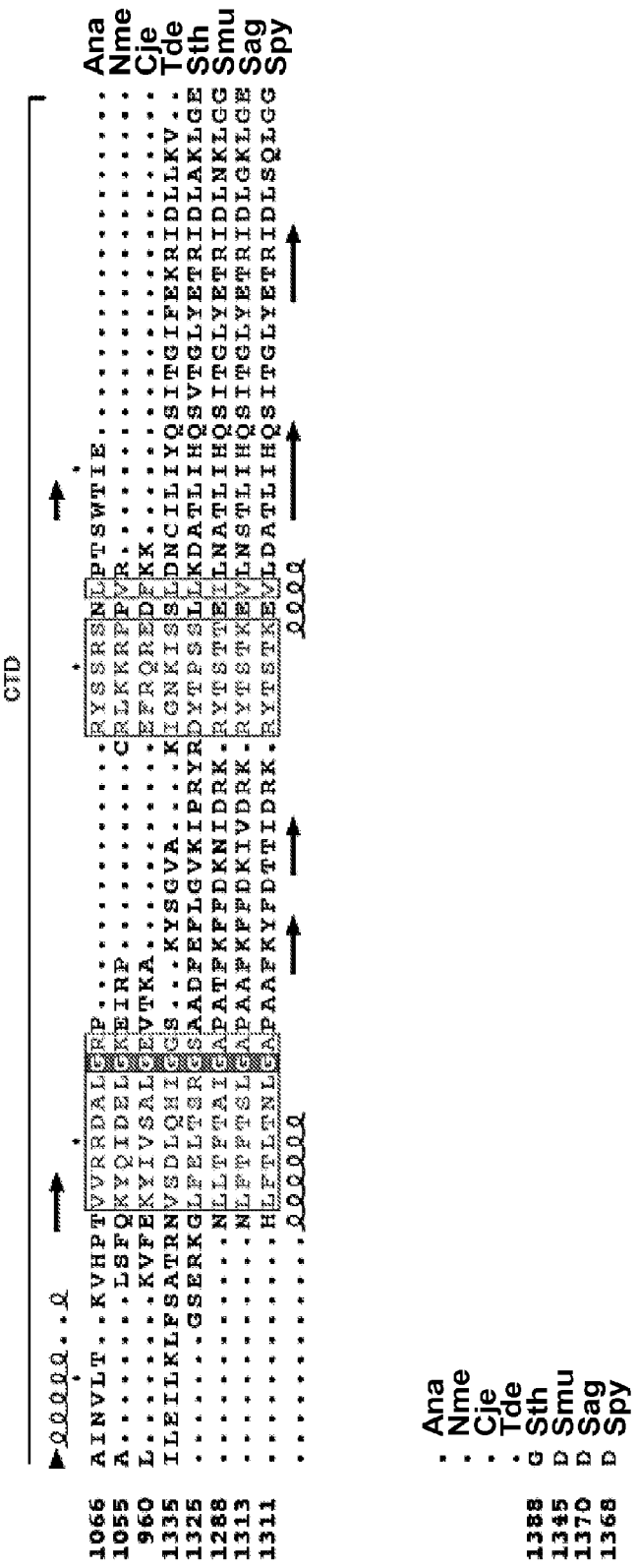

FIG. 10 provides the results of a DNA cleavage assay performed with wild type (WT) and catalytically inactive (d) Cas9 and analyzed by denaturing PAGE.

FIGS. 11A-I provide multiple sequence alignment of Cas9 orthologs associated with Type II-A CRISPR loci. Primary sequences of Cas9 proteins from Ana (*Actinomyces naeslundii* str. Howell 279, EJN84392.1; SEQ ID NO:7), Nme (*Neisseria meningitidis*, WP_019742773.1; SEQ ID NO:8), Cje (*Campylobacter jejuni*, WP_002876341.1; SEQ ID NO:9), Tde (*Treponema denticola*, WP_002676671.1; SEQ ID NO:10), Sth (*Streptococcus thermophilus* LMD-9, YP_820832.1; SEQ ID NO:11), Smu (*Streptococcus mutans*, WP_019803776.1; SEQ ID NO:12), Sag (*Streptococcus agalactiae*, WP_001040088.1; SEQ ID NO:13), and Spy (*Streptococcus pyogenes*, YP_282132.1; SEQ ID NO:14) were aligned using CLUSTALW and generated in ESPript.

Figure 12:
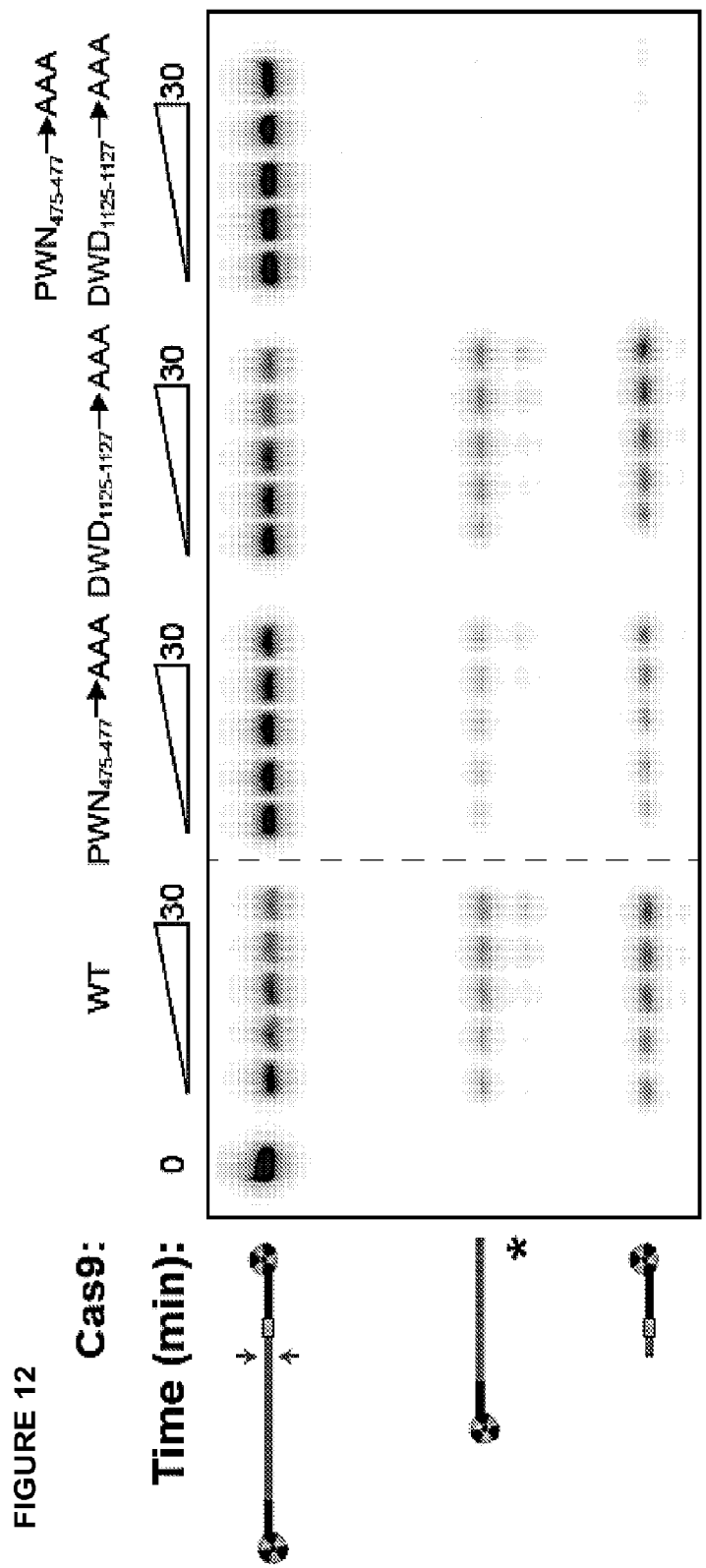

FIG. 12 provides DNA cleavage activity assays with SpyCas9 constructs containing mutations in residues identified by crosslinking and LC-MS/MS experiments.

Figure 13A:
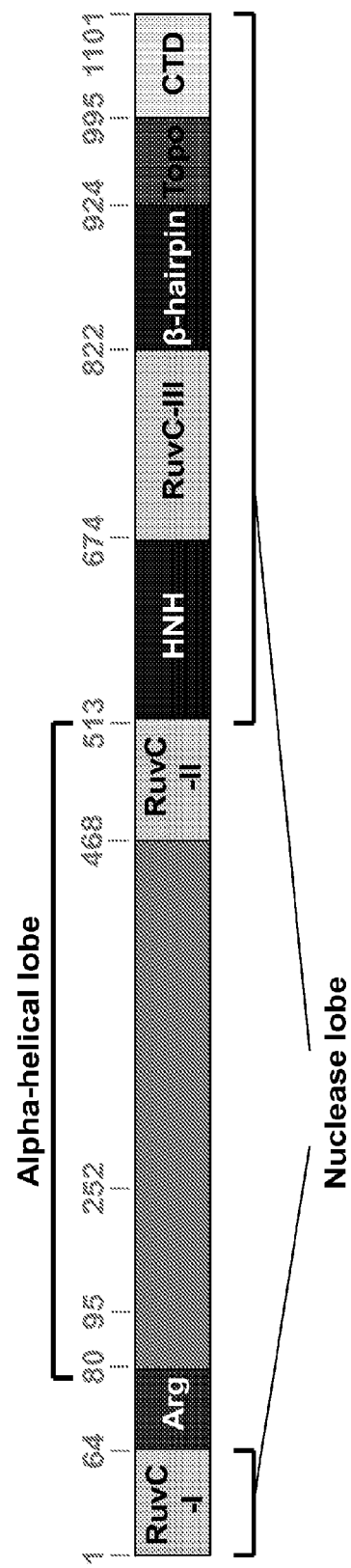
Figure 13B:
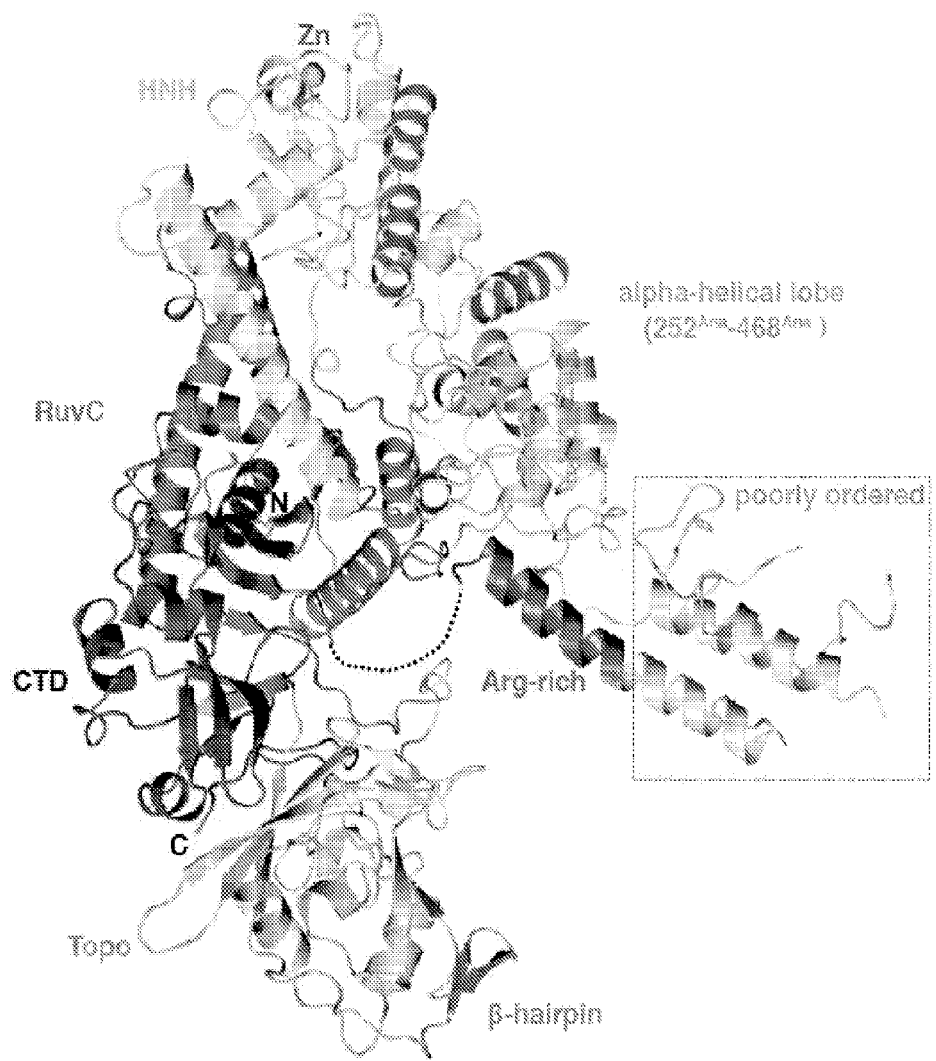
Figure 13C:
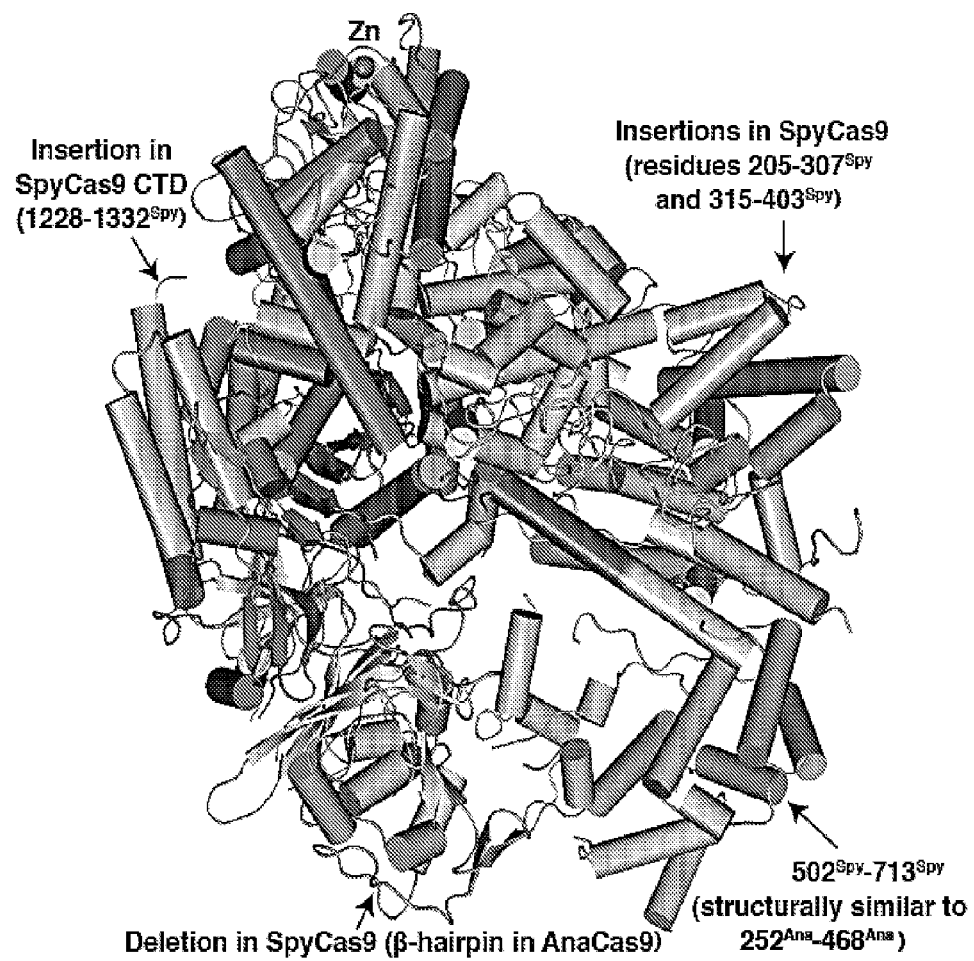

FIGS. 13A-C provide (A) a cartoon of schematic of the polypeptide sequence and domain organization of the Cas9 protein from *A. naeslundii* (AnaCas9), (B) orthogonal views of the overall structure of AnaCas9 shown in ribbon representation, (C) superposition of AnaCas9 with SpyCas9.

Figure 14:
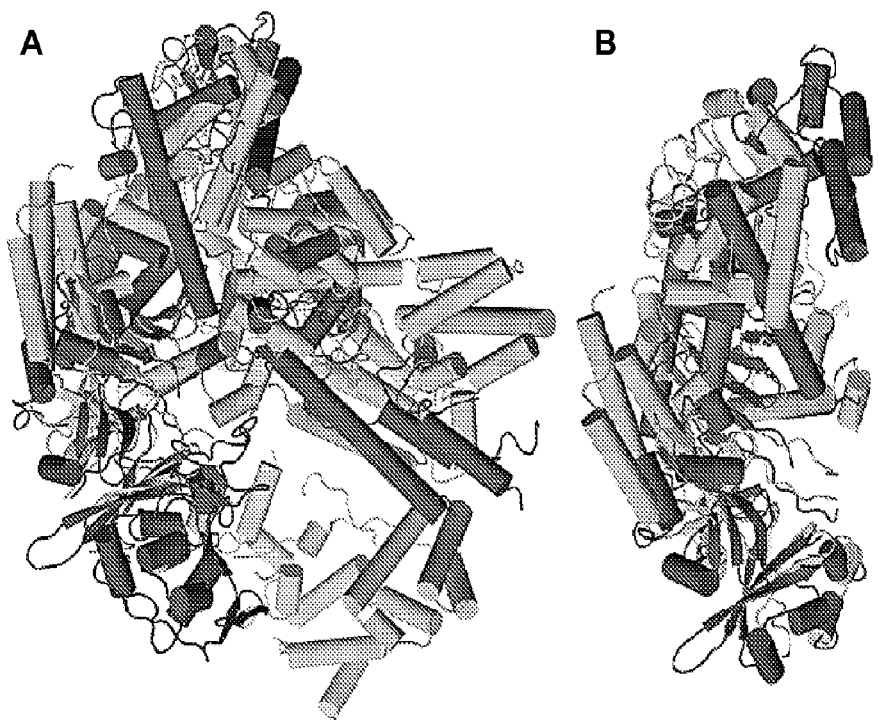
Figure 14C:
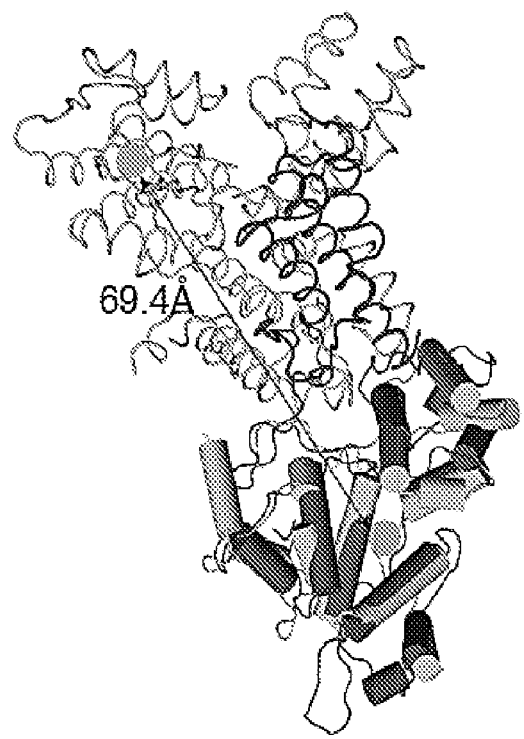

FIGS. 14A-C provide superpositions of AnaCas9 and SpyCas9 showing the structural alignment of (A) the overall proteins, (B) the catalytic core, and (C) the alpha-helical lobe.

Figure 15:
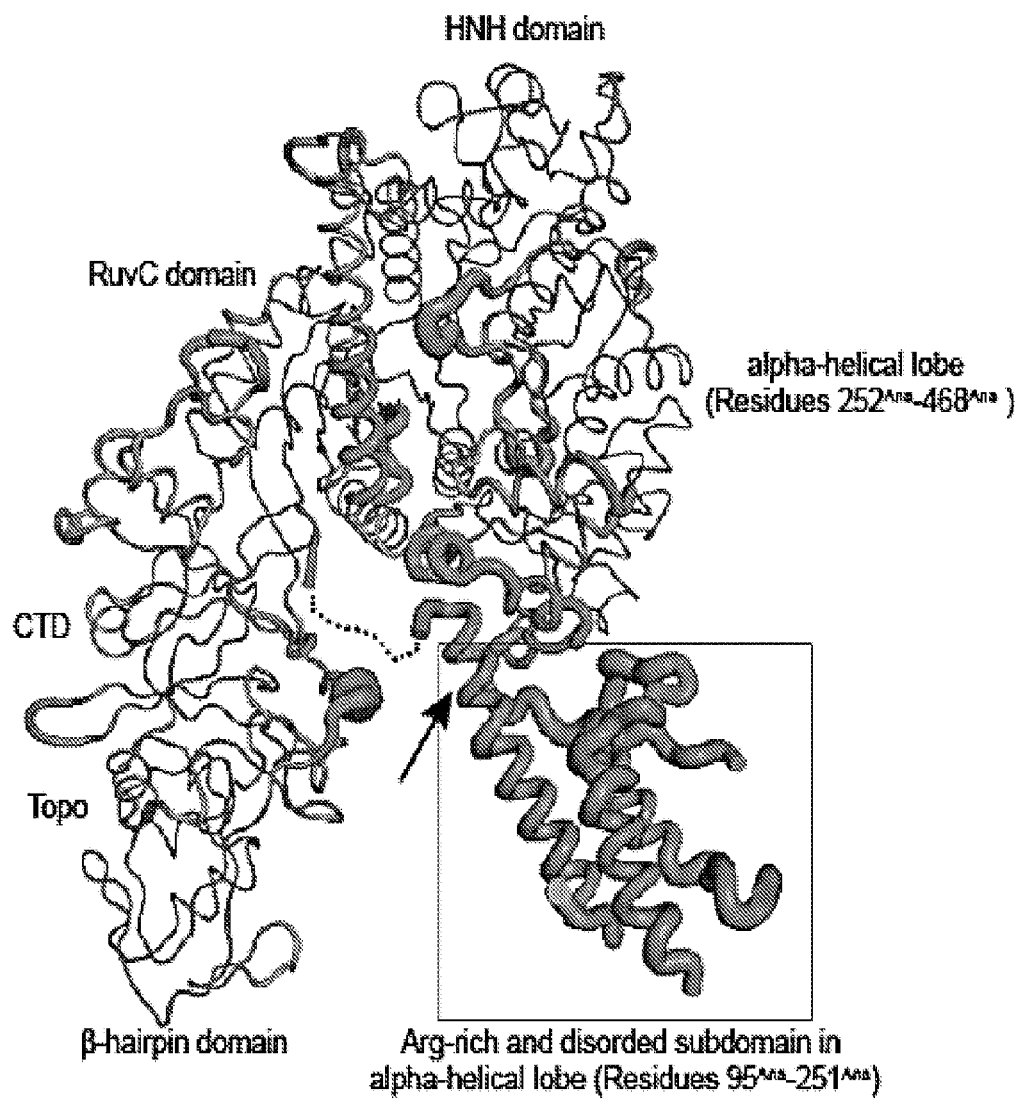

FIG. 15 provides a B-factor putty plot of AnaCas9 wherein thin loops represent low B-values, while broad tubes represent high B-values.

Figure 16:
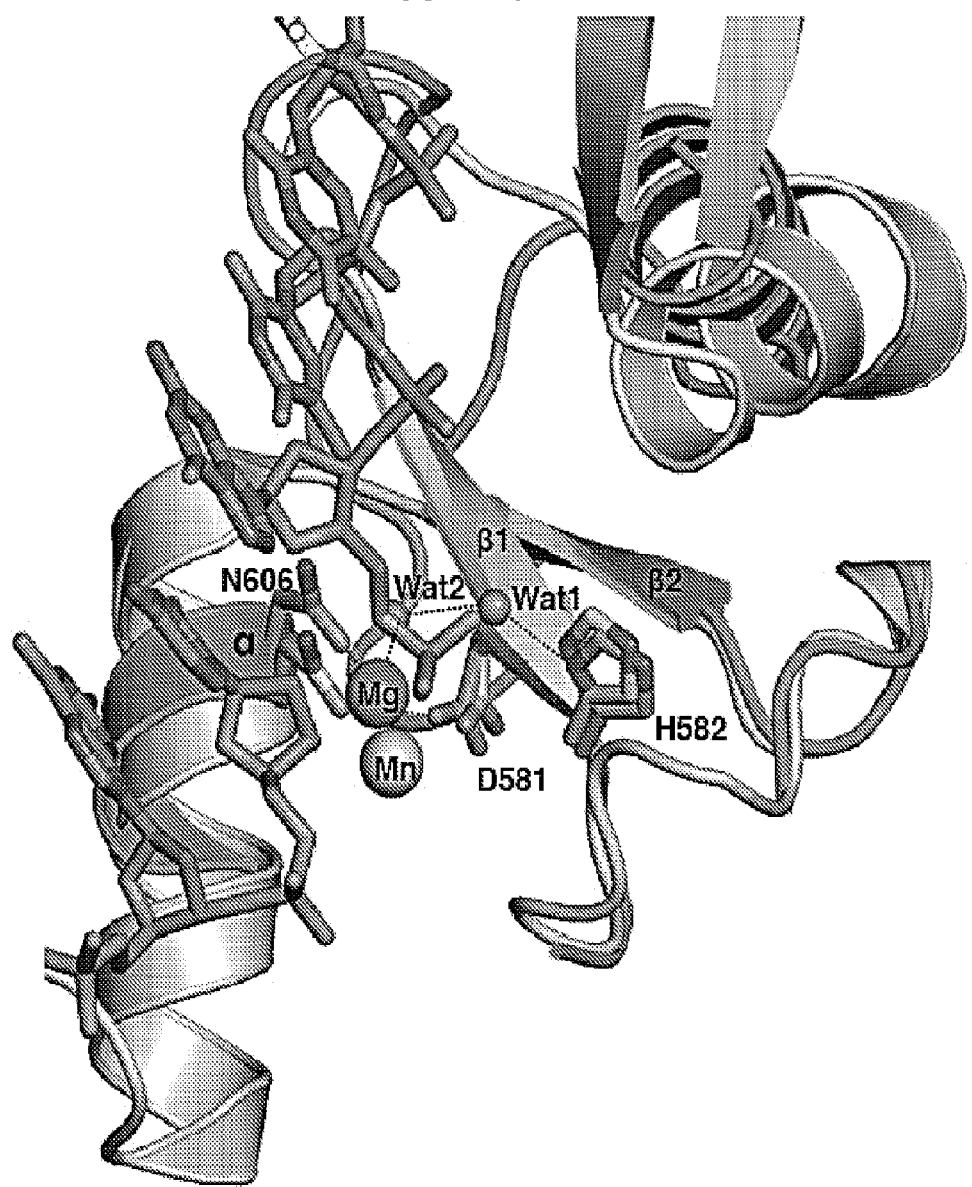

FIG. 16 provides a close-up view of the active site of AnaCas9 HNH domain superimposed with the structure of I-HmuI-DNA complex (PDB entry 1U3E).

Figure 17:
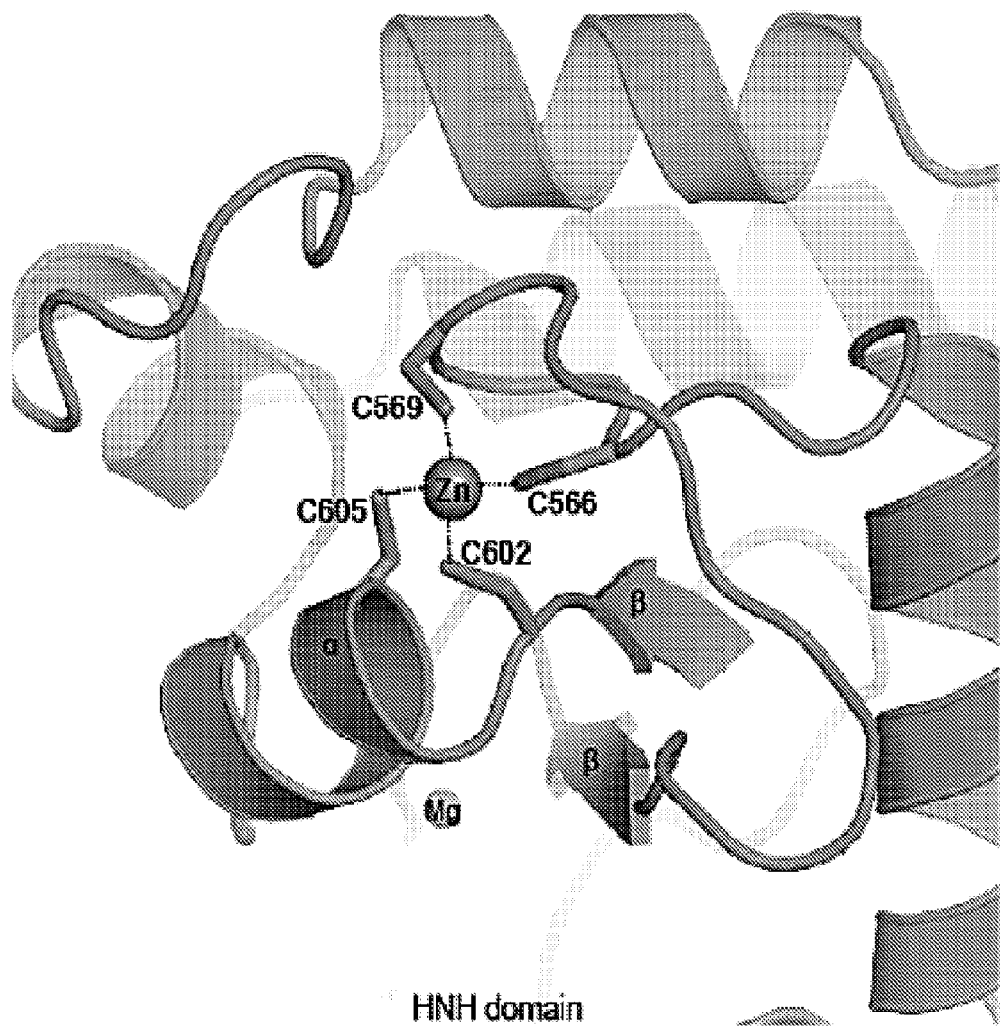

FIG. 17 provides a close-up view of the zinc-binding site in the HNH domain of AnaCas9 and the coordinating resides.

Figure 18:
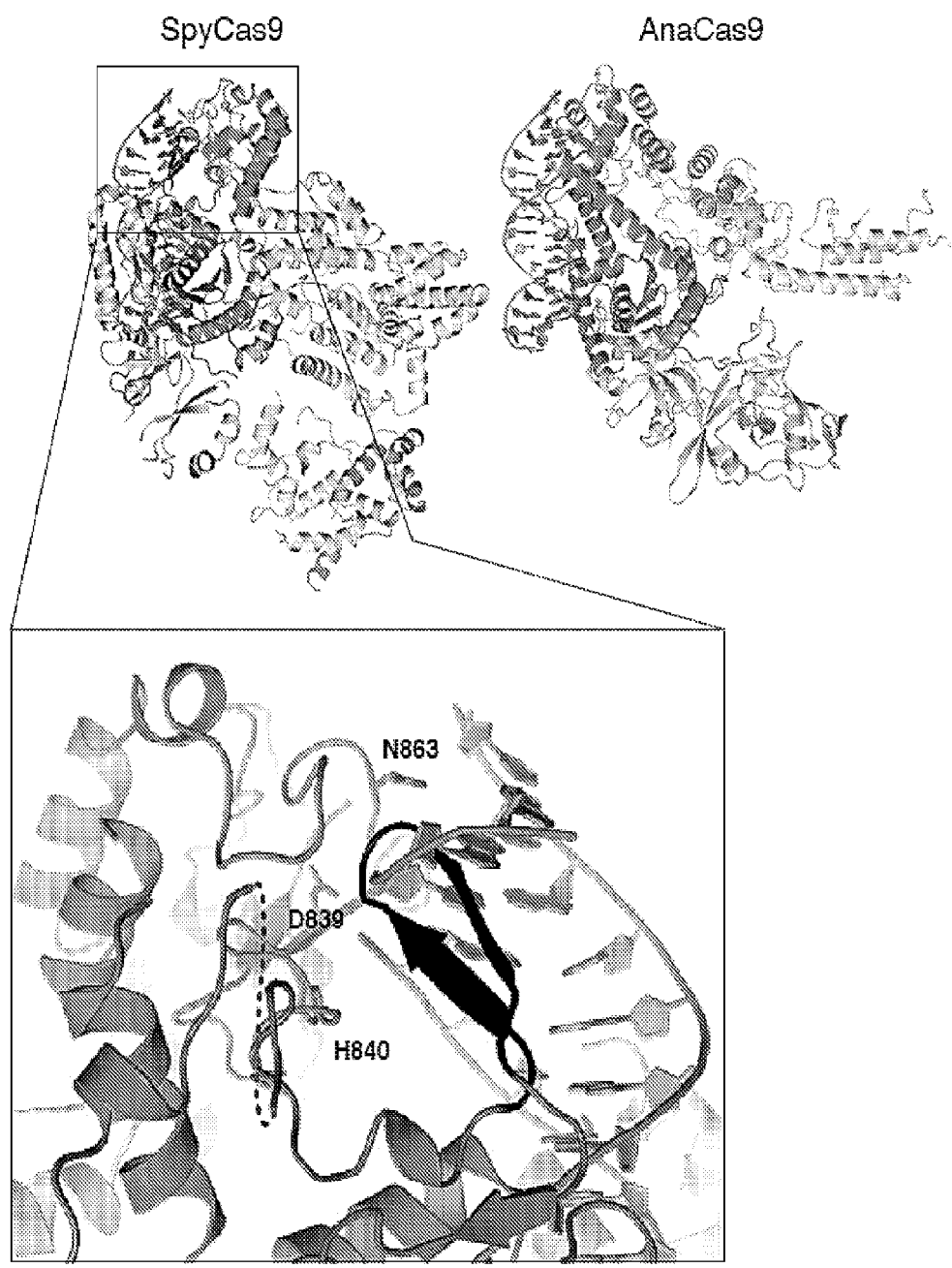

FIG. 18 provides models showing the (A) overall auto-inhibited conformations of SpyCas9 and AnaCas9 in the outbound state and a (B) zoomed in view of the HNH domain (yellow) active site in SpyCas9 occluded by the $1049^{Spy}$-$1059^{Spy}$ beta-hairpin (black).

Figure 19:
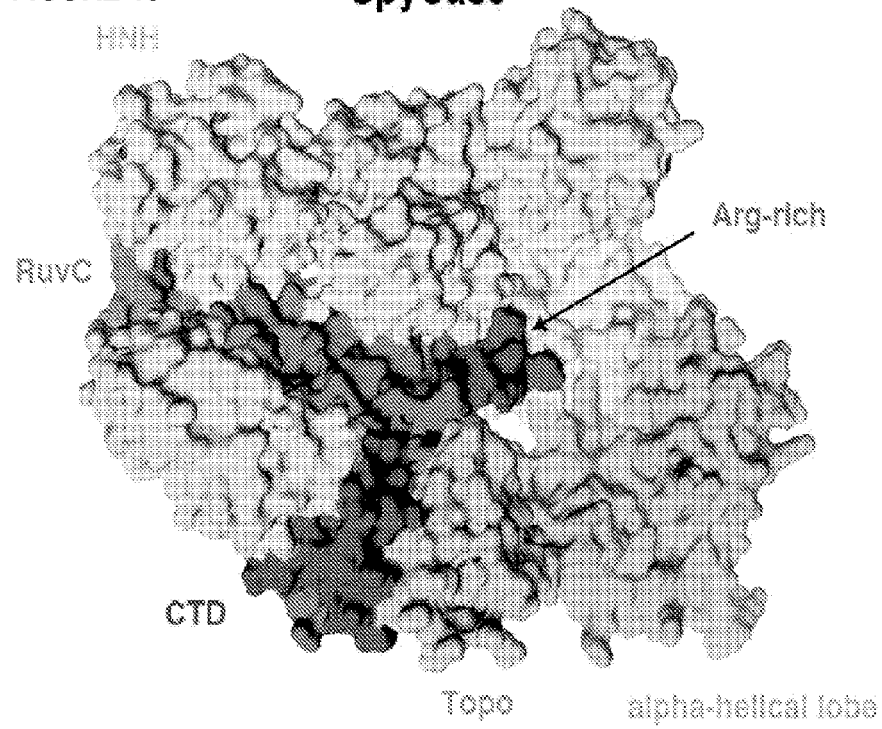
Figure 19:
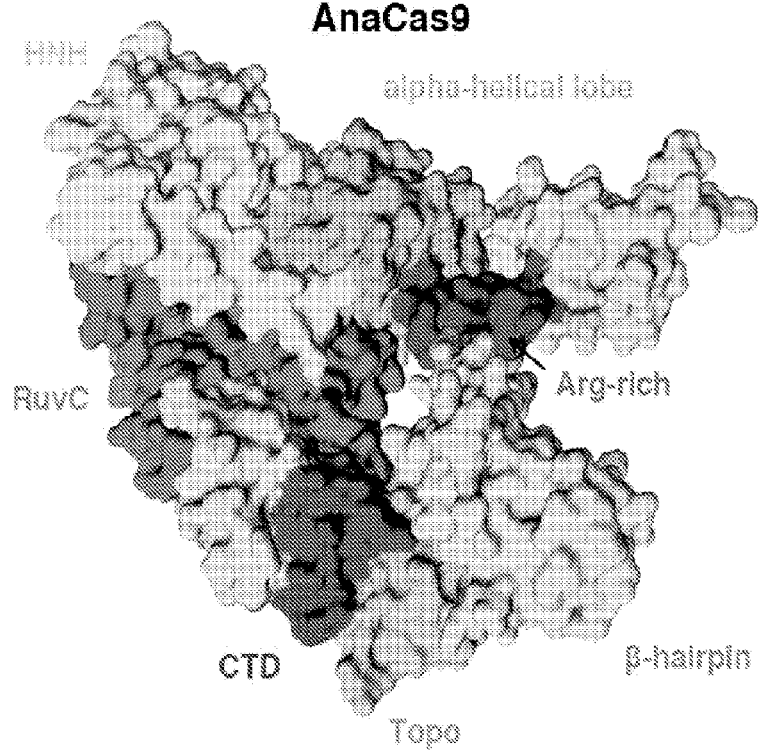

FIG. 19 provides a common Cas9 functional core through structural comparison of surface representations of SpyCas9 and AnaCas9 with conserved RuvC, HNH, Arg-rich, Topo-homology and CTD domains.

Figure 20:
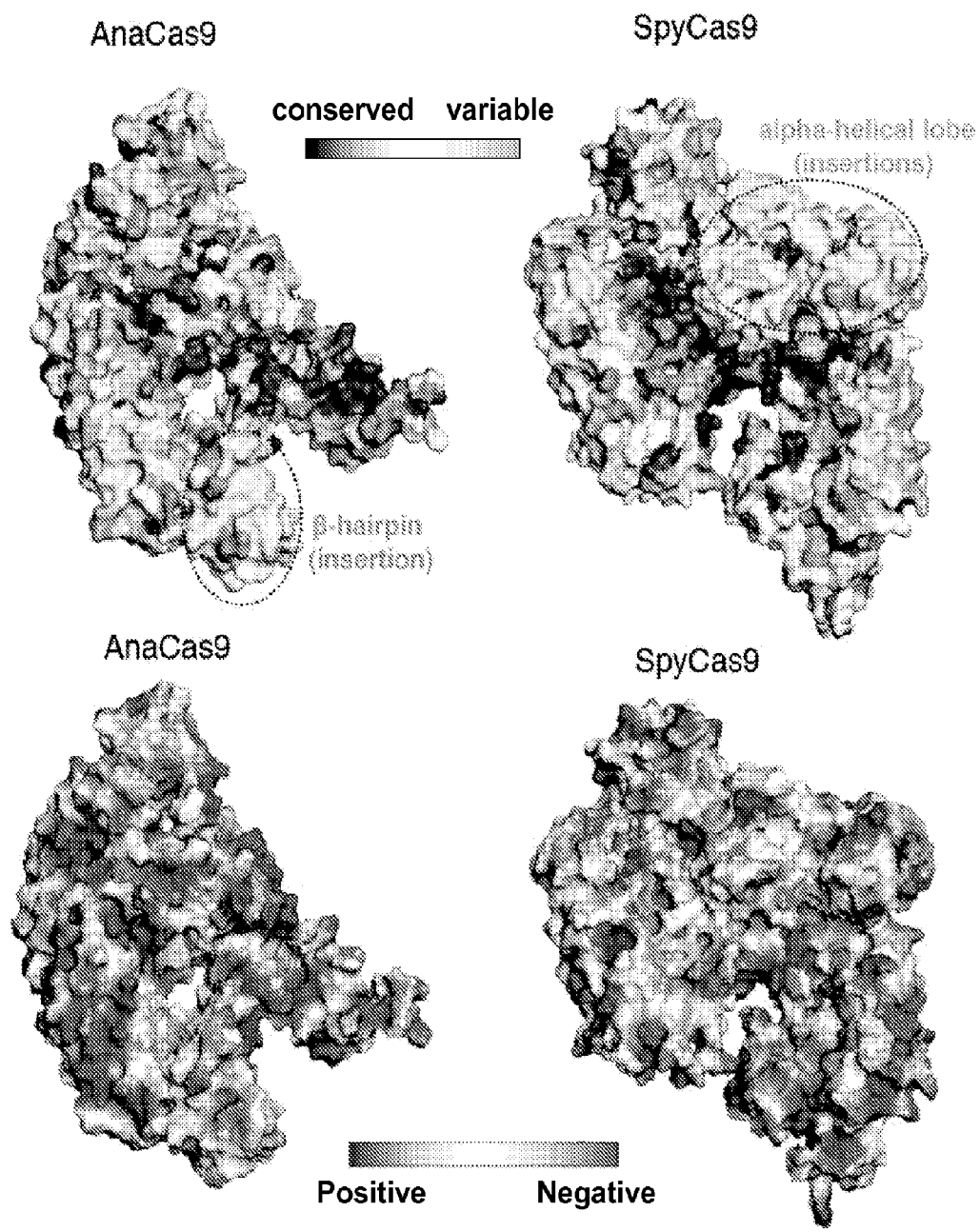

FIG. 20 provides surface feature comparison of SpyCas9 and AnaCas9 evolutionary amino acid residue conservation and electrostatic potential.

Figure 21:
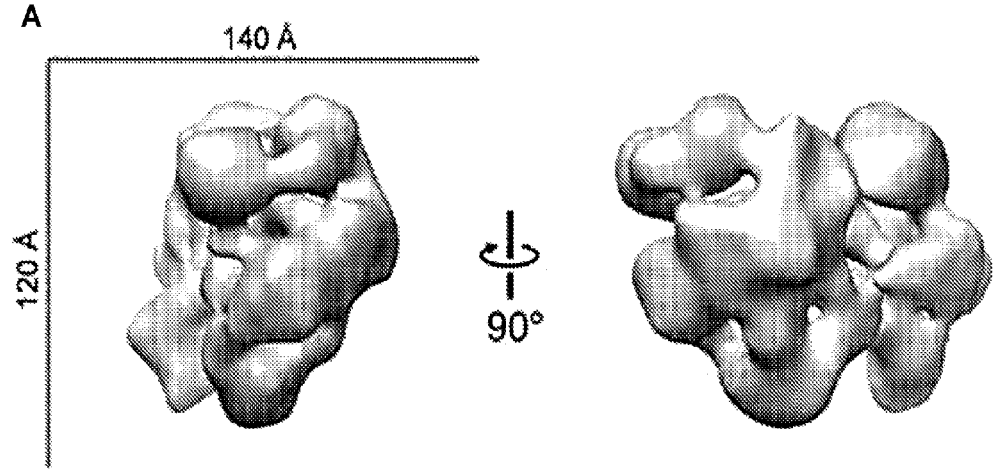
Figure 21:
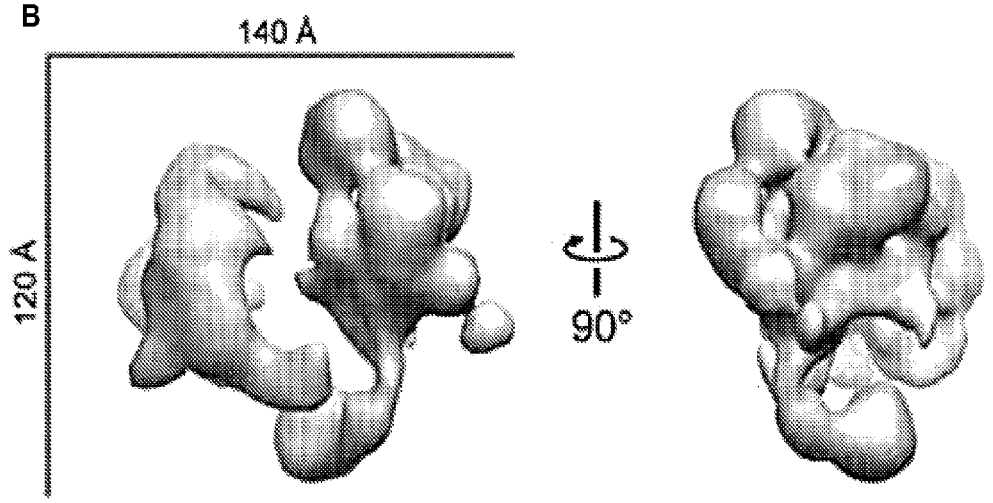

FIGS. 21A-B provide reconstructions of (A) apo-Cas9 and (B) Cas9:RNA:DNA produced from negative-stain electron microscopy.

Figure 22:
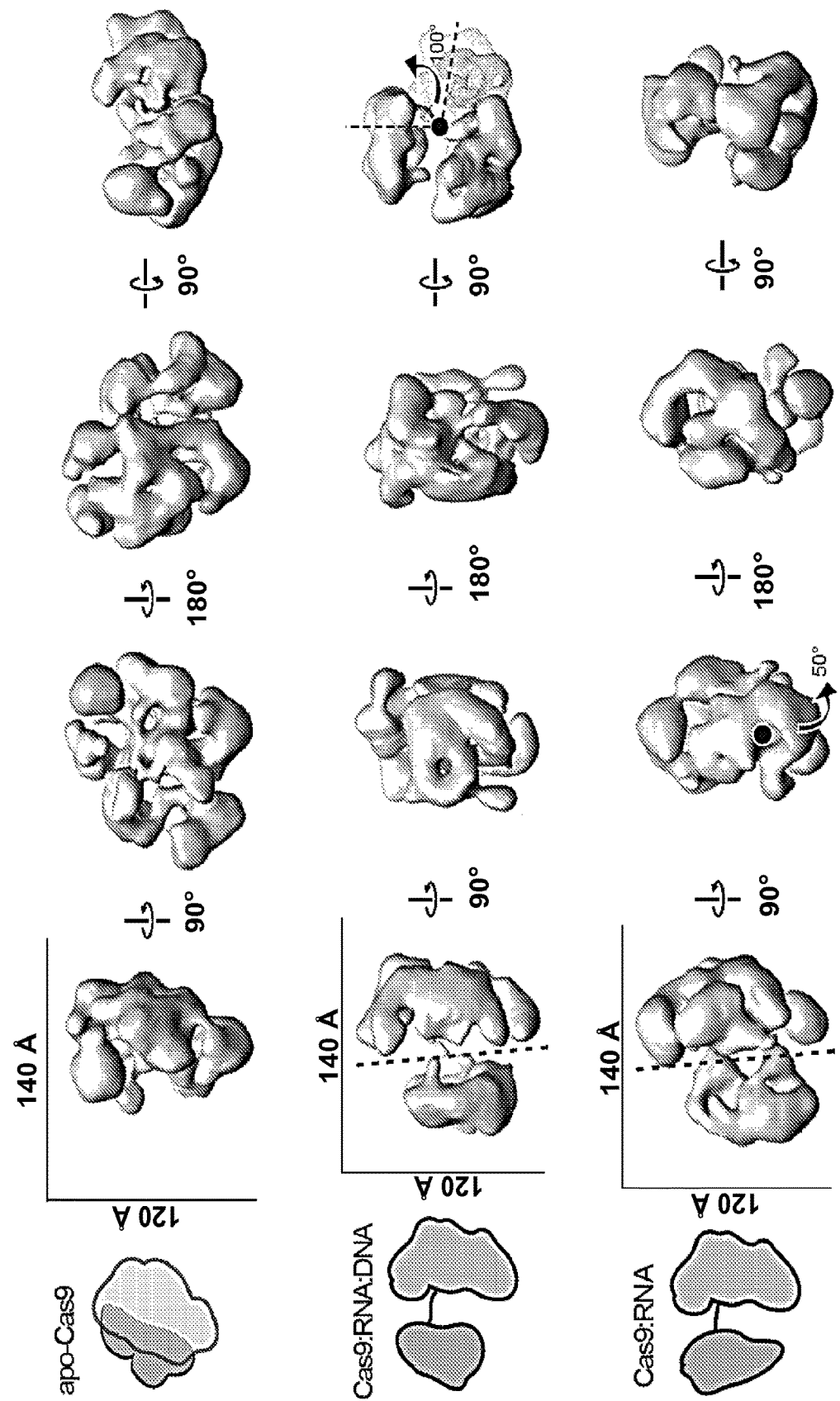

FIG. 22 provides cartoon representations and single particle EM reconstructions of negatively stained apo-Cas9, Cas9:RNA:DNA, and Cas9:RNA at 19-, 19-, and 21-Å resolution, respectively.

Figure 23A:
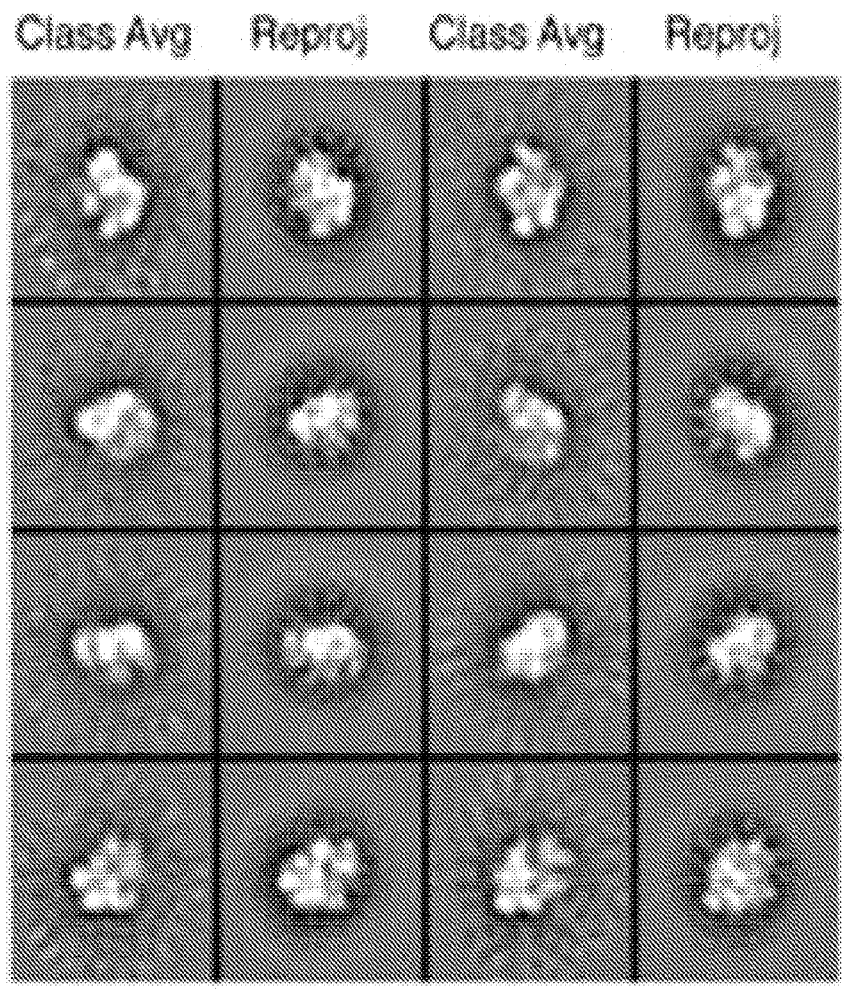
Figure 23B:
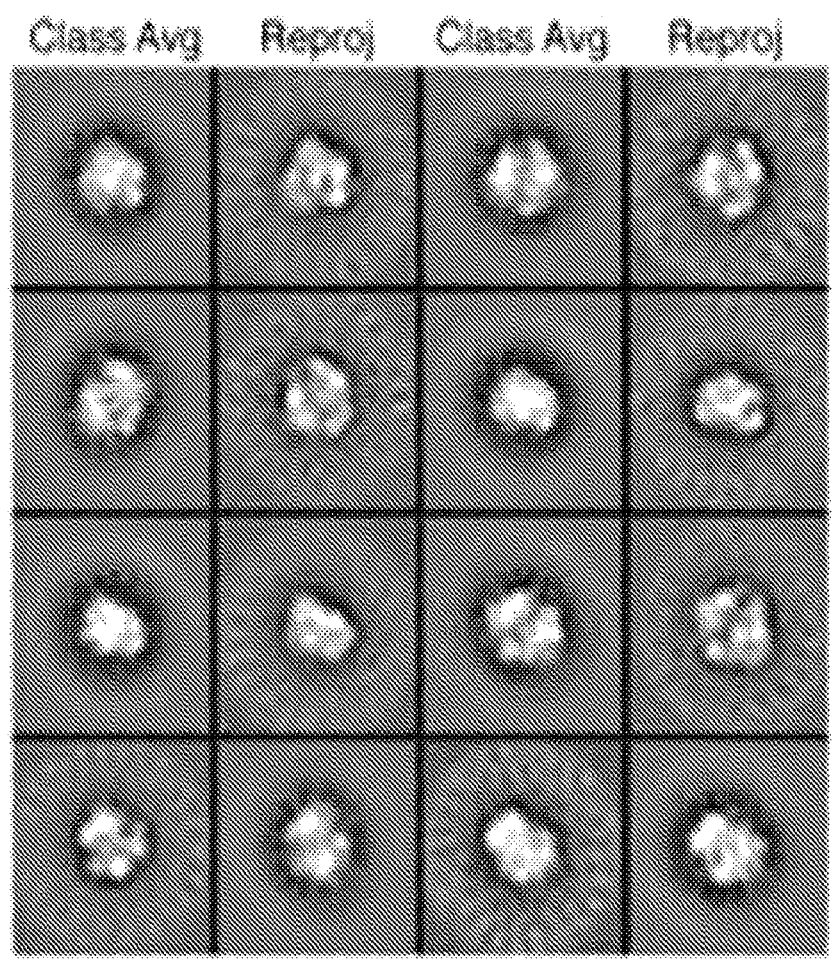

FIGS. 23A-B provide reference free 2D class averages of (A) apo-Cas9 and (B) Cas9:RNA:DNA matched to projections of the final reconstructions.

Figure 24:
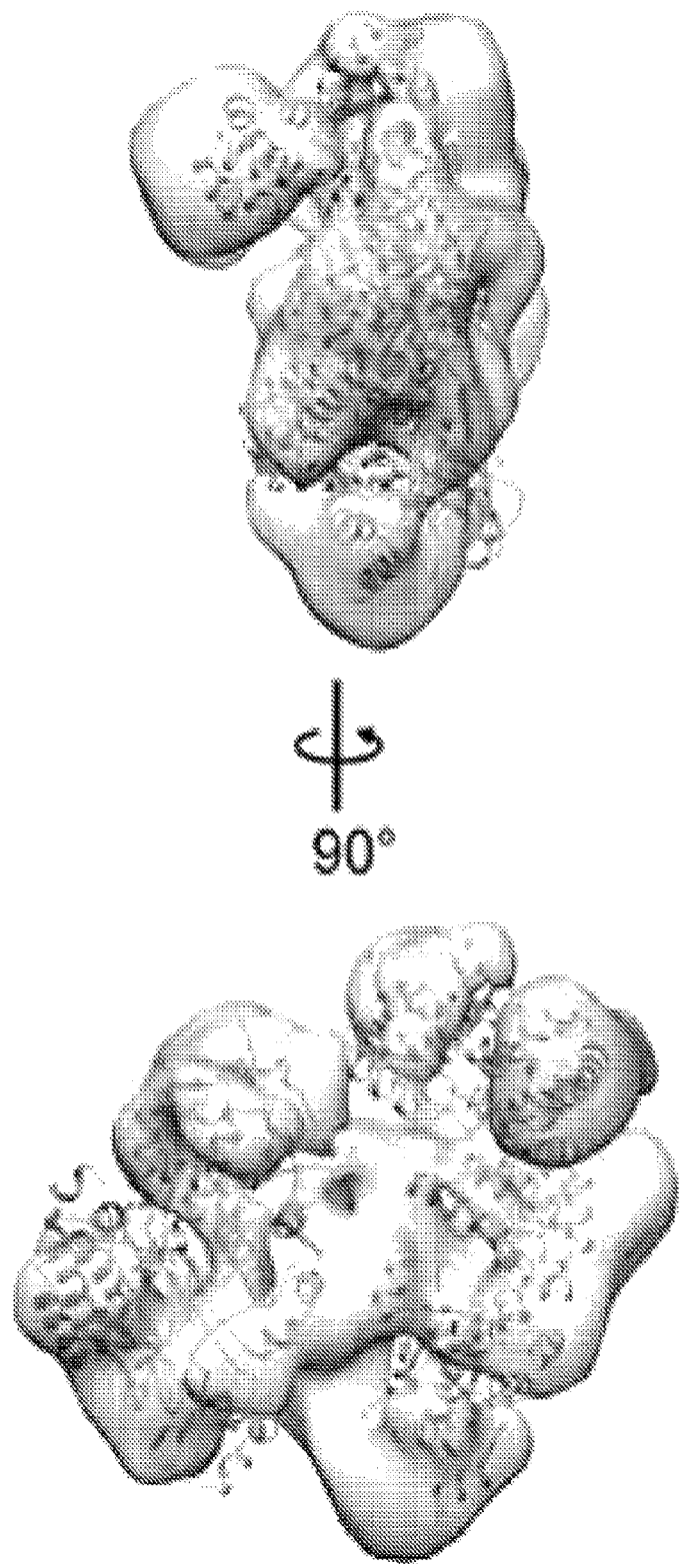

FIG. 24 provides computational docking of X-ray crystal structure of *S. pyogenes* apo-Cas9 into the apo-Cas9 EM density model.

Figure 25:
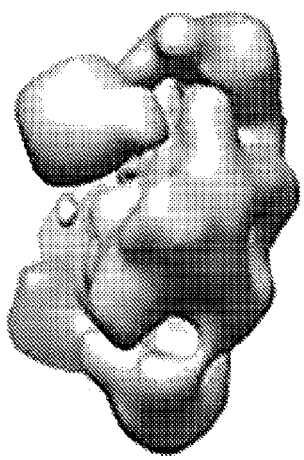
Figure 25:
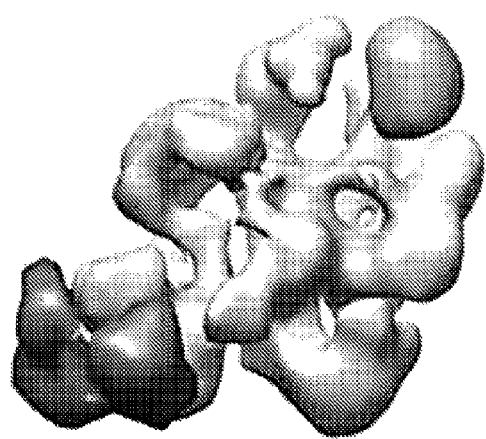
Figure 25:
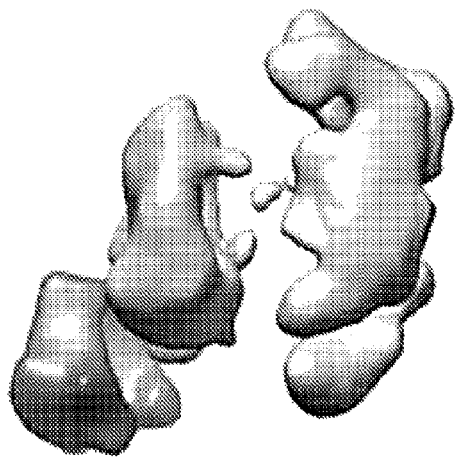
Figure 25:
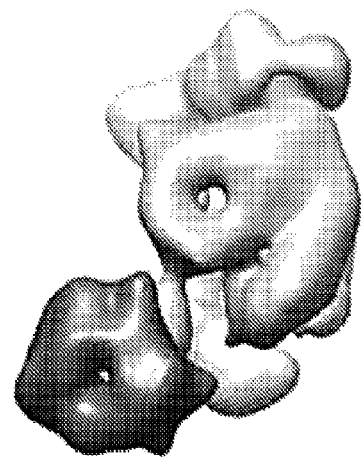

FIG. 25 provides 3D difference maps between the N-terminal MBP-labeled and unlabeled reconstructions of apo-Cas9 and Cas9:RNA:DNA mapped onto the corresponding unlabeled reconstructions.

Figure 26:
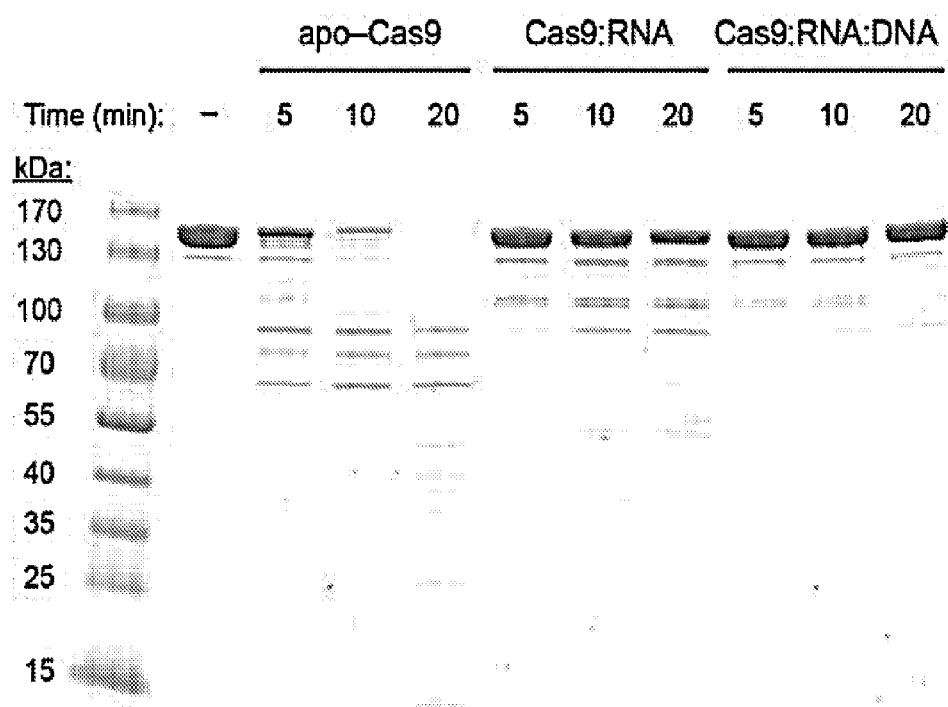

FIG. 26 provides a proteolysis assay performed on apo-Cas9, Cas9:RNA, and Cas9:RNA:DNA resolved by SDS-PAGE.

Figure 27:
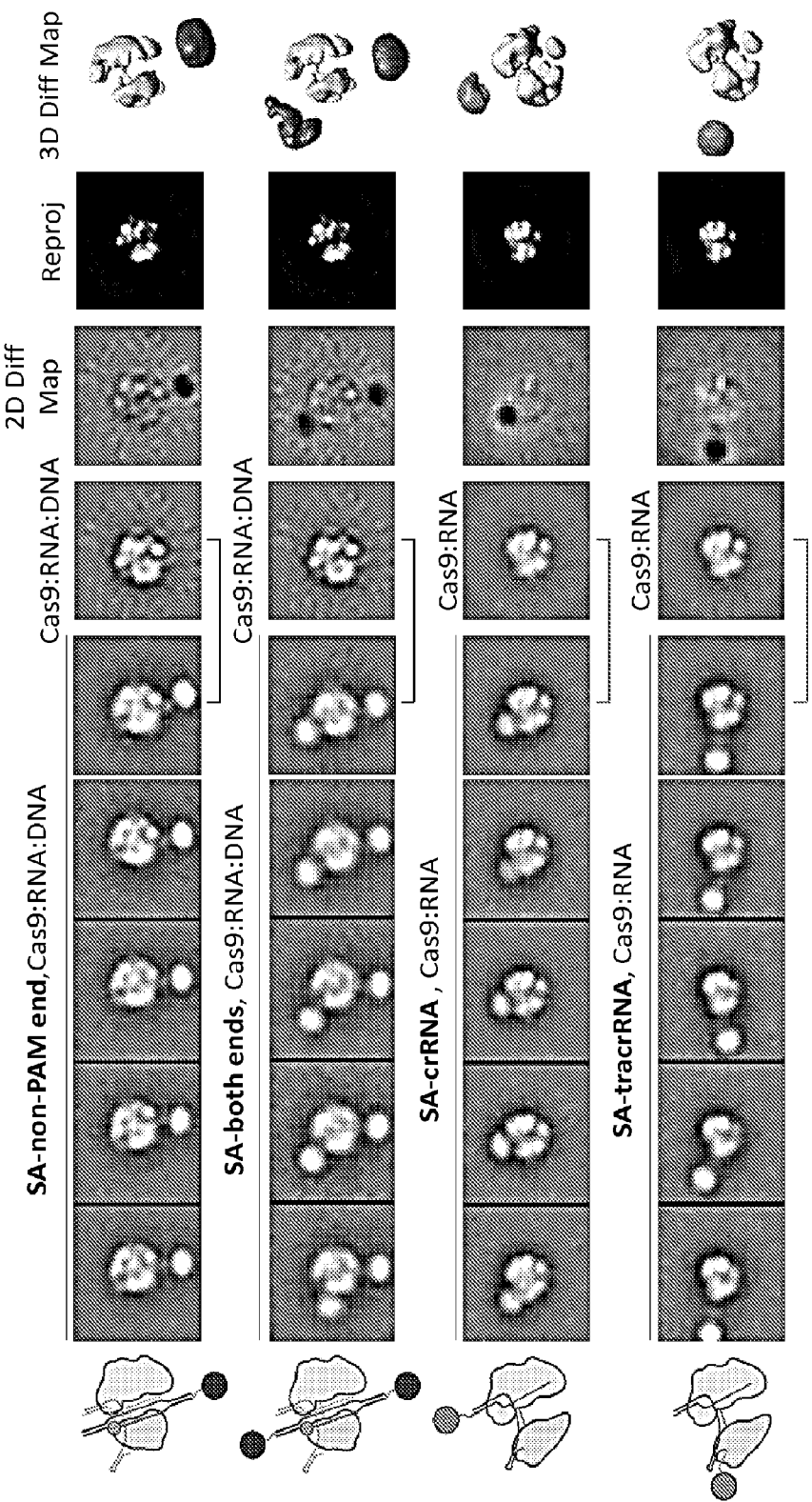

FIG. 27 provides single particle EM analyses of streptavidin (SA) labelled nucleic acids bound to Cas9. For each combination of labelled nucleic acid and Cas9 included are schematics of structures and labels, five representative reference-free 2D class averages, the corresponding reference-free 2D class average of unlabeled Cas9 bound to nucleic acid, a 2D difference map between the unlabeled and labeled structures, the corresponding reprojection of the Cas9 bound to nucleic acid, and corresponding reconstructions.

Figure 28:
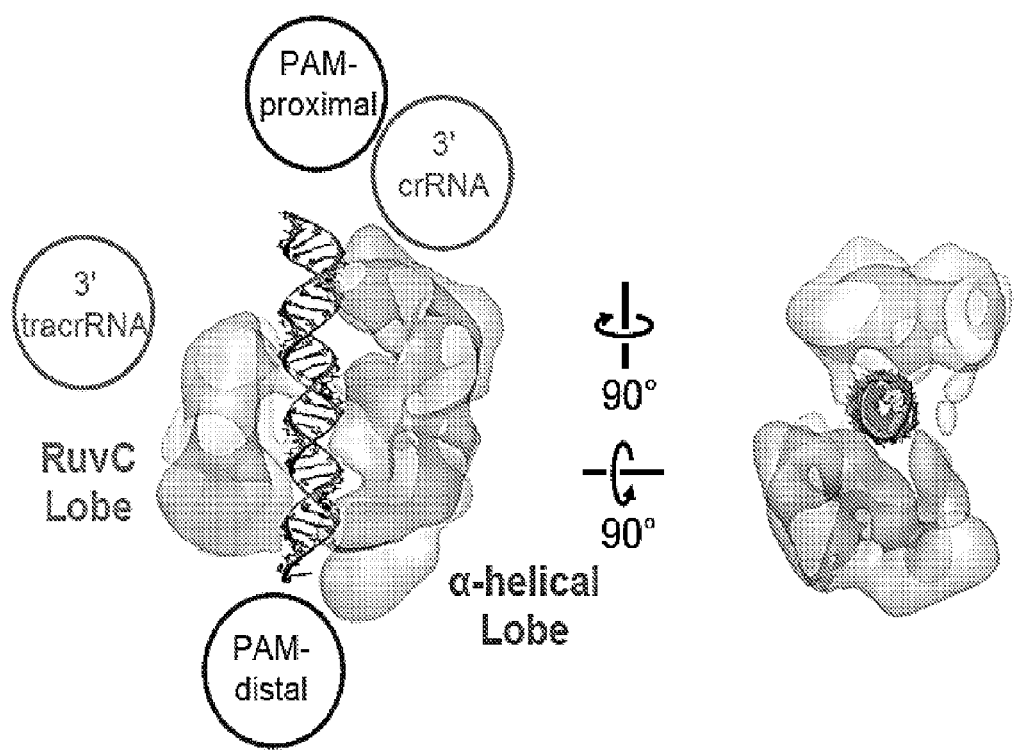

FIG. 28 provide a reconstruction of the central channel of the Cas9:RNA:DNA (transparent surface) with ~25 bp of an A-form duplex. The positions of DNA and guide RNA termini based on our labelling experiments are marked.

Figure 29A:
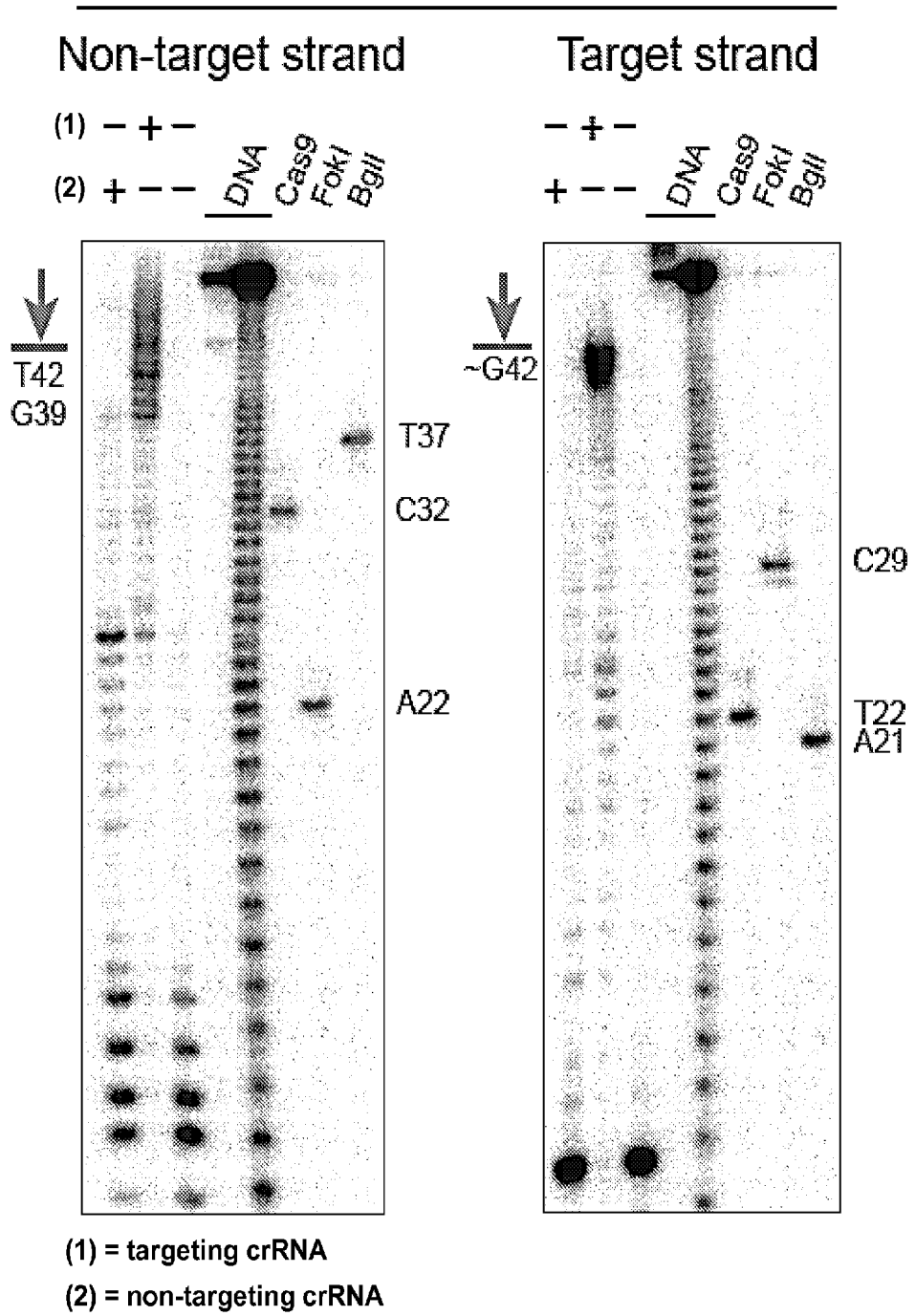

FIGS. 29A-B provide footprinting assays resolved by polyacrylamide gel electrophoresis with target DNA bound by Cas9:RNA where a 55-bp DNA substrate was 5'-radiolabeled on either the target (SEQ ID NO:18) or non-target strand (SEQ ID NO:17) and incubated with catalytically inactive Cas9:RNA containing a complementary crRNA (targeting) (SEQ ID NO:16) or a mismatched control crRNA (non-targeting) (SEQ ID NO:24), before being subjected to (A) exonuclease III or (B) nuclease P1 treatment.

Figure 30:
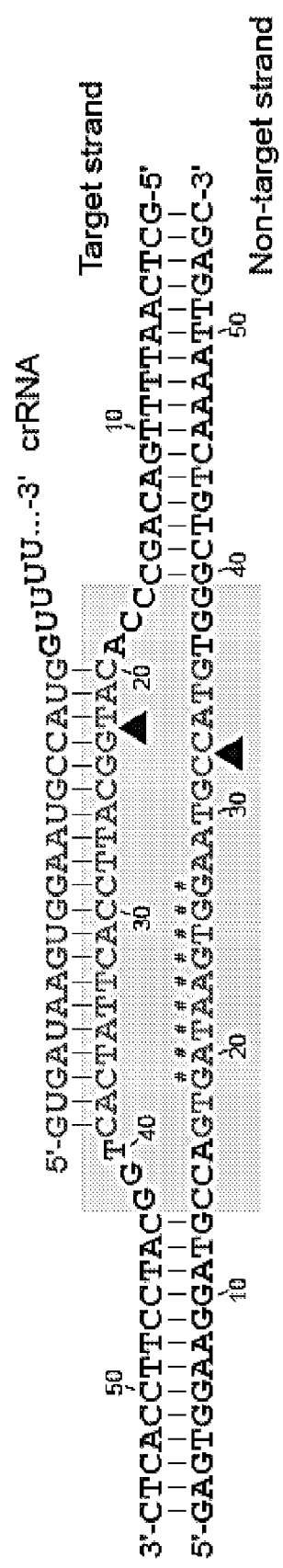

FIG. 30 provides a schematic representation of the results from the footprinting assays in FIGS. 29A-B showing the boarders of the DNA target protected by Cas9:RNA (gray box) and the nucleotides susceptible to P1 digestion (hash tags) in respect to the crRNA (SEQ ID NO:16), Target strand (SEQ ID NO:25), and Non-target strand (SEQ ID NO:17).

FIG. 31 provides Table 2, Data collection, refinement and model statistics for Spy Cas9.

FIG. 32 provides Table 4, Data collection, refinement and model statistics for AnaCas9.

DEFINITIONS

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. "Oligonucleotide" generally refers to polynucleotides of between about 5 and about 100 nucleotides of single- or double-stranded DNA. However, for the purposes of this disclosure, there is no upper limit to the length of an oligonucleotide. Oligonucleotides are also known as "oligomers" or "oligos" and may be isolated from genes, or chemically synthesized by methods known in the art. The terms "polynucleotide" and "nucleic acid" should be understood to include, as applicable to the embodiments being described, single-stranded (such as sense or antisense) and double-stranded polynucleotides.

By "hybridizable" or "complementary" or "substantially complementary" it is meant that a nucleic acid (e.g. RNA) comprises a sequence of nucleotides that enables it to non-covalently bind, i.e. form Watson-Crick base pairs and/or G/U base pairs, "anneal", or "hybridize," to another nucleic acid in a sequence-specific, antiparallel, manner (i.e., a nucleic acid specifically binds to a complementary nucleic acid) under the appropriate in vitro and/or in vivo conditions of temperature and solution ionic strength. As is known in the art, standard Watson-Crick base-pairing includes: adenine (A) pairing with thymidine (T), adenine (A) pairing with uracil (U), and guanine (G) pairing with cytosine (C) [DNA, RNA]. In addition, it is also known in the art that for hybridization between two RNA molecules (e.g., dsRNA), guanine (G) base pairs with uracil (U). For example, G/U base-pairing is partially responsible for the degeneracy (i.e., redundancy) of the genetic code in the context of tRNA anti-codon base-pairing with codons in mRNA. In the context of this disclosure, a guanine (G) of a protein-binding segment (dsRNA duplex) of a subject DNA-targeting RNA molecule is considered complementary to a uracil (U), and vice versa. As such, when a G/U base-pair can be made at a given nucleotide position a protein-binding segment (dsRNA duplex) of a subject DNA-targeting RNA molecule, the position is not considered to be non-complementary, but is instead considered to be complementary.

Hybridization and washing conditions are well known and exemplified in Sambrook, J., Fritsch, E. F. and Maniatis, T. Molecular Cloning: A Laboratory Manual, Second Edition, Cold Spring Harbor Laboratory Press, Cold Spring Harbor (1989), particularly Chapter 11 and Table 11.1 therein; and Sambrook, J. and Russell, W., Molecular Cloning: A Laboratory Manual, Third Edition, Cold Spring Harbor Laboratory Press, Cold Spring Harbor (2001). The conditions of temperature and ionic strength determine the "stringency" of the hybridization.

Hybridization requires that the two nucleic acids contain complementary sequences, although mismatches between bases are possible. The conditions appropriate for hybridization between two nucleic acids depend on the length of the nucleic acids and the degree of complementation, variables well known in the art. The greater the degree of complementation between two nucleotide sequences, the greater the value of the melting temperature (Tm) for hybrids of nucleic acids having those sequences. For hybridizations between nucleic acids with short stretches of complementarity (e.g. complementarity over 35 or less, 30 or less, 25 or less, 22 or less, 20 or less, or 18 or less nucleotides) the position of mismatches becomes important (see Sambrook et al., supra, 11.7-11.8). Typically, the length for a hybridizable nucleic acid is at least about 10 nucleotides. Illustrative minimum lengths for a hybridizable nucleic acid are: at least about 15 nucleotides; at least about 20 nucleotides; at least about 22 nucleotides; at least about 25 nucleotides; and at least about 30 nucleotides). Furthermore, the skilled artisan will recognize that the temperature and wash solution salt concentration may be adjusted as necessary according to factors such as length of the region of complementation and the degree of complementation.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones "Binding" as used herein (e.g. with reference to an RNA-binding domain of a polypeptide) refers to a non-covalent interaction between macromolecules (e.g., between a protein and a nucleic acid). While in a state of non-covalent interaction, the macromolecules are said to be "associated" or "interacting" or "binding" (e.g., when a molecule X is said to interact with a molecule Y, it is meant the molecule X binds to molecule Y in a non-covalent manner). Not all components of a binding interaction need be sequence-specific (e.g., contacts with phosphate residues in a DNA backbone), but some portions of a binding interaction may be sequence-specific. Binding interactions are generally characterized by a dissociation constant (Kd) of less than $10^{-6}$ M, less than $10^{-7}$ M, less than $10^{-8}$ M, less than $10^{-9}$ M, less than $10^{-10}$ M, less than $10^{-11}$ M, less than $10^{-12}$ M, less than $10^{-13}$ M, less than $10^{-14}$ M, or less than $10^{-15}$ M. "Affinity" refers to the strength of binding, increased binding affinity being correlated with a lower Kd.

By "binding domain" it is meant a protein domain that is able to bind non-covalently to another molecule. A binding domain can bind to, for example, a DNA molecule (a DNA-binding protein), an RNA molecule (an RNA-binding protein) and/or a protein molecule (a protein-binding protein). In the case of a protein domain-binding protein, it can bind to itself (to form homodimers, homotrimers, etc.) and/or it can bind to one or more molecules of a different protein or proteins.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide containing side chains consisting of asparagine and glutamine; a group of amino acids having aromatic side chains consists of phenylalanine, tyrosine, and tryptophan; a group of amino acids having basic side chains consists of lysine, arginine, and histidine; a group of amino acids having acidic side chains consists of glutamate and aspartate; and a group of amino acids having sulfur containing side chains consists of cysteine and methionine. Exemplary conservative amino acid substitution groups are valine-leucine-isoleucine, phenylalanine-tyrosine, lysine-arginine, alanine-valine, and asparagine-glutamine.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence identity can be determined in a number of different manners. To determine sequence identity, sequences can be aligned using various methods and computer programs (e.g., BLAST, T-COFFEE, MUSCLE, MAFFT, etc.), available over the world wide web at sites including ncbi.nlm.nili.gov/BLAST, ebi.ac.uk/Tools/msa/tcoffee/, ebi.ac.uk/Tools/msa/muscle/, mafft.cbrc.jp/alignment/software/. See, e.g., Altschul et al. (1990), J. Mol. Bioi. 215:403-10.

The term "naturally-occurring" or "unmodified" or "native" as used herein as applied to a nucleic acid, a polypeptide, a cell, or an organism, refers to a nucleic acid, polypeptide, cell, or organism that is found in nature. For example, a polypeptide or polynucleotide sequence that is present in an organism (including viruses) that can be isolated from a source in nature and which has not been intentionally modified by a human in the laboratory is naturally occurring.

The term "chimeric" as used herein as applied to a nucleic acid or polypeptide refers to two components that are defined by structures derived from different sources. For example, where "chimeric" is used in the context of a chimeric polypeptide (e.g., a chimeric Cas9 protein), the chimeric polypeptide includes amino acid sequences that are derived from different polypeptides. A chimeric polypeptide may comprise either modified or naturally-occurring polypeptide sequences (e.g., a first amino acid sequence from a modified or unmodified Cas9 protein; and a second amino acid sequence other than the Cas9 protein). In some cases, the two different sources of a chimeric polypeptide may also refer to two different Cas9 proteins (e.g., a first amino acid sequence from a *Streptococcus pyogenes* Cas9 protein and a second amino acid sequence from an *Actinomyces naeslundii* Cas9), for example. Similarly, "chimeric" in the context of a polynucleotide encoding a chimeric polypeptide includes nucleotide sequences derived from different coding regions (e.g., a first nucleotide sequence encoding a modified or unmodified Cas9 protein; and a second nucleotide sequence encoding a polypeptide other than a Cas9 protein).

The term "chimeric polypeptide" or "chimeric protein" refers to a polypeptide which is made by the combination (i.e., "fusion") of two otherwise separated segments of amino sequence, usually through human intervention. A polypeptide that comprises a chimeric amino acid sequence is a chimeric polypeptide. Chimeric polypeptides may be derived in may ways; e.g., through the fusion of two or more amino acid sequences end-to-end, or e.g., through the insertion of one or more amino acid sequences into another amino acid sequence, or e.g., through the mutation or removal of individual amino acid residues in a polypeptide such that motifs or domains within the polypeptide more similarly resemble motifs or domains within a different polypeptide.

"Heterologous," as used herein, means a nucleotide or polypeptide sequence that is not found in the native nucleic acid or protein, respectively. For example, in a chimeric Cas9 protein, the RNA-binding domain of a naturally-occurring bacterial Cas9 polypeptide (or a variant thereof) may be fused to a heterologous polypeptide sequence (i.e. a polypeptide sequence from a protein other than Cas9 or a polypeptide sequence from another organism). The heterologous polypeptide sequence may exhibit an activity (e.g., enzymatic activity) that will also be exhibited by the chimeric Cas9 protein (e.g., methyltransferase activity, acetyltransferase activity, kinase activity, ubiquitinating activity, etc.). A heterologous nucleic acid sequence may be linked to a naturally-occurring nucleic acid sequence (or a variant thereof) (e.g., by genetic engineering) to generate a chimeric nucleotide sequence encoding a chimeric polypeptide. As another example, in a fusion variant Cas9 site-directed polypeptide, a variant Cas9 site-directed polypeptide may be fused to a heterologous polypeptide (i.e. a polypeptide other than Cas9), which exhibits an activity that will also be exhibited by the fusion variant Cas9 site-directed polypeptide. A heterologous nucleic acid sequence may be linked to a variant Cas9 site-directed polypeptide (e.g., by genetic engineering) to generate a nucleotide sequence encoding a fusion variant Cas9 site-directed polypeptide.

"Recombinant," as used herein, means that a particular nucleic acid (DNA or RNA) is the product of various combinations of cloning, restriction, polymerase chain reaction (PCR) and/or ligation steps resulting in a construct having a structural coding or non-coding sequence distinguishable from endogenous nucleic acids found in natural systems. DNA sequences encoding polypeptides can be assembled from cDNA fragments or from a series of synthetic oligonucleotides, to provide a synthetic nucleic acid which is capable of being expressed from a recombinant transcriptional unit contained in a cell or in a cell-free transcription and translation system. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "DNA regulatory sequences", below). Alternatively, DNA sequences encoding RNA (e.g., DNA-targeting RNA) that is not translated may also be considered recombinant. Thus, e.g., the term "recombinant" nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a codon encoding the same amino acid, a conservative amino acid, or a non-conservative amino acid. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques. When a recombinant polynucleotide encodes a polypeptide, the sequence of the encoded polypeptide can be naturally occurring ("wild type") or can be a variant (e.g., a mutant) of the naturally occurring sequence. Thus, the term "recombinant" polypeptide does not necessarily refer to a polypeptide whose sequence does not naturally occur. Instead, a "recombinant" polypeptide is encoded by a recombinant DNA sequence, but the sequence of the polypeptide can be naturally occurring ("wild type") or non-naturally occurring (e.g., a variant, a mutant, etc.). Thus, a "recombinant" polypeptide is the result of human intervention, but may be a naturally occurring amino acid sequence.

A "vector" or "expression vector" is a replicon, such as plasmid, phage, virus, or cosmid, to which another DNA segment, i.e. an "insert", may be attached so as to bring about the replication of the attached segment in a cell.

Figure 1:
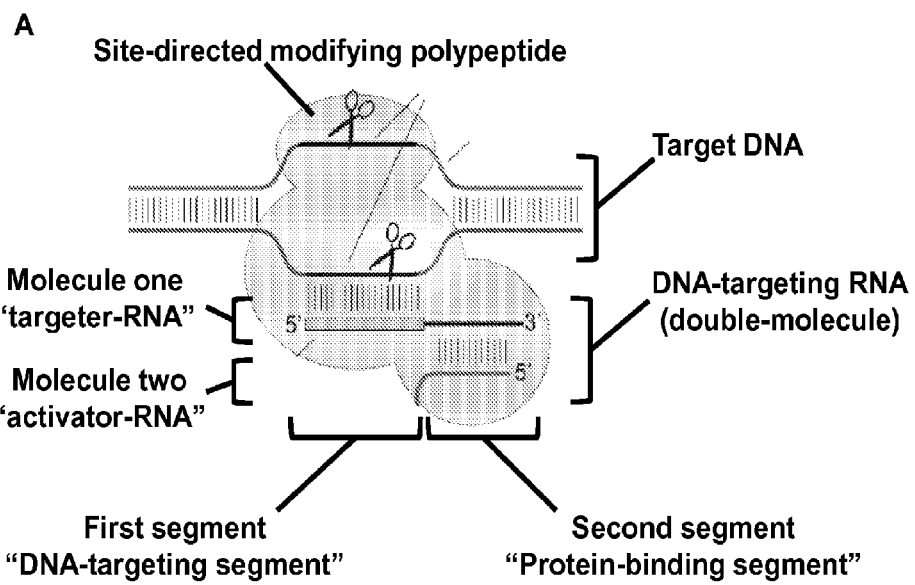
FIGS. 1A-B provide a general schematic drawing of a generalized site-directed modifying polypeptide associated with two exemplary subject DNA-targeting RNAs and target DNA.
Figure 1:
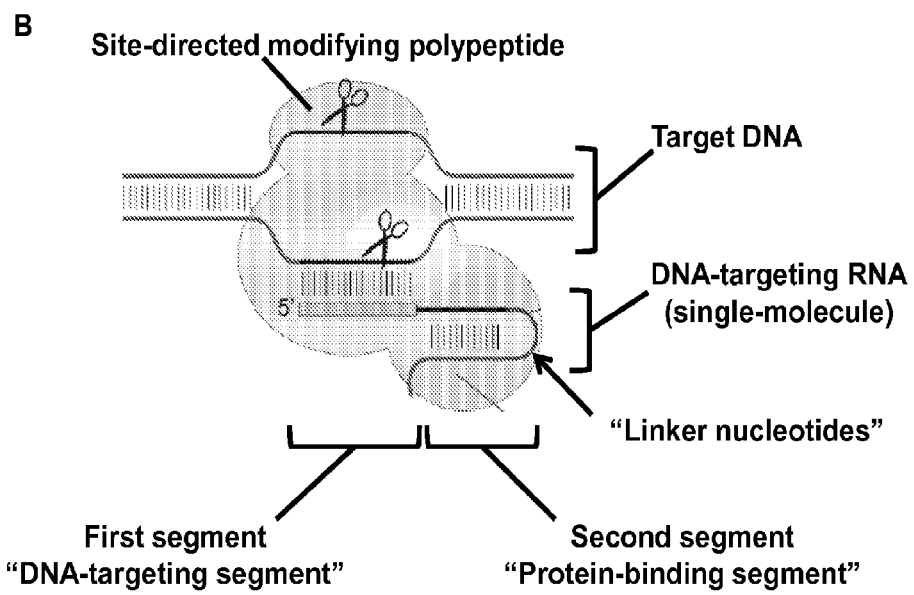

A "target DNA" as used herein is a DNA polynucleotide that comprises a "target site" or "target sequence." The terms "target site" or "target sequence" or "target protospacer DNA" are used interchangeably herein to refer to a nucleic acid sequence present in a target DNA to which a DNA-targeting segment of a subject DNA-targeting RNA will bind (see FIG. 1), provided sufficient conditions for binding exist.

For example, the target site (or target sequence) 5'-GAG-CATATC-3' within a target DNA is targeted by (or is bound by, or hybridizes with, or is complementary to) the RNA sequence 5'-GAUAUGCUC-3'. Suitable DNA/RNA binding conditions include physiological conditions normally present in a cell. Other suitable DNA/RNA binding conditions (e.g., conditions in a cell-free system) are known in the art; see, e.g., Sambrook, supra. The strand of the target DNA that is complementary to and hybridizes with the DNA-targeting RNA is referred to as the "complementary strand" and the strand of the target DNA that is complementary to the "complementary strand" (and is therefore not complementary to the DNA-targeting RNA) is referred to as the "noncomplementary strand" or "non-complementary strand."

By "cleavage" it is meant the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, a complex comprising a DNA-targeting RNA and a site-directed modifying polypeptide is used for targeted double-stranded DNA cleavage.

By "cleavage domain" or "nuclease domain" of a nuclease it is meant the polypeptide sequence or domain within the nuclease which possesses the catalytic activity for nucleic acid cleavage. A cleavage domain can be contained in a single polypeptide chain or cleavage activity can result from the association of two (or more) polypeptides. A single nuclease domain may consist of more than one isolated stretch of amino acids within a given polypeptide.

The RNA molecule that binds to the site-directed modifying polypeptide and targets the polypeptide to a specific location within the target DNA is referred to herein as the "DNA-targeting RNA" or "DNA-targeting RNA polynucleotide" (also referred to herein as a "guide RNA" or "gRNA"). A subject DNA-targeting RNA comprises two segments, a "DNA-targeting segment" and a "protein-binding segment." By "segment" it is meant a segment/section/region of a molecule, e.g., a contiguous stretch of nucleotides in an RNA. A segment can also mean a region/section of a complex such that a segment may comprise regions of more than one molecule. For example, in some cases the protein-binding segment (described below) of a DNA-targeting RNA is one RNA molecule and the protein-binding segment therefore comprises a region of that RNA molecule. In other cases, the protein-binding segment (described below) of a DNA-targeting RNA comprises two separate molecules that are hybridized along a region of complementarity. As an illustrative, non-limiting example, a protein-binding segment of a DNA-targeting RNA that comprises two separate molecules can comprise (i) base pairs 40-75 of a first RNA molecule that is 100 base pairs in length; and (ii) base pairs 10-25 of a second RNA molecule that is 50 base pairs in length. The definition of "segment," unless otherwise specifically defined in a particular context, is not limited to a specific number of total base pairs, is not limited to any particular number of base pairs from a given RNA molecule, is not limited to a particular number of separate molecules within a complex, and may include regions of RNA molecules that are of any total length and may or may not include regions with complementarity to other molecules.

The DNA-targeting segment (or "DNA-targeting sequence") comprises a nucleotide sequence that is complementary to a specific sequence within a target DNA (the complementary strand of the target DNA). The protein-binding segment (or "protein-binding sequence") interacts with a site-directed modifying polypeptide. When the site-directed modifying polypeptide is a Cas9 or Cas9 related polypeptide (described in more detail below), site-specific cleavage of the target DNA occurs at locations determined by both (i) base-pairing complementarity between the DNA-targeting RNA and the target DNA; and (ii) a short motif (referred to as the protospacer adjacent motif (PAM)) in the target DNA.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference.

Structural similarity may be inferred from, e.g., sequence similarity, which can be determined by one of ordinary skill through visual inspection and comparison of the sequences, or through the use of well-known alignment software programs such as CLUSTAL (Wilbur, W. J. and Lipman, D. J. Proc. Natl. Acad. Sci. USA, 80, 726-730 (1983)) or CLUSTALW (Thompson, J. D., Higgins, D. G. and Gibson, T. J., CLUSTAL W: improving the sensitivity of progressive multiple sequence alignment through sequence weighting, positions-specific gap penalties and weight matrix choice, Nucleic Acids Research, 22:4673-4680 (1994)) or BLAST (Altschul S F, Gish W, et al., J. Mol. Biol., October 5; 215(3):403-10 (1990)), a set of similarity search programs designed to explore all of the available sequence databases regardless of whether the query is protein or DNA. CLUSTAL W is available on the internet at ebi.ac.uk/clustalw/; BLAST is available on the internet at ncbi.nlm.nih.gov/BLAST/. A residue within a first protein or nucleic acid sequence corresponds to a residue within a second protein or nucleic acid sequence if the two residues occupy the same position when the first and second sequences are aligned.

The term "atomic coordinates" refers to the Cartesian coordinates corresponding to an atom's spatial relationship to other atoms in a molecule or molecular complex. Atomic coordinates may be obtained using x-ray crystallography techniques or nuclear magnetic resonance techniques, or may be derived using molecular replacement analysis or homology modeling. Reconstructions of atomic coordinates may be informed from practical data, for example from electron microscopy. Various software programs allow for the graphical representation of a set of structural coordinates to obtain a three dimensional representation of a molecule or molecular complex. The atomic coordinates of the present disclosure may be modified from the original set by mathematical manipulation, such as by inversion or integer additions or subtractions. As such, it is recognized that the structural coordinates of the present disclosure are relative, and are in no way specifically limited by the actual x, y, z coordinates.

The term "atomic structure" refers to a three dimensional representation of the atoms in a molecule or molecular complex. An atomic structure may be derived from atomic coordinates as described above. An atomic structure may also be derived from computational manipulation of a received or previously obtained set of atomic coordinates. Such computational manipulation may be performed to produce an alternative or new atomic structure of a previously derived atomic structure based on new information. An alternative or new atomic structure of an initially modeled molecule may represent an alternate conformation of the modeled molecule or the conformation of a second molecule that is closely related to the initially modeled molecule. The new information used to inform manipulation may be obtained from practical data, for example electron density maps derived from electron microscopy. New information that may inform computational manipulation may also be obtained from computational data, for example the results of computationally docking two atomic structures or molecular models. A computationally manipulated atomic structure may be utilized to produce a new set of atomic coordinates representing the newly derived three dimensional molecule or molecular complex.

"Root mean square deviation" is the square root of the arithmetic mean of the squares of the deviations from the mean, and is a way of expressing deviation or variation from the structural coordinates described herein. The present disclosure includes all embodiments comprising conservative substitutions of the noted amino acid residues resulting in same structural coordinates within the stated root mean square deviation. It will be apparent to the skilled practitioner that the numbering of the amino acid residues of *Streptococcus pyogenes* Cas9 endonuclease (SpyCas9) or *Actinomyces naeslundii* Cas9 endonuclease (AnaCas9) may be different than that set forth herein, and may contain certain conservative amino acid substitutions that yield the same three dimensional structures as those defined by Table 1. Corresponding amino acids and conservative substitutions in other isoforms or analogues are easily identified by visual inspection of the relevant amino acid sequences or by using commercially available homology software programs (e.g., MODELLER, Accelrys, San Diego, Calif.; Sali and Blundell (1993) *J Mol Biol* 234:779-815; Sanchez and Sali (1997) *Curr Opin Struct Biol* 7: 206-214; and Sanchez and Sali (1998) *Proc Natl Acad Sci USA* 95: 13597-13602).

The terms "system" and "computer-based system" refer to the hardware means, software means, and data storage means used to analyze the information of the present disclosure. The minimum hardware of the computer-based systems of the present disclosure comprises a central processing unit (CPU), input means, output means, and data storage means. As such, any convenient computer-based system may be employed in the present disclosure. The data storage means may comprise any manufacture comprising a recording of the present information as described above, or a memory access means that can access such a manufacture.

A "processor" references any hardware and/or software combination which will perform the functions required of it. For example, any processor herein may be a programmable digital microprocessor such as available in the form of an electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

"Computer readable medium" as used herein refers to any storage or transmission medium that participates in providing instructions and/or data to a computer for execution and/or processing. Examples of storage media include floppy disks, magnetic tape, USB, CD-ROM, a hard disk drive, a ROM or integrated circuit, a magneto-optical disk, or a computer readable card such as a PCMCIA card and the like, whether or not such devices are internal or external to the computer. A file containing information may be "stored" on computer readable medium, where "storing" means recording information such that it is accessible and retrievable at a later date by a computer. A file may be stored in permanent memory.

With respect to computer readable media, "permanent memory" refers to memory that is permanently stored on a data storage medium. Permanent memory is not erased by termination of the electrical supply to a computer or processor. Computer hard-drive ROM (i.e. ROM not used as virtual memory), CD-ROM, floppy disk and DVD are all examples of permanent memory. Random Access Memory (RAM) is an example of non-permanent memory. A file in permanent memory may be editable and re-writable.

To "record" data, programming or other information on a computer readable medium refers to a process for storing information, using any convenient method. Any convenient data storage structure may be chosen, based on the means used to access the stored information. A variety of data processor programs and formats can be used for storage, e.g., word processing text file, database format, etc.

A "memory" or "memory unit" refers to any device which can store information for subsequent retrieval by a processor, and may include magnetic or optical devices (such as a hard disk, floppy disk, CD, or DVD), or solid state memory devices (such as volatile or non-volatile RAM). A memory or memory unit may have more than one physical memory device of the same or different types (for example, a memory may have multiple memory devices such as multiple hard drives or multiple solid state memory devices or some combination of hard drives and solid state memory devices).

A system can include hardware components which take the form of one or more platforms, e.g., in the form of servers, such that any functional elements of the system, i.e., those elements of the system that carry out specific tasks (such as managing input and output of information, processing information, etc.) of the system may be carried out by the execution of software applications on and across the one or more computer platforms represented of the system. The one or more platforms present in the subject systems may be any convenient type of computer platform, e.g., such as a server, main-frame computer, a work station, etc. Where more than one platform is present, the platforms may be connected via any convenient type of connection, e.g., cabling or other communication system including wireless systems, either networked or otherwise. Where more than one platform is present, the platforms may be co-located or they may be physically separated. Various operating systems may be employed on any of the computer platforms, where representative operating systems include Windows, MacOS, Sun Solaris, Linux, OS/400, Compaq Tru64 Unix, SGI IRIX, Siemens Reliant Unix, and others. The functional elements of system may also be implemented in accordance with a variety of software facilitators, platforms, or other convenient method.

Items of data are "linked" to one another in a memory when the same data input (for example, filename or directory name or search term) retrieves the linked items (in a same file or not) or an input of one or more of the linked items retrieves one or more of the others.

Subject computer readable media may be at a "remote location", where "remote location," means a location other than the location at which the x-ray crystallographic or other analysis is carried out. For example, a remote location could be another location (e.g., office, lab, etc.) in the same city, another location in a different city, another location in a different state, another location in a different country, etc. As such, when one item is indicated as being "remote" from another, what is meant is that the two items may be in the same room but separated, or at least in different rooms or different buildings, and may be at least one mile, ten miles, or at least one hundred miles apart.

"Communicating" information references transmitting the data representing that information as, e.g., electrical or optical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the Internet or Intranets including email transmissions and information recorded on websites and the like.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a Cas9 polypeptide" includes a plurality of such polypeptides and reference to "the atomic structure" includes reference to one or more atomic structures and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides atomic structures of Cas9 with and without polynucleotides bound thereto. Also provided is a computer readable medium comprising atomic coordinates for Cas9 polypeptides in both an unbound configuration and a configuration wherein the Cas9 polypeptide is bound to one or more polynucleotides. The present disclosure provides crystals comprising Cas9 polypeptides; and compositions comprising the crystals. The present disclosure provides methods for the engineering of Cas9 polypeptides wherein Cas9 activity has been altered, ablated, or preserved and amended with additional activities.

The present disclosure provides a computer readable medium comprising: atomic coordinates for a Cas9 polypeptide, wherein said Cas9 polypeptide comprises an amino acid sequence having at least 75%, at least 80%, at least 85%, at least 90%, at least 95%, at least 98%, at least 99%, or 100%, amino acid sequence identity to an amino acid sequence depicted in FIG. 5 or FIG. 11. In some cases, the computer readable medium further comprises programming for displaying a molecular model of said Cas9 polypeptide. In some cases, the Cas9 polypeptide comprises an amino acid sequence having at least 75%, at least 80%, at least 85%, at least 90%, at least 95%, at least 98%, at least 99%, or 100%, amino acid sequence identity to an amino acid sequence of a *Streptococcus pyogenes* Cas9 polypeptide or an *Actinomyces naeslundii* Cas9 polypeptide. In some cases, the atomic coordinates for said Cas9 polypeptide further comprise a polynucleotide bound to a nucleic acid binding site in said Cas9 polypeptide. In some cases, the computer-readable medium further comprises programming for identifying amino acid residues of said Cas9 polypeptide that bind the polynucleotide. In some cases, the computer-readable medium further comprises programming for identifying amino acid substitutions of said Cas9 polypeptide that alter the binding of the Cas9 polypeptide to the polynucleotide.

The present disclosure provides a computer comprising a computer-readable medium of the present disclosure, as described herein.

The present disclosure provides a crystal comprising a Cas9 polypeptide in crystalline form, wherein the crystal is characterized with space group $P2_12_12$, and has unit cell parameters of a=160 Å, b=209 Å, c=91 Å, $\alpha=\beta=\gamma=90°$. The present disclosure provides a composition comprising the crystal. In some cases, the Cas9 polypeptide shares at least 75%, at least 80%, at least 85%, at least 90%, at least 95%, at least 98%, at least 99%, or 100%, amino acid sequence identity with SEQ ID NO:1.

The present disclosure provides a crystal comprising a Cas9 polypeptide in crystalline form, wherein the crystal is characterized with space group $P1\ 2_11$, and has unit cell parameters of a=75 Å, b=133 Å, c=80 Å, $\alpha=\gamma=90°$ and $\beta=95°$. The present disclosure provides a composition comprising the crystal. In some cases, the Cas9 polypeptide shares at least 75%, at least 80%, at least 85%, at least 90%, at least 95%, at least 98%, at least 99%, or 100%, amino acid sequence identity with SEQ ID NO:7.

The present disclosure provides a method comprising: a) receiving a set of atomic coordinates for a Cas9 polypeptide, wherein said Cas9 polypeptide comprises an amino acid sequence having at least 75%, at least 80%, at least 85%, at least 90%, at least 95%, at least 98%, at least 99%, or 100%, amino acid sequence identity to an amino acid sequence depicted in FIG. 5 or FIG. 11; and b) identifying a site within said Cas9 polypeptide for the insertion of a heterologous amino acid sequence using said coordinates. In some cases, the insertion of the heterologous amino acid sequence results in the preservation of at least one biological activity of said Cas9 polypeptide. In some cases, the insertion of the heterologous amino acid sequence results in the addition of at least one non-native activity to said Cas9 polypeptide.

The present disclosure provides a method of engineering a chimeric Cas9, the method comprising: a) receiving a set of atomic coordinates for a Cas9 polypeptide, wherein said Cas9 polypeptide comprises an amino acid sequence having at least 75%, at least 80%, at least 85%, at least 90%, at least 95%, at least 98%, at least 99%, or 100%, amino acid sequence identity to an amino acid sequence depicted in FIG. 5 or FIG. 11; and b) identifying a site within said Cas9 polypeptide for replacement of a Cas9 domain of a first Cas9 species with a Cas9 domain of a second species. In some cases, the replacement of a Cas9 domain of a first Cas9 species with a Cas9 domain of a second species results in altered activity of said first Cas9.

The present disclosure provides a method comprising: a) receiving a set of atomic coordinates for a Cas9 polypeptide; and b) identifying a site within said Cas9 polypeptide for the substitution, insertion, or deletion of one or more amino acid residues resulting in altered activity of said Cas9 polypeptide. In some cases, the Cas9 polypeptide comprises an amino acid sequence having at least 75%, at least 80%, at least 85%, at least 90%, at least 95%, at least 98%, at least 99%, or 100%, amino acid sequence identity to an amino acid sequence depicted in FIG. 5 or FIG. 11.

The present disclosure provides a method comprising: a) forwarding to a remote location a set of atomic coordinates for a Cas9 polypeptide, wherein said Cas9 polypeptide comprises an amino acid sequence having at least 75%, at least 80%, at least 85%, at least 90%, at least 95%, at least 98%, at least 99%, or 100%, amino acid sequence identity to an amino acid sequence depicted in FIG. 5 or FIG. 11; and b) receiving the identity of a site within Cas9 for the insertion or substitution of heterologous sequence, wherein the insertion of heterologous sequence results in the preservation of Cas9 activities and the addition of chimeric activities to Cas9.

Atomic Structures

The present disclosure provides the atomic structures of the SpyCas9 and AnaCas9 endonucleases. The present disclosure provides the atomic structures of a complex comprising: i) a Cas9 polypeptide; and ii) a polynucleotide (a "target") bound to the Cas9 polypeptide.

The terms "Cas9" and "Cas9 polypeptide" are used interchangeably herein to refer to an enzyme that exhibits at least endonuclease activity (e.g. cleaving the phosphodiester bond within a polynucleotide) guided by a CRISPR RNA (crRNA) bearing complementary sequence to a target polynucleotide. Cas9 polypeptides are known in the art, and include Cas9 polypeptides from any of a variety of biological sources, including, e.g., prokaryotic sources such as bacteria and archaea. Bacterial Cas9 includes, Actinobacteria (e.g., *Actinomyces naeslundii*) Cas9, Aquificae Cas9, Bacteroidetes Cas 9, Chlamydiae Cas9, Chloroflexi Cas9, Cyanobacteria Cas9, Elusimicrobia Cas9, Fibrobacteres Cas9, Firmicutes Cas9 (e.g., *Streptococcus pyogenes* Cas9, *Streptococcus thermophilus* Cas9, *Listeria innocua* Cas9, *Streptococcus agalactiae* Cas9, *Streptococcus mutans* Cas9, and *Enterococcus faecium* Cas9), Fusobacteria Cas9, Proteobacteria (e.g., *Neisseria meningitides, Campylobacter jejuni*) Cas9, Spirochaetes (e.g., *Treponema denticola*) Cas9, and the like. Archaea Cas 9 includes Euryarchaeota Cas9 (e.g., *Methanococcus maripaludis* Cas9) and the like. A variety of Cas9 polypeptides are known, and are reviewed in, e.g., Makarova et al. (2011) *Nature Reviews Microbiology* 9:467-477, Makarova et al. (2011) *Biology Direct* 6:38, Haft et al. (2005) *PLOS Computational Biology* 1:e60 and Chylinski et al. (2013) *RNA Biology* 10:726-737. The term "Cas9" includes a Cas9 polypeptide of any Cas9 family, including any isoform of Cas9.

Amino acid sequences of various Cas9 homologs are known in the art and are publicly available. See, e.g., GenBank Accession No. AGM26527.1, GenBank Accession No. AGZ01981.1, GenBank Accession No. ERJ56406.1, GenBank Accession No. ERM89468.1, GenBank Accession No. G3ECR1.2, GenBank Accession No. Q03JI6.1, GenBank Accession No. Q927P4.1, GenBank Accession No. WP_002664048.1, GenBank Accession No. WP_002665199.1, GenBank Accession No. WP_002678519.1, GenBank Accession No. WP_002837826.1, GenBank Accession No. WP_002841804.1, GenBank Accession No. WP_003004889.1, GenBank Accession No. WP_003710997.1, GenBank Accession No. WP_004369789.1, GenBank Accession No. WP_004918207.1, GenBank Accession No. WP_005399084.1, GenBank Accession No.

WP_005728738.1, GenBank Accession No.
WP_005728739.1, GenBank Accession No.
WP_005729619.1, GenBank Accession No.
WP_005760293.1, GenBank Accession No.
WP_005791619.1, GenBank Accession No.
WP_005855543.1, GenBank Accession No.
WP_007093045.1, GenBank Accession No.
WP_007210085.1, GenBank Accession No.
WP_007407075.1, GenBank Accession No.
WP_007711412.1, GenBank Accession No.
WP_008146746.1, GenBank Accession No.
WP_008582100.1, GenBank Accession No.
WP_008610988.1, GenBank Accession No.
WP_008770229.1, GenBank Accession No.
WP_008780913.1, GenBank Accession No.
WP_008822925.1, GenBank Accession No.
WP_008991033.1, GenBank Accession No.
WP_008997907.1, GenBank Accession No.
WP_009035786.1, GenBank Accession No.
WP_009217841.1, GenBank Accession No.
WP_009293010.1, GenBank Accession No.
WP_009392516.1, GenBank Accession No.
WP_009417297.1, GenBank Accession No.
WP_009434997.1, GenBank Accession No.
WP_010254321.1, GenBank Accession No.
WP_011963637.1, GenBank Accession No.
WP_012290141.1, GenBank Accession No.
WP_013073784.1, GenBank Accession No.
WP_013997568.1, GenBank Accession No.
WP_014411267.1, GenBank Accession No.
WP_014708934.1, GenBank Accession No.
WP_014773653.1, GenBank Accession No.
WP_014938037.1, GenBank Accession No.
WP_015781852.1, GenBank Accession No.
WP_016341167.1, GenBank Accession No.
WP_018280040.1, GenBank Accession No.
WP_018626154.1, GenBank Accession No.
WP_022599516.1, GenBank Accession No.
WP_022832948.1, and GenBank Accession No. YP_008027038.1.

The term "SpyCas9" as used herein encompasses wild type *Streptococcus pyogenes* Cas9, e.g. a polypeptide comprising an amino acid sequence having at least about 75%, at least about 80%, at least about 85%, at least about 90%, at least about 95%, at least about 98%, at least about 99%, or 100%, amino acid sequence identity to amino acids 1-1368 of the amino acid sequence set forth in SEQ ID NO:1, and having at least about 75%, at least about 80%, at least about 85%, at least about 90%, at least about 95%, at least about 98%, at least about 99%, or 100% of the enzymatic activity of a polypeptide comprising amino acids 1-1368 of SEQ ID NO:1.

The term "AnaCas9" as used herein encompasses wild type *Actinomyces naeslundii* Cas9, e.g. a polypeptide comprising an amino acid sequence having at least about 75%, at least about 80%, at least about 85%, at least about 90%, at least about 95%, at least about 98%, at least about 99%, or 100%, amino acid sequence identity to amino acids 1-1101 of the amino acid sequence set forth in SEQ ID NO:7, and having at least about 75%, at least about 80%, at least about 85%, at least about 90%, at least about 95%, at least about 98%, at least about 99%, or 100% of the enzymatic activity of a polypeptide comprising amino acids 1-1101 of SEQ ID NO:7.

The term "Cas9" as used herein encompasses wild type Cas9, e.g. a polypeptide comprising an amino acid sequence having at least about 75%, at least about 80%, at least about 85%, at least about 90%, at least about 95%, at least about 98%, at least about 99%, or 100%, amino acid sequence identity to a Cas9 polypeptide represented in FIG. 5 or FIG. 11 (SEQ ID NOs:1-14), and having at least about 75%, at least about 80%, at least about 85%, at least about 90%, at least about 95%, at least about 98%, at least about 99%, or 100% of the enzymatic activity of a polypeptide represented in FIG. 5 or FIG. 11 (SEQ ID NOs:1-14).

A Cas9 polypeptide can exhibit one or more of the following native enzymatic activities: hydrolase activity, nuclease activity; standard DNA endonuclease and/or exonuclease activity (e.g. cleavage of linear double stranded DNA (dsDNA) and circular dsDNA); non-standard DNA endonuclease and/or exonuclease activity (e.g. cleavage of single stranded DNA (ssDNA), branched DNA (e.g. Holliday junctions, replication forks, 5'-flaps, and the like), Triple-stranded DNA, G-quadruplex DNA, synthetic DNA, artificial DNA, and double stranded hybrids of DNA and RNA), and ribonuclease activity.

A Cas9 polypeptide can exhibit one or more of the following binding activities: binding of a dsDNA target sequence; binding of a ssDNA target sequence; binding of a branched DNA target sequence; binding of a CRISPR RNA (crRNA) (e.g. a pre-crRNA, a trans-encoded small RNA (tracrRNA); binding of non-crRNA target; binding of a polypeptide; binding of a small molecule, and the like.

The atomic structures described herein are useful as models for rationally designing Cas9 derivatives, either de novo or by modification of known Cas9 polypeptides. One or more amino acid residues or sites within the polypeptide, represented by atomic coordinates, may be identified that are useful for mutation by replacement, insertion, or deletion of one or more amino acid resides. Such mutations may have utility for altering, enhancing, or ablating Cas9 activities.

Replacement of amino acid residues may be performed by conservative or non-conservative amino acid substitution. Amino acid residues may be signally replaced within a protein, domain, or motif, or multiple individual replacements may be performed within a protein, domain, or motif. In some embodiments single or multiple sequences or stretches of sequential amino acids may be replaced. In some cases, naturally occurring amino acids may be replaced with naturally occurring amino acids. Such replacement of naturally occurring amino acids may be performed to alter, either increasing or decreasing, the charge or hydrophobicity of a three dimensional site, region, or domain, of a Cas9 polypeptide, thus altering local or global Cas9 polypeptide chemical properties or activity.

In other cases, naturally occurring amino acids may be replaced with synthetic amino acids or modified amino acids. Synthetic or unnatural amino acids may contain functional side chains Non-limiting examples of functional side chains include: fluorophores, post-translational modifications, metal ion chelators, photocaged and photocrosslinking moieties, reactive functional groups, and NMR (nuclear magnetic resonance), IR (infrared) and X-ray crystallographic probes, and the like. The replacement of naturally occurring amino acids with synthetic amino acids may have utility in rendering a Cas9 polypeptide traceable at the cellular, molecular, or atomic level. Synthetic amino acid substitution may also have utility for adding additional physical, chemical, or biological activities to a Cas9 polypeptide.

Insertion or deletion of amino acid residues into or out of a Cas9 protein, domain, or motif may be performed singly, such as one at a time, or multiply, such as more than one at a time. Naturally occurring or synthetic amino acids may be inserted, as described above for amino acid residue replacement or substitution. In some embodiments one or more amino acid residues may be inserted or deleted at or from a single location. In other cases, one or more amino acid residues may be inserted or deleted at or from multiple locations. Insertion or deletion of amino acid residues may have utility in altering the conformation or three dimensional structure of a Cas9 polypeptide. Such a change in structure may ablate or alter Cas9 activities, such as nucleic acid binding, nuclease activity, DNA target site recognition (e.g. protospacer adjacent motif recognition), and the like.

Furthermore, sites within the polypeptide, represented by atomic coordinates, may be identified wherein insertion of heterologous amino acids or polypeptides does not alter or ablate Cas9 activities; such sites are useful for the addition of heterologous activities to Cas9. Non-limiting examples of heterologous activities include: fluorescence, phosphorylation, dephosphorylation, acetylation, deacetylation, methylation, demethylation, ubiquitination, deubiquitination, glycosylation, deglycosylation, membrane transduction, and the like. In some cases, sites within the polynucleotide may be identified wherein insertion of heterologous sequence does not alter Cas9 function.

In other embodiments, domains or motifs within the polynucleotide, represented by atomic coordinates, may be identified that may be substituted or exchanged with orthologous domains or motifs from a related CRISPR-Cas polypeptide, e.g., Cas9 polypeptides. Domains or motifs may be represented by linear sequence of 2 or more sequential amino acids or may comprise discontinuous or non-sequential amino acids related in three dimensional space. Such substitutions may have utility for altering the overall performance characteristics of a particular Cas9, such as increasing or decreasing binding affinity, processivity, and the like. Such substitutions may also have utility for exchanging the activity of one species of Cas9 with another by exchanging domains or motifs, e.g., exchanging protospacer adjacent motif (PAM) recognition domains, PAM-binding loops, catalytic domains, nuclease domains, DNA binding domains, crRNA binding domains, tracrRNA binding domains, RuvC-I domains, RuvC-II domains, RuvC-III domains, Arginine rich domains, alpha-helical lobes, beta-hairpin domains, HNH domains, Topo (Topoisomerase) domains, C-terminal domains, N-terminal domains, and the like. Such exchange of domains between different Cas9 polypeptides may be performed by the engineering of chimeric Cas9 proteins.

In other embodiments, sites within the polypeptide may be identified wherein deletion of amino acids does not alter or ablate Cas9 activities locally or globally; such sites are useful for decreasing the size of a Cas9 polypeptide while retaining Cas9 activities. Such atomic locations may be determined according to any method known in the art, including the methods described herein.

Crystals and Crystal Compositions

The present disclosure provides crystals that include wild type and mutant Cas9 polypeptides. In some embodiments, the crystal has a unit cell dimension of a=160 Å, b=209 Å, c=90 Å, and $\alpha=\beta=\gamma=90°$, and belongs to space group $P2_12_12$. In some embodiments, the crystal has a unit cell dimension of a=74 Å, b=133 Å, c=80 Å, and $\alpha=\gamma=90°$ and $\beta=95°$, and belongs to space group $P1\ 2_11$. The present disclosure also provides a composition comprising a subject crystal.

The Cas9 polypeptide can be produced using any of a variety of well known methods, including, e.g., synthetic methods, such as solid phase, liquid phase and combination solid phase/liquid phase syntheses; recombinant DNA methods, including cDNA cloning, optionally combined with site directed mutagenesis; and purification of the polypeptide from a natural source.

Computer Models, Computer-Readable Media, and Computer Systems

In certain embodiments, a computer readable medium may comprise programming for displaying a molecular model of Cas9, programming for identifying candidate sites for mutagenesis or insertion of heterologous sequence as described above, for example. In certain embodiments, the atomic coordinates of the computer readable medium may comprise the atomic coordinates provided in Table 1. A computer system comprising the computer-readable medium is also provided.

As noted above, the atomic coordinates may be employed in conjunction with a modeling program to provide a model of Cas9. As used herein, the term "model" refers to a representation in a tangible medium of the three dimensional structure of Cas9. For example, a model can be a representation of the three dimensional structure in an electronic file, on a display, e.g., a computer screen, on a piece of paper (i.e., on a two dimensional medium), and/or as a ball-and-stick figure. Physical three-dimensional models are tangible and include, but are not limited to, stick models and space-filling models. The phrase "imaging the model on a computer screen" refers to the ability to express (or represent) and manipulate the model on a computer screen using appropriate computer hardware and software technology known to those skilled in the art. Such technology is available from a variety of sources including, for example, Evans and Sutherland, Salt Lake City, Utah, and Biosym Technologies, San Diego, Calif. The phrase "providing a picture of the model" refers to the ability to generate a "hard copy" of the model. Hard copies include both motion and still pictures. Computer screen images and pictures of the model can be visualized in a number of formats including space-filling representations, backbone traces, ribbon diagrams, and electron density maps. Exemplary modeling programs include, but are not limited to PYMOL, GRASP, or O software, for example.

Atomic coordinates may derived by a variety of means. Generally, atomic coordinates can be derived from electron density maps derived by experimental means. Such electron density maps may be produced through X-ray crystallographic methods or electron microscopic methods. Atomic structures may be generated from electron density maps. Two or more atomic structures of related molecules, e.g., molecules related between different species or the same molecule in different conformations, may be computationally compared and the atomic coordinates of one may be used to inform the other. In one embodiment of the present disclosure the atomic coordinates of a Cas9 polypeptide derived from a first species are used to determine the atomic coordinates of a Cas9 polypeptide of a second species. In yet another embodiment, atomic coordinates from a Cas9 polypeptide in an unbound conformation are used to determine the atomic coordinates of a Cas9 polypeptide in a bound conformation. Computational comparison of atomic structures and/or electron density maps can be performed as described herein.

One embodiment of the present disclosure relates to a computer readable medium with Cas9 structural data and/or information stored thereon. As used herein, the phrase "computer readable medium" refers to storage media readable by a computer, which media may be used to store and retrieve data and software programs incorporating computer code. Exemplary computer readable media include floppy disk, CD-ROM, tape, memory (such as flash memory or system memory), hard drive, and the like.

In another embodiment, the disclosure provides a computer system having a memory comprising the above-described atomic coordinates; and a processor in communication with the memory, wherein the processor generates a molecular model having a three dimensional structure representative of Cas9. The processor can be adapted for identifying candidate sites for mutagenesis or insertion of heterologous sequence for example.

Methods of Designing Modified Cas9 Polypeptides or Cas9 Derivatives

The present disclosure provides methods for designing modified Cas9 polypeptides or Cas9 derivatives, as well as methods for studying the Cas9 mechanism. A subject method generally involves computationally identifying candidate sites for mutation and/or insertion of heterologous sequence within the atomic structure and/or amino acid sequence of a polypeptide of Cas9 using atomic coordinates for a Cas9 polypeptide or atomic structures of a Cas9 polypeptide with or without a bound polynucleotide. For example, in some embodiments, the atomic coordinates are as disclosed in Table 1.

The present disclosure provides methods for identifying candidate sites for the mutation of Cas9 such that substitution, insertion, or deletion of amino acids at the candidate site will affect an activity of Cas9. The method generally involves determining the atomic locations of amino acid residues that are essential to the enzymatic and/or binding activities of Cas9, involving determining the three dimensional location of a residue or residues relative to known Cas9 enzymatic or catalytic motifs and/or the binding groups of a bound polynucleotide. The method further involves computationally substituting, inserting or deleting one or more essential amino acid residues and modeling and/or testing the resulting altered Cas9 polypeptide.

In certain cases, a subject method will involve identifying amino acid residues critical to the activity or structure of Cas9 and computationally engineering mutations at those critical amino acid residues. In some embodiments the method will further comprise computationally determining an amino acid insertion, deletion, or substitution or multiple amino acid insertions, deletions, or substitutions that will affect Cas9 activity using the atomic coordinates or atomic structures provided herein. In particular embodiments, a subject method involves engineering mutations at SpyCas9 critical sites including the Topo-homology domain (residues $1136^{Spy}$-$1200^{Spy}$, wherein the superscript "Spy" indicates reference to the amino acid sequence of *S. pyogenes* previously disclosed, SEQ ID NO:1), the C-terminal domain (residues $1201^{Spy}$-$1363^{Spy}$), the Arginine-rich region (residues $59^{Spy}$-$76^{Spy}$), the disordered linker (residues $714^{Spy}$-$717^{Spy}$), PAM loop 1 (residues $448^{Spy}$-$501^{Spy}$; including $W476^{Spy}$), PAM loop 2 (residues $1102^{Spy}$-$1136^{Spy}$, $W1126^{Spy}$), basic amino acid residues in the nucleic acid binding groove (residues $R69^{Spy}$, $R70^{Spy}$, $R71^{Spy}$, $R75^{Spy}$ $K76^{Spy}$, $His160^{Spy}$, $Lys163^{Spy}$, $Lys288^{Spy}$, $Arg400^{Spy}$, $Lys401^{Spy}$, and $Arg403^{Spy}$), the auto-inhibitory beta hairpin of the RuvC domain (residues $1049^{Spy}$-$1059^{Spy}$), as well as those atoms that are close thereto, e.g., within 5 Å, within 10 Å, within 20 Å or within 30 Å of those amino acids. In particular embodiments, a subject method involves engineering mutations at AnaCas9 critical sites including the beta-hairpin domain (residues $822^{Ana}$-$924^{Ana}$, wherein the superscript "Ana" indicates reference to the amino acid sequence of *A. naeslundii* previously disclosed, SEQ ID NO:7), the Arginine-rich region (residues $64^{Ana}$-$80^{Ana}$), the non-conserved zinc site (residues $Cys566^{Ana}$, $Cys569^{Ana}$, $Cys602^{Ana}$ and $Cys605^{Ana}$), the HNH active site (residues $Asp581^{Ana}$ and $Asn606^{Ana}$), the RuvC domain (residues $Asp17^{Ana}$, $Glu505^{Ana}$, $His736^{Ana}$ and $Asp739^{Ana}$), the catalytic residue $His582^{Ana}$, as well as those atoms that are close thereto, e.g., within 5 Å, within 10 Å, within 20 Å or within 30 Å of those amino acids.

The present disclosure also provides a method of identifying candidate sites for the insertion of heterologous sequence within the amino acid sequence of a polynucleotide of Cas9 such that the inserted heterologous sequence does not affect a desired activity of Cas9. The method generally involves determining the atomic locations of amino acid residues that are non-essential to the enzymatic and/or binding activities of Cas9, involving determining the three dimensional location of a residue or residues relative to known Cas9 enzymatic or catalytic motifs and/or the binding groups of a bound polynucleotide. The method further involves computationally inserting a heterologous sequence near or next to a non-essential amino acid residue or between non-essential residues and modeling and/or testing the resulting altered Cas9 polypeptide.

In certain cases, a subject method will further comprise a test performed computationally or in silico with or without comparison to the atomic coordinates provided herein. In some embodiments, computer models are analyzed to determine whether an altered Cas9 retains its three dimensional structure or whether altered Cas9 performs a desired enzymatic activity or binding function. In other embodiments, the testing is performed by obtaining a physical polypeptide of the altered Cas9 (e.g., purchasing or synthesizing the polypeptide, or utilizing cloning and protein expression) and performing an in vitro or in vivo chemical, biochemical, or biological assay to determine if the altered Cas9 demonstrates altered activity (e.g., a loss of endonuclease activity, increased or decreased binding of a polynucleotide, or the presence of an activity novel to Cas9 (e.g., (de)acetylation, (de)phosphorylation, (de)methylation, (de)ubiquitination, peptide binding, transduction)).

The present disclosure provides methods for identifying candidate sites within a Cas9 polypeptide for the exchange of orthologous protein domains or motifs between different Cas9 polypeptides for the purpose of engineering a chimeric Cas9 polypeptide that includes activities from 2 or more native Cas9 polypeptides. A subject method generally involves computationally identifying a candidate site within a donor Cas9 polypeptide that includes a protein domain or motif that provides for a desirable activity, e.g., binding of a particular protospacer sequence or DNA-targeting sequence, using the atomic coordinates disclosed herein. The method further includes computationally identifying a candidate site within the recipient Cas9 polypeptide for receiving the donor candidate site. The recipient candidate site may contain a domain or motif that is orthologous to the domain or motif within the candidate donor site. In other cases, the recipient site may not contain domains or motifs orthologous to the domains or motifs present in the donor site. An identified candidate site may consist of a continuous sequence of 2 or more sequential amino acid residues, discontinuous sequences of 2 or more amino acids, or 2 or more amino acids that are dispersed in primary protein sequence. The method further includes computationally replacing the recipient candidate site with the donor candidate site thus producing a model of a chimeric Cas9 polypeptide consisting of the recipient Cas9 polypeptide containing the desirable domain or motif of the donor Cas9 polypeptide. In some embodiments, the resulting model chimeric Cas9 may be used to computationally test activity of the polypeptide and to further refine the donor and recipient candidate sites. The method may further include testing performed by obtaining a physical polypeptide of the chimeric Cas9 (e.g., purchasing or synthesizing the polypeptide, or utilizing cloning and protein expression) and performing an in vitro or in vivo chemical, biochemical, or biological assay to determine if the chimeric Cas9 demonstrates chimeric activity (e.g., binding of non-native DNA-target sequence).

In certain cases, a subject method will further comprise testing a mutated, altered, or chimeric Cas9 polypeptide to determine if it physically binds a polynucleotide as represented by a computational model derived from the atomic coordinates or atomic structures provided herein. In some embodiments, a subject method will further comprise obtaining the polynucleotide (e.g., purchasing, synthesizing, isolating, or generating the polynucleotide through cloning, PCR or in vitro transcription) and testing the polynucleotide to determine if it binds a mutated, altered, or chimeric Cas9. In certain cases, binding of the polynucleotide to the Cas9 may be tested using any method described herein or known to the art (e.g., immunoprecipitation (IP), chromatin immunoprecipitation (ChIP), DNA immunoprecipitation (DIP), electrophoretic mobility shift assay (EMSA), exonuclease footprinting assay, nuclease protection assay, polynucleotide labeling with negative-stain electron microscopy, and the like).

A method that comprises receiving a set of atomic coordinates for a Cas9 polypeptide; and identifying sites for mutation, insertion of heterologous sequences, or exchange of orthologous domains using the coordinates is also provided, as is a method comprising: forwarding to a remote location a set of atomic coordinates for a Cas9 polypeptide; and receiving the identity of sites for mutation, insertion of heterologous sequences, or exchange of orthologous domains.

A subject method can provide for one or more of: 1) reducing a native activity of a Cas9 polypeptide; 2) ablating a native activity of a Cas9 polypeptide; 3) increasing a native activity of a Cas9 polypeptide; 4) altering a native DNA binding activity of a Cas9 polypeptide; 5) altering a DNA-targeting activity of a Cas9 polypeptide; 6) altering a native RNA binding activity of a Cas9 polypeptide; 7) altering a native nuclease activity of a Cas9 polypeptide; 8) altering a native endonuclease activity of a Cas9 polypeptide; 9) conferring a non-native enzymatic activity to a Cas9 polypeptide; 10) improving or altering desirable activities of a Cas9 polypeptide by producing a chimeric Cas9 polypeptide; 11) improving or altering a desirable chemical property of a Cas9 polypeptide by producing a chimeric Cas9 polypeptide; 12) designing a compact Cas9 polypeptide that retains desirable activities by producing a chimeric Cas9 polypeptide.

In certain embodiments, a computer system comprising a memory comprising the atomic coordinates of a Cas9 polypeptide with or without a bound ligand polynucleotide is provided. The atomic coordinates are useful as models for rationally identifying derivatives of a Cas9 polypeptide. Such derivatives may be designed either de novo, or by modification of a disclosed Cas9 polypeptide, for example. In other cases, derivatives may be identified by testing known polynucleotide sequences to determine if they "bind" with a molecular model of a Cas9 polypeptide. Such computational binding methods are generally well known in the art.

Software programs also may be used to aid one skilled in the art in visualizing or designing Cas9 derivatives. These include, but are not limited to, Abalone (Agile Molecule), ACEMD (Acellera Ltd), ADUN (adun.imim.es), AMBER (ambermd.org), Ascalaph Designer (Ascalaph Project), Automated Topology Builder (Automated Topology Builder), Avogadro (Avogadro), Balloon (Åbo Akademi), BOSS (Yale University), CHARMM (charmm.org), Chemitorium (weltweitimnetz.de), ChemSketch (Advanced Chemistry Development, Inc.), COSMOS (COSMOS Software), Culgi (Culgi BV), Deneb (AtelGraphics inc.), Desmond (D. E. Shaw Research Schrödinger), Discovery Studio (Accelrys), fold.it (fold.it), FoldX (CRG), GoVASP (Windiks Consulting), GPIUTMD (GPIUTMD), GROMACS (gromacs.org), GROMOS (GROMOS.net), GULP (projects.ivec.org), HOOMD-blue (codeblue.umich.edu), ICM (Molsoft), LAMMPS (Sandia), MacroModel (Schrödinger), MAPS (Scienomics), Materials Studio (Accelrys), MedeA (Materials Design), MCCCS Towhee (Towhee Project), MDynaMix (Stockholm University), MOE (Chemical Computing Group), MOIL (cbsu.tc.cornell.edu), MOLDY (Moldy), ORAC (chim.unifi.it), NAB (Case group), Packmol (ime.unicamp.br), Prime (Schrödinger), Protein Local Optimization Program (PLOP wiki), p4vasp (p4vasp.at), PyMOL (PyMol.org), QMOL (DNASTAR, Inc.), RasMol (RasMol), Raster3D (University of Washington), RedMD (University of Warsaw, ICM), StruMM3D (STR3DI32) (Exorga, Inc.), Selvita Protein Modeling Platform (Selvita Ltd), SCIGRESS (SCIGRESS.com), SimBioSys' MoDeST (SimBioSys Inc.), Spartan (Wavefunction, Inc.), SwissParam (SwissParam.), TeraChem (PetaChem LLC), TINKER (Washington University), Tremolo-X (Tremolo-X), UCSF Chimera (University of California), VEGA ZZ (VEGA ZZ Web site), VLifeMDS (Vlife Sciences Technologies), VMD+NAMD (Beckman Institute), WHAT IF (swift.cmbisu.nl ), xeo (xeo.sourceforge.net), YASARA (YASARA.org), and Zodiac (zeden.org). These programs may be implemented, for instance, using a computer workstation, as are well known in the art, for example, a Windows, Macintosh, LINUX, SGI or Sun workstation. Other hardware systems and software packages will be known to those skilled in the art.

The structure data provided herein can be used in conjunction with computer-modeling techniques to design Cas9 derivatives with or without altered Cas9 activity. The models characterize the three-dimensional surface topography of a Cas9 derivative, as well as factors including van der Waals contacts, electrostatic interactions, hydrogen-bonding opportunities, and electron density. Computer simulation techniques are then used to map intramolecular and intermolecular interaction positions for functional groups including but not limited to protons, hydroxyl groups, amine groups, divalent cations, aromatic and aliphatic functional groups, amide groups, alcohol groups, etc. that are modified to produce the Cas9 derivative.

The ability of an altered Cas9 to bind to a particular polynucleotide can be analyzed prior to actual synthesis using computer modeling techniques. Only those candidate Cas9 derivatives that are indicated by computer modeling to bind the target polynucleotide (e.g., a particular DNA sequence) with sufficient binding energy may be synthesized and tested for their ability to bind the target polynucleotide using binding assays known to those of skill in the art and/or described herein. The computational evaluation step thus avoids the unnecessary synthesis or cloning of Cas9 derivatives that are unlikely to bind a particular polynucleotide target with adequate affinity.

Specific computer software is available in the art to evaluate binding deformation energy and electrostatic interaction. Examples of programs designed for such uses include: Gaussian 94, revision C (Frisch, Gaussian, Inc., Pittsburgh, Pa. (1995); AMBER, version 7. (Kollman, University of California at San Francisco, (2002); QUANTA/CHARMM (Accelrys, Inc., San Diego, Calif., (1995); Insight II/Discover (Accelrys, Inc., San Diego, Calif., (1995); DelPhi (Accelrys, Inc., San Diego, Calif., (1995); and AMSOL (University of Minnesota) (Quantum Chemistry Program Exchange, Indiana University). These programs may be implemented, for instance, using a computer workstation, as are well known in the art, for example, a Windows, Macintosh, LINUX, SGI or Sun workstation. Other hardware systems and software packages will be known to those skilled in the art.

Once a candidate Cas9 derivative has been optimally selected or designed, as described above, substitutions may then be made in some of its amino acid residues, atoms, or side groups to improve or modify its binding properties. Generally, initial substitutions are conservative in that the replacement group will have either approximately same size, or overall structure, or hydrophobicity, or charge as the original group. Components known in the art to alter conformation should be avoided in making substitutions. Substituted candidates may be analyzed for efficiency of binding to a target polynucleotide using the same methods described above.

Once a candidate Cas9 derivative has been identified using any of the methods described above, it can be screened for biological activity. Any one of a number of assays of for Cas9 polynucleotide binding or nuclease activity disclosed here or known to those of skill in the art may be used.

Utility

A method for identifying sites for the mutation, insertion of heterologous domains, or replacement with chimeric domains within a Cas9 polypeptide according to the present disclosure finds use in a variety of applications, which are also provided. Applications include research applications and industrial applications.

Research and industrial applications include, e.g., identifying a site within Cas9 that renders a Cas9 domain inactive and thus produces a Cas9 derivative useful in research or industrial processes, e.g., identifying a site for the insertion of heterologous sequence to alter the enzymatic activity of or add enzymatic activity to a Cas9 polypeptide and thus producing a Cas9 derivative useful in research or industrial processes, and the like.

In some cases, the Cas9 enzymatic activity or the enzymatic activity of the heterologous sequence modifies the target DNA. In some cases, the Cas9 enzymatic activity or the enzymatic activity of the heterologous sequence is nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity or glycosylase activity. In some cases, the Cas9 enzymatic activity or the enzymatic activity of the heterologous sequence is nuclease activity. In some cases, the nuclease activity introduces a double strand break in the target DNA. In some cases, the Cas9 enzymatic activity or the enzymatic activity of the heterologous sequence modifies a target polypeptide associated with the target DNA. In some cases, the Cas9 enzymatic activity or the enzymatic activity of the heterologous sequence is methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity (small ubiquitin-related modifier), deSUMOylating activity, ribosylation activity, deribosylation activity, myristoylation activity or demyristoylation activity.

Sites identified for the deletion of amino acid resides that do not alter Cas9 activity or sites identified for the engineering of chimeric Cas9 polypeptides using a method as described above are useful, for example in producing a smaller or more compact Cas9 polypeptide. The above described methods have utility in research applications for determining how large and small Cas9 variants are related and how related Cas9 variants carry out similar catalytic functions, e.g., computational comparison of AnaCas9 domains with domains of Cas9 from a different species, e.g., computational comparison of SpyCas9 domains with domains of Cas9 from a different species, e.g., computational comparison between SpyCas9 and AnaCas9.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); and the like.

Example 1

SpyCas9

SpyCas9 Expression and Purification

*Streptococcus pyogenes* Cas9 (SpyCas9) was cloned into a custom pET-based expression vector encoding an N-terminal His$_6$-tag followed by Maltose-Binding Protein (MBP) and a tobacco etch virus (TEV) protease cleavage site (plasmid pMJ806, SEQ ID NO:33). Point mutations were introduced into SpyCas9 using site-directed mutagenesis and verified by DNA sequencing.

For crystallization, wild-type (WT) (SEQ ID NO:1) and K848C mutant SpyCas9 (SEQ ID NO:26) proteins were expressed and purified. The protein was purified by a combination of Ni-NTA (nitrilotriacetic acid) affinity, cation exchange (SP sepharose) and gel filtration (Superdex 200) chromatography steps. The final gel filtration step was carried out in elution buffer containing 20 mM HEPES(4-(2-hydroxyethyl)-1-piperazineethanesulfonic acid)-KOH pH 7.5, 250 mM KCl and 1 mM TCEP (tris(2-carboxyethyl) phosphine). The protein was concentrated to 4-6 mg ml$^{-1}$ and flash frozen in liquid N$_2$. Selenomethionine (SeMet)-substituted SpyCas9 was expressed and purified as for native SpyCas9, except that all chromatographic solutions were supplemented with 5 mM TCEP.

SpyCas9 Crystallization and Structure Determination

SpyCas9 crystals were grown using the hanging drop vapor diffusion method at 20° C. by mixing equal volumes (1.5 µl+1.5 µl) of protein solution and crystallization buffer (0.1 M Tris-Cl pH 8.5, 0.2-0.3 M Li$_2$SO$_4$ and 14-15% (w/v) PEG 3350). Crystal nucleation and growth was gradually improved using iterative microseeding. For diffraction experiments, the crystals were cryoprotected in situ by stepwise exchange into a solution containing 0.1 M Tris-Cl pH 8.5, 0.1 M Li$_2$SO$_4$, 35% (w/v) PEG (polyethylene glycol) 3350, and 10% ethylene glycol in five steps executed at 5 min intervals. In each step, 0.5 µl of mother liquor was removed from the crystal drop and replaced with 0.5 µl cryoprotectant. After the final cryoprotectant addition, the crystals were incubated for an additional 5 min, transferred to a drop containing 100% cryoprotectant for 30 s, and then flash cooled in liquid N$_2$. Diffraction data were measured at beamlines 8.2.1 and 8.2.2 of the Advanced Light Source (Lawrence Berkeley National Laboratory), and beamlines PXI and PXIII of the Swiss Light Source (Paul Scherer Institute) and processed using XDS. Data collection statistics are shown in Table 2. The crystals belonged to space group P2$_1$2$_1$2 and contained two molecules of SpyCas9 in the asymmetric unit related by pseudotranslational, non-crystallographic symmetry. High-resolution native data to 2.62 Å resolution were measured from an unusually large crystal cryoprotected in the presence of 1 mM MgCl$_2$. A complete native data set was obtained by collecting four datasets (40° rotation per dataset) from different exposed parts of the crystal.

Phasing was performed as follows. A 4.2 Å resolution single-wavelength anomalous diffraction (SAD) dataset was measured at the selenium peak wavelength using a SeMet-substituted SpyCas9 crystal. However, due to small crystal size and low resolution, the anomalous signal in this dataset was too weak to locate the selenium sites. Additional phases were therefore obtained from SpyCas9 crystals soaked in sodium tungstate. The crystals were soaked by stepwise exchange of the lithium sulfate containing mother liquor with 0.1 M Tris-Cl pH 8.5, 0.1 M Na$_2$WO$_4$, 15% (w/v) PEG 3350, and then cryoprotected by stepwise exchange (as described above) of the soak solution with cryoprotectant solution supplemented with 10 mM Na$_2$WO$_4$. Using these crystals, a highly redundant SAD 3.9 Å dataset was measured at the tungsten L-III absorption edge (1.2149 Å), and 16 tungstate sites were located using SHELXD. Further phase information came from peak-wavelength SAD datasets obtained from a crystal of SpyCas9 K848C mutant soaked in 1 mM thimerosal for 6 hr prior to cryoprotection (thimerosal soak), a WT SpyCas9 crystal soaked with 10 mM CoCl$_2$ during the cryoprotection procedure (Co soak), and a WT SpyCas9 crystal grown in the presence of 1 mM Er(III)-acetate. Refinement of the substructures and phase calculations were performed using the MIRAS procedure in AutoSHARP by combining initial tungstate SAD phases with the additional SAD data sets (SeMet, Co, Er and thimerosal) and the high-resolution native data. Phases were improved by density modification and two-fold non-crystallographic symmetry averaging using the Resolve module of the Phenix suite. The resulting electron density maps were of excellent quality and allowed manual model building in COOT. Selenium positions aided in assigning the sequence register. The atomic model of SpyCas9 was completed by iterative model building in COOT and refinement using Phenix.refine. Refinement and model statistics are provided in Table 2 (provided in FIG. 31).

The final atomic model has R$_{work}$ and R$_{free}$ values of 0.245 and 0.290, respectively, and good stereochemistry, as assessed with MolProbity, with 96.2% of the residues in the most favored regions of the Ramachandran plot and no outliers. The model contains two SpyCas9 molecules that superimpose with an overall rmsd of 1.1 Å over 1060 Cα atoms, the major difference being a ~5° hinge-like rotation of the HNH domain. In the atomic model, molecule A contains residues 4-102, 116-307, 314-447, 503-527, 539-570, 587-672, 677-714, 718-765, 774-791, 800-859, 862-902, 908-1027, 1036-1102, 1137-1147, 1159-1186, 1192-1242, and 1259-1363 of SEQ ID NO:1. Molecule B contains residues 4-103, 116-308, 310-447, 502-527, 539-570, 587-673, 678-713, 718-764, 773-791, 800-859, 862-902, 908-1025, 1036-1102, 1137-1148, 1160-1185, 1188-1241, and 1256-1363 of SEQ ID NO:1. The remaining residues do not appear ordered in electron density maps and could not be built. The description of the SpyCas9 structure herein is based on molecule B, which is better ordered.

Figure 2A:
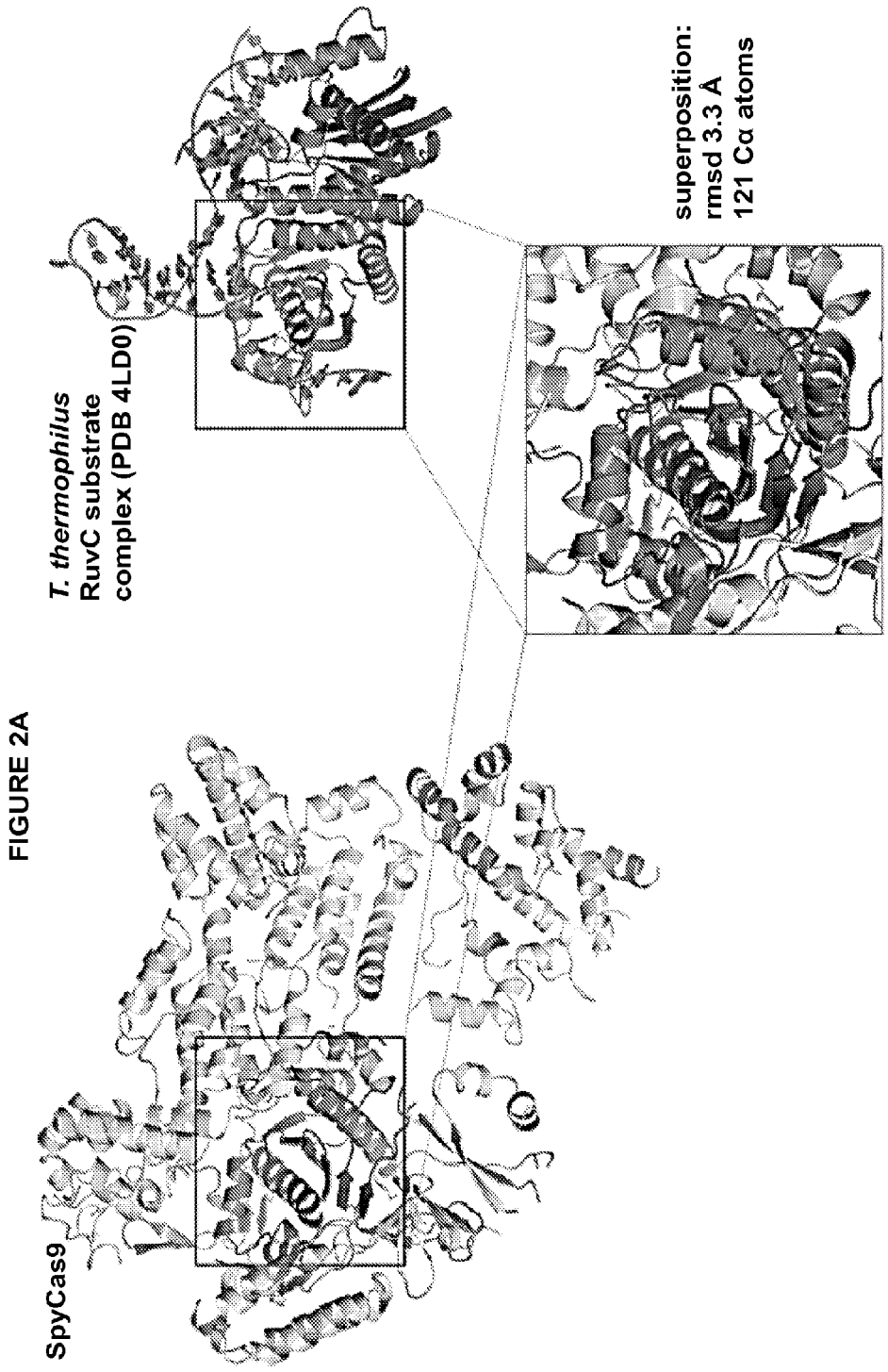
FIGS. 2A-C provide a crystal structure of SpyCas9 and structural superposition of SpyCas9 with *Thermus thermophilus* RuvC resolvase bound to a Holliday junction substrate (PDB entry 4LD0) including close-up views of the RuvC active site (A) without and (B) with six nucleotides of DNA modeled in the active site and (C) close-up views of the catalytic sites.

An additional dataset (at 3.1 Å resolution) was measured using a SpyCas9 crystal soaked in 20 mM MnCl$_2$ during the cryoprotection procedure. Fo-Fc difference maps calculated using the high-resolution model revealed two Mn$^{2+}$ ions bound in the RuvC domain active site (FIG. 2) and 4 additional Mn$^{2+}$ ions bound to each of the two SpyCas9 molecules. The HNH domain active site remained poorly ordered in this structure, and no Mn$^{2+}$ binding was observed. The model was refined to an R$_{work}$ and R$_{free}$ of 0.255 and 0.280, respectively.

Endonuclease Cleavage Assays with SpyCas9

A synthetic 42-nt crRNA targeting a protospacer from the bacteriophage γ genome was purchased from Integrated DNA Technologies (IDT) and purified via 10% denaturing PAGE (polyacrylamide gel electrophoresis). tracrRNA was in vitro transcribed from a synthetic DNA template (IDT) using T7 RNA polymerase and corresponds to nucleotides 15-87 as described previously. crRNA:tracrRNA duplexes (10 µM) were prepared by mixing equimolar amounts of crRNA and tracrRNA in Hybridization Buffer (20 mM Tris-Cl pH 7.5, 100 mM KCl, 5 mM MgCl$_2$), heating at 95° C. for 30 sec, and slow-cooling on the benchtop. SpyCas9:RNA complexes were reconstituted by mixing SpyCas9 with a 2× molar excess of the crRNA:tracrRNA duplex in Reconstitution Buffer (20 mM Tris-Cl pH 7.5, 100 mM KCl, 5 mM MgCl$_2$, 1 mM DTT) and incubating at 37° C. for 10 minutes.

A 55 base-pair (bp) DNA target derived from the bacteriophage 2 genome was prepared by mixing equimolar amounts of individual synthetic oligonucleotides (IDT) in Hybridization Buffer supplemented with 5% glycerol, heating for 1-2 minutes, and slow-cooling on the benchtop. Duplexes were separated from single-stranded DNA by 6% native PAGE conducted at 4° C., with 5 mM MgCl$_2$ added to the gel and the running buffer. The DNA was excised, eluted into 10 mM Tris-Cl, pH 8 at 4° C. overnight, ethanol precipitated, and resuspended in Hybridization Buffer. BrdU (bromodeoxyuridine) containing ssDNAs used in analytical crosslinking reactions were radiolabeled and hybridized with a 5× molar excess of the unlabeled complementary strand. Cleavage reactions were performed at room temperature in Reaction Buffer (20 mM Tris-Cl pH 7.5, 100 mM KCl, 5 mM MgCl$_2$, 5% glycerol, 1 mM DTT (dithiothreitol)) using 1 nM radiolabeled dsDNA substrates and 1 nM or 10 nM Cas9:RNA. Aliquots (10 µl) were removed at various time points and quenched by mixing with an equal volume of formamide gel loading buffer supplemented with 50 mM EDTA (ethylenediaminetetraacetic acid). Cleavage products were resolved by 10% denaturing PAGE and visualized by phosphorimaging (GE Healthcare). The sequences of DNA and RNA oligonucleotides used in this study are listed in Table 3.

TABLE 3

List of nucleic acid reagents used in this study:

| # | Description | SEQ ID NO.: | Sequence (5'-3') |
|---|---|---|---|
| 1 | tracrRNA (nts 15-87) | 15 | GGACAGCAUAGCAAGU UAAAAUAAGGCUAGUC CGUUAUCAACUUGAAA AAGUGGCACCGAGUCG GUGCUUUUU |
| 2 | Targeting crRNA | 16 | GUGAUAAGUGGAAUGC CAUGGUUUUAGAGCUA UGCUGUUUUG |
| 3 | 55-bp DNA substrate, non-target strand[a] | 17 | GAGTGGAAGGATGCCA GTGATAAGTGGAATGC CAT<u>G</u>TGGGCTGTCAAA ATTGAGC |
| 4 | 55-bp DNA substrate, target strand[a] | 18 | GCTCAATTTTGACAGC CCACATGGCATTCCAC TTATCACTGGCATCCT TCCACTC |
| 5 | Br-dU1 containing 55 nt DNA substrate, non-target strand[a] | 19 | GAGTGGAAGGATGCCA GTGATAAGTGGAATGC CATG(BrdU1)GGGCT GTCAAAATTGAGC |
| 6 | Br-dU2 containing 55 nt DNA substrate, target strand[a] | 20 | GCTCAATTTTGACAGC CC(BrdU2)CATGGCA TTCCACTTATCACTGG CATCCTTCCACTC |
| 7 | reverse complement for #6[a] | 21 | GAGTGGAAGGATGCCA GTGATAAGTGGAATGC CAT<u>G</u>AGGGCTGTCAAA ATTGAGC |
| 8 | Br-dU3 containing 55 nt DNA substrate, non-target strand[a] | 22 | GAGTGGAAGGATGCCA GTGATAAGTGGAATGC CAT<u>GTGG</u>(BrdU3)CT GTCAAAATTGAGC |
| 9 | reverse complement for #8[a] | 23 | GCTCAATTTTGACAGA CCACATGGCATTCCAC TTATCACTGGCATCCT TCCACTC |

[a]The protospacer is in italics and the PAM is underlined.

S. pyogenes Cas9 Structure Reveals a Two-lobed Architecture with Adjacent Active Sites

Figure 3:
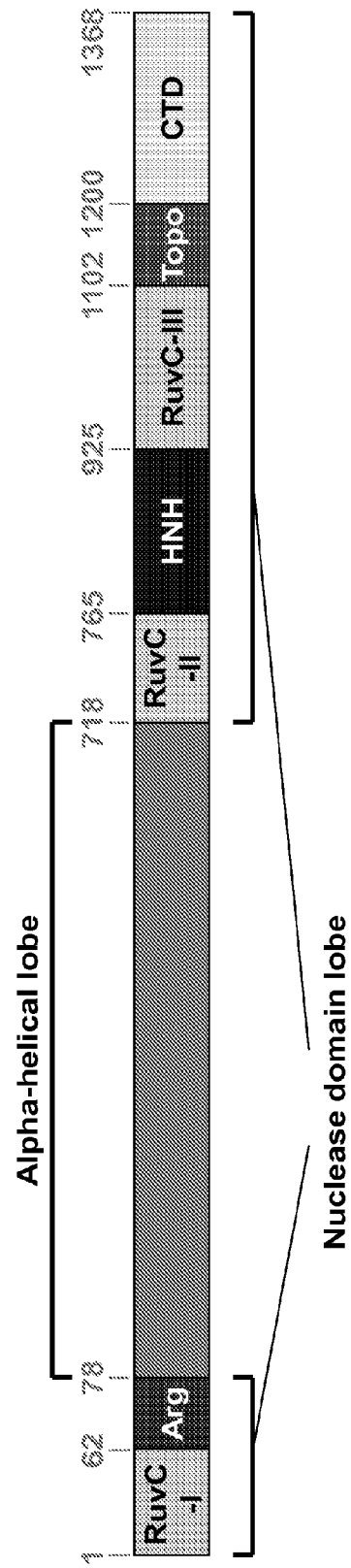
FIG. 3 provides a cartoon of schematic of the polypeptide sequence and domain organization of the Type II-A Cas9 protein from *S. pyogenes* (SpyCas9).
Figure 4A:
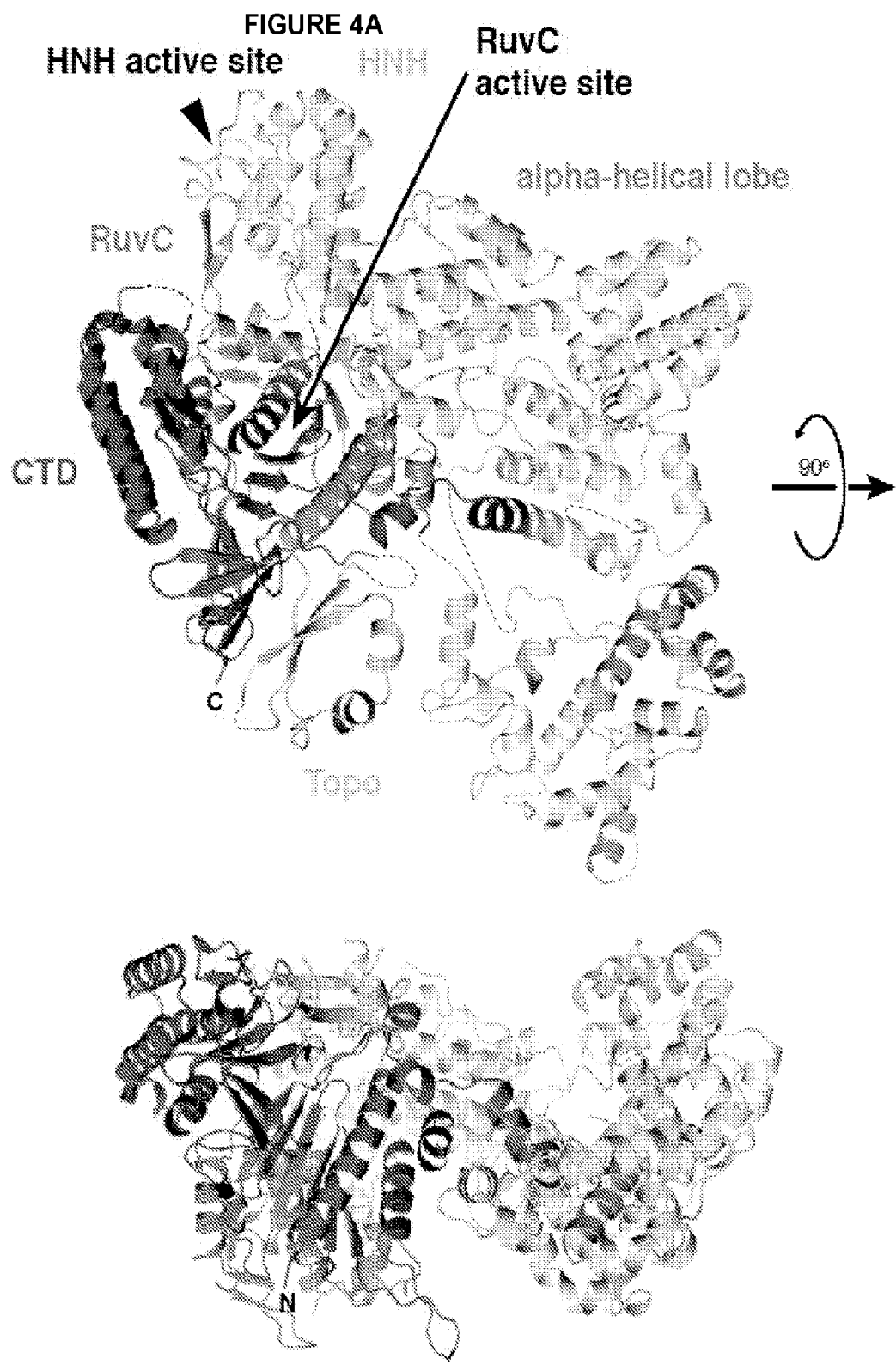
FIGS. 4A-B provide orthogonal views of the overall structure of SpyCas9 shown in (A) ribbon and (b) surface representations.

*Streptococcus pyogenes* Cas9 (SpyCas9; SEQ ID NO:1) is a prototypical Type II-A Cas9 protein consisting of well-conserved RuvC motifs and an HNH domain, as well as flanking regions that lack apparent sequence similarity to known protein structures (FIG. 3). SpyCas9 was the first biochemically characterized Cas9 and has been employed in the majority of current CRISPR-based genetic engineering methodologies. To obtain structural insights into the multidomain architecture of SpyCas9, the 2.6 Å resolution crystal structure of the enzyme as determined, see Table 2. The structure reveals that SpyCas9 is a crescent-shaped molecule with approximate dimensions of ~100 Å×~100 Å×~50 Å (FIG. 4 and FIG. 5). The enzyme adopts a distinct bi-lobed architecture comprising the nuclease domains and C-terminal domain in one lobe (the nuclease lobe) and a large alpha-helical domain in the other. The RuvC domain forms the structural core of the nuclease lobe, a six-stranded beta sheet surrounded by four alpha helices, with all three conserved motifs contributing catalytic residues to the active site (FIG. 5). In the Cas9 primary sequence (SEQ ID NO:1), the HNH domain is inserted between the second and third RuvC domain motifs. The HNH and RuvC domains are juxtaposed in the SpyCas9 structure, with their active sites located ~25 Å apart. The HNH domain active site is poorly ordered in apo-SpyCas9 crystals, showing that the active site undergoes conformational ordering upon nucleic acid binding. The C-terminal region of SpyCas9 contains a β-β-α-β Greek key domain that is structurally similar to a domain found in topoisomerase II (hereafter referred to as the Topo-homology domain, residues $1136^{Spy}$-$1200^{Spy}$). A mixed α/βregion (C-terminal domain, residues $1201^{Spy}$-$1363^{Spy}$) forms a protrusion on the nuclease domain lobe. The structural halves of SpyCas9 are connected by two linking segments, one formed by the Arginine-rich region (residues $59^{Spy}$-$76^{Spy}$) and the other by a disordered linker comprising residues $714^{Spy}$-$717^{Spy}$ (FIG. 4A).

SpyCas9 Contains Two Putative Nucleic Acid Binding Grooves

The SpyCas9 structure contains two prominent clefts on one face of the molecule: a deep and narrow groove located within the nuclease lobe and a wider groove within the alpha-helical lobe (FIG. 6). The nuclease lobe cleft is approximately 40 Å long, 15-20 Å wide and 15 Å deep, with the RuvC active site located at its bottom. The C-terminal domain forms one side of the cleft, while the HNH domain and a protrusion of the alpha-helical lobe forms the other. The concave surface of the alpha-helical lobe creates a wider, shallower groove that extends over almost its entire length (FIG. 6). The groove is more than 25 Å across at its widest point, which is sufficient to accommodate an RNA-RNA or DNA-RNA duplex. Its surface is highly positively charged (FIG. 6), especially at the Arg-rich segment comprising $R69^{Spy}$, $R70^{Spy}$, $R71^{Spy}$, $R75^{Spy}$ and $K76^{Spy}$. Additional basic residues that are conserved in Type II-A proteins project their side chains into the groove: $His160^{Spy}$, $Lys163^{Spy}$, $Lys288^{Spy}$, $Arg400^{Spy}$, $Lys401^{Spy}$, and $Arg403^{Spy}$ (FIG. 7). Multiple sulfate or tungstate ions are bound to the alpha-helical lobe in the SpyCas9 crystals (FIG. 7), showing a role for this lobe in nucleic acid recognition. Amino acid residues located in both the nuclease and alpha-helical lobe clefts are highly conserved within Type II-A Cas9 proteins (FIG. 6), while the opposite face of the SpyCas9 molecule lacks extensive surface conservation. The above observations demonstrate that both clefts play important functional roles. The RuvC domain mediates cleavage of the non-target DNA strand and the nuclease domain cleft is the binding site of the displaced non-target strand. Conversely, the alpha-helical lobe, which contains the Arg-rich segment, is involved in binding the crRNA:tracrRNA guide RNA and/or the crRNA-target DNA heteroduplex.

Identification of Cas9 PAM Binding Site

Figure 2B:
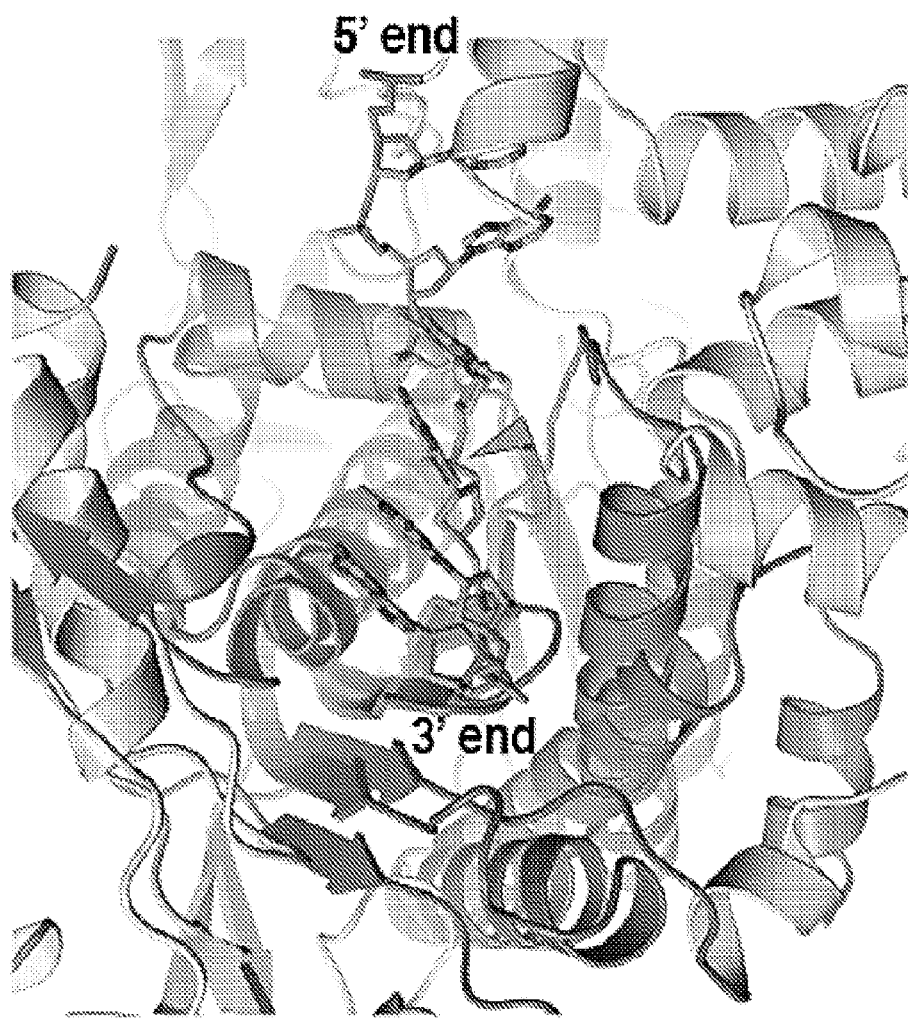
Figure 2C:
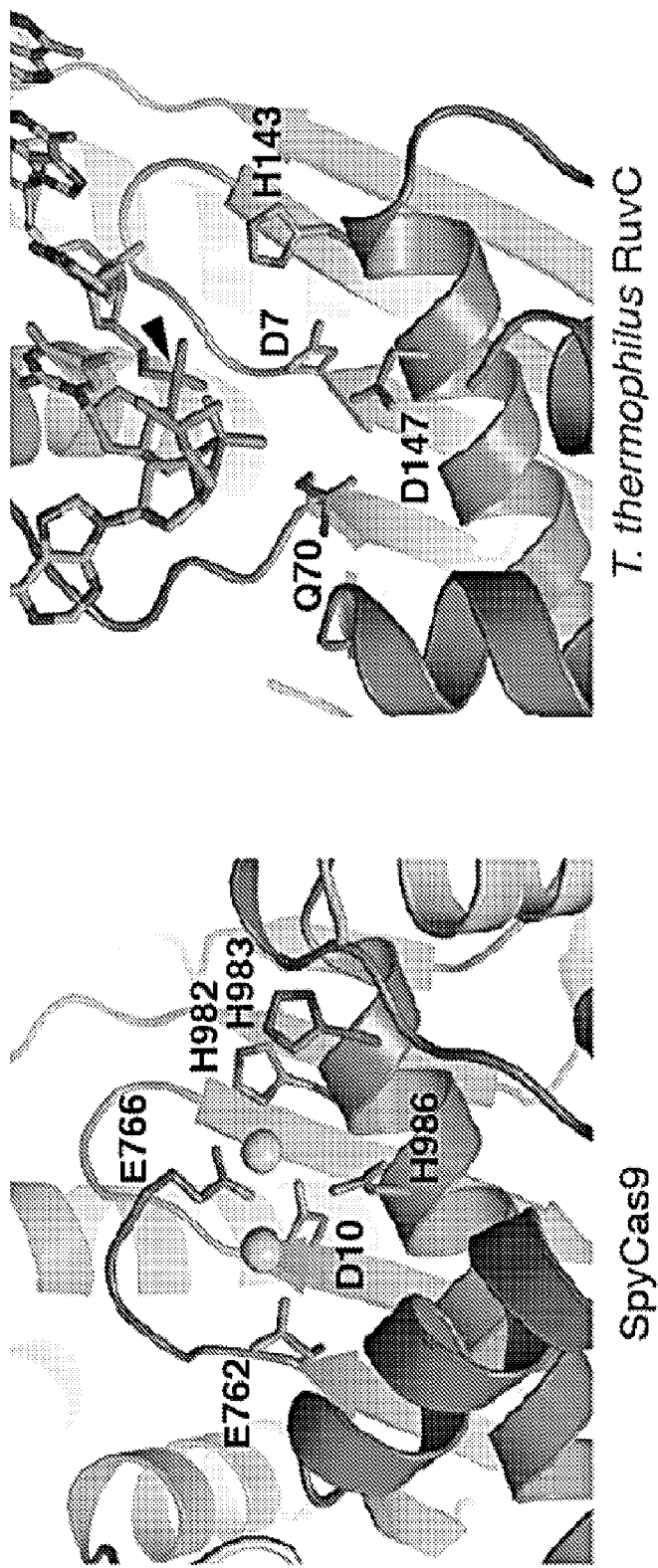

SpyCas9 recognizes a 5'-NGG-3' PAM sequence located three base pairs to the 3' side of the cleavage site on the non-complementary DNA strand, whereas other Cas9 orthologs have different PAM requirements. To gain insight into PAM binding by SpyCas9, the SpyCas9 RuvC nuclease domain structure was compared to that of the RuvC Holliday junction resolvase-substrate complex (FIG. 8). Superposition of these RuvC structures enabled us to model the trajectory of the non-target DNA strand in the SpyCas9 holoenzyme (FIG. 8, FIG. 2B-C). The DNA strand is located along the length of the nuclease lobe cleft in an orientation that would position the 3' end of the DNA, and hence the PAM, at the junction of the two lobes, in the vicinity of the Arg-rich segment and the Topo-homology domain (FIG. 8).

To directly identify regions of Cas9 involved in PAM binding, the catalytically inactive SpyCas9 (D10A/H840A; SEQ. ID NO:27) was reconstituted with a crRNA:tracrRNA guide RNA and bound to DNA targets carrying a photoactivatable 5-bromodeoxyuridine (Br-dU) nucleotide adjacent to either end of the GG PAM motif on the non-target strand (FIG. 9). Following UV irradiation and trypsin digestion, covalent peptide-DNA crosslinks were detected (FIG. 9 and FIG. 10), whereas a DNA substrate containing Br-dU on the target strand opposite the PAM failed to produce a crosslink (FIG. 10). After treatment with nuclease and phosphatase to digest cross-linked DNA, nano-HPLC (high-performance liquid chromatography) MS/MS (tandem mass spectrometry) was performed to identify tryptic peptides containing an extra mass resulting from covalent dU or p-dU adducts (FIG. 9). The nucleotide immediately 5' to the GG motif was found to be cross-linked to residue $W476^{Spy}$, whereas the residue immediately 3' to the motif was found to be cross-linked to residue $W1126^{Spy}$. Both tryptophans are located in disordered regions of the SpyCas9 structure that are ~30 Å apart. $W476^{Spy}$ resides in a 53-aa loop at the edge of the alpha helical lobe underneath the Arg-rich region, whereas $W1126^{Spy}$ is in a 33-aa loop that connects the RuvC domain and the Topo-homology domain (FIG. 8). These tryptophan residues are conserved among Type II-A Cas9 proteins that utilize the same NGG PAM to cleave target DNA in vitro, but are absent from the *Neisseria meningitidis* and *Streptococcus thermophilus* Type II-C Cas9 proteins, which are known to recognize different PAMs (FIG. 5 and FIG. 11).

To test the roles of both loops in DNA target recognition and cleavage, triple alanine substitutions of residues $475^{Spy}$-$477^{Spy}$ (P-W-N) and $1125^{Spy}$-$1127^{Spy}$ (D-W-D) were made and cleavage assays with double-stranded DNA targets were performed (FIG. 12). SpyCas9 mutated in residues $1125^{Spy}$-$1127^{Spy}$ showed wild-type cleavage activity, whereas mutations in residues $475^{Spy}$-$477^{Spy}$ caused a decrease of activity compared to wild-type. Mutating both loops simultaneously almost completely abolished SpyCas9 activity (FIG. 12). These data demonstrate that at least one tryptophan is necessary to promote the DNA cleavage reaction. The spatial constraints of crosslink formation and the distance of both tryptophan residues from either nuclease domain show that they are involved in PAM binding.

Example 2

Ana Cas9

AnaCas9 Expression and Purification

Full-length *Actinomyces naeslundii* Cas9 (AnaCas9; SEQ ID NO:7, residues 1-1101) was subcloned into a custom pET-based expression vector with an N-terminal $His_{10}$-tag followed by Maltose-Binding Protein (MBP) and a TEV protease cleavage site. The protein was overexpressed in *Escherichia coli* strain Rosetta (DE3) and was purified to homogeneity by immobilized metal ion affinity chromatography and heparin affinity chromatography. An additional gel filtration chromatography step (HiLoad 16/60 Superdex200, GE Healthcare) was added to further purify Ana-Cas9 and remove trace nucleic acid contaminants prior to crystallization. Purified AnaCas9 protein in gel filtration buffer (50 mM HEPES 7.5, 300 mM KCl, 2 mM TCEP, 5% glycerol) was snap frozen in liquid nitrogen and stored at −80° C. Selenomethionine-labeled AnaCas9 protein was expressed in Rosetta (DE3) cells grown in M9 minimal medium supplemented with 50 mg ml$^{-1}$ L-SeMet (L-selenomethionine) (Sigma) and specific amino acids to inhibit endogenous methionine synthesis. The SeMet-substituted protein was then purified using the same procedure as for the native AnaCas9 protein.

AnaCas9 Crystallization and Structure Determination

Crystals of native and SeMet-substituted AnaCas9 were grown by the hanging drop vapor diffusion method at 20° C. Aliquots (2.5 µl) of 4.5 mg ml$^{-1}$ native AnaCas9 protein in 50 mM HEPES 7.5, 300 mM KCl, 2 mM TCEP, 5% glycerol were mixed with 2.5 µl of reservoir solution containing 10% (w/v) PEG 8000, 0.25 M calcium acetate, 50 mM magnesium acetate and 5 mM spermidine. Crystals appeared after 1-2 days, and they grew to a maximum size of 0.15×0.20× 0.35 mm over the course of 6 days. SeMet-substituted AnaCas9 crystals were grown and optimized under the same conditions. Crystals of AnaCas9 bound to manganese (II) ions were prepared by soaking AnaCas9 native crystals in mother liquor supplemented with 20 mM $MnCl_2$ for 2 hr. For cryogenic data collection, crystals were transferred into crystallization solutions containing 30% (v/v) glycerol as the cryoprotectant and then flash-cooled at 100 K. Native and SeMet single-wavelength anomalous diffraction (SAD) datasets were collected at beamline 8.3.1 of the Advanced Light Source, Lawrence Berkeley National Laboratory. Data from manganese-soaked AnaCas9 crystals were collected at the 8.2.2 beamline of the Advanced Light Source, Lawrence Berkeley National Laboratory. All diffraction data were integrated using Mosflm and scaled in SCALA.

The AnaCas9 structure was solved using the single anomalous dispersion phasing method. Using SeMet data between 79.0 and 3.2 Å resolution, both SHELXD/ HKL2MAP and HySS in Phenix detected a total of 13 out of 18 possible selenium sites in the asymmetric unit. Initial phases were calculated using SOLVE followed by solvent flattening with RESOLVE to produce an electron-density map into which most of the protein residues could be unambiguously built. The initial model automatically generated from Phenix AutoBuild module was subjected to subsequent iterative rounds of manual building with COOT and refinement against the 2.2 Å native data in Refmac and Phenix. The final model contains one zinc ion, two magnesium ions, AnaCas9 residues 8-49, 65-98, 134-170, and 225-1101 of SEQ ID NO:7, and has $R_{work}$ and $R_{free}$ values of 0.19 and 0.23, respectively. The N terminus (residues 1-7), loop regions (residues 50-64), and a portion of the alpha-helical lobe (residues 99-133, 171-224) are completely disordered. Model validation showed 94% of the residues in the most favored and 5.8% in the allowed regions of the Ramachandran plot. The structure of $Mn^{2+}$-bound AnaCas9 was obtained by molecular replacement using the program Phaser, which revealed two unambiguously refined $Mn^{2+}$ ions present in the RuvC active site. All statistics of the data processing and structure refinement of AnaCas9 are summarized in Table 4 (provided in FIG. 32

*A. naeslundii* Cas9 Structure Reveals the Architecture of a Smaller Cas9 Variant The 2.2 Å resolution crystal structure of the Type II-C Cas9 enzyme from *Actinomyces naeslundii* (AnaCas9) was determined (Table 4). AnaCas9 folds into a bi-lobed structure with approximate dimensions 105 Å×80 Å×55 Å. The RuvC and HNH nuclease domains, a Topo-homology domain, and the C-terminal domain form an extended nuclease lobe with the RuvC domain located at its center (FIG. 13A-B). Similar to SpyCas9, the RuvC and HNH domains comprise a compact catalytic core, with the two active sites positioned ~30 Å apart. In contrast to SpyCas9, an additional domain (residues $822^{Ana}$-$924^{Ana}$, hereafter referred to as the beta-hairpin domain) is found between the RuvC-III motif and the Topo-homology domain, and adopts a novel fold composed primarily of three anti-parallel beta-hairpins. As in SpyCas9, the polypeptide sequence found between the RuvC-I and RuvC-II motifs forms an alpha-helical lobe. However, the AnaCas9 alpha-helical lobe is much smaller in size, and its relative orientation to the nuclease lobe is different (FIG. 13C and FIG. 14A-C). The Arg-rich region (residues $64^{Ana}$-$80^{Ana}$) connecting the nuclease lobe and the alpha-helical lobe is highly flexible, as indicated by elevated B-factors (FIG. 15). Comparison of the helical lobes in AnaCas9 and SpyCas9 reveals that regions $95^{Ana}$-$251^{Ana}$ and $77^{Spy}$-$447^{Spy}$ are highly divergent and do not align in sequence and structure (FIG. 11). Moreover, the $95^{Ana}$-$251^{Ana}$ region is poorly ordered, and only parts of it could be modeled. By contrast, residues $252^{Ana}$-$468^{Ana}$ and $502^{Spy}$-$713^{Spy}$, which share ~32% sequence identity, superimpose with a root mean square deviation (rmsd) of ~3.6 Å over 149 Cα (FIG. 13C and FIG. 14). The position and orientation of this portion of the alpha-helical domain with respect to the RuvC domain in the AnaCas9 and SpyCas9 structures are substantially different, with a large displacement of ~70 Å towards the RuvC domain and an approximately 35° rotation about the junction between two domains in AnaCas9 (FIG. 14C).

The higher resolution of the AnaCas9 structure provides insights into active-site chemistries for both nuclease domains. The well-defined AnaCas9 HNH active site contains a two-stranded antiparallel β-sheet flanked by two α-helices on each side, as well as a non-conserved zinc site coordinated by $Cys566^{Ana}$, $Cys569^{Ana}$, $Cys602^{Ana}$ and $Cys605^{Ana}$ (FIG. 16 and FIG. 17). The HNH active site reveals $Asp581^{Ana}$ and $Asn606^{Ana}$ coordinating a hydrated magnesium ion (FIG. 16) that is involved in binding the scissile phosphate in the target DNA strand. The imidazole side chain of the catalytic residue $His582^{Ana}$ (corresponding to $His840^{Spy}$) acts as a general base in deprotonating the attacking water nucleophile, in agreement with a one-metal-ion catalytic mechanism common to endonucleases containing the ββα-Metal motif. In the RuvC domain, two $Mn^{2+}$ ions, spaced 3.8 Å apart and coordinated by the invariant residues $Asp17^{Ana}$, $Glu505^{Ana}$, $His736^{Ana}$ and $Asp739^{Ana}$ are consistent with a two-metal ion mechanism.

Example 3

SpyCap9 and AnaCap9 Adopt Auto-Inhibited Conformations in the Apo State

Figure 4B:
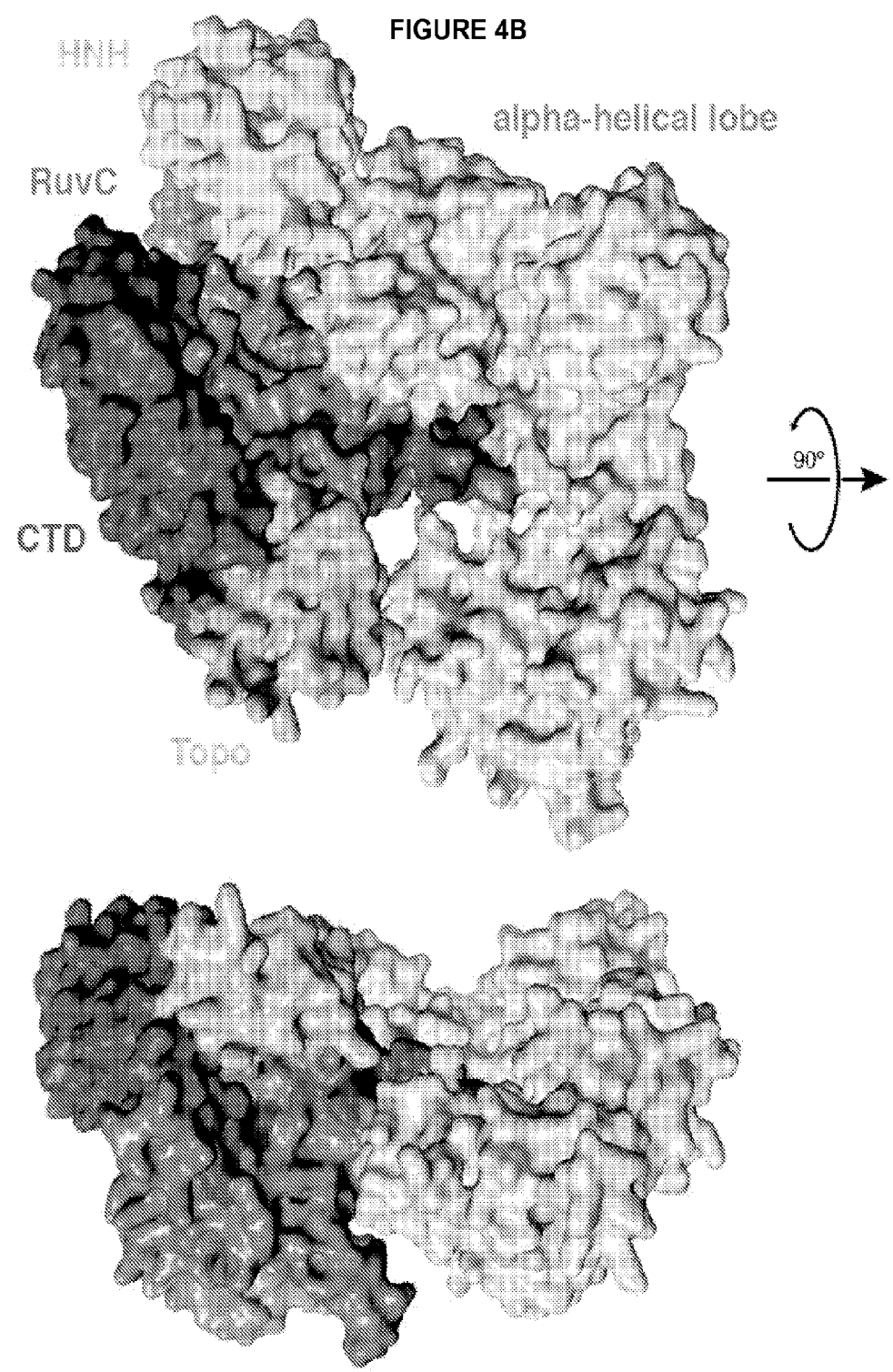
Figure 5A:
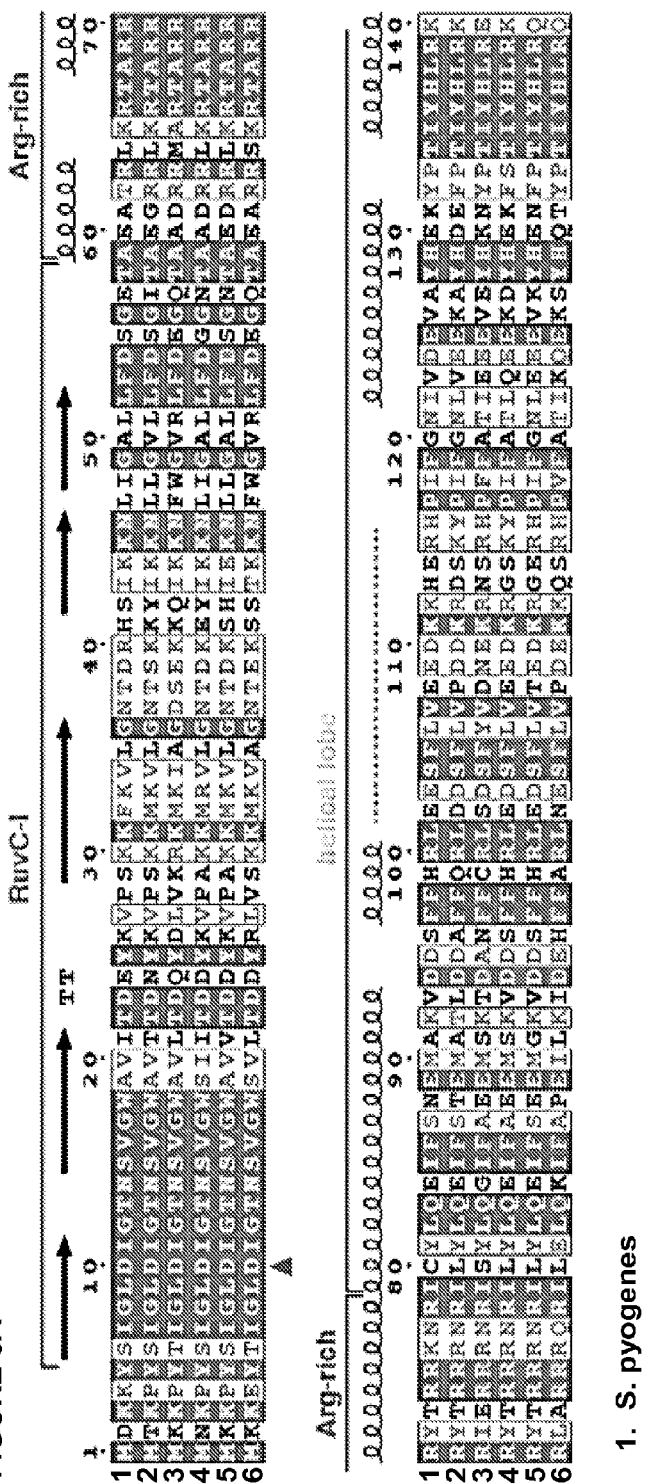
FIGS. 5A-K provide multiple sequence alignment of Cas9 proteins associated with Type II-A CRISPR loci. Primary sequences of Cas9 proteins from *Streptococcus pyogenes*
Figure 5B:
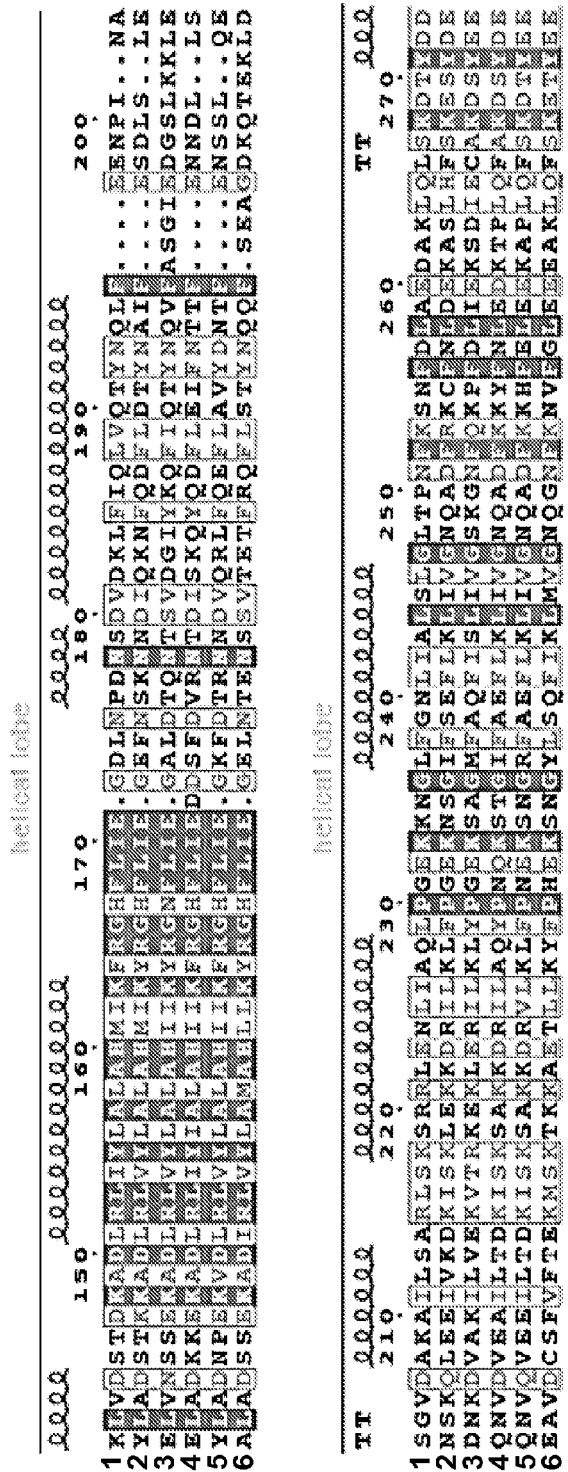
Figure 5C:
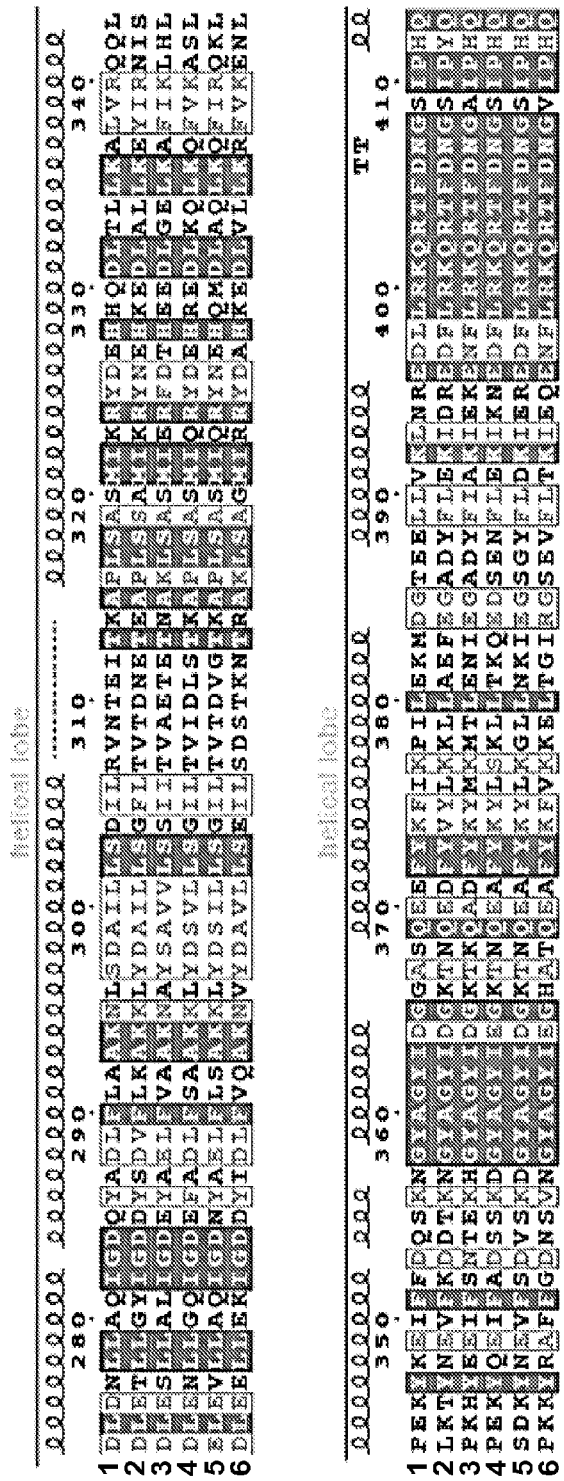
Figure 5D:
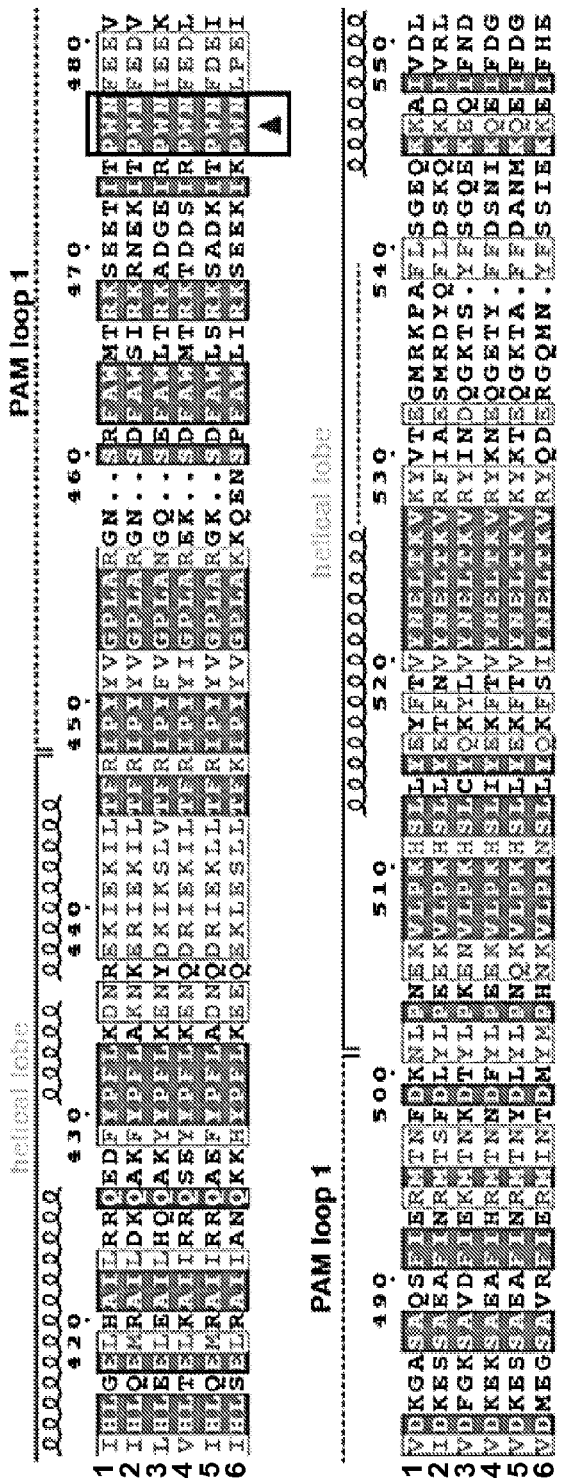
Figure 5E:
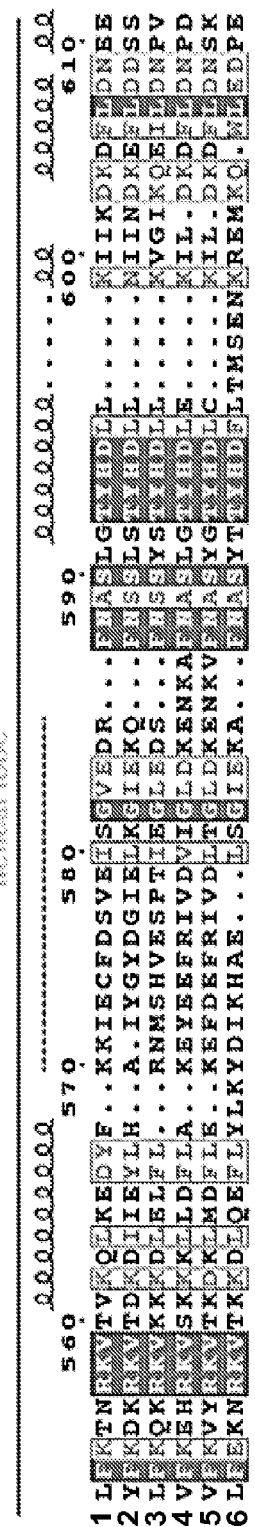
Figure 5F:
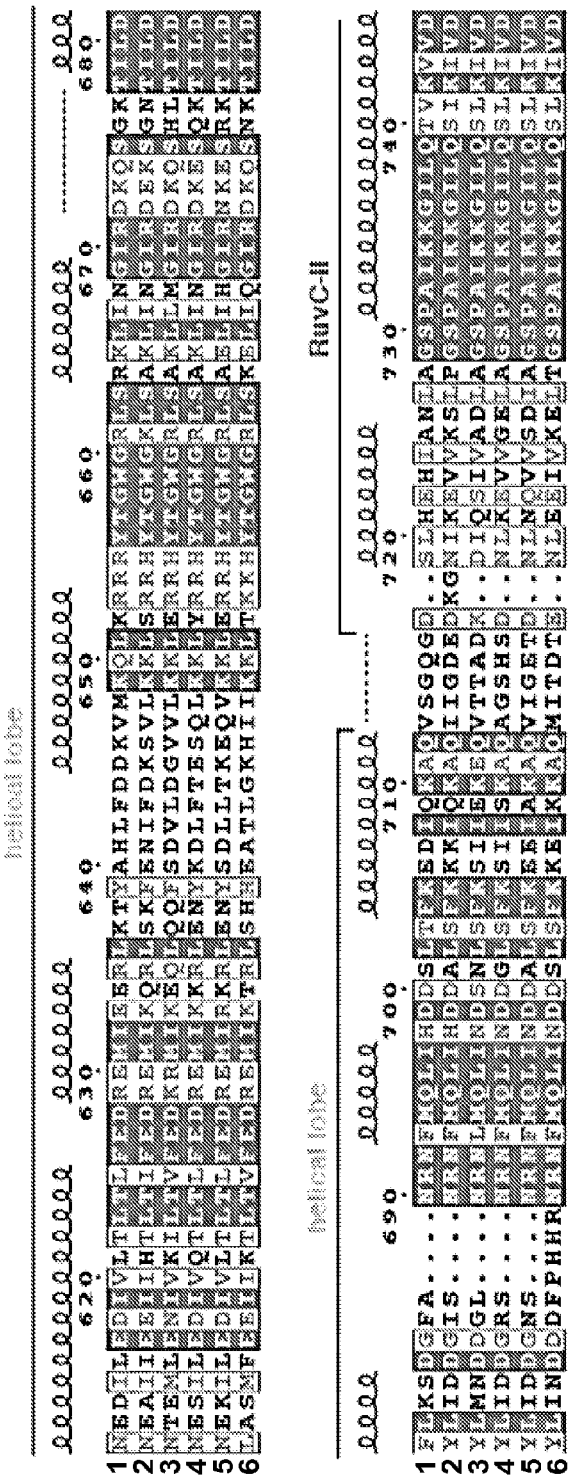
Figure 5G:
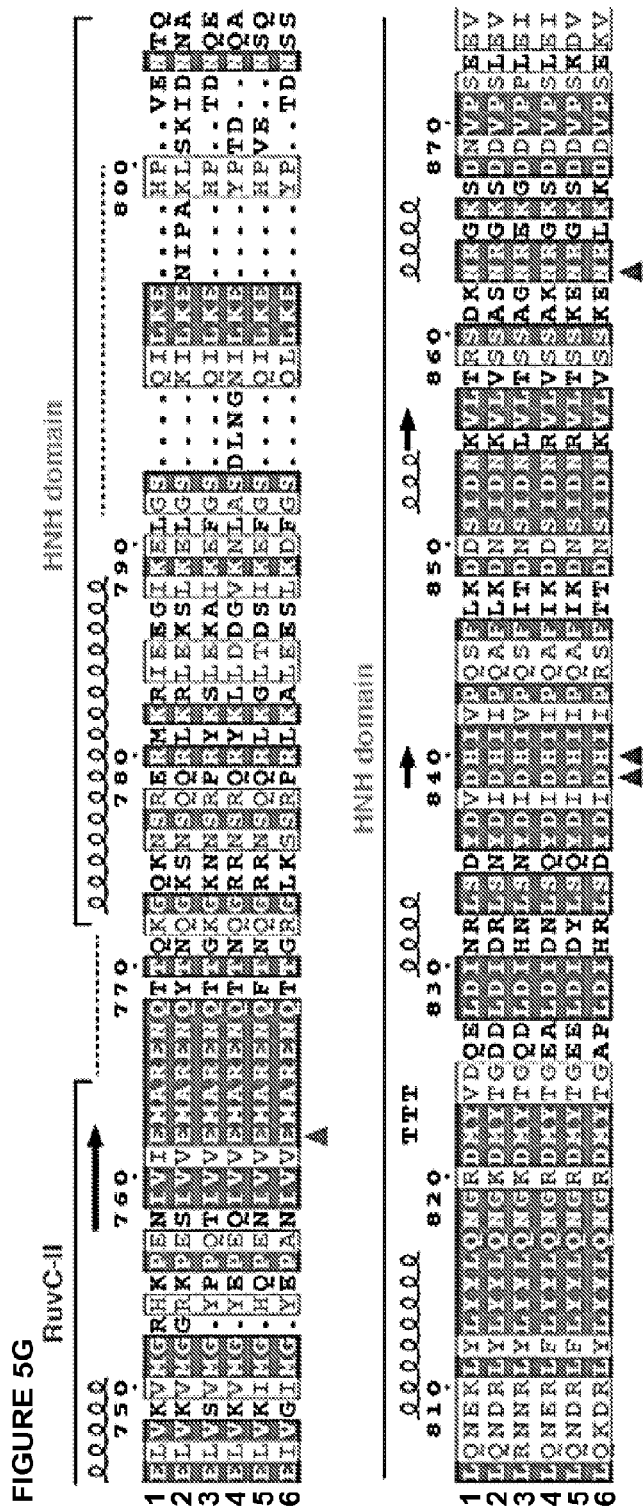
Figure 5H:
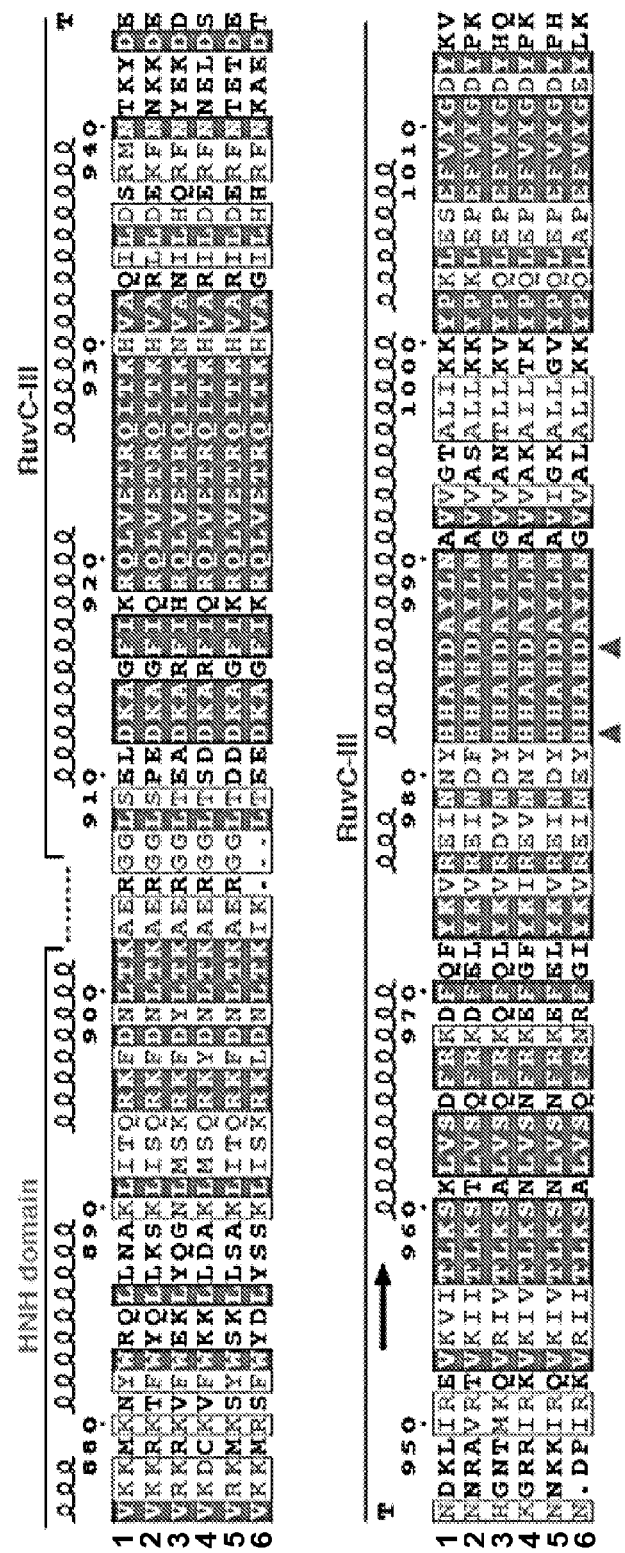
Figure 5I:
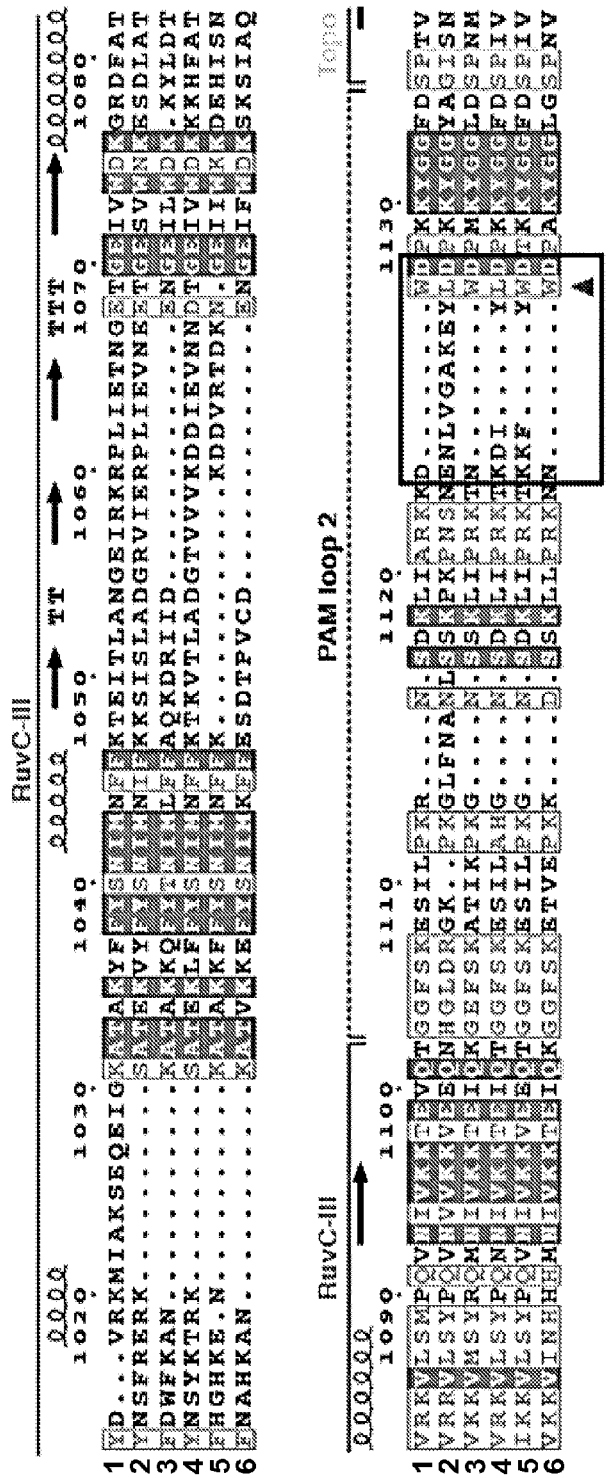
Figure 5J:
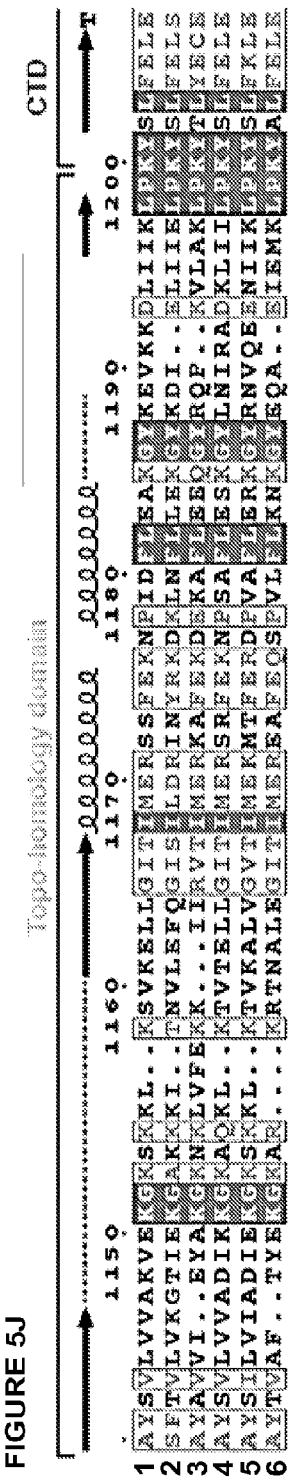
Figure 5K:
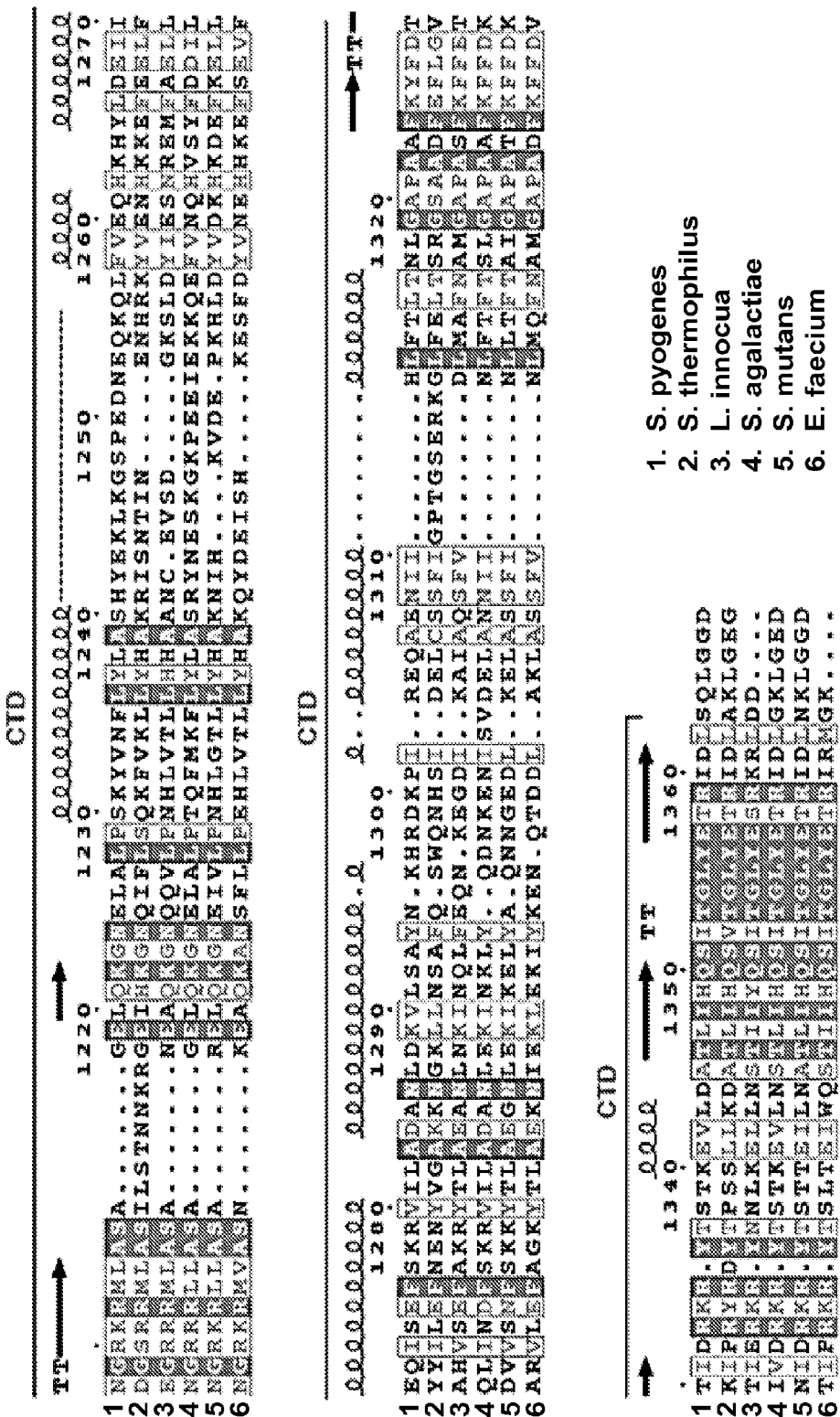

Target DNA cleavage by Cas9 enzymes requires the concerted nuclease activities of the RuvC and HNH domains following base-pairing between the crRNA guide and the target DNA to induce R-loop formation. Although SpyCas9 and AnaCas9 adopt distinct conformations in their helical lobes, the relative orientations of the RuvC and HNH active sites within the nuclease lobes are very similar (FIG. 13C and FIG. 14). In both structures, the HNH active sites face outwards, away from the putative nucleic acid binding clefts (FIG. 4A-B). Structural superpositions with the DNA-bound complex of the HNH homing endonuclease I-HmuI (FIG. 16) shows that this orientation is unlikely to be compatible with target DNA binding and cleavage (FIG. 18). In SpyCas9, the HNH domain active site is blocked by a beta-hairpin formed by residues $1049^{Spy}$-$1059^{Spy}$ of the RuvC domain, and the RNA-DNA heteroduplex would additionally clash sterically with the C-terminal domain (FIG. 18). In AnaCas9, the bound crRNA-target DNA heteroduplex would conversely make few contacts with the protein outside of the HNH domain in the absence of HNH domain reorientation (FIG. 18). The two Cas9 structures in similar auto-inhibited states shows the general feature of auto-inhibition of Cas9 enzymes that is consistent with the observation that Cas9 enzymes are inactive as nucleases in the absence of bound guide RNAs. Cas9 enzymes clearly undergo a conformational rearrangement upon guide RNA and/or target DNA binding.

Example 4

A Common Cas9 Functional Core Shows Structural Plasticity that Supports RNA-Guided DNA Cleavage Comparison of the SpyCas9 and AnaCas9 structures reveals a conserved functional core consisting of the RuvC and HNH domains, the Arg-rich region, and the Topo-homology domain, with divergent C-terminal and alpha-helical domains (FIG. 19). In both SpyCas9 and AnaCas9 structures, the Arg-rich region connects the nuclease and helical lobes of the proteins. The central position of the Arg-rich segment and its proximity to the PAM-binding loops in SpyCas9 shows that this is involved in guide RNA and/or target DNA binding and functions as a hinge to enable conformational rearrangements in the enzyme.

Differences between SpyCas9 and AnaCas9 illustrate the structural divergence that allows Cas9 enzymes to associate with different guide RNAs and have different PAM requirements. Although the helical lobes of SpyCas9 and AnaCas9 share a common region (residues $252^{Ana}$-$468^{Ana}$ versus $502^{Spy}$-$713^{Spy}$), the orientation of this part of the protein relative to the nuclease lobe varies widely between the two structures (FIG. 19). The divergent conformations of the alpha helical lobes controls recognition of diverse guide RNAs present in Type II-A versus II-C CRISPR-Cas9 systems. The PAM interacting regions identified in SpyCas9 are located in loops that are highly variable within Cas9 enzymes. In AnaCas9, the beta-hairpin domain (residues $822^{Ana}$-$924^{Ana}$) is inserted at a position corresponding to one of the SpyCas9 PAM loops ($1102^{Spy}$-$1136^{Spy}$), showing that AnaCas9 employs a distinct mechanism of PAM recognition (FIG. 13C and FIG. 11). The beta-hairpin domain is not conserved in all Type II-C Cas9 proteins (FIG. 11 and FIG. 20), further underscoring the notion that the sequence- and structurally-divergent regions of Cas9 proteins may have co-evolved with specific guide RNA structures and PAM sequences.

Example 5

Determination of the Structures of Nucleotide Bound Cas9

Preparation of crRNA and tracrRNA

A 42-nucleotide (nt) crRNA targeting a protospacer found in the bacteriophage γ genome was ordered synthetically (Integrated DNA Technologies; IDT; SEQ ID NO:16) and purified by 10% denaturing PAGE. Biotinylated crRNA was prepared similarly and contained a 5-adenosine linker followed by biotin at its 3' end. tracrRNA was in vitro transcribed from a synthetic DNA template using T7 polymerase (SEQ ID NO:15). crRNA:tracrRNA duplexes (5 μM) were prepared by mixing equimolar amounts of crRNA and tracrRNA in Hybridization Buffer (20 mM Tris-Cl pH 7.5, 100 mM KCl, 5 mM MgCl$_2$), heating at 95° C. for 30 seconds, and slow-cooling on the benchtop. To attach a biotin moiety to the tracrRNA, a modified tracrRNA was transcribed that carries the following additional sequence at its 3' end beyond residue U89: 5'-GCUCGUGCGC-3' (SEQ ID NO:28). A complementary biotinylated DNA oligonucleotide, 5'-biotin-TTGCGCACGAGCAAA-3' (IDT; SEQ ID NO:29), was included during the crRNA:tracrRNA hybridization reaction at a 2× molar excess over tracrRNA.

Preparation of Double-stranded DNA Substrates

A 55 base-pair (bp) DNA target (SEQ ID NO:17-18) derived from the bacteriophage γ genome was prepared by mixing 5 nmol of individual synthetic oligonucleotides (IDT) in Hybridization Buffer supplemented with 5% glycerol, heating for 1-2 minutes, and slow-cooling on the benchtop. Duplexes were separated from single-stranded DNA by 5% native PAGE conducted at 4° C., with 5 mM MgCl$_2$ added to the gel and the running buffer. The DNA was excised, eluted into 10 mM Tris-Cl pH 7.5 overnight at 4° C., ethanol precipitated, and resuspended in Hybridization Buffer. Duplexes containing a 3'-biotin on one or both strands were prepared similarly.

Activity Assays

Cas9:RNA complexes were reconstituted by mixing equimolar amounts of Cas9 and the crRNA:tracrRNA duplex in Reaction Buffer (20 mM Tris-Cl pH 7.5, 100 mM KCl, 5 mM MgCl$_2$, 5% glycerol, 1 mM DTT) and incubating at 37° C. for 10 minutes. Cleavage reactions were conducted at room temperature in Reaction Buffer using 1-2 nM radiolabeled DNA substrates and 100 nM Cas9:RNA. Aliquots were removed at various time points and quenched by mixing with an equal volume of formamide gel loading buffer supplemented with 50 mM EDTA. Cleavage products were resolved by 10% denaturing PAGE and visualized by phosphorimaging. The fraction of DNA cleaved at each time point was quantified using ImageQuant (GE Healthcare), and kinetic time courses were fit with a single exponential decay using Kaleidagraph (Synergy Software) to extract pseudo first-order rate constants. Each modified Cas9, RNA, and DNA construct was tested in three independent experiments.

Binding reactions (15 μl) were conducted in Reaction Buffer and contained ~0.25 nM radiolabeled DNA and increasing concentrations of D10A/H840A Cas9:RNA complex that was reconstituted with a 10× molar excess of crRNA:tracrRNA duplex over Cas9. Reactions were incubated at 37° C. for one hour and resolved by 5% native PAGE conducted at 4° C., with 5 mM MgCl$_2$ added to the gel and the running buffer. Bound and unbound DNA was visualized by phosphorimaging, and the fraction of DNA bound at each Cas9 concentration was quantified using ImageQuant (GE Healthcare). Binding curves were fit using Kaleidagraph (Synergy Software).

Complex Reconstitution for Negative-stain EM

All samples for EM (electron microscopy) (10 μl volumes) were prepared in Reaction Buffer at a final Cas9 concentration of 1 μM. Cas9:RNA complexes contained 2 μM crRNA:tracrRNA duplex and were incubated at 37° C. for 10 minutes before storing on ice until grid preparation. Cas9:RNA:DNA complexes were prepared by first generating Cas9:RNA as before and then adding the DNA duplex at 5 μM (unlabeled) or 2 μM (biotin labeled) and incubating an additional 10 minutes at 37° C. When present, streptavidin (New England Biolabs) was added after formation of Cas9:RNA or Cas9:RNA:DNA complexes at a 2× unit excess over the biotinylated species, according to the manufacturer's unit definition (~65 ng/μL in the final reaction volume), followed by an additional 10 minute incubation at 37° C. before storing on ice. Catalytically inactive Cas9 (D10A/H840A) was used to generate the following samples: unlabeled Cas9:RNA:DNA, Cas9:RNA:DNA containing biotin modifications on one or both ends of the duplex, and Cas9:RNA:DNA containing an N-terminal MBP. Wild-type Cas9 was used to generate apo-Cas9 and all Cas9:RNA complexes.

Negative-stain Electron Microscopy

Cas9 complexes were diluted for negative-stain EM to a concentration of ~25-60 nM in 20 mM Tris-HCl pH 7.5, 200 mM KCl, 1 mM DTT, and 5% glycerol immediately before applying the sample to glow-discharged 400 mesh continuous carbon grids. After adsorption for 1 min, the samples were stained consecutively with six droplets of 2% (w/v) uranyl acetate solution. Then the residual stain was gently blotted off and the samples were air-dried in a fume hood. Data were acquired using a Tecnai F20 Twin transmission electron microscope operated at 120 keV (kiloelectron volt) at a nominal magnification of either 80,000× (1.45 Å at the specimen level) or 100,000× (1.08 Å at the specimen level) using low-dose exposures (~20 e$^-$Å$^{-2}$) with a randomly set defocus ranging from –0.5 to –1.3 μm. A total of 300-400 images of each Cas9 sample were automatically recorded on a Gatan 4 k×4 k CCD camera using the MSI-Raster application within the automated macromolecular microscopy software LEGINON.

Single-particle Pre-processing

All image pre-processing and two-dimensional classification was performed in Appion. The contrast transfer function (CTF) of each micrograph was estimated, and particles were selected concurrently with data collection using ACE2 and a template-based particle picker, respectively. Micrograph phases were corrected using ACE2, and the negatively-stained Cas9 particles were extracted using a 288×288-pixel box size. The particle stacks were binned by a factor of 2 for processing, and particles were normalized to remove pixels whose values were above or below 4.5-σ of the mean pixel value using XMIPP.

Random Conical Tilt Reconstruction

Initial models for reconstructions of both apo-Cas9 and Cas9:RNA:DNA samples were determined using random conical tilt (RCT) methodology. Tilt-pairs of micrographs were recorded manually at 0° and 55°, and ab initio models were generated using the RCT module in Appion. Particles were correlated between tilt-pairs using TiltPicker, binned by 2, and extracted from raw micrographs. Reference-free class averages were produced from untilted particle images by iterative 2D alignment and classification using MSA-MRA in IMAGIC. These class averages served as references for SPIDER reference-based alignment and classification, and RCT volumes were calculated for each class average using back-projection in SPIDER based on these angles and shifts. The RCT model from the most representative class (largest number of particles) was low-pass filtered to 60-Å resolution and used to assign Euler angles to the entire data set of reference-free class averages. The resulting low-resolution model was again low-pass filtered to 60-Å resolution and used as the initial model for refinement of the three-dimensional structure by iterative projection matching using the untilted particle images as previously described, with libraries from EMAN2 and SPARX software packages.

Domain Mapping and Localization of RNA- and DNA-ends

Particle stacks were binned by a factor of 2 and subjected to five rounds of iterative multivariate statistical analysis (MSA) and multi-reference alignment (MRA) using the IMAGIC software package, to generate two-dimensional class averages of each complex. The resulting set of class averages for each species was normalized using 'proc2d' in EMAN. The EMAN classification program 'classesbymra' was used to match the labeled class average to the best-matching unlabeled class average based on cross-correlation coefficients. The difference maps were calculating by subtracting the unlabeled class average from the labeled class averages using 'proc2d' in EMAN. This same strategy was used to match the unlabeled class average to the best-matching reprojection of the corresponding structure. The Euler angles used for creating the reprojection were applied to the 3D electron density using 'proc3d,' and the surface representation visualized in Chimera is shown along with its corresponding reprojection.

3D Reconstruction and Analysis

Three-dimensional reconstructions were all performed using an iterative projection-matching refinement with libraries from the EMAN2 and SPARX software packages. Refinement of the RCT starting models began using an angular increment of 25°, progressing down to 4° for all reconstructions. The resulting model was again low-pass filtered to 60-Å resolution and subjected to iterative projection-matching refinement to obtain the final structure. In an alternative approach for apo-Cas9 and Cas9:RNA:DNA, we used a low-pass filtered model of the other structure after initial refinement with untilted particles as an initial model for the above-mentioned projection matching refinement. This led to EM densities with similar structural features as the RCT models (FIG. 21A-B), and the structures converged to the final models presented in FIG. 22. The resolution was estimated by splitting the particle stack into two equally sized data sets and calculating the Fourier shell correlation (FSC) between each of the back-projected volumes. The final reconstructions of Cas9, Cas9:RNA, and Cas9:RNA:DNA showed structural features to ~19-Å, ~21-Å, and ~19-Å resolution, respectively, based on the 0.5 Fourier shell correlation criterion. Reprojections of the final three-dimensional reconstruction showed excellent agreement with the reference-free class averages (FIG. 23A-C) and displayed a large distribution of Euler angles, despite some preferential orientations of the particles on the carbon film.

The final reconstruction was segmented using Segger in Chimera based on inspection of the similarities between lobes in the apo-Cas9 and Cas9:RNA:DNA reconstructions. A modeled A-form duplex was manually docked into the map with Chimera, using information from the labeling experiments and map segmentation, and by accommodating the substrate within the channel in the EM reconstruction.

The EM-derived density map correlated closely with the structural features present in the X-ray crystal structure. The alpha-helical and nuclease domain lobes of the X-ray crystal structure were computationally docked as rigid bodies into the larger and smaller lobes of our EM structure using SITUS with cross-correlation coefficients (CCC) of 0.74 and 0.66, respectively (FIG. 24).

Determination of Cas9 Domain Reorientation Due to Nucleic Acid Binding

Using a catalytically inactive D10A/H840A-Cas9 mutant that retains DNA binding activity, ribonucleoprotein complexes containing full-length crRNA and tracrRNA (Cas9:RNA) were prepared and bound to a 55 base-pair (bp) double-stranded DNA substrate. Reconstitutions were conducted at substrate concentrations expected to saturate Cas9, given an equilibrium dissociation constant of ~4 nM. Reference-free 2D class averages of the DNA-bound complex (Cas9:RNA:DNA) showed a large-scale conformational change, with both lobes separating from one another into discrete structural units. Using the apo-Cas9 structure low-pass filtered to 60 Å as a starting model, we obtained a 3D reconstruction of Cas9:RNA:DNA at ~19 Å resolution (using the 0.5 FSC criterion) that reveals a substantial reorganization of the major lobes (FIG. 22). The shape of the larger lobe remains relatively unchanged from that in apo-Cas9 (CCC of 0.78), but the smaller lobe rotates by ~100 degrees with respect to its position in the apo structure (FIG. 22). A reconstruction of Cas9:RNA:DNA using the N-terminal MBP fusion (FIG. 25) confirmed that the nuclease domain-containing lobe is rearranged with respect to the alpha-helical lobe in this complex. This rearrangement forms a central channel with a width of ~25-Å that spans the length of both lobes.

Determination of Cas9 Domain Reorientation Due to RNA Binding

The architecture of Cas9:RNA in the absence of a bound target DNA molecule was analysed and reference-free 2D class averages of the Cas9:RNA showed a clear central channel similar to Cas9:RNA:DNA. Using the 3D reconstruction of Cas9:RNA:DNA low-pass filtered to 60 Å as a starting model, a reconstruction of Cas9:RNA at ~21 Å resolution (using the 0.5 FSC criterion) was obtained, which revealed a conformation similar to that of the DNA-bound complex (CCC of 0.89 with DNA-bound vs. 0.81 with apo), with a central channel extending between the two lobes (FIG. 22). Limited proteolysis experiments show that both the Cas9:RNA and Cas9:RNA:DNA complexes are more resistant to trypsin than apo-Cas9 and display similar digestion patterns, in agreement with these nucleic acid-bound complexes occupying a similar structural state (FIG. 26). While the smaller lobe undergoes an additional ~50 degree rotation along an axis perpendicular to the channel in the DNA-bound complex compared to Cas9:RNA, the same ~100 degree rotation around the channel is present in both structures. Thus, loading of crRNA and tracrRNA alone is sufficient to convert the endonuclease into an active conformation for target surveillance.

Determination of Bound DNA and RNA Orientation within Cas9

Cas9:RNA:DNA complexes were formed using DNA substrates containing 3'-biotin modifications (Table 5) to visualize the duplex ends via streptavidin labeling. Negative-stain EM analysis of samples labeled at either the PAM-distal (non-PAM) end or both ends showed additional circular density below, or both above and below the complex, respectively, along the central channel positioned between the two structural lobes (FIG. 27). These data show that the major lobes of Cas9 enclose the target DNA, positioning the RNA:DNA heteroduplex along the central channel with the PAM oriented near the top. Finally, the orientation of RNA within Cas9:RNA complexes was determined using streptavidin labeling of crRNA and tracrRNA containing biotin at their 3' termini, after ensuring that Cas9 retains full activity with these modified RNAs. Using the same 2D and 3D difference mapping approach, the 3' end of the crRNA was localized to the top of the channel (FIG. 27) and the 3' end of the tracrRNA was shown to extend roughly perpendicular to the central channel from the side of the nuclease domain lobe (FIG. 27). The similar positions above the channel of the 3' end of the crRNA and the PAM-proximal side of the target shows that the crRNA:DNA heteroduplex orients roughly in parallel with the crRNA:tracrRNA duplex.

TABLE 5

Sequences of nucleic acids used.

| Description | SEQ ID NO: | Sequence (5'-3') |
|---|---|---|
| Oligo for preparing doublestranded T7 promoters for in vitro transcription | 30 | TAATACGACTCACTATA |
| ssDNA template for transcribing tracrRNA | 31 | AAAAAGCACCGACTCGGTG CCACTTTTTCAAGTTGATA ACGGACTAGCCTTATTTTA ACTTGCTATGCTGTCCTAT AGTGAGTCGTATTA |
| tracrRNA (nts 15-87) | 15 | GGACAGCAUAGCAAGUUAA AAUAAGGCUAGUCCGUUAU CAACUUGAAAAAGUGGCAC CGAGUCGGUGCUUUUU |
| ssDNA template for transcribing tracrRNA_ext | 32 | GCGCACGAGCAAAAAAAGC ACCGACTCGGTGCCACTTT TTCAAGTTGATAACGGACT AGCCTTATTTTAACTTGCT ATGCTGTCCTATAGTGAGT CGTATTA |
| tracrRNA_ext | 28 | GGACAGCAUAGCAAGUUAA AAUAAGGCUAGUCCGUUAU CAACUUGAAAAAGUGGCAC CGAGUCGGUGCUUUU*UUUG CUCGUGCGC* |
| Biotinylated DNA oligo to hybridize to tracrRNA_ext | 29 | Biotin-TT*GCGCACGAGC AAA* |
| Targeting crRNA | 16 | GUGAUAAGUGGAAUGCCAU GGUUUUAGAGCUAUGCUGU UUUG |
| Non-targeting crRNA (control) | 24 | GACGCAUAAAGAUGAGACG CGUUUUAGAGCUAUGCUGU UUUG |
| 55-bp DNA substrate, non-target strand | 17 | GAGTGGAAGGATGCCA<u>GTG ATAAGTGGAATGCCATG</u>tg gCTGTCAAAATTGAGC |
| 55-bp DNA substrate, target strand | 18 | GCTCAATTTTGACAGCCCA <u>CATGGCATTCCACTTATCA C</u>TGGCATCCTTCCACTC |
| 3'-Biotinylated DNA, non-target strand | 17 | GAGTGGAAGGATGCCA<u>GTG ATAAGTGGAATGCCATG</u>tg gGCTGTCAAAATTGAGC-Biotin |
| 3'-Biotinylated DNA, target strand | 18 | GCTCAATTTTGACAGCCCA <u>CATGGCATTCCACTTATCA C</u>TGGCATCCTTCCACTC-Biotin |

Reverse complement of the T7 promoter is in bold uppercase
Nucleoltides hybridizing between the tracrRNA_ext and biotin-DNA are in italics
Protospacer is underlined and the PAM is in bold lowercase The channel between the lobes of Cas9 accommodates ~25 bp of a modeled A-form helix (FIG. 28). Exonuclease III footprinting experiments show that Cas9 protects a ~26-bp segment of the target DNA (FIG. 29A-B). Additionally, P1 nuclease mapping experiments reveal that the displaced non-target strand is susceptible to degradation towards the 5' end of the protospacer, while the target strand that hybridizes to crRNA is protected along nearly its entire length. These results are consistent with the formation of an R-loop structure (FIG. 29A-B).

RNA loading drives critical rearrangements of the Cas9 enzyme to enable productive encounters with target DNA (FIG. 30). Binding of crRNA:tracrRNA to Cas9 causes a substantial rotation of the small nuclease lobe relative to the larger lobe to form a central channel. This RNA-induced conformational change occurs either through allostery or via direct interactions between the RNA and both lobes, and this reorganization aids in positioning the two major catalytic centers of the enzyme on opposite sides of the channel, where the two separated strands are threaded into either active site.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A crystal comprising a Type II-A Cas9 polypeptide in crystalline form, wherein the crystal is characterized with space group $P2_12_12$, has unit cell parameters of a=160 Å, b=209 Å, c=91 Å, $\alpha=\beta=\gamma=90°$ and wherein the polypeptide shares at least 90% sequence identity with SEQ ID NO: 1 and comprises a nuclease lobe, an alpha-helical lobe, a RuvC domain, an arginine-rich region, an HNH domain, a Topo-homology domain and a C-terminal domain.

2. A crystal comprising a Type II-C Cas9 polypeptide in crystalline form, wherein the crystal is characterized with space group $P1\,2_11$, has unit cell parameters of a=75 Å, b=133 Å, c=80 Å, $\alpha=\gamma=90°$ and $\beta=95°$ and wherein the polypeptide shares at least 90% sequence identity with SEQ ID NO: 7 and comprises a nuclease lobe, an alpha-helical lobe, a RuvC domain, an arginine-rich region, an HNH domain, a beta-hairpin domain, a Topo-homology domain and a C-terminal domain.

3. A composition comprising the crystal of claim 1.

4. A composition comprising the crystal of claim 2.

5. The composition of claim 3, wherein the polypeptide shares at least 99% sequence identity with SEQ ID NO:1.

6. The composition of claim 4, wherein the polypeptide shares at least 99% sequence identity with SEQ ID NO:7.

* * * * *

SEQUENCE LISTING

<160> NUMBER OF SEQ ID NOS: 33

<210> SEQ ID NO 1
<211> LENGTH: 1368
<212> TYPE: PRT
<213> ORGANISM: Streptococcus pyogenes

<400> SEQUENCE: 1

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

```
Lys Val Leu Gly Asn Thr Asp Arg His Ser Ile Lys Lys Asn Leu Ile
            35                  40                  45

Gly Ala Leu Leu Phe Asp Ser Gly Glu Thr Ala Glu Ala Thr Arg Leu
 50                  55                  60

Lys Arg Thr Ala Arg Arg Tyr Thr Arg Arg Lys Asn Arg Ile Cys
 65                  70                  75                  80

Tyr Leu Gln Glu Ile Phe Ser Asn Glu Met Ala Lys Val Asp Asp Ser
                    85                  90                  95

Phe Phe His Arg Leu Glu Glu Ser Phe Leu Val Glu Glu Asp Lys Lys
                100                 105                 110

His Glu Arg His Pro Ile Phe Gly Asn Ile Val Asp Glu Val Ala Tyr
                115                 120                 125

His Glu Lys Tyr Pro Thr Ile Tyr His Leu Arg Lys Lys Leu Val Asp
130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
                180                 185                 190

Asn Gln Leu Phe Glu Glu Asn Pro Ile Asn Ala Ser Gly Val Asp Ala
                195                 200                 205

Lys Ala Ile Leu Ser Ala Arg Leu Ser Lys Ser Arg Arg Leu Glu Asn
                210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
                260                 265                 270

Asp Asp Leu Asp Asn Leu Leu Ala Gln Ile Gly Asp Gln Tyr Ala Asp
                275                 280                 285

Leu Phe Leu Ala Ala Lys Asn Leu Ser Asp Ala Ile Leu Leu Ser Asp
                290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
                340                 345                 350

Asp Gln Ser Lys Asn Gly Tyr Ala Gly Tyr Ile Asp Gly Gly Ala Ser
                355                 360                 365

Gln Glu Glu Phe Tyr Lys Phe Ile Lys Pro Ile Leu Glu Lys Met Asp
                370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
                435                 440                 445

Pro Tyr Tyr Val Gly Pro Leu Ala Arg Gly Asn Ser Arg Phe Ala Trp
```

```
            450                 455                 460
Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
                515                 520                 525

Tyr Val Thr Glu Gly Met Arg Lys Pro Ala Phe Leu Ser Gly Glu Gln
            530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
            610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
            690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
                755                 760                 765

Thr Thr Gln Lys Gly Gln Lys Asn Ser Arg Glu Arg Met Lys Arg Ile
            770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
            835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880
```

-continued

Asn Tyr Trp Arg Gln Leu Leu Asn Ala Lys Leu Ile Thr Gln Arg Lys
                885                 890                 895
Phe Asp Asn Leu Thr Lys Ala Glu Arg Gly Gly Leu Ser Glu Leu Asp
                900                 905                 910
Lys Ala Gly Phe Ile Lys Arg Gln Leu Val Glu Thr Arg Gln Ile Thr
                915                 920                 925
Lys His Val Ala Gln Ile Leu Asp Ser Arg Met Asn Thr Lys Tyr Asp
            930                 935                 940
Glu Asn Asp Lys Leu Ile Arg Glu Val Lys Val Ile Thr Leu Lys Ser
945                 950                 955                 960
Lys Leu Val Ser Asp Phe Arg Lys Asp Phe Gln Phe Tyr Lys Val Arg
                965                 970                 975
Glu Ile Asn Asn Tyr His His Ala His Asp Ala Tyr Leu Asn Ala Val
                980                 985                 990
Val Gly Thr Ala Leu Ile Lys Lys Tyr Pro Lys Leu Glu Ser Glu Phe
            995                 1000                1005
Val Tyr Gly Asp Tyr Lys Val Tyr Asp Val Arg Lys Met Ile Ala
        1010                1015                1020
Lys Ser Glu Gln Glu Ile Gly Lys Ala Thr Ala Lys Tyr Phe Phe
        1025                1030                1035
Tyr Ser Asn Ile Met Asn Phe Phe Lys Thr Glu Ile Thr Leu Ala
        1040                1045                1050
Asn Gly Glu Ile Arg Lys Arg Pro Leu Ile Glu Thr Asn Gly Glu
        1055                1060                1065
Thr Gly Glu Ile Val Trp Asp Lys Gly Arg Asp Phe Ala Thr Val
        1070                1075                1080
Arg Lys Val Leu Ser Met Pro Gln Val Asn Ile Val Lys Lys Thr
        1085                1090                1095
Glu Val Gln Thr Gly Gly Phe Ser Lys Glu Ser Ile Leu Pro Lys
        1100                1105                1110
Arg Asn Ser Asp Lys Leu Ile Ala Arg Lys Lys Asp Trp Asp Pro
        1115                1120                1125
Lys Lys Tyr Gly Gly Phe Asp Ser Pro Thr Val Ala Tyr Ser Val
        1130                1135                1140
Leu Val Val Ala Lys Val Glu Lys Gly Lys Ser Lys Lys Leu Lys
        1145                1150                1155
Ser Val Lys Glu Leu Leu Gly Ile Thr Ile Met Glu Arg Ser Ser
        1160                1165                1170
Phe Glu Lys Asn Pro Ile Asp Phe Leu Glu Ala Lys Gly Tyr Lys
        1175                1180                1185
Glu Val Lys Lys Asp Leu Ile Ile Lys Leu Pro Lys Tyr Ser Leu
        1190                1195                1200
Phe Glu Leu Glu Asn Gly Arg Lys Arg Met Leu Ala Ser Ala Gly
        1205                1210                1215
Glu Leu Gln Lys Gly Asn Glu Leu Ala Leu Pro Ser Lys Tyr Val
        1220                1225                1230
Asn Phe Leu Tyr Leu Ala Ser His Tyr Glu Lys Leu Lys Gly Ser
        1235                1240                1245
Pro Glu Asp Asn Glu Gln Lys Gln Leu Phe Val Glu Gln His Lys
        1250                1255                1260
His Tyr Leu Asp Glu Ile Ile Glu Gln Ile Ser Glu Phe Ser Lys
        1265                1270                1275

-continued

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

<210> SEQ ID NO 2
<211> LENGTH: 1388
<212> TYPE: PRT
<213> ORGANISM: Streptococcus thermophilus

<400> SEQUENCE: 2

Met Thr Lys Pro Tyr Ser Ile Gly Leu Asp Ile Gly Thr Asn Ser Val
1               5                   10                  15

Gly Trp Ala Val Thr Thr Asp Asn Tyr Lys Val Pro Ser Lys Lys Met
            20                  25                  30

Lys Val Leu Gly Asn Thr Ser Lys Lys Tyr Ile Lys Lys Asn Leu Leu
        35                  40                  45

Gly Val Leu Leu Phe Asp Ser Gly Ile Thr Ala Glu Gly Arg Arg Leu
    50                  55                  60

Lys Arg Thr Ala Arg Arg Arg Tyr Thr Arg Arg Arg Asn Arg Ile Leu
65              70                  75                  80

Tyr Leu Gln Glu Ile Phe Ser Thr Glu Met Ala Thr Leu Asp Asp Ala
            85                  90                  95

Phe Phe Gln Arg Leu Asp Asp Ser Phe Leu Val Pro Asp Asp Lys Arg
        100                 105                 110

Asp Ser Lys Tyr Pro Ile Phe Gly Asn Leu Val Glu Glu Lys Ala Tyr
    115                 120                 125

His Asp Glu Phe Pro Thr Ile Tyr His Leu Arg Lys Tyr Leu Ala Asp
    130                 135                 140

Ser Thr Lys Lys Ala Asp Leu Arg Leu Val Tyr Leu Ala Leu Ala His
145             150                 155                 160

Met Ile Lys Tyr Arg Gly His Phe Leu Ile Glu Gly Glu Phe Asn Ser
            165                 170                 175

Lys Asn Asn Asp Ile Gln Lys Asn Phe Gln Asp Phe Leu Asp Thr Tyr
        180                 185                 190

Asn Ala Ile Phe Glu Ser Asp Leu Ser Leu Glu Asn Ser Lys Gln Leu
    195                 200                 205

Glu Glu Ile Val Lys Asp Lys Ile Ser Lys Leu Glu Lys Lys Asp Arg
    210                 215                 220

Ile Leu Lys Leu Phe Pro Gly Glu Lys Asn Ser Gly Ile Phe Ser Glu
225             230                 235                 240

Phe Leu Lys Leu Ile Val Gly Asn Gln Ala Asp Phe Arg Lys Cys Phe
            245                 250                 255

Asn Leu Asp Glu Lys Ala Ser Leu His Phe Ser Lys Glu Ser Tyr Asp
        260                 265                 270

Glu Asp Leu Glu Thr Leu Leu Gly Tyr Ile Gly Asp Asp Tyr Ser Asp
    275                 280                 285

```
Val Phe Leu Lys Ala Lys Lys Leu Tyr Asp Ala Ile Leu Leu Ser Gly
    290                 295                 300

Phe Leu Thr Val Thr Asp Asn Glu Thr Glu Ala Pro Leu Ser Ser Ala
305                 310                 315                 320

Met Ile Lys Arg Tyr Asn Glu His Lys Glu Asp Leu Ala Leu Leu Lys
                325                 330                 335

Glu Tyr Ile Arg Asn Ile Ser Leu Lys Thr Tyr Asn Glu Val Phe Lys
                340                 345                 350

Asp Asp Thr Lys Asn Gly Tyr Ala Gly Tyr Ile Asp Gly Lys Thr Asn
            355                 360                 365

Gln Glu Asp Phe Tyr Val Tyr Leu Lys Lys Leu Leu Ala Glu Phe Glu
370                 375                 380

Gly Ala Asp Tyr Phe Leu Glu Lys Ile Asp Arg Glu Asp Phe Leu Arg
385                 390                 395                 400

Lys Gln Arg Thr Phe Asp Asn Gly Ser Ile Pro Tyr Gln Ile His Leu
                405                 410                 415

Gln Glu Met Arg Ala Ile Leu Asp Lys Gln Ala Lys Phe Tyr Pro Phe
                420                 425                 430

Leu Ala Lys Asn Lys Glu Arg Ile Glu Lys Ile Leu Thr Phe Arg Ile
            435                 440                 445

Pro Tyr Tyr Val Gly Pro Leu Ala Arg Gly Asn Ser Asp Phe Ala Trp
        450                 455                 460

Ser Ile Arg Lys Arg Asn Glu Lys Ile Thr Pro Trp Asn Phe Glu Asp
465                 470                 475                 480

Val Ile Asp Lys Glu Ser Ser Ala Glu Ala Phe Ile Asn Arg Met Thr
                485                 490                 495

Ser Phe Asp Leu Tyr Leu Pro Glu Glu Lys Val Leu Pro Lys His Ser
                500                 505                 510

Leu Leu Tyr Glu Thr Phe Asn Val Tyr Asn Glu Leu Thr Lys Val Arg
            515                 520                 525

Phe Ile Ala Glu Ser Met Arg Asp Tyr Gln Phe Leu Asp Ser Lys Gln
        530                 535                 540

Lys Lys Asp Ile Val Arg Leu Tyr Phe Lys Asp Lys Arg Lys Val Thr
545                 550                 555                 560

Asp Lys Asp Ile Ile Glu Tyr Leu His Ala Ile Tyr Gly Tyr Asp Gly
                565                 570                 575

Ile Glu Leu Lys Gly Ile Glu Lys Gln Phe Asn Ser Ser Leu Ser Thr
            580                 585                 590

Tyr His Asp Leu Leu Asn Ile Ile Asn Asp Lys Glu Phe Leu Asp Asp
        595                 600                 605

Ser Ser Asn Glu Ala Ile Ile Glu Glu Ile Ile His Thr Leu Thr Ile
610                 615                 620

Phe Glu Asp Arg Glu Met Ile Lys Gln Arg Leu Ser Lys Phe Glu Asn
625                 630                 635                 640

Ile Phe Asp Lys Ser Val Leu Lys Lys Leu Ser Arg Arg His Tyr Thr
                645                 650                 655

Gly Trp Gly Lys Leu Ser Ala Lys Leu Ile Asn Gly Ile Arg Asp Glu
            660                 665                 670

Lys Ser Gly Asn Thr Ile Leu Asp Tyr Leu Ile Asp Asp Gly Ile Ser
        675                 680                 685

Asn Arg Asn Phe Met Gln Leu Ile His Asp Asp Ala Leu Ser Phe Lys
690                 695                 700
```

```
Lys Lys Ile Gln Lys Ala Gln Ile Ile Gly Asp Glu Asp Lys Gly Asn
705                 710                 715                 720

Ile Lys Glu Val Val Lys Ser Leu Pro Gly Ser Pro Ala Ile Lys Lys
            725                 730                 735

Gly Ile Leu Gln Ser Ile Lys Ile Val Asp Glu Leu Val Lys Val Met
                740                 745                 750

Gly Gly Arg Lys Pro Glu Ser Ile Val Val Glu Met Ala Arg Glu Asn
            755                 760                 765

Gln Tyr Thr Asn Gln Gly Lys Ser Asn Ser Gln Gln Arg Leu Lys Arg
        770                 775                 780

Leu Glu Lys Ser Leu Lys Glu Leu Gly Ser Lys Ile Leu Lys Glu Asn
785                 790                 795                 800

Ile Pro Ala Lys Leu Ser Lys Ile Asp Asn Asn Ala Leu Gln Asn Asp
                805                 810                 815

Arg Leu Tyr Leu Tyr Tyr Leu Gln Asn Gly Lys Asp Met Tyr Thr Gly
            820                 825                 830

Asp Asp Leu Asp Ile Asp Arg Leu Ser Asn Tyr Asp Ile Asp His Ile
            835                 840                 845

Ile Pro Gln Ala Phe Leu Lys Asp Asn Ser Ile Asp Asn Lys Val Leu
850                 855                 860

Val Ser Ser Ala Ser Asn Arg Gly Lys Ser Asp Asp Val Pro Ser Leu
865                 870                 875                 880

Glu Val Val Lys Lys Arg Lys Thr Phe Trp Tyr Gln Leu Leu Lys Ser
                885                 890                 895

Lys Leu Ile Ser Gln Arg Lys Phe Asp Asn Leu Thr Lys Ala Glu Arg
                900                 905                 910

Gly Gly Leu Ser Pro Glu Asp Lys Ala Gly Phe Ile Gln Arg Gln Leu
            915                 920                 925

Val Glu Thr Arg Gln Ile Thr Lys His Val Ala Arg Leu Leu Asp Glu
930                 935                 940

Lys Phe Asn Asn Lys Lys Asp Glu Asn Asn Arg Ala Val Arg Thr Val
945                 950                 955                 960

Lys Ile Ile Thr Leu Lys Ser Thr Leu Val Ser Gln Phe Arg Lys Asp
                965                 970                 975

Phe Glu Leu Tyr Lys Val Arg Glu Ile Asn Asp Phe His His Ala His
            980                 985                 990

Asp Ala Tyr Leu Asn Ala Val Val  Ala Ser Ala Leu Leu Lys Lys Tyr
        995                 1000                1005

Pro Lys Leu Glu Pro Glu Phe  Val Tyr Gly Asp Tyr  Pro Lys Tyr
    1010                1015                1020

Asn Ser  Phe Arg Glu Arg Lys  Ser Ala Thr Glu Lys  Val Tyr Phe
    1025                1030                1035

Tyr Ser  Asn Ile Met Asn Ile  Phe Lys Lys Ser Ile  Ser Leu Ala
    1040                1045                1050

Asp Gly  Arg Val Ile Glu Arg  Pro Leu Ile Glu Val  Asn Glu Glu
    1055                1060                1065

Thr Gly  Glu Ser Val Trp Asn  Lys Glu Ser Asp Leu  Ala Thr Val
    1070                1075                1080

Arg Arg  Val Leu Ser Tyr Pro  Gln Val Asn Val Val  Lys Lys Val
    1085                1090                1095

Glu Glu  Gln Asn His Gly Leu  Asp Arg Gly Lys Pro  Lys Gly Leu
    1100                1105                1110

Phe Asn  Ala Asn Leu Ser Ser  Lys Pro Lys Pro Asn  Ser Asn Glu
```

```
                    1115                1120                1125

Asn Leu Val Gly Ala Lys Glu Tyr Leu Asp Pro Lys Lys Tyr Gly
        1130                1135                1140

Gly Tyr Ala Gly Ile Ser Asn Ser Phe Thr Val Leu Val Lys Gly
        1145                1150                1155

Thr Ile Glu Lys Gly Ala Lys Lys Ile Thr Asn Val Leu Glu
        1160                1165                1170

Phe Gln Gly Ile Ser Ile Leu Asp Arg Ile Asn Tyr Arg Lys Asp
        1175                1180                1185

Lys Leu Asn Phe Leu Leu Glu Lys Gly Tyr Lys Asp Ile Glu Leu
        1190                1195                1200

Ile Ile Glu Leu Pro Lys Tyr Ser Leu Phe Glu Leu Ser Asp Gly
        1205                1210                1215

Ser Arg Arg Met Leu Ala Ser Ile Leu Ser Thr Asn Asn Lys Arg
        1220                1225                1230

Gly Glu Ile His Lys Gly Asn Gln Ile Phe Leu Ser Gln Lys Phe
        1235                1240                1245

Val Lys Leu Leu Tyr His Ala Lys Arg Ile Ser Asn Thr Ile Asn
        1250                1255                1260

Glu Asn His Arg Lys Tyr Val Glu Asn His Lys Lys Glu Phe Glu
        1265                1270                1275

Glu Leu Phe Tyr Tyr Ile Leu Glu Phe Asn Glu Asn Tyr Val Gly
        1280                1285                1290

Ala Lys Lys Asn Gly Lys Leu Leu Asn Ser Ala Phe Gln Ser Trp
        1295                1300                1305

Gln Asn His Ser Ile Asp Glu Leu Cys Ser Ser Phe Ile Gly Pro
        1310                1315                1320

Thr Gly Ser Glu Arg Lys Gly Leu Phe Glu Leu Thr Ser Arg Gly
        1325                1330                1335

Ser Ala Ala Asp Phe Glu Phe Leu Gly Val Lys Ile Pro Arg Tyr
        1340                1345                1350

Arg Asp Tyr Thr Pro Ser Ser Leu Leu Lys Asp Ala Thr Leu Ile
        1355                1360                1365

His Gln Ser Val Thr Gly Leu Tyr Glu Thr Arg Ile Asp Leu Ala
        1370                1375                1380

Lys Leu Gly Glu Gly
        1385

<210> SEQ ID NO 3
<211> LENGTH: 1334
<212> TYPE: PRT
<213> ORGANISM: Listeria innocua

<400> SEQUENCE: 3

Met Lys Lys Pro Tyr Thr Ile Gly Leu Asp Ile Gly Thr Asn Ser Val
1               5                   10                  15

Gly Trp Ala Val Leu Thr Asp Gln Tyr Asp Leu Val Lys Arg Lys Met
            20                  25                  30

Lys Ile Ala Gly Asp Ser Glu Lys Lys Gln Ile Lys Lys Asn Phe Trp
        35                  40                  45

Gly Val Arg Leu Phe Asp Glu Gly Gln Thr Ala Ala Asp Arg Arg Met
    50                  55                  60

Ala Arg Thr Ala Arg Arg Arg Ile Glu Arg Arg Arg Asn Arg Ile Ser
65                  70                  75                  80
```

```
                                    -continued

Tyr Leu Gln Gly Ile Phe Ala Glu Glu Met Ser Lys Thr Asp Ala Asn
                    85                  90                  95

Phe Phe Cys Arg Leu Ser Asp Ser Phe Tyr Val Asp Asn Glu Lys Arg
            100                 105                 110

Asn Ser Arg His Pro Phe Phe Ala Thr Ile Glu Glu Val Glu Tyr
        115                 120                 125

His Lys Asn Tyr Pro Thr Ile Tyr His Leu Arg Glu Glu Leu Val Asn
    130                 135                 140

Ser Ser Glu Lys Ala Asp Leu Arg Leu Val Tyr Leu Ala Leu Ala His
145                 150                 155                 160

Ile Ile Lys Tyr Arg Gly Asn Phe Leu Ile Glu Gly Ala Leu Asp Thr
                165                 170                 175

Gln Asn Thr Ser Val Asp Gly Ile Tyr Lys Gln Phe Ile Gln Thr Tyr
                180                 185                 190

Asn Gln Val Phe Ala Ser Gly Ile Glu Asp Gly Ser Leu Lys Lys Leu
            195                 200                 205

Glu Asp Asn Lys Asp Val Ala Lys Ile Leu Val Glu Lys Val Thr Arg
    210                 215                 220

Lys Glu Lys Leu Glu Arg Ile Leu Lys Leu Tyr Pro Gly Glu Lys Ser
225                 230                 235                 240

Ala Gly Met Phe Ala Gln Phe Ile Ser Leu Ile Val Gly Ser Lys Gly
                245                 250                 255

Asn Phe Gln Lys Pro Phe Asp Leu Ile Glu Lys Ser Asp Ile Glu Cys
            260                 265                 270

Ala Lys Asp Ser Tyr Glu Glu Asp Leu Glu Ser Leu Leu Ala Leu Ile
        275                 280                 285

Gly Asp Glu Tyr Ala Glu Leu Phe Val Ala Ala Lys Asn Ala Tyr Ser
    290                 295                 300

Ala Val Val Leu Ser Ser Ile Ile Thr Val Ala Glu Thr Glu Thr Asn
305                 310                 315                 320

Ala Lys Leu Ser Ala Ser Met Ile Glu Arg Phe Asp Thr His Glu Glu
                325                 330                 335

Asp Leu Gly Glu Leu Lys Ala Phe Ile Lys Leu His Leu Pro Lys His
            340                 345                 350

Tyr Glu Glu Ile Phe Ser Asn Thr Glu Lys His Gly Tyr Ala Gly Tyr
        355                 360                 365

Ile Asp Gly Lys Thr Lys Gln Ala Asp Phe Tyr Lys Tyr Met Lys Met
    370                 375                 380

Thr Leu Glu Asn Ile Glu Gly Ala Asp Tyr Phe Ile Ala Lys Ile Glu
385                 390                 395                 400

Lys Glu Asn Phe Leu Arg Lys Gln Arg Thr Phe Asp Asn Gly Ala Ile
                405                 410                 415

Pro His Gln Leu His Leu Glu Glu Leu Glu Ala Ile Leu His Gln Gln
            420                 425                 430

Ala Lys Tyr Tyr Pro Phe Leu Lys Glu Asn Tyr Asp Lys Ile Lys Ser
        435                 440                 445

Leu Val Thr Phe Arg Ile Pro Tyr Phe Val Gly Pro Leu Ala Asn Gly
    450                 455                 460

Gln Ser Glu Phe Ala Trp Leu Thr Arg Lys Ala Asp Gly Glu Ile Arg
465                 470                 475                 480

Pro Trp Asn Ile Glu Glu Lys Val Asp Phe Gly Lys Ser Ala Val Asp
                485                 490                 495

Phe Ile Glu Lys Met Thr Asn Lys Asp Thr Tyr Leu Pro Lys Glu Asn
```

-continued

```
                500                 505                 510
    Val Leu Pro Lys His Ser Leu Cys Tyr Gln Lys Tyr Leu Val Tyr Asn
            515                 520                 525
    Glu Leu Thr Lys Val Arg Tyr Ile Asn Asp Gln Gly Lys Thr Ser Tyr
            530                 535                 540
    Phe Ser Gly Gln Glu Lys Glu Gln Ile Phe Asn Asp Leu Phe Lys Gln
    545                 550                 555                 560
    Lys Arg Lys Val Lys Lys Asp Leu Glu Leu Phe Leu Arg Asn Met
                    565                 570                 575
    Ser His Val Glu Ser Pro Thr Ile Glu Gly Leu Glu Asp Ser Phe Asn
                580                 585                 590
    Ser Ser Tyr Ser Thr Tyr His Asp Leu Leu Lys Val Gly Ile Lys Gln
                595                 600                 605
    Glu Ile Leu Asp Asn Pro Val Asn Thr Glu Met Leu Glu Asn Ile Val
            610                 615                 620
    Lys Ile Leu Thr Val Phe Glu Asp Lys Arg Met Ile Lys Glu Gln Leu
    625                 630                 635                 640
    Gln Gln Phe Ser Asp Val Leu Asp Gly Val Val Leu Lys Lys Leu Glu
                    645                 650                 655
    Arg Arg His Tyr Thr Gly Trp Gly Arg Leu Ser Ala Lys Leu Leu Met
                660                 665                 670
    Gly Ile Arg Asp Lys Gln Ser His Leu Thr Ile Leu Asp Tyr Leu Met
                675                 680                 685
    Asn Asp Asp Gly Leu Asn Arg Asn Leu Met Gln Leu Ile Asn Asp Ser
            690                 695                 700
    Asn Leu Ser Phe Lys Ser Ile Ile Glu Lys Glu Gln Val Thr Thr Ala
    705                 710                 715                 720
    Asp Lys Asp Ile Gln Ser Ile Val Ala Asp Leu Ala Gly Ser Pro Ala
                    725                 730                 735
    Ile Lys Lys Gly Ile Leu Gln Ser Leu Lys Ile Val Asp Glu Leu Val
                740                 745                 750
    Ser Val Met Gly Tyr Pro Pro Gln Thr Ile Val Val Glu Met Ala Arg
                755                 760                 765
    Glu Asn Gln Thr Thr Gly Lys Gly Lys Asn Asn Ser Arg Pro Arg Tyr
            770                 775                 780
    Lys Ser Leu Glu Lys Ala Ile Lys Glu Phe Gly Ser Gln Ile Leu Lys
    785                 790                 795                 800
    Glu His Pro Thr Asp Asn Gln Glu Leu Arg Asn Asn Arg Leu Tyr Leu
                    805                 810                 815
    Tyr Tyr Leu Gln Asn Gly Lys Asp Met Tyr Thr Gly Gln Asp Leu Asp
                820                 825                 830
    Ile His Asn Leu Ser Asn Tyr Asp Ile Asp His Ile Val Pro Gln Ser
                835                 840                 845
    Phe Ile Thr Asp Asn Ser Ile Asp Asn Leu Val Leu Thr Ser Ser Ala
            850                 855                 860
    Gly Asn Arg Glu Lys Gly Asp Asp Val Pro Pro Leu Glu Ile Val Arg
    865                 870                 875                 880
    Lys Arg Lys Val Phe Trp Glu Lys Leu Tyr Gln Gly Asn Leu Met Ser
                    885                 890                 895
    Lys Arg Lys Phe Asp Tyr Leu Thr Lys Ala Glu Arg Gly Gly Leu Thr
                900                 905                 910
    Glu Ala Asp Lys Ala Arg Phe Ile His Arg Gln Leu Val Glu Thr Arg
                915                 920                 925
```

```
Gln Ile Thr Lys Asn Val Ala Asn Ile Leu His Gln Arg Phe Asn Tyr
    930                 935                 940
Glu Lys Asp Asp His Gly Asn Thr Met Lys Gln Val Arg Ile Val Thr
945                 950                 955                 960
Leu Lys Ser Ala Leu Val Ser Gln Phe Arg Lys Gln Phe Gln Leu Tyr
                965                 970                 975
Lys Val Arg Asp Val Asn Asp Tyr His His Ala His Asp Ala Tyr Leu
            980                 985                 990
Asn Gly Val Val Ala Asn Thr Leu Leu Lys Val Tyr Pro Gln Leu Glu
        995                 1000                1005
Pro Glu Phe Val Tyr Gly Asp Tyr His Gln Phe Asp Trp Phe Lys
    1010                1015                1020
Ala Asn Lys Ala Thr Ala Lys Lys Gln Phe Tyr Thr Asn Ile Met
    1025                1030                1035
Leu Phe Phe Ala Gln Lys Asp Arg Ile Ile Asp Glu Asn Gly Glu
    1040                1045                1050
Ile Leu Trp Asp Lys Lys Tyr Leu Asp Thr Val Lys Lys Val Met
    1055                1060                1065
Ser Tyr Arg Gln Met Asn Ile Val Lys Lys Thr Glu Ile Gln Lys
    1070                1075                1080
Gly Glu Phe Ser Lys Ala Thr Ile Lys Pro Lys Gly Asn Ser Ser
    1085                1090                1095
Lys Leu Ile Pro Arg Lys Thr Asn Trp Asp Pro Met Lys Tyr Gly
    1100                1105                1110
Gly Leu Asp Ser Pro Asn Met Ala Tyr Ala Val Val Ile Glu Tyr
    1115                1120                1125
Ala Lys Gly Lys Asn Lys Leu Val Phe Glu Lys Lys Ile Ile Arg
    1130                1135                1140
Val Thr Ile Met Glu Arg Lys Ala Phe Glu Lys Asp Glu Lys Ala
    1145                1150                1155
Phe Leu Glu Glu Gln Gly Tyr Arg Gln Pro Lys Val Leu Ala Lys
    1160                1165                1170
Leu Pro Lys Tyr Thr Leu Tyr Glu Cys Glu Glu Gly Arg Arg Arg
    1175                1180                1185
Met Leu Ala Ser Ala Asn Glu Ala Gln Lys Gly Asn Gln Gln Val
    1190                1195                1200
Leu Pro Asn His Leu Val Thr Leu Leu His His Ala Ala Asn Cys
    1205                1210                1215
Glu Val Ser Asp Gly Lys Ser Leu Asp Tyr Ile Glu Ser Asn Arg
    1220                1225                1230
Glu Met Phe Ala Glu Leu Leu Ala His Val Ser Glu Phe Ala Lys
    1235                1240                1245
Arg Tyr Thr Leu Ala Glu Ala Asn Leu Asn Lys Ile Asn Gln Leu
    1250                1255                1260
Phe Glu Gln Asn Lys Glu Gly Asp Ile Lys Ala Ile Ala Gln Ser
    1265                1270                1275
Phe Val Asp Leu Met Ala Phe Asn Ala Met Gly Ala Pro Ala Ser
    1280                1285                1290
Phe Lys Phe Phe Glu Thr Thr Ile Glu Arg Lys Arg Tyr Asn Asn
    1295                1300                1305
Leu Lys Glu Leu Leu Asn Ser Thr Ile Ile Tyr Gln Ser Ile Thr
    1310                1315                1320
```

```
Gly Leu Tyr Glu Ser Arg Lys Arg Leu Asp Asp
    1325                1330

<210> SEQ ID NO 4
<211> LENGTH: 1370
<212> TYPE: PRT
<213> ORGANISM: Streptococcus agalactiae

<400> SEQUENCE: 4

Met Asn Lys Pro Tyr Ser Ile Gly Leu Asp Ile Gly Thr Asn Ser Val
1               5                   10                  15

Gly Trp Ser Ile Ile Thr Asp Asp Tyr Lys Val Pro Ala Lys Lys Met
            20                  25                  30

Arg Val Leu Gly Asn Thr Asp Lys Glu Tyr Ile Lys Lys Asn Leu Ile
        35                  40                  45

Gly Ala Leu Leu Phe Asp Gly Asn Thr Ala Ala Asp Arg Arg Leu
    50                  55                  60

Lys Arg Thr Ala Arg Arg Arg Tyr Thr Arg Arg Arg Asn Arg Ile Leu
65                  70                  75                  80

Tyr Leu Gln Glu Ile Phe Ala Glu Glu Met Ser Lys Val Asp Asp Ser
                85                  90                  95

Phe Phe His Arg Leu Glu Asp Ser Phe Leu Val Glu Glu Asp Lys Arg
            100                 105                 110

Gly Ser Lys Tyr Pro Ile Phe Ala Thr Leu Gln Glu Glu Lys Asp Tyr
        115                 120                 125

His Glu Lys Phe Ser Thr Ile Tyr His Leu Arg Lys Glu Leu Ala Asp
    130                 135                 140

Lys Lys Glu Lys Ala Asp Leu Arg Leu Ile Tyr Ile Ala Leu Ala His
145                 150                 155                 160

Ile Ile Lys Phe Arg Gly His Phe Leu Ile Glu Asp Asp Ser Phe Asp
                165                 170                 175

Val Arg Asn Thr Asp Ile Ser Lys Gln Tyr Gln Asp Phe Leu Glu Ile
            180                 185                 190

Phe Asn Thr Thr Phe Glu Asn Asn Asp Leu Leu Ser Gln Asn Val Asp
        195                 200                 205

Val Glu Ala Ile Leu Thr Asp Lys Ile Ser Lys Ser Ala Lys Lys Asp
    210                 215                 220

Arg Ile Leu Ala Gln Tyr Pro Asn Gln Lys Ser Thr Gly Ile Phe Ala
225                 230                 235                 240

Glu Phe Leu Lys Leu Ile Val Gly Asn Gln Ala Asp Phe Lys Lys Tyr
                245                 250                 255

Phe Asn Leu Glu Asp Lys Thr Pro Leu Gln Phe Ala Lys Asp Ser Tyr
            260                 265                 270

Asp Glu Asp Leu Glu Asn Leu Leu Gly Gln Ile Gly Asp Glu Phe Ala
        275                 280                 285

Asp Leu Phe Ser Ala Ala Lys Lys Leu Tyr Asp Ser Val Leu Leu Ser
    290                 295                 300

Gly Ile Leu Thr Val Ile Asp Leu Ser Thr Lys Ala Pro Leu Ser Ala
305                 310                 315                 320

Ser Met Ile Gln Arg Tyr Asp Glu His Arg Glu Asp Leu Lys Gln Leu
                325                 330                 335

Lys Gln Phe Val Lys Ala Ser Leu Pro Glu Lys Tyr Gln Glu Ile Phe
            340                 345                 350

Ala Asp Ser Ser Lys Asp Gly Tyr Ala Gly Tyr Ile Glu Gly Lys Thr
        355                 360                 365
```

```
Asn Gln Glu Ala Phe Tyr Lys Tyr Leu Ser Lys Leu Leu Thr Lys Gln
    370                 375                 380

Glu Asp Ser Glu Asn Phe Leu Glu Lys Ile Lys Asn Glu Asp Phe Leu
385                 390                 395                 400

Arg Lys Gln Arg Thr Phe Asp Asn Gly Ser Ile Pro His Gln Val His
                405                 410                 415

Leu Thr Glu Leu Lys Ala Ile Ile Arg Arg Gln Ser Glu Tyr Tyr Pro
                420                 425                 430

Phe Leu Lys Glu Asn Gln Asp Arg Ile Glu Lys Ile Leu Thr Phe Arg
            435                 440                 445

Ile Pro Tyr Tyr Ile Gly Pro Leu Ala Arg Glu Lys Ser Asp Phe Ala
    450                 455                 460

Trp Met Thr Arg Lys Thr Asp Asp Ser Ile Arg Pro Trp Asn Phe Glu
465                 470                 475                 480

Asp Leu Val Asp Lys Glu Lys Ser Ala Glu Ala Phe Ile His Arg Met
                485                 490                 495

Thr Asn Asn Asp Phe Tyr Leu Pro Glu Glu Lys Val Leu Pro Lys His
            500                 505                 510

Ser Leu Ile Tyr Glu Lys Phe Thr Val Tyr Asn Glu Leu Thr Lys Val
    515                 520                 525

Arg Tyr Lys Asn Glu Gln Gly Glu Thr Tyr Phe Phe Asp Ser Asn Ile
530                 535                 540

Lys Gln Glu Ile Phe Asp Gly Val Phe Lys Glu His Arg Lys Val Ser
545                 550                 555                 560

Lys Lys Lys Leu Leu Asp Phe Leu Ala Lys Glu Tyr Glu Glu Phe Arg
                565                 570                 575

Ile Val Asp Val Ile Gly Leu Asp Lys Glu Asn Lys Ala Phe Asn Ala
            580                 585                 590

Ser Leu Gly Thr Tyr His Asp Leu Glu Lys Ile Leu Asp Lys Asp Phe
    595                 600                 605

Leu Asp Asn Pro Asp Asn Glu Ser Ile Leu Glu Asp Ile Val Gln Thr
610                 615                 620

Leu Thr Leu Phe Glu Asp Arg Glu Met Ile Lys Lys Arg Leu Glu Asn
625                 630                 635                 640

Tyr Lys Asp Leu Phe Thr Glu Ser Gln Leu Lys Lys Leu Tyr Arg Arg
                645                 650                 655

His Tyr Thr Gly Trp Gly Arg Leu Ser Ala Lys Leu Ile Asn Gly Ile
            660                 665                 670

Arg Asp Lys Glu Ser Gln Lys Thr Ile Leu Asp Tyr Leu Ile Asp Asp
    675                 680                 685

Gly Arg Ser Asn Arg Asn Phe Met Gln Leu Ile Asn Asp Asp Gly Leu
690                 695                 700

Ser Phe Lys Ser Ile Ile Ser Lys Ala Gln Ala Gly Ser His Ser Asp
705                 710                 715                 720

Asn Leu Lys Glu Val Val Gly Glu Leu Ala Gly Ser Pro Ala Ile Lys
                725                 730                 735

Lys Gly Ile Leu Gln Ser Leu Lys Ile Val Asp Glu Leu Val Lys Val
            740                 745                 750

Met Gly Tyr Glu Pro Glu Gln Ile Val Val Glu Met Ala Arg Glu Asn
    755                 760                 765

Gln Thr Thr Asn Gln Gly Arg Arg Asn Ser Arg Gln Tyr Lys Leu
770                 775                 780
```

```
Leu Asp Asp Gly Val Lys Asn Leu Ala Ser Asp Leu Asn Gly Asn Ile
785                 790                 795                 800

Leu Lys Glu Tyr Pro Thr Asp Asn Gln Ala Leu Gln Asn Glu Arg Leu
                805                 810                 815

Phe Leu Tyr Tyr Leu Gln Asn Gly Arg Asp Met Tyr Thr Gly Glu Ala
            820                 825                 830

Leu Asp Ile Asp Asn Leu Ser Gln Tyr Asp Ile Asp His Ile Ile Pro
            835                 840                 845

Gln Ala Phe Ile Lys Asp Ser Ile Asp Asn Arg Val Leu Val Ser
    850                 855                 860

Ser Ala Lys Asn Arg Gly Lys Ser Asp Asp Val Pro Ser Leu Glu Ile
865                 870                 875                 880

Val Lys Asp Cys Lys Val Phe Trp Lys Lys Leu Leu Asp Ala Lys Leu
                885                 890                 895

Met Ser Gln Arg Lys Tyr Asp Asn Leu Thr Lys Ala Glu Arg Gly Gly
                900                 905                 910

Leu Thr Ser Asp Asp Lys Ala Arg Phe Ile Gln Arg Gln Leu Val Glu
            915                 920                 925

Thr Arg Gln Ile Thr Lys His Val Ala Arg Ile Leu Asp Glu Arg Phe
930                 935                 940

Asn Asn Glu Leu Asp Ser Lys Gly Arg Arg Ile Arg Lys Val Lys Ile
945                 950                 955                 960

Val Thr Leu Lys Ser Asn Leu Val Ser Asn Phe Arg Lys Glu Phe Gly
                965                 970                 975

Phe Tyr Lys Ile Arg Glu Val Asn Asn Tyr His His Ala His Asp Ala
            980                 985                 990

Tyr Leu Asn Ala Val Val Ala Lys Ala Ile Leu Thr Lys Tyr Pro Gln
            995                 1000                1005

Leu Glu Pro Glu Phe Val Tyr Gly Asp Tyr Pro Lys Tyr Asn Ser
    1010                1015                1020

Tyr Lys Thr Arg Lys Ser Ala Thr Glu Lys Leu Phe Phe Tyr Ser
    1025                1030                1035

Asn Ile Met Asn Phe Phe Lys Thr Lys Val Thr Leu Ala Asp Gly
    1040                1045                1050

Thr Val Val Val Lys Asp Asp Ile Glu Val Asn Asn Asp Thr Gly
    1055                1060                1065

Glu Ile Val Trp Asp Lys Lys Lys His Phe Ala Thr Val Arg Lys
    1070                1075                1080

Val Leu Ser Tyr Pro Gln Asn Asn Ile Val Lys Lys Thr Glu Ile
    1085                1090                1095

Gln Thr Gly Gly Phe Ser Lys Glu Ser Ile Leu Ala His Gly Asn
    1100                1105                1110

Ser Asp Lys Leu Ile Pro Arg Lys Thr Lys Asp Ile Tyr Leu Asp
    1115                1120                1125

Pro Lys Lys Tyr Gly Gly Phe Asp Ser Pro Ile Val Ala Tyr Ser
    1130                1135                1140

Val Leu Val Val Ala Asp Ile Lys Lys Gly Lys Ala Gln Lys Leu
    1145                1150                1155

Lys Thr Val Thr Glu Leu Leu Gly Ile Thr Ile Met Glu Arg Ser
    1160                1165                1170

Arg Phe Glu Lys Asn Pro Ser Ala Phe Leu Glu Ser Lys Gly Tyr
    1175                1180                1185

Leu Asn Ile Arg Ala Asp Lys Leu Ile Ile Leu Pro Lys Tyr Ser
```

-continued

```
                1190                1195                1200

Leu Phe Glu Leu Glu Asn Gly Arg Arg Arg Leu Leu Ala Ser Ala
    1205                1210                1215

Gly Glu Leu Gln Lys Gly Asn Glu Leu Ala Leu Pro Thr Gln Phe
    1220                1225                1230

Met Lys Phe Leu Tyr Leu Ala Ser Arg Tyr Asn Glu Ser Lys Gly
    1235                1240                1245

Lys Pro Glu Glu Ile Glu Lys Lys Gln Glu Phe Val Asn Gln His
    1250                1255                1260

Val Ser Tyr Phe Asp Asp Ile Leu Gln Leu Ile Asn Asp Phe Ser
    1265                1270                1275

Lys Arg Val Ile Leu Ala Asp Ala Asn Leu Glu Lys Ile Asn Lys
    1280                1285                1290

Leu Tyr Gln Asp Asn Lys Glu Asn Ile Ser Val Asp Glu Leu Ala
    1295                1300                1305

Asn Asn Ile Ile Asn Leu Phe Thr Phe Thr Ser Leu Gly Ala Pro
    1310                1315                1320

Ala Ala Phe Lys Phe Phe Asp Lys Ile Val Asp Arg Lys Arg Tyr
    1325                1330                1335

Thr Ser Thr Lys Glu Val Leu Asn Ser Thr Leu Ile His Gln Ser
    1340                1345                1350

Ile Thr Gly Leu Tyr Glu Thr Arg Ile Asp Leu Gly Lys Leu Gly
    1355                1360                1365

Glu Asp
    1370

<210> SEQ ID NO 5
<211> LENGTH: 1345
<212> TYPE: PRT
<213> ORGANISM: Streptococcus mutans

<400> SEQUENCE: 5

Met Lys Lys Pro Tyr Ser Ile Gly Leu Asp Ile Gly Thr Asn Ser
1               5                   10                  15

Gly Trp Ala Val Val Thr Asp Asp Tyr Lys Val Pro Ala Lys Lys Met
                20                  25                  30

Lys Val Leu Gly Asn Thr Asp Lys Ser His Ile Glu Lys Asn Leu Leu
            35                  40                  45

Gly Ala Leu Leu Phe Asp Ser Gly Asn Thr Ala Glu Asp Arg Arg Leu
        50                  55                  60

Lys Arg Thr Ala Arg Arg Arg Tyr Thr Arg Arg Asn Arg Ile Leu
65                  70                  75                  80

Tyr Leu Gln Glu Ile Phe Ser Glu Glu Met Gly Lys Val Asp Asp Ser
                85                  90                  95

Phe Phe His Arg Leu Glu Asp Ser Phe Leu Val Thr Glu Asp Lys Arg
            100                 105                 110

Gly Glu Arg His Pro Ile Phe Gly Asn Leu Glu Glu Val Lys Tyr
        115                 120                 125

His Glu Asn Phe Pro Thr Ile Tyr His Leu Arg Gln Tyr Leu Ala Asp
    130                 135                 140

Asn Pro Glu Lys Val Asp Leu Arg Leu Val Tyr Leu Ala Leu Ala His
145                 150                 155                 160

Ile Ile Lys Phe Arg Gly His Phe Leu Ile Glu Gly Lys Phe Asp Thr
                165                 170                 175
```

```
Arg Asn Asn Asp Val Gln Arg Leu Phe Gln Glu Phe Leu Ala Val Tyr
            180                 185                 190

Asp Asn Thr Phe Glu Asn Ser Ser Leu Gln Glu Gln Asn Val Gln Val
        195                 200                 205

Glu Glu Ile Leu Thr Asp Lys Ile Ser Lys Ser Ala Lys Lys Asp Arg
    210                 215                 220

Val Leu Lys Leu Phe Pro Asn Glu Lys Ser Asn Gly Arg Phe Ala Glu
225                 230                 235                 240

Phe Leu Lys Leu Ile Val Gly Asn Gln Ala Asp Phe Lys His Phe
                245                 250                 255

Glu Leu Glu Glu Lys Ala Pro Leu Gln Phe Ser Lys Asp Thr Tyr Glu
        260                 265                 270

Glu Glu Leu Glu Val Leu Leu Ala Gln Ile Gly Asp Asn Tyr Ala Glu
    275                 280                 285

Leu Phe Leu Ser Ala Lys Lys Leu Tyr Asp Ser Ile Leu Leu Ser Gly
290                 295                 300

Ile Leu Thr Val Thr Asp Val Gly Thr Lys Ala Pro Leu Ser Ala Ser
305                 310                 315                 320

Met Ile Gln Arg Tyr Asn Glu His Gln Met Asp Leu Ala Gln Leu Lys
            325                 330                 335

Gln Phe Ile Arg Gln Lys Leu Ser Asp Lys Tyr Asn Glu Val Phe Ser
        340                 345                 350

Asp Val Ser Lys Asp Gly Tyr Ala Gly Tyr Ile Asp Gly Lys Thr Asn
    355                 360                 365

Gln Glu Ala Phe Tyr Lys Tyr Leu Lys Gly Leu Leu Asn Lys Ile Glu
370                 375                 380

Gly Ser Gly Tyr Phe Leu Asp Lys Ile Glu Arg Glu Asp Phe Leu Arg
385                 390                 395                 400

Lys Gln Arg Thr Phe Asp Asn Gly Ser Ile Pro His Gln Ile His Leu
            405                 410                 415

Gln Glu Met Arg Ala Ile Ile Arg Arg Gln Ala Glu Phe Tyr Pro Phe
        420                 425                 430

Leu Ala Asp Asn Gln Asp Arg Ile Glu Lys Leu Leu Thr Phe Arg Ile
    435                 440                 445

Pro Tyr Tyr Val Gly Pro Leu Ala Arg Gly Lys Ser Asp Phe Ala Trp
450                 455                 460

Leu Ser Arg Lys Ser Ala Asp Lys Ile Thr Pro Trp Asn Phe Asp Glu
465                 470                 475                 480

Ile Val Asp Lys Glu Ser Ser Ala Glu Ala Phe Ile Asn Arg Met Thr
            485                 490                 495

Asn Tyr Asp Leu Tyr Leu Pro Asn Gln Lys Val Leu Pro Lys His Ser
        500                 505                 510

Leu Leu Tyr Glu Lys Phe Thr Val Tyr Asn Glu Leu Thr Lys Val Lys
    515                 520                 525

Tyr Lys Thr Glu Gln Gly Lys Thr Ala Phe Phe Asp Ala Asn Met Lys
530                 535                 540

Gln Glu Ile Phe Asp Gly Val Phe Lys Val Tyr Arg Lys Val Thr Lys
545                 550                 555                 560

Asp Lys Leu Met Asp Phe Leu Glu Lys Glu Phe Asp Glu Phe Arg Ile
            565                 570                 575

Val Asp Leu Thr Gly Leu Asp Lys Glu Asn Lys Val Phe Asn Ala Ser
        580                 585                 590

Tyr Gly Thr Tyr His Asp Leu Cys Lys Ile Leu Asp Lys Asp Phe Leu
```

```
                         595                 600                 605
Asp Asn Ser Lys Asn Glu Lys Ile Leu Glu Asp Ile Val Leu Thr Leu
610                 615                 620

Thr Leu Phe Glu Asp Arg Glu Met Ile Arg Lys Arg Leu Glu Asn Tyr
625                 630                 635                 640

Ser Asp Leu Leu Thr Lys Glu Gln Val Lys Lys Leu Glu Arg Arg His
                645                 650                 655

Tyr Thr Gly Trp Gly Arg Leu Ser Ala Glu Leu Ile His Gly Ile Arg
                660                 665                 670

Asn Lys Glu Ser Arg Lys Thr Ile Leu Asp Tyr Leu Ile Asp Asp Gly
            675                 680                 685

Asn Ser Asn Arg Asn Phe Met Gln Leu Ile Asn Asp Asp Ala Leu Ser
690                 695                 700

Phe Lys Glu Glu Ile Ala Lys Ala Gln Val Ile Gly Glu Thr Asp Asn
705                 710                 715                 720

Leu Asn Gln Val Val Ser Asp Ile Ala Gly Ser Pro Ala Ile Lys Lys
                725                 730                 735

Gly Ile Leu Gln Ser Leu Lys Ile Val Asp Glu Leu Val Lys Ile Met
            740                 745                 750

Gly His Gln Pro Glu Asn Ile Val Val Glu Met Ala Arg Glu Asn Gln
        755                 760                 765

Phe Thr Asn Gln Gly Arg Arg Asn Ser Gln Gln Arg Leu Lys Gly Leu
770                 775                 780

Thr Asp Ser Ile Lys Glu Phe Gly Ser Gln Ile Leu Lys Glu His Pro
785                 790                 795                 800

Val Glu Asn Ser Gln Leu Gln Asn Asp Arg Leu Phe Leu Tyr Tyr Leu
                805                 810                 815

Gln Asn Gly Arg Asp Met Tyr Thr Gly Glu Glu Leu Asp Ile Asp Tyr
            820                 825                 830

Leu Ser Gln Tyr Asp Ile Asp His Ile Ile Pro Gln Ala Phe Ile Lys
        835                 840                 845

Asp Asn Ser Ile Asp Asn Arg Val Leu Thr Ser Ser Lys Glu Asn Arg
850                 855                 860

Gly Lys Ser Asp Asp Val Pro Ser Lys Asp Val Val Arg Lys Met Lys
865                 870                 875                 880

Ser Tyr Trp Ser Lys Leu Leu Ser Ala Lys Leu Ile Thr Gln Arg Lys
                885                 890                 895

Phe Asp Asn Leu Thr Lys Ala Glu Arg Gly Gly Leu Thr Asp Asp Asp
            900                 905                 910

Lys Ala Gly Phe Ile Lys Arg Gln Leu Val Glu Thr Arg Gln Ile Thr
        915                 920                 925

Lys His Val Ala Arg Ile Leu Asp Glu Arg Phe Asn Thr Glu Thr Asp
    930                 935                 940

Glu Asn Asn Lys Lys Ile Arg Gln Val Lys Ile Val Thr Leu Lys Ser
945                 950                 955                 960

Asn Leu Val Ser Asn Phe Arg Lys Glu Phe Glu Leu Tyr Lys Val Arg
                965                 970                 975

Glu Ile Asn Asp Tyr His His Ala His Asp Ala Tyr Leu Asn Ala Val
            980                 985                 990

Ile Gly Lys Ala Leu Leu Gly Val Tyr Pro Gln Leu Glu Pro Glu Phe
        995                 1000                1005

Val Tyr Gly Asp Tyr Pro His Phe His Gly His Lys Glu Asn Lys
    1010                1015                1020
```

```
Ala Thr Ala Lys Lys Phe Phe Tyr Ser Asn Ile Met Asn Phe Phe
    1025                1030                1035

Lys Lys Asp Asp Val Arg Thr Asp Lys Asn Gly Glu Ile Ile Trp
    1040                1045                1050

Lys Lys Asp Glu His Ile Ser Asn Ile Lys Lys Val Leu Ser Tyr
    1055                1060                1065

Pro Gln Val Asn Ile Val Lys Lys Val Glu Glu Gln Thr Gly Gly
    1070                1075                1080

Phe Ser Lys Glu Ser Ile Leu Pro Lys Gly Asn Ser Asp Lys Leu
    1085                1090                1095

Ile Pro Arg Lys Thr Lys Lys Phe Tyr Trp Asp Thr Lys Lys Tyr
    1100                1105                1110

Gly Gly Phe Asp Ser Pro Ile Val Ala Tyr Ser Ile Leu Val Ile
    1115                1120                1125

Ala Asp Ile Glu Lys Gly Lys Ser Lys Lys Leu Lys Thr Val Lys
    1130                1135                1140

Ala Leu Val Gly Val Thr Ile Met Glu Lys Met Thr Phe Glu Arg
    1145                1150                1155

Asp Pro Val Ala Phe Leu Glu Arg Lys Gly Tyr Arg Asn Val Gln
    1160                1165                1170

Glu Glu Asn Ile Ile Lys Leu Pro Lys Tyr Ser Leu Phe Lys Leu
    1175                1180                1185

Glu Asn Gly Arg Lys Arg Leu Leu Ala Ser Ala Arg Glu Leu Gln
    1190                1195                1200

Lys Gly Asn Glu Ile Val Leu Pro Asn His Leu Gly Thr Leu Leu
    1205                1210                1215

Tyr His Ala Lys Asn Ile His Lys Val Asp Glu Pro Lys His Leu
    1220                1225                1230

Asp Tyr Val Asp Lys His Lys Asp Glu Phe Lys Glu Leu Leu Asp
    1235                1240                1245

Val Val Ser Asn Phe Ser Lys Lys Tyr Thr Leu Ala Glu Gly Asn
    1250                1255                1260

Leu Glu Lys Ile Lys Glu Leu Tyr Ala Gln Asn Asn Gly Glu Asp
    1265                1270                1275

Leu Lys Glu Leu Ala Ser Ser Phe Ile Asn Leu Leu Thr Phe Thr
    1280                1285                1290

Ala Ile Gly Ala Pro Ala Thr Phe Lys Phe Phe Asp Lys Asn Ile
    1295                1300                1305

Asp Arg Lys Arg Tyr Thr Ser Thr Thr Glu Ile Leu Asn Ala Thr
    1310                1315                1320

Leu Ile His Gln Ser Ile Thr Gly Leu Tyr Glu Thr Arg Ile Asp
    1325                1330                1335

Leu Asn Lys Leu Gly Gly Asp
    1340                1345

<210> SEQ ID NO 6
<211> LENGTH: 1340
<212> TYPE: PRT
<213> ORGANISM: Enterococcus faecium

<400> SEQUENCE: 6

Met Lys Lys Glu Tyr Thr Ile Gly Leu Asp Ile Gly Thr Asn Ser Val
1               5                   10                  15

Gly Trp Ser Val Leu Thr Asp Asp Tyr Arg Leu Val Ser Lys Lys Met
```

```
                    20                  25                  30
Lys Val Ala Gly Asn Thr Glu Lys Ser Thr Lys Lys Asn Phe Trp
            35                  40                  45
Gly Val Arg Leu Phe Asp Glu Gly Gln Thr Ala Glu Ala Arg Ser
        50                  55                  60
Lys Arg Thr Ala Arg Arg Leu Ala Arg Arg Gln Arg Ile Leu
65                  70                  75                  80
Glu Leu Gln Lys Ile Phe Ala Pro Glu Ile Leu Lys Ile Asp Glu His
                    85                  90                  95
Phe Phe Ala Arg Leu Asn Glu Ser Phe Leu Val Pro Asp Glu Lys Lys
                100                 105                 110
Gln Ser Arg His Pro Val Phe Ala Thr Ile Lys Gln Glu Lys Ser Tyr
            115                 120                 125
His Gln Thr Tyr Pro Thr Ile Tyr His Leu Arg Gln Ala Leu Ala Asp
        130                 135                 140
Ser Ser Glu Lys Ala Asp Ile Arg Leu Val Tyr Leu Ala Met Ala His
145                 150                 155                 160
Leu Leu Lys Tyr Arg Gly His Phe Leu Ile Glu Gly Glu Leu Asn Thr
                165                 170                 175
Glu Asn Ser Ser Val Thr Glu Thr Phe Arg Gln Phe Leu Ser Thr Tyr
                180                 185                 190
Asn Gln Gln Phe Ser Glu Ala Gly Asp Lys Gln Thr Glu Lys Leu Asp
            195                 200                 205
Glu Ala Val Asp Cys Ser Phe Val Phe Thr Glu Lys Met Ser Lys Thr
        210                 215                 220
Lys Lys Ala Glu Thr Leu Leu Lys Tyr Phe Pro His Glu Lys Ser Asn
225                 230                 235                 240
Gly Tyr Leu Ser Gln Phe Ile Lys Leu Met Val Gly Asn Gln Gly Asn
                245                 250                 255
Phe Lys Asn Val Phe Gly Leu Glu Glu Glu Ala Lys Leu Gln Phe Ser
                260                 265                 270
Lys Glu Thr Tyr Glu Glu Asp Leu Glu Glu Leu Leu Glu Lys Ile Gly
            275                 280                 285
Asp Asp Tyr Ile Asp Leu Phe Val Gln Ala Lys Asn Val Tyr Asp Ala
290                 295                 300
Val Leu Leu Ser Glu Ile Leu Ser Asp Ser Thr Lys Asn Thr Arg Ala
305                 310                 315                 320
Lys Leu Ser Ala Gly Met Ile Arg Arg Tyr Asp Ala His Lys Glu Asp
                325                 330                 335
Leu Val Leu Leu Lys Arg Phe Val Lys Glu Asn Leu Pro Lys Lys Tyr
            340                 345                 350
Arg Ala Phe Phe Gly Asp Asn Ser Val Asn Gly Tyr Ala Gly Tyr Ile
            355                 360                 365
Glu Gly His Ala Thr Gln Glu Ala Phe Tyr Lys Phe Val Lys Lys Glu
        370                 375                 380
Leu Thr Gly Ile Arg Gly Ser Glu Val Phe Leu Thr Lys Ile Glu Gln
385                 390                 395                 400
Glu Asn Phe Leu Arg Lys Gln Arg Thr Phe Asp Asn Gly Val Ile Pro
                405                 410                 415
His Gln Ile His Leu Ser Glu Leu Arg Ala Ile Ile Ala Asn Gln Lys
            420                 425                 430
Lys His Tyr Pro Phe Leu Lys Glu Glu Gln Glu Lys Leu Glu Ser Leu
            435                 440                 445
```

-continued

Leu Thr Phe Lys Ile Pro Tyr Tyr Val Gly Pro Leu Ala Lys Lys Gln
            450                 455                 460

Glu Asn Ser Pro Phe Ala Trp Leu Ile Arg Lys Ser Glu Glu Lys Ile
465                 470                 475                 480

Lys Pro Trp Asn Leu Pro Glu Ile Val Asp Met Glu Gly Ser Ala Val
                485                 490                 495

Arg Phe Ile Glu Arg Met Ile Asn Thr Asp Met Tyr Met Pro His Asn
                500                 505                 510

Lys Val Leu Pro Lys Asn Ser Leu Leu Tyr Gln Lys Phe Ser Ile Tyr
                515                 520                 525

Asn Glu Leu Thr Lys Val Arg Tyr Gln Asp Glu Arg Gly Gln Met Asn
530                 535                 540

Tyr Phe Ser Ser Ile Glu Lys Lys Glu Ile Phe His Glu Leu Phe Glu
545                 550                 555                 560

Lys Asn Arg Lys Val Thr Lys Lys Asp Leu Gln Glu Phe Leu Tyr Leu
                565                 570                 575

Lys Tyr Asp Ile Lys His Ala Glu Leu Ser Gly Ile Glu Lys Ala Phe
                580                 585                 590

Asn Ala Ser Tyr Thr Thr Tyr His Asp Phe Leu Thr Met Ser Glu Asn
                595                 600                 605

Lys Arg Glu Met Lys Gln Trp Leu Glu Asp Pro Glu Leu Ala Ser Met
610                 615                 620

Phe Glu Glu Ile Ile Lys Thr Leu Thr Val Phe Glu Asp Arg Glu Met
625                 630                 635                 640

Ile Lys Thr Arg Leu Ser His His Glu Ala Thr Leu Gly Lys His Ile
                645                 650                 655

Ile Lys Lys Leu Thr Lys Lys His Tyr Thr Gly Trp Gly Arg Leu Ser
                660                 665                 670

Lys Glu Leu Ile Gln Gly Ile Arg Asp Lys Gln Ser Asn Lys Thr Ile
                675                 680                 685

Leu Asp Tyr Leu Ile Asn Asp Asp Phe Pro His His Arg Asn Arg
690                 695                 700

Asn Phe Met Gln Leu Ile Asn Asp Asp Ser Leu Ser Phe Lys Lys Glu
705                 710                 715                 720

Ile Lys Lys Ala Gln Met Ile Thr Asp Thr Glu Asn Leu Glu Glu Ile
                725                 730                 735

Val Lys Glu Leu Thr Gly Ser Pro Ala Ile Lys Lys Gly Ile Leu Gln
                740                 745                 750

Ser Leu Lys Ile Val Asp Glu Ile Val Gly Ile Met Gly Tyr Glu Pro
                755                 760                 765

Ala Asn Ile Val Val Glu Met Ala Arg Glu Asn Gln Thr Thr Gly Arg
                770                 775                 780

Gly Leu Lys Ser Ser Arg Pro Arg Leu Lys Ala Leu Glu Glu Ser Leu
785                 790                 795                 800

Lys Asp Phe Gly Ser Gln Leu Leu Lys Glu Tyr Pro Thr Asp Asn Ser
                805                 810                 815

Ser Leu Gln Lys Asp Arg Leu Tyr Leu Tyr Leu Gln Asn Gly Arg
                820                 825                 830

Asp Met Tyr Thr Gly Ala Pro Leu Asp Ile His Arg Leu Ser Asp Tyr
                835                 840                 845

Asp Ile Asp His Ile Ile Pro Arg Ser Phe Thr Thr Asp Asn Ser Ile
                850                 855                 860

```
Asp Asn Lys Val Leu Val Ser Ser Lys Glu Asn Arg Leu Lys Lys Asp
865                 870                 875                 880

Asp Val Pro Ser Glu Lys Val Lys Lys Met Arg Ser Phe Trp Tyr
                885                 890                 895

Asp Leu Tyr Ser Ser Lys Leu Ile Ser Lys Arg Lys Leu Asp Asn Leu
                900                 905                 910

Thr Lys Ile Lys Leu Thr Glu Glu Asp Lys Ala Gly Phe Ile Lys Arg
        915                 920                 925

Gln Leu Val Glu Thr Arg Gln Ile Thr Lys His Val Ala Gly Ile Leu
        930                 935                 940

His His Arg Phe Asn Lys Ala Glu Asp Thr Asn Asp Pro Ile Arg Lys
945                 950                 955                 960

Val Arg Ile Ile Thr Leu Lys Ser Ala Leu Val Ser Gln Phe Arg Asn
                965                 970                 975

Arg Phe Gly Ile Tyr Lys Val Arg Glu Ile Asn Glu Tyr His His Ala
                980                 985                 990

His Asp Ala Tyr Leu Asn Gly Val Val Ala Leu Ala Leu Leu Lys Lys
            995                 1000                1005

Tyr Pro Gln Leu Ala Pro Glu Phe Val Tyr Gly Glu Tyr Leu Lys
    1010                1015                1020

Phe Asn Ala His Lys Ala Asn Lys Ala Thr Val Lys Lys Glu Phe
    1025                1030                1035

Tyr Ser Asn Ile Met Lys Phe Phe Glu Ser Asp Thr Pro Val Cys
    1040                1045                1050

Asp Glu Asn Gly Glu Ile Phe Trp Asp Lys Ser Lys Ser Ile Ala
    1055                1060                1065

Gln Val Lys Lys Val Ile Asn His His Met Asn Ile Val Lys
    1070                1075                1080

Lys Thr Glu Ile Gln Lys Gly Gly Phe Ser Lys Glu Thr Val Glu
    1085                1090                1095

Pro Lys Lys Asp Ser Ser Lys Leu Leu Pro Arg Lys Asn Asn Trp
    1100                1105                1110

Asp Pro Ala Lys Tyr Gly Gly Leu Gly Ser Pro Asn Val Ala Tyr
    1115                1120                1125

Thr Val Ala Phe Thr Tyr Glu Lys Gly Lys Ala Arg Lys Arg Thr
    1130                1135                1140

Asn Ala Leu Glu Gly Ile Thr Ile Met Glu Arg Glu Ala Phe Glu
    1145                1150                1155

Gln Ser Pro Val Leu Phe Leu Lys Asn Lys Gly Tyr Glu Gln Ala
    1160                1165                1170

Glu Ile Glu Met Lys Leu Pro Lys Tyr Ala Leu Phe Glu Leu Glu
    1175                1180                1185

Asn Gly Arg Lys Arg Met Val Ala Ser Asn Lys Glu Ala Gln Lys
    1190                1195                1200

Ala Asn Ser Phe Leu Leu Pro Glu His Leu Val Thr Leu Leu Tyr
    1205                1210                1215

His Ala Lys Gln Tyr Asp Glu Ile Ser His Lys Glu Ser Phe Asp
    1220                1225                1230

Tyr Val Asn Glu His His Lys Glu Phe Ser Glu Val Phe Ala Arg
    1235                1240                1245

Val Leu Glu Phe Ala Gly Lys Tyr Thr Leu Ala Glu Lys Asn Ile
    1250                1255                1260

Glu Lys Leu Glu Lys Ile Tyr Lys Glu Asn Gln Thr Asp Asp Leu
```

```
                    1265                1270                1275

Ala Lys Leu Ala Ser Ser Phe Val Asn Leu Met Gln Phe Asn Ala
        1280                1285                1290

Met Gly Ala Pro Ala Asp Phe Lys Phe Phe Asp Val Thr Ile Pro
    1295                1300                1305

Arg Lys Arg Tyr Thr Ser Leu Thr Glu Ile Trp Gln Ser Thr Ile
    1310                1315                1320

Ile His Gln Ser Ile Thr Gly Leu Tyr Glu Thr Arg Ile Arg Met
    1325                1330                1335

Gly Lys
    1340

<210> SEQ ID NO 7
<211> LENGTH: 1101
<212> TYPE: PRT
<213> ORGANISM: Actinomyces naeslundii

<400> SEQUENCE: 7

Met Trp Tyr Ala Ser Leu Met Ser Ala His His Leu Arg Val Gly Ile
1               5                   10                  15

Asp Val Gly Thr His Ser Val Gly Leu Ala Thr Leu Arg Val Asp Asp
            20                  25                  30

His Gly Thr Pro Ile Glu Leu Leu Ser Ala Leu Ser His Ile His Asp
        35                  40                  45

Ser Gly Val Gly Lys Glu Gly Lys Lys Asp His Asp Thr Arg Lys Lys
    50                  55                  60

Leu Ser Gly Ile Ala Arg Arg Ala Arg Arg Leu His Arg Arg
65                  70                  75                  80

Thr Gln Leu Gln Gln Leu Asp Glu Val Leu Arg Asp Leu Gly Phe Pro
                85                  90                  95

Ile Pro Thr Pro Gly Glu Phe Leu Asp Leu Asn Glu Gln Thr Asp Pro
            100                 105                 110

Tyr Arg Val Trp Arg Val Arg Ala Arg Leu Val Glu Glu Lys Leu Pro
        115                 120                 125

Glu Glu Leu Arg Gly Pro Ala Ile Ser Met Ala Val Arg His Ile Ala
    130                 135                 140

Arg His Arg Gly Trp Arg Asn Pro Tyr Ser Lys Val Glu Ser Leu Leu
145                 150                 155                 160

Ser Pro Ala Glu Glu Ser Pro Phe Met Lys Ala Leu Arg Glu Arg Ile
                165                 170                 175

Leu Ala Thr Thr Gly Glu Val Leu Asp Asp Gly Ile Thr Pro Gly Gln
            180                 185                 190

Ala Met Ala Gln Val Ala Leu Thr His Asn Ile Ser Met Arg Gly Pro
        195                 200                 205

Glu Gly Ile Leu Gly Lys Leu His Gln Ser Asp Asn Ala Asn Glu Ile
    210                 215                 220

Arg Lys Ile Cys Ala Arg Gln Gly Val Ser Pro Asp Val Cys Lys Gln
225                 230                 235                 240

Leu Leu Arg Ala Val Phe Lys Ala Asp Ser Pro Arg Gly Ser Ala Val
                245                 250                 255

Ser Arg Val Ala Pro Asp Pro Leu Pro Gly Gln Gly Ser Phe Arg Arg
            260                 265                 270

Ala Pro Lys Cys Asp Pro Glu Phe Gln Arg Phe Arg Ile Ile Ser Ile
        275                 280                 285
```

-continued

```
Val Ala Asn Leu Arg Ile Ser Glu Thr Lys Gly Glu Asn Arg Pro Leu
    290                 295                 300

Thr Ala Asp Glu Arg Arg His Val Val Thr Phe Leu Thr Glu Asp Ser
305                 310                 315                 320

Gln Ala Asp Leu Thr Trp Val Asp Val Ala Glu Lys Leu Gly Val His
                    325                 330                 335

Arg Arg Asp Leu Arg Gly Thr Ala Val His Thr Asp Asp Gly Glu Arg
                340                 345                 350

Ser Ala Ala Arg Pro Pro Ile Asp Ala Thr Asp Arg Ile Met Arg Gln
                355                 360                 365

Thr Lys Ile Ser Ser Leu Lys Thr Trp Trp Glu Glu Ala Asp Ser Glu
370                 375                 380

Gln Arg Gly Ala Met Ile Arg Tyr Leu Tyr Glu Asp Pro Thr Asp Ser
385                 390                 395                 400

Glu Cys Ala Glu Ile Ile Ala Glu Leu Pro Glu Glu Asp Gln Ala Lys
                    405                 410                 415

Leu Asp Ser Leu His Leu Pro Ala Gly Arg Ala Ala Tyr Ser Arg Glu
                420                 425                 430

Ser Leu Thr Ala Leu Ser Asp His Met Leu Ala Thr Thr Asp Asp Leu
                435                 440                 445

His Glu Ala Arg Lys Arg Leu Phe Gly Val Asp Asp Ser Trp Ala Pro
    450                 455                 460

Pro Ala Glu Ala Ile Asn Ala Pro Val Gly Asn Pro Ser Val Asp Arg
465                 470                 475                 480

Thr Leu Lys Ile Val Gly Arg Tyr Leu Ser Ala Val Glu Ser Met Trp
                    485                 490                 495

Gly Thr Pro Glu Val Ile His Val Glu His Val Arg Asp Gly Phe Thr
                500                 505                 510

Ser Glu Arg Met Ala Asp Glu Arg Asp Lys Ala Asn Arg Arg Tyr
                515                 520                 525

Asn Asp Asn Gln Glu Ala Met Lys Lys Ile Gln Arg Asp Tyr Gly Lys
    530                 535                 540

Glu Gly Tyr Ile Ser Arg Gly Asp Ile Val Arg Leu Asp Ala Leu Glu
545                 550                 555                 560

Leu Gln Gly Cys Ala Cys Leu Tyr Cys Gly Thr Thr Ile Gly Tyr His
                    565                 570                 575

Thr Cys Gln Leu Asp His Ile Val Pro Gln Ala Gly Pro Gly Ser Asn
                580                 585                 590

Asn Arg Arg Gly Asn Leu Val Ala Val Cys Glu Arg Cys Asn Arg Ser
                595                 600                 605

Lys Ser Asn Thr Pro Phe Ala Val Trp Ala Gln Lys Cys Gly Ile Pro
    610                 615                 620

His Val Gly Val Lys Glu Ala Ile Gly Arg Val Arg Gly Trp Arg Lys
625                 630                 635                 640

Gln Thr Pro Asn Thr Ser Ser Glu Asp Leu Thr Arg Leu Lys Lys Glu
                    645                 650                 655

Val Ile Ala Arg Leu Arg Arg Thr Gln Glu Asp Pro Glu Ile Asp Glu
                660                 665                 670

Arg Ser Met Glu Ser Val Ala Trp Met Ala Asn Glu Leu His His Arg
                675                 680                 685

Ile Ala Ala Ala Tyr Pro Glu Thr Thr Val Met Val Tyr Arg Gly Ser
    690                 695                 700

Ile Thr Ala Ala Ala Arg Lys Ala Ala Gly Ile Asp Ser Arg Ile Asn
```

-continued

```
            705                 710                 715                 720
        Leu Ile Gly Glu Lys Gly Arg Lys Asp Arg Ile Asp Arg Arg His His
                        725                 730                 735

Ala Val Asp Ala Ser Val Val Ala Leu Met Glu Ala Ser Val Ala Lys
                        740                 745                 750

Thr Leu Ala Glu Arg Ser Ser Leu Arg Gly Glu Gln Arg Leu Thr Gly
                        755                 760                 765

Lys Glu Gln Thr Trp Lys Gln Tyr Thr Gly Ser Thr Val Gly Ala Arg
                        770                 775                 780

Glu His Phe Glu Met Trp Arg Gly His Met Leu His Leu Thr Glu Leu
        785                 790                 795                 800

Phe Asn Glu Arg Leu Ala Glu Asp Lys Val Tyr Val Thr Gln Asn Ile
                        805                 810                 815

Arg Leu Arg Leu Ser Asp Gly Asn Ala His Thr Val Asn Pro Ser Lys
                        820                 825                 830

Leu Val Ser His Arg Leu Gly Asp Gly Leu Thr Val Gln Gln Ile Asp
                        835                 840                 845

Arg Ala Cys Thr Pro Ala Leu Trp Cys Ala Leu Thr Arg Glu Lys Asp
        850                 855                 860

Phe Asp Glu Lys Asn Gly Leu Pro Ala Arg Glu Asp Arg Ala Ile Arg
        865                 870                 875                 880

Val His Gly His Glu Ile Lys Ser Ser Asp Tyr Ile Gln Val Phe Ser
                        885                 890                 895

Lys Arg Lys Lys Thr Asp Ser Asp Arg Asp Glu Thr Pro Phe Gly Ala
                        900                 905                 910

Ile Ala Val Arg Gly Gly Phe Val Glu Ile Gly Pro Ser Ile His His
                        915                 920                 925

Ala Arg Ile Tyr Arg Val Glu Gly Lys Lys Pro Val Tyr Ala Met Leu
                        930                 935                 940

Arg Val Phe Thr His Asp Leu Leu Ser Gln Arg His Gly Asp Leu Phe
        945                 950                 955                 960

Ser Ala Val Ile Pro Pro Gln Ser Ile Ser Met Arg Cys Ala Glu Pro
                        965                 970                 975

Lys Leu Arg Lys Ala Ile Thr Thr Gly Asn Ala Thr Tyr Leu Gly Trp
                        980                 985                 990

Val Val Val Gly Asp Glu Leu Glu Ile Asn Val Asp Ser Phe Thr Lys
                        995                 1000                1005

Tyr Ala Ile Gly Arg Phe Leu Glu Asp Phe Pro Asn Thr Thr Arg
                    1010                1015                1020

Trp Arg Ile Cys Gly Tyr Asp Thr Asn Ser Lys Leu Thr Leu Lys
                    1025                1030                1035

Pro Ile Val Leu Ala Ala Glu Gly Leu Glu Asn Pro Ser Ser Ala
                    1040                1045                1050

Val Asn Glu Ile Val Glu Leu Lys Gly Trp Arg Val Ala Ile Asn
                    1055                1060                1065

Val Leu Thr Lys Val His Pro Thr Val Val Arg Arg Asp Ala Leu
                    1070                1075                1080

Gly Arg Pro Arg Tyr Ser Ser Arg Ser Asn Leu Pro Thr Ser Trp
                    1085                1090                1095

Thr Ile Glu
                    1100

<210> SEQ ID NO 8
```

<211> LENGTH: 1082
<212> TYPE: PRT
<213> ORGANISM: Neisseria meningitidis

<400> SEQUENCE: 8

```
Met Ala Ala Phe Lys Pro Asn Pro Ile Asn Tyr Ile Leu Gly Leu Asp
1               5                   10                  15

Ile Gly Ile Ala Ser Val Gly Trp Ala Met Val Glu Ile Asp Glu Asp
            20                  25                  30

Glu Asn Pro Ile Cys Leu Ile Asp Leu Gly Val Arg Val Phe Glu Arg
        35                  40                  45

Ala Glu Val Pro Lys Thr Gly Asp Ser Leu Ala Met Ala Arg Arg Leu
50                  55                  60

Ala Arg Ser Val Arg Arg Leu Thr Arg Arg Arg Ala His Arg Leu Leu
65                  70                  75                  80

Arg Ala Cys Arg Leu Leu Lys Arg Glu Gly Val Leu Gln Ala Ala Asp
                85                  90                  95

Phe Asp Glu Asn Gly Leu Ile Lys Ser Leu Pro Asn Thr Pro Trp Gln
            100                 105                 110

Leu Arg Ala Ala Ala Leu Asp Arg Lys Leu Thr Pro Leu Glu Trp Ser
        115                 120                 125

Ala Val Leu Leu His Leu Ile Lys His Arg Gly Tyr Leu Ser Gln Arg
130                 135                 140

Lys Asn Glu Gly Glu Thr Ala Asp Lys Glu Leu Gly Ala Leu Leu Lys
145                 150                 155                 160

Gly Val Ala Asp Asn Ala His Ala Leu Gln Thr Gly Asp Phe Arg Thr
                165                 170                 175

Pro Ala Glu Leu Ala Leu Asn Lys Phe Glu Lys Glu Ser Gly His Ile
            180                 185                 190

Arg Asn Gln Arg Gly Asp Tyr Ser His Thr Phe Ser Arg Lys Asp Leu
        195                 200                 205

Gln Ala Glu Leu Ile Leu Leu Phe Glu Lys Gln Lys Glu Phe Gly Asn
210                 215                 220

Pro His Val Ser Gly Gly Leu Lys Glu Gly Ile Glu Thr Leu Leu Met
225                 230                 235                 240

Thr Gln Arg Pro Ala Leu Ser Gly Asp Ala Val Gln Lys Met Leu Gly
                245                 250                 255

His Cys Thr Phe Glu Pro Ala Glu Pro Lys Ala Ala Lys Asn Thr Tyr
            260                 265                 270

Thr Ala Glu Arg Phe Ile Trp Leu Thr Lys Leu Asn Asn Leu Arg Ile
        275                 280                 285

Leu Glu Gln Gly Ser Glu Arg Pro Leu Thr Asp Thr Glu Arg Ala Thr
290                 295                 300

Leu Met Asp Glu Pro Tyr Arg Lys Ser Lys Leu Thr Tyr Ala Gln Ala
305                 310                 315                 320

Arg Lys Leu Leu Gly Leu Glu Asp Thr Ala Phe Phe Lys Gly Leu Arg
                325                 330                 335

Tyr Gly Lys Asp Asn Ala Glu Ala Ser Thr Leu Met Glu Met Lys Ala
            340                 345                 350

Tyr His Ala Ile Ser Arg Ala Leu Glu Lys Glu Gly Leu Lys Asp Lys
        355                 360                 365

Lys Ser Pro Leu Asn Leu Ser Pro Glu Leu Gln Asp Glu Ile Gly Thr
370                 375                 380

Ala Phe Ser Leu Phe Lys Thr Asp Glu Asp Ile Thr Gly Arg Leu Lys
```

```
            385                 390                 395                 400
Asp Arg Ile Gln Pro Glu Ile Leu Glu Ala Leu Leu Lys His Ile Ser
                405                 410                 415
Phe Asp Lys Phe Val Gln Ile Ser Leu Lys Ala Leu Arg Arg Ile Val
                420                 425                 430
Pro Leu Met Glu Gln Gly Lys Arg Tyr Asp Glu Ala Cys Ala Glu Ile
                435                 440                 445
Tyr Gly Asp His Tyr Gly Lys Lys Asn Thr Glu Glu Lys Ile Tyr Leu
            450                 455                 460
Pro Pro Ile Pro Ala Asp Glu Ile Arg Asn Pro Val Val Leu Arg Ala
465                 470                 475                 480
Leu Ser Gln Ala Arg Lys Val Ile Asn Gly Val Val Arg Tyr Gly
                485                 490                 495
Ser Pro Ala Arg Ile His Ile Glu Thr Ala Arg Glu Val Gly Lys Ser
                500                 505                 510
Phe Lys Asp Arg Lys Glu Ile Glu Lys Arg Gln Glu Glu Asn Arg Lys
            515                 520                 525
Asp Arg Glu Lys Ala Ala Ala Lys Phe Arg Glu Tyr Phe Pro Asn Phe
        530                 535                 540
Val Gly Glu Pro Lys Ser Lys Asp Ile Leu Lys Leu Arg Leu Tyr Glu
545                 550                 555                 560
Gln Gln His Gly Lys Cys Leu Tyr Ser Gly Lys Glu Ile Asn Leu Gly
                565                 570                 575
Arg Leu Asn Glu Lys Gly Tyr Val Glu Ile Asp His Ala Leu Pro Phe
            580                 585                 590
Ser Arg Thr Trp Asp Asp Ser Phe Asn Asn Lys Val Leu Val Leu Gly
        595                 600                 605
Ser Glu Asn Gln Asn Lys Gly Asn Gln Thr Pro Tyr Glu Tyr Phe Asn
    610                 615                 620
Gly Lys Asp Asn Ser Arg Glu Trp Gln Glu Phe Lys Ala Arg Val Glu
625                 630                 635                 640
Thr Ser Arg Phe Pro Arg Ser Lys Lys Gln Arg Ile Leu Leu Gln Lys
                645                 650                 655
Phe Asp Glu Asp Gly Phe Lys Glu Arg Asn Leu Asn Asp Thr Arg Tyr
            660                 665                 670
Val Asn Arg Phe Leu Cys Gln Phe Val Ala Asp Arg Met Arg Leu Thr
        675                 680                 685
Gly Lys Gly Lys Lys Arg Val Phe Ala Ser Asn Gly Gln Ile Thr Asn
        690                 695                 700
Leu Leu Arg Gly Phe Trp Gly Leu Arg Lys Val Arg Ala Glu Asn Asp
705                 710                 715                 720
Arg His His Ala Leu Asp Ala Val Val Val Ala Cys Ser Thr Val Ala
                725                 730                 735
Met Gln Gln Lys Ile Thr Arg Phe Val Arg Tyr Lys Glu Met Asn Ala
                740                 745                 750
Phe Asp Gly Lys Thr Ile Asp Lys Glu Thr Gly Glu Val Leu His Gln
            755                 760                 765
Lys Thr His Phe Pro Gln Pro Trp Glu Phe Phe Ala Gln Glu Val Met
        770                 775                 780
Ile Arg Val Phe Gly Lys Pro Asp Gly Lys Pro Glu Phe Glu Glu Ala
785                 790                 795                 800
Asp Thr Pro Glu Lys Leu Arg Thr Leu Leu Ala Glu Lys Leu Ser Ser
                805                 810                 815
```

```
Arg Pro Glu Ala Val His Glu Tyr Val Thr Pro Leu Phe Val Ser Arg
            820                 825                 830

Ala Pro Asn Arg Lys Met Ser Gly Gln Gly His Met Glu Thr Val Lys
            835                 840                 845

Ser Ala Lys Arg Leu Asp Glu Gly Val Ser Val Leu Arg Val Pro Leu
    850                 855                 860

Thr Gln Leu Lys Leu Lys Asp Leu Gly Lys Met Val Asn Arg Glu Arg
865                 870                 875                 880

Glu Pro Lys Leu Tyr Glu Ala Leu Lys Ala Arg Leu Glu Ala His Lys
                885                 890                 895

Asp Asp Pro Ala Lys Ala Phe Ala Glu Pro Phe Tyr Lys Tyr Asp Lys
            900                 905                 910

Ala Gly Asn Arg Thr Gln Gln Val Lys Ala Val Arg Val Glu Gln Val
            915                 920                 925

Gln Lys Thr Gly Val Trp Val Arg Asn His Asn Gly Ile Ala Asp Asn
930                 935                 940

Ala Thr Met Val Arg Val Asp Val Phe Glu Lys Gly Asp Lys Tyr Tyr
945                 950                 955                 960

Leu Val Pro Ile Tyr Ser Trp Gln Val Ala Lys Gly Ile Leu Pro Asp
                965                 970                 975

Arg Ala Val Val Gln Gly Lys Asp Glu Glu Asp Trp Gln Leu Ile Asp
            980                 985                 990

Asp Ser Phe Asn Phe Lys Phe Ser Leu His Pro Asn Asp Leu Val Glu
            995                 1000                1005

Val Ile Thr Lys Lys Ala Arg Met Phe Gly Tyr Phe Ala Ser Cys
    1010                1015                1020

His Arg Gly Thr Gly Asn Ile Asn Ile Arg Ile His Asp Leu Asp
    1025                1030                1035

His Lys Ile Gly Lys Asn Gly Ile Leu Glu Gly Ile Gly Val Lys
    1040                1045                1050

Thr Ala Leu Ser Phe Gln Lys Tyr Gln Ile Asp Glu Leu Gly Lys
    1055                1060                1065

Glu Ile Arg Pro Cys Arg Leu Lys Lys Arg Pro Pro Val Arg
    1070                1075                1080
```

<210> SEQ ID NO 9
<211> LENGTH: 987
<212> TYPE: PRT
<213> ORGANISM: Campylobacter jejuni

<400> SEQUENCE: 9

```
Met Ala Arg Ile Leu Ala Phe Asp Ile Gly Ile Ser Ser Ile Gly Trp
1               5                   10                  15

Ala Phe Ser Glu Asn Asp Glu Leu Lys Asp Cys Gly Val Arg Ile Phe
                20                  25                  30

Thr Lys Ala Glu Asn Pro Lys Thr Gly Glu Ser Leu Ala Leu Pro Arg
            35                  40                  45

Arg Leu Ala Arg Ser Ala Arg Lys Arg Leu Ala Arg Lys Ala Arg
    50                  55                  60

Leu Asn His Leu Lys His Leu Ile Ala Asn Glu Phe Lys Leu Asn Tyr
65                  70                  75                  80

Glu Asp Tyr Gln Ser Phe Asp Glu Ser Leu Ala Lys Ala Tyr Lys Gly
                85                  90                  95

Ser Leu Ile Ser Pro Tyr Glu Leu Arg Phe Arg Ala Leu Asn Glu Leu
```

```
            100                 105                 110
Leu Ser Lys Gln Asp Phe Ala Arg Val Ile Leu His Ile Ala Lys Arg
        115                 120                 125

Arg Gly Tyr Asp Asp Ile Lys Asn Asn Gly Asp Glu Glu Lys Ser Glu
        130                 135                 140

Ile Leu Lys Ala Ile Lys Gln Asn Glu Glu Lys Leu Val Asn Tyr Gln
145                 150                 155                 160

Ser Val Gly Glu Tyr Leu Tyr Lys Glu Tyr Phe Gln Lys Phe Lys Glu
                165                 170                 175

Asn Ser Lys Glu Phe Ile Asn Val Arg Asn Lys Glu Ser Tyr Glu
            180                 185                 190

Arg Cys Ile Ala Gln Ser Phe Leu Lys Asp Glu Leu Lys Leu Ile Phe
        195                 200                 205

Gln Lys Gln Arg Glu Phe Gly Phe Ser Phe Ser Lys Lys Phe Glu Glu
        210                 215                 220

Glu Val Leu Ser Val Ala Phe Tyr Lys Arg Ala Leu Lys Asp Phe Ser
225                 230                 235                 240

His Leu Val Gly Asn Cys Ser Phe Phe Thr Asp Glu Lys Arg Ala Pro
                245                 250                 255

Lys Asn Ser Pro Leu Ala Phe Met Phe Val Ala Leu Thr Arg Ile Ile
            260                 265                 270

Asn Leu Leu Asn Asn Leu Lys Asn Thr Glu Gly Ile Leu Tyr Thr Lys
        275                 280                 285

Asp Asp Leu Asn Thr Leu Leu Asn Glu Val Leu Lys Asn Gly Thr Leu
        290                 295                 300

Thr Tyr Lys Gln Thr Lys Lys Leu Leu Gly Leu Ser Asp Asp Tyr Glu
305                 310                 315                 320

Phe Lys Gly Glu Lys Gly Thr Tyr Phe Ile Glu Phe Lys Lys Tyr Lys
                325                 330                 335

Glu Phe Ile Lys Ala Leu Gly Glu His Asn Leu Ser Gln Asp Asn Leu
            340                 345                 350

Asn Glu Ile Ala Lys Asp Ile Thr Leu Ile Lys Asp Glu Ile Lys Leu
        355                 360                 365

Lys Lys Ala Leu Ala Lys Tyr Asp Leu Asn Gln Asn Gln Ile Asp Ser
        370                 375                 380

Leu Ser Lys Leu Glu Phe Lys Asp His Leu Asn Ile Ser Phe Lys Ala
385                 390                 395                 400

Leu Lys Leu Ile Thr Pro Leu Met Leu Glu Gly Lys Lys Tyr Asp Glu
                405                 410                 415

Ala Tyr Asn Glu Leu Asn Leu Lys Val Ala Ile Asn Glu Asp Lys Lys
            420                 425                 430

Asp Phe Leu Pro Ala Phe Asn Glu Thr Tyr Tyr Lys Asp Glu Val Thr
        435                 440                 445

Asn Pro Val Val Leu Arg Ala Ile Lys Glu Tyr Arg Lys Val Leu Asn
        450                 455                 460

Ala Leu Leu Lys Lys Tyr Gly Lys Val His Lys Ile Asn Ile Glu Leu
465                 470                 475                 480

Ala Arg Glu Val Gly Lys Asn His Ser Gln Arg Ala Lys Ile Glu Lys
                485                 490                 495

Glu Gln Asn Glu Asn Tyr Lys Ala Lys Lys Asp Ala Glu Leu Glu Cys
            500                 505                 510

Glu Lys Leu Gly Leu Lys Ile Asn Ser Lys Asn Ile Leu Lys Leu Arg
        515                 520                 525
```

```
Leu Phe Lys Glu Gln Lys Glu Phe Cys Ala Tyr Ser Gly Glu Lys Ile
    530                 535                 540

Lys Ile Ser Asp Leu Gln Asp Glu Lys Met Leu Glu Ile Asp His Ile
545                 550                 555                 560

Tyr Pro Tyr Ser Arg Ser Phe Asp Asp Ser Tyr Met Asn Lys Val Leu
                565                 570                 575

Val Phe Thr Lys Gln Asn Gln Glu Lys Leu Asn Gln Thr Pro Phe Glu
            580                 585                 590

Ala Phe Gly Asn Asp Ser Ala Lys Trp Gln Lys Ile Glu Val Leu Ala
        595                 600                 605

Lys Asn Leu Pro Thr Lys Gln Lys Arg Ile Leu Asp Lys Asn Tyr
610                 615                 620

Lys Asp Lys Glu Gln Lys Asp Phe Lys Asp Arg Asn Leu Asn Asp Thr
625                 630                 635                 640

Arg Tyr Ile Ala Arg Leu Val Leu Asn Tyr Thr Lys Asp Tyr Leu Asp
                645                 650                 655

Phe Leu Pro Leu Ser Asp Asp Glu Asn Thr Lys Leu Asn Asp Thr Gln
            660                 665                 670

Lys Gly Ser Lys Val His Val Glu Ala Lys Ser Gly Met Leu Thr Ser
        675                 680                 685

Ala Leu Arg His Thr Trp Gly Phe Ser Ala Lys Asp Arg Asn Asn His
690                 695                 700

Leu His His Ala Ile Asp Ala Val Ile Ile Ala Tyr Ala Asn Asn Ser
705                 710                 715                 720

Ile Val Lys Ala Phe Ser Asp Phe Lys Lys Glu Gln Glu Ser Asn Ser
                725                 730                 735

Ala Glu Leu Tyr Ala Lys Lys Ile Ser Glu Leu Asp Tyr Lys Asn Lys
            740                 745                 750

Arg Lys Phe Phe Glu Pro Phe Ser Gly Phe Arg Gln Lys Val Leu Asp
        755                 760                 765

Lys Ile Asp Glu Ile Phe Val Ser Lys Pro Glu Arg Lys Lys Pro Ser
770                 775                 780

Gly Ala Leu His Glu Glu Thr Phe Arg Lys Glu Glu Phe His Gln
785                 790                 795                 800

Ser Tyr Gly Gly Lys Glu Gly Val Leu Lys Ala Leu Glu Leu Gly Lys
                805                 810                 815

Ile Arg Lys Val Asn Gly Lys Ile Val Lys Asn Gly Asp Met Phe Arg
            820                 825                 830

Val Asp Ile Phe Lys His Lys Lys Thr Asn Lys Phe Tyr Ala Val Pro
        835                 840                 845

Ile Tyr Thr Met Asp Phe Ala Leu Lys Val Leu Pro Asn Lys Ala Val
850                 855                 860

Val Gln Gly Lys Asp Lys Lys Ser Gly Leu Ile Lys Asp Trp Ile Leu
865                 870                 875                 880

Met Asp Glu Asn Tyr Glu Phe Cys Phe Ser Leu Tyr Lys Asp Ser Leu
                885                 890                 895

Ile Leu Ile Gln Thr Lys Asp Met Gln Glu Pro Glu Leu Val Tyr Phe
            900                 905                 910

Asn Ala Phe Thr Ser Ser Thr Val Ser Leu Ile Val Ser Lys His Asp
        915                 920                 925

Asn Lys Phe Glu Thr Leu Ser Lys Asn Gln Lys Ile Leu Phe Lys Asn
930                 935                 940
```

```
Ala Asn Glu Lys Glu Val Ile Ala Lys Ser Ile Gly Ile Gln Asn Leu
945                 950                 955                 960

Lys Val Phe Glu Lys Tyr Ile Val Ser Ala Leu Gly Glu Val Thr Lys
            965                 970                 975

Ala Glu Phe Arg Gln Arg Glu Asp Phe Lys Lys
        980                 985

<210> SEQ ID NO 10
<211> LENGTH: 1395
<212> TYPE: PRT
<213> ORGANISM: Treponema denticola

<400> SEQUENCE: 10

Met Lys Lys Glu Ile Lys Asp Tyr Phe Leu Gly Leu Asp Val Gly Thr
1               5                   10                  15

Gly Ser Val Gly Trp Ala Val Thr Asp Thr Asp Tyr Lys Leu Leu Lys
            20                  25                  30

Ala Asn Arg Lys Asp Leu Trp Gly Met Arg Cys Phe Glu Thr Ala Glu
        35                  40                  45

Thr Ala Glu Val Arg Arg Leu His Arg Gly Ala Arg Arg Arg Ile Glu
    50                  55                  60

Arg Arg Lys Lys Arg Ile Lys Leu Leu Gln Glu Leu Phe Ser Gln Glu
65                  70                  75                  80

Ile Ala Lys Ile Asp Glu Gly Phe Phe Gln Arg Met Lys Glu Ser Pro
                85                  90                  95

Leu Tyr Ala Glu Asp Lys Thr Ile Leu Gln Glu Asn Thr Leu Phe Asn
            100                 105                 110

Asp Lys Asp Phe Thr Asp Lys Thr Tyr His Lys Ala Tyr Pro Thr Ile
        115                 120                 125

Asn His Leu Ile Lys Ala Trp Ile Glu Asn Lys Val Lys Pro Asp Pro
    130                 135                 140

Arg Leu Leu Tyr Leu Ala Cys His Asn Ile Ile Lys Lys Arg Gly His
145                 150                 155                 160

Phe Leu Phe Glu Gly Asp Phe Asp Ser Glu Asn Gln Phe Asp Thr Ser
                165                 170                 175

Ile Gln Ala Leu Phe Glu Tyr Leu Arg Glu Asp Met Glu Val Asp Ile
            180                 185                 190

Asp Ala Asp Ser Gln Lys Val Lys Glu Ile Leu Lys Asp Ser Ser Leu
        195                 200                 205

Lys Asn Ser Glu Lys Gln Ser Arg Leu Asn Lys Met Leu Gly Leu Lys
    210                 215                 220

Pro Ser Asp Lys Gln Lys Lys Ala Ile Thr Asn Leu Ile Ser Gly Asn
225                 230                 235                 240

Lys Ile Asn Phe Ala Asp Leu Tyr Asp Asn Pro Asp Leu Lys Asp Ala
                245                 250                 255

Glu Lys Asn Ser Ile Ser Phe Ser Lys Asp Asp Phe Asp Ala Leu Ser
            260                 265                 270

Asp Asp Leu Ala Ser Ile Leu Gly Asp Ser Phe Glu Leu Leu Leu Lys
        275                 280                 285

Ala Lys Ala Val Tyr Asn Cys Ser Val Leu Ser Lys Val Ile Gly Asp
    290                 295                 300

Glu Gln Tyr Leu Ser Phe Ala Lys Val Lys Ile Tyr Glu Lys His Lys
305                 310                 315                 320

Thr Asp Leu Thr Lys Leu Lys Asn Val Ile Lys Lys His Phe Pro Lys
                325                 330                 335
```

```
Asp Tyr Lys Lys Val Phe Gly Tyr Asn Lys Asn Glu Lys Asn Asn Asn
                340                 345                 350

Asn Tyr Ser Gly Tyr Val Gly Val Cys Lys Thr Lys Ser Lys Lys Leu
                355                 360                 365

Ile Ile Asn Asn Ser Val Asn Gln Glu Asp Phe Tyr Lys Phe Leu Lys
370                 375                 380

Thr Ile Leu Ser Ala Lys Ser Glu Ile Lys Glu Val Asn Asp Ile Leu
385                 390                 395                 400

Thr Glu Ile Glu Thr Gly Thr Phe Leu Pro Lys Gln Ile Ser Lys Ser
                405                 410                 415

Asn Ala Glu Ile Pro Tyr Gln Leu Arg Lys Met Glu Leu Glu Lys Ile
                420                 425                 430

Leu Ser Asn Ala Glu Lys His Phe Ser Phe Leu Lys Gln Lys Asp Glu
                435                 440                 445

Lys Gly Leu Ser His Ser Glu Lys Ile Ile Met Leu Leu Thr Phe Lys
                450                 455                 460

Ile Pro Tyr Tyr Ile Gly Pro Ile Asn Asp Asn His Lys Lys Ser Phe
465                 470                 475                 480

Pro Asp Arg Cys Trp Val Val Lys Lys Glu Lys Ser Pro Ser Gly Lys
                485                 490                 495

Thr Thr Pro Trp Asn Phe Phe Asp His Ile Asp Lys Glu Lys Thr Ala
                500                 505                 510

Glu Glu Phe Ile Thr Ser Arg Thr Asn Phe Cys Thr Tyr Leu Ile Gly
                515                 520                 525

Glu Ser Val Leu Pro Lys Asn Ser Leu Leu Tyr Ser Glu Tyr Thr Val
                530                 535                 540

Leu Asn Glu Ile Asn Asn Leu Gln Ile Ile Ile Asp Gly Lys Asn Ile
545                 550                 555                 560

Cys Asp Thr Lys Leu Lys Gln Lys Ile Tyr Glu Glu Leu Phe Lys Lys
                565                 570                 575

Tyr Lys Lys Ile Thr Gln Lys Gln Ile Ser Thr Phe Ile Lys His Glu
                580                 585                 590

Gly Ile Cys Asn Lys Thr Asp Glu Val Ile Ile Leu Gly Ile Asp Lys
                595                 600                 605

Glu Cys Thr Ser Ser Leu Lys Ser Tyr Ile Glu Leu Lys Asn Ile Phe
                610                 615                 620

Gly Lys Gln Val Asp Glu Ile Ser Thr Lys Asn Met Leu Glu Glu Ile
625                 630                 635                 640

Ile Arg Trp Ala Thr Ile Tyr Asp Glu Gly Glu Gly Lys Thr Ile Leu
                645                 650                 655

Lys Thr Lys Ile Lys Ala Glu Tyr Gly Lys Tyr Cys Ser Asp Glu Gln
                660                 665                 670

Ile Lys Lys Ile Leu Asn Leu Lys Phe Ser Gly Trp Gly Arg Leu Ser
                675                 680                 685

Arg Lys Phe Leu Glu Thr Val Thr Ser Glu Met Pro Gly Phe Ser Glu
                690                 695                 700

Pro Val Asn Ile Ile Thr Ala Met Arg Glu Thr Gln Asn Asn Leu Met
705                 710                 715                 720

Glu Leu Leu Ser Ser Glu Phe Lys Phe Thr Glu Asn Ile Lys Lys Ile
                725                 730                 735

Asn Ser Gly Phe Glu Asp Val Glu Lys Gln Phe Ser Tyr Asp Gly Leu
                740                 745                 750
```

-continued

Val Lys Pro Leu Phe Leu Ser Pro Ser Val Lys Lys Met Leu Trp Gln
                755                 760                 765

Thr Leu Lys Leu Val Lys Glu Ile Ser His Ile Thr Gln Ala Pro Pro
    770                 775                 780

Lys Lys Ile Phe Ile Glu Met Ala Lys Gly Ala Glu Leu Asp Pro Val
785                 790                 795                 800

Arg Thr Lys Thr Arg Leu Lys Ile Leu Gln Asp Leu Tyr Asn Asn Cys
        805                 810                 815

Lys Asn Asp Ala Asp Ala Phe Ser Ser Glu Ile Lys Asp Leu Ser Gly
            820                 825                 830

Lys Ile Glu Asn Glu Asp Asn Leu Arg Leu Arg Ser Asp Lys Leu Tyr
                835                 840                 845

Leu Tyr Tyr Thr Gln Leu Gly Lys Cys Met Tyr Cys Gly Lys Pro Ile
    850                 855                 860

Glu Ile Gly His Val Phe Asp Thr Ser Asn Tyr Asp Ile Asp His Ile
865                 870                 875                 880

Tyr Pro Gln Ser Lys Ile Lys Asp Asp Ser Ile Ser Asn Arg Val Leu
            885                 890                 895

Val Cys Ser Ser Cys Asn Lys Asn Lys Glu Asp Lys Tyr Pro Leu Lys
                900                 905                 910

Ala Glu Ile Gln Ser Lys Gln Arg Gly Phe Trp Asn Phe Leu Gln Arg
    915                 920                 925

Asn Asn Phe Ile Ser Leu Glu Lys Phe Asn Arg Leu Thr Arg Ala Thr
    930                 935                 940

Pro Ile Ser Asp Asp Glu Thr Ala Lys Phe Ile Ala Arg Gln Leu Val
945                 950                 955                 960

Glu Thr Arg Gln Ala Thr Lys Val Ala Ala Arg Val Leu Glu Lys Met
            965                 970                 975

Phe Pro Glu Thr Lys Ile Val Tyr Ser Lys Ala Glu Thr Val Ser Met
                980                 985                 990

Phe Arg Asn Lys Phe Asp Ile Val Lys Cys Arg Glu Ile Asn Asp Phe
            995                 1000                1005

His His Ala His Asp Ala Tyr Leu Asn Ile Val Val Gly Asn Val
    1010                1015                1020

Tyr Asn Thr Lys Phe Thr Asn Leu Trp Asn Phe Ile Lys Glu
    1025                1030                1035

Lys Arg Asp Asn Pro Lys Ile Ala Asp Thr Tyr Asn Tyr Tyr Lys
    1040                1045                1050

Val Phe Asp Tyr Asp Val Lys Arg Asn Asn Ile Thr Ala Trp Glu
    1055                1060                1065

Lys Gly Lys Thr Ile Ile Thr Val Lys Asp Met Leu Lys Arg Asn
    1070                1075                1080

Thr Pro Ile Tyr Thr Arg Gln Ala Ala Cys Lys Lys Gly Gly Leu
    1085                1090                1095

Phe Asp Gln Thr Ile Met Lys Lys Gly Leu Gly Gln His Pro Leu
    1100                1105                1110

Lys Lys Glu Gly Pro Phe Ser Asn Ile Ser Lys Tyr Gly Gly Tyr
    1115                1120                1125

Asn Lys Val Ser Ala Ala Tyr Tyr Thr Leu Ile Glu Tyr Glu Glu
    1130                1135                1140

Lys Gly Asn Lys Ile Arg Ser Leu Glu Thr Ile Pro Leu Tyr Leu
    1145                1150                1155

Val Lys Asp Ile Gln Lys Asp Gln Asp Val Leu Lys Ser Tyr Leu

```
            1160                1165                1170

Thr Asp Leu Leu Gly Lys Lys Glu Phe Lys Ile Leu Val Pro Lys
    1175                1180                1185

Ile Lys Ile Asn Ser Leu Leu Lys Ile Asn Gly Phe Pro Cys His
    1190                1195                1200

Ile Thr Gly Lys Thr Asn Asp Ser Phe Leu Leu Arg Pro Ala Val
    1205                1210                1215

Gln Phe Cys Cys Ser Asn Asp Glu Val Leu Tyr Phe Lys Lys Ile
    1220                1225                1230

Ile Arg Phe Ser Glu Ile Arg Ser Gln Arg Glu Lys Ile Gly Lys
    1235                1240                1245

Thr Ile Ser Pro Tyr Glu Asp Leu Ser Phe Arg Ser Tyr Ile Lys
    1250                1255                1260

Glu Asn Leu Cys Lys Lys Thr Lys Asn Asp Glu Ile Gly Glu Lys
    1265                1270                1275

Glu Phe Tyr Asp Leu Leu Gln Lys Lys Asn Leu Glu Ile Tyr Asp
    1280                1285                1290

Met Leu Leu Thr Lys His Lys Asp Thr Ile Tyr Lys Lys Arg Pro
    1295                1300                1305

Asn Ser Ala Thr Ile Asp Ile Leu Val Lys Gly Lys Glu Lys Phe
    1310                1315                1320

Lys Ser Leu Ile Ile Glu Asn Gln Phe Glu Val Ile Leu Glu Ile
    1325                1330                1335

Leu Lys Leu Phe Ser Ala Thr Arg Asn Val Ser Asp Leu Gln His
    1340                1345                1350

Ile Gly Gly Ser Lys Tyr Ser Gly Val Ala Lys Ile Gly Asn Lys
    1355                1360                1365

Ile Ser Ser Leu Asp Asn Cys Ile Leu Ile Tyr Gln Ser Ile Thr
    1370                1375                1380

Gly Ile Phe Glu Lys Arg Ile Asp Leu Leu Lys Val
    1385                1390                1395

<210> SEQ ID NO 11
<211> LENGTH: 1388
<212> TYPE: PRT
<213> ORGANISM: Streptococcus thermophilus

<400> SEQUENCE: 11

Met Thr Lys Pro Tyr Ser Ile Gly Leu Asp Ile Gly Thr Asn Ser Val
1               5                   10                  15

Gly Trp Ala Val Thr Thr Asp Asn Tyr Lys Val Pro Ser Lys Lys Met
            20                  25                  30

Lys Val Leu Gly Asn Thr Ser Lys Lys Tyr Ile Lys Lys Asn Leu Leu
        35                  40                  45

Gly Val Leu Leu Phe Asp Ser Gly Ile Thr Ala Glu Gly Arg Arg Leu
    50                  55                  60

Lys Arg Thr Ala Arg Arg Arg Tyr Thr Arg Arg Arg Asn Arg Ile Leu
65                  70                  75                  80

Tyr Leu Gln Glu Ile Phe Ser Thr Glu Met Ala Thr Leu Asp Asp Ala
                85                  90                  95

Phe Phe Gln Arg Leu Asp Asp Ser Phe Leu Val Pro Asp Asp Lys Arg
            100                 105                 110

Asp Ser Lys Tyr Pro Ile Phe Gly Asn Leu Val Glu Glu Lys Ala Tyr
        115                 120                 125
```

```
His Asp Glu Phe Pro Thr Ile Tyr His Leu Arg Lys Tyr Leu Ala Asp
        130                 135                 140

Ser Thr Lys Lys Ala Asp Leu Arg Leu Val Tyr Leu Ala Leu Ala His
145                 150                 155                 160

Met Ile Lys Tyr Arg Gly His Phe Leu Ile Glu Gly Glu Phe Asn Ser
                165                 170                 175

Lys Asn Asn Asp Ile Gln Lys Asn Phe Gln Asp Phe Leu Asp Thr Tyr
            180                 185                 190

Asn Ala Ile Phe Glu Ser Asp Leu Ser Leu Glu Asn Ser Lys Gln Leu
        195                 200                 205

Glu Glu Ile Val Lys Asp Lys Ile Ser Lys Leu Glu Lys Lys Asp Arg
210                 215                 220

Ile Leu Lys Leu Phe Pro Gly Glu Lys Asn Ser Gly Ile Phe Ser Glu
225                 230                 235                 240

Phe Leu Lys Leu Ile Val Gly Asn Gln Ala Asp Phe Arg Lys Cys Phe
                245                 250                 255

Asn Leu Asp Glu Lys Ala Ser Leu His Phe Ser Lys Glu Ser Tyr Asp
            260                 265                 270

Glu Asp Leu Glu Thr Leu Leu Gly Tyr Ile Gly Asp Asp Tyr Ser Asp
        275                 280                 285

Val Phe Leu Lys Ala Lys Lys Leu Tyr Asp Ala Ile Leu Leu Ser Gly
290                 295                 300

Phe Leu Thr Val Thr Asp Asn Glu Thr Glu Ala Pro Leu Ser Ser Ala
305                 310                 315                 320

Met Ile Lys Arg Tyr Asn Glu His Lys Glu Asp Leu Ala Leu Leu Lys
                325                 330                 335

Glu Tyr Ile Arg Asn Ile Ser Leu Lys Thr Tyr Asn Glu Val Phe Lys
            340                 345                 350

Asp Asp Thr Lys Asn Gly Tyr Ala Gly Tyr Ile Asp Gly Lys Thr Asn
        355                 360                 365

Gln Glu Asp Phe Tyr Val Tyr Leu Lys Lys Leu Leu Ala Glu Phe Glu
370                 375                 380

Gly Ala Asp Tyr Phe Leu Glu Lys Ile Asp Arg Glu Asp Phe Leu Arg
385                 390                 395                 400

Lys Gln Arg Thr Phe Asp Asn Gly Ser Ile Pro Tyr Gln Ile His Leu
                405                 410                 415

Gln Glu Met Arg Ala Ile Leu Asp Lys Gln Ala Lys Phe Tyr Pro Phe
            420                 425                 430

Leu Ala Lys Asn Lys Glu Arg Ile Glu Lys Ile Leu Thr Phe Arg Ile
        435                 440                 445

Pro Tyr Tyr Val Gly Pro Leu Ala Arg Gly Asn Ser Asp Phe Ala Trp
450                 455                 460

Ser Ile Arg Lys Arg Asn Glu Lys Ile Thr Pro Trp Asn Phe Glu Asp
465                 470                 475                 480

Val Ile Asp Lys Glu Ser Ser Ala Glu Ala Phe Ile Asn Arg Met Thr
                485                 490                 495

Ser Phe Asp Leu Tyr Leu Pro Glu Glu Lys Val Leu Pro Lys His Ser
            500                 505                 510

Leu Leu Tyr Glu Thr Phe Asn Val Tyr Asn Glu Leu Thr Lys Val Arg
        515                 520                 525

Phe Ile Ala Glu Ser Met Arg Asp Tyr Gln Phe Leu Asp Ser Lys Gln
530                 535                 540

Lys Lys Asp Ile Val Arg Leu Tyr Phe Lys Asp Lys Arg Lys Val Thr
```

```
            545                 550                 555                 560
Asp Lys Asp Ile Ile Glu Tyr Leu His Ala Ile Tyr Gly Tyr Asp Gly
                565                 570                 575
Ile Glu Leu Lys Gly Ile Glu Lys Gln Phe Asn Ser Ser Leu Ser Thr
                580                 585                 590
Tyr His Asp Leu Leu Asn Ile Asn Asp Lys Glu Phe Leu Asp Asp
                595                 600                 605
Ser Ser Asn Glu Ala Ile Ile Glu Glu Ile Ile His Thr Leu Thr Ile
610                 615                 620
Phe Glu Asp Arg Glu Met Ile Lys Gln Arg Leu Ser Lys Phe Glu Asn
625                 630                 635                 640
Ile Phe Asp Lys Ser Val Leu Lys Lys Leu Ser Arg Arg His Tyr Thr
                645                 650                 655
Gly Trp Gly Lys Leu Ser Ala Lys Leu Ile Asn Gly Ile Arg Asp Glu
                660                 665                 670
Lys Ser Gly Asn Thr Ile Leu Asp Tyr Leu Ile Asp Asp Gly Ile Ser
                675                 680                 685
Asn Arg Asn Phe Met Gln Leu Ile His Asp Asp Ala Leu Ser Phe Lys
                690                 695                 700
Lys Lys Ile Gln Lys Ala Gln Ile Ile Gly Asp Glu Asp Lys Gly Asn
705                 710                 715                 720
Ile Lys Glu Val Val Lys Ser Leu Pro Gly Ser Pro Ala Ile Lys Lys
                725                 730                 735
Gly Ile Leu Gln Ser Ile Lys Ile Val Asp Glu Leu Val Lys Val Met
                740                 745                 750
Gly Gly Arg Lys Pro Glu Ser Ile Val Val Glu Met Ala Arg Glu Asn
                755                 760                 765
Gln Tyr Thr Asn Gln Gly Lys Ser Asn Ser Gln Arg Leu Lys Arg
                770                 775                 780
Leu Glu Lys Ser Leu Lys Glu Leu Gly Ser Lys Ile Leu Lys Glu Asn
785                 790                 795                 800
Ile Pro Ala Lys Leu Ser Lys Ile Asp Asn Asn Ala Leu Gln Asn Asp
                805                 810                 815
Arg Leu Tyr Leu Tyr Tyr Leu Gln Asn Gly Lys Asp Met Tyr Thr Gly
                820                 825                 830
Asp Asp Leu Asp Ile Asp Arg Leu Ser Asn Tyr Asp Ile Asp His Ile
                835                 840                 845
Ile Pro Gln Ala Phe Leu Lys Asp Asn Ser Ile Asp Asn Lys Val Leu
                850                 855                 860
Val Ser Ser Ala Ser Asn Arg Gly Lys Ser Asp Asp Val Pro Ser Leu
865                 870                 875                 880
Glu Val Val Lys Lys Arg Lys Thr Phe Trp Tyr Gln Leu Leu Lys Ser
                885                 890                 895
Lys Leu Ile Ser Gln Arg Lys Phe Asp Asn Leu Thr Lys Ala Glu Arg
                900                 905                 910
Gly Gly Leu Ser Pro Glu Asp Lys Ala Gly Phe Ile Gln Arg Gln Leu
                915                 920                 925
Val Glu Thr Arg Gln Ile Thr Lys His Val Ala Arg Leu Leu Asp Glu
                930                 935                 940
Lys Phe Asn Asn Lys Lys Asp Glu Asn Asn Arg Ala Val Arg Thr Val
945                 950                 955                 960
Lys Ile Ile Thr Leu Lys Ser Thr Leu Val Ser Gln Phe Arg Lys Asp
                965                 970                 975
```

-continued

```
Phe Glu Leu Tyr Lys Val Arg Glu Ile Asn Asp Phe His His Ala His
            980                 985                 990

Asp Ala Tyr Leu Asn Ala Val Val Ala Ser Ala Leu Leu Lys Lys Tyr
            995                1000                1005

Pro Lys Leu Glu Pro Glu Phe Val Tyr Gly Asp Tyr Pro Lys Tyr
    1010                1015                1020

Asn Ser Phe Arg Glu Arg Lys Ser Ala Thr Glu Lys Val Tyr Phe
    1025                1030                1035

Tyr Ser Asn Ile Met Asn Ile Phe Lys Lys Ser Ile Ser Leu Ala
    1040                1045                1050

Asp Gly Arg Val Ile Glu Arg Pro Leu Ile Glu Val Asn Glu Glu
    1055                1060                1065

Thr Gly Glu Ser Val Trp Asn Lys Glu Ser Asp Leu Ala Thr Val
    1070                1075                1080

Arg Arg Val Leu Ser Tyr Pro Gln Val Asn Val Val Lys Lys Val
    1085                1090                1095

Glu Glu Gln Asn His Gly Leu Asp Arg Gly Lys Pro Lys Gly Leu
    1100                1105                1110

Phe Asn Ala Asn Leu Ser Ser Lys Pro Lys Pro Asn Ser Asn Glu
    1115                1120                1125

Asn Leu Val Gly Ala Lys Glu Tyr Leu Asp Pro Lys Lys Tyr Gly
    1130                1135                1140

Gly Tyr Ala Gly Ile Ser Asn Ser Phe Thr Val Leu Val Lys Gly
    1145                1150                1155

Thr Ile Glu Lys Gly Ala Lys Lys Lys Ile Thr Asn Val Leu Glu
    1160                1165                1170

Phe Gln Gly Ile Ser Ile Leu Asp Arg Ile Asn Tyr Arg Lys Asp
    1175                1180                1185

Lys Leu Asn Phe Leu Leu Glu Lys Gly Tyr Lys Asp Ile Glu Leu
    1190                1195                1200

Ile Ile Glu Leu Pro Lys Tyr Ser Leu Phe Glu Leu Ser Asp Gly
    1205                1210                1215

Ser Arg Arg Met Leu Ala Ser Ile Leu Ser Thr Asn Asn Lys Arg
    1220                1225                1230

Gly Glu Ile His Lys Gly Asn Gln Ile Phe Leu Ser Gln Lys Phe
    1235                1240                1245

Val Lys Leu Leu Tyr His Ala Lys Arg Ile Ser Asn Thr Ile Asn
    1250                1255                1260

Glu Asn His Arg Lys Tyr Val Glu Asn His Lys Lys Glu Phe Glu
    1265                1270                1275

Glu Leu Phe Tyr Tyr Ile Leu Glu Phe Asn Glu Asn Tyr Val Gly
    1280                1285                1290

Ala Lys Lys Asn Gly Lys Leu Leu Asn Ser Ala Phe Gln Ser Trp
    1295                1300                1305

Gln Asn His Ser Ile Asp Glu Leu Cys Ser Ser Phe Ile Gly Pro
    1310                1315                1320

Thr Gly Ser Glu Arg Lys Gly Leu Phe Glu Leu Thr Ser Arg Gly
    1325                1330                1335

Ser Ala Ala Asp Phe Glu Phe Leu Gly Val Lys Ile Pro Arg Tyr
    1340                1345                1350

Arg Asp Tyr Thr Pro Ser Ser Leu Leu Lys Asp Ala Thr Leu Ile
    1355                1360                1365
```

```
His Gln Ser Val Thr Gly Leu Tyr Glu Thr Arg Ile Asp Leu Ala
    1370                1375                1380

Lys Leu Gly Glu Gly
    1385

<210> SEQ ID NO 12
<211> LENGTH: 1345
<212> TYPE: PRT
<213> ORGANISM: Streptococcus mutans

<400> SEQUENCE: 12

Met Lys Lys Pro Tyr Ser Ile Gly Leu Asp Ile Gly Thr Asn Ser Val
1               5                   10                  15

Gly Trp Ala Val Val Thr Asp Asp Tyr Lys Val Pro Ala Lys Lys Met
            20                  25                  30

Lys Val Leu Gly Asn Thr Asp Lys Ser His Ile Glu Lys Asn Leu Leu
35                  40                  45

Gly Ala Leu Leu Phe Asp Ser Gly Asn Thr Ala Glu Asp Arg Arg Leu
50                  55                  60

Lys Arg Thr Ala Arg Arg Arg Tyr Thr Arg Arg Arg Asn Arg Ile Leu
65                  70                  75                  80

Tyr Leu Gln Glu Ile Phe Ser Glu Glu Met Gly Lys Val Asp Asp Ser
                85                  90                  95

Phe Phe His Arg Leu Glu Asp Ser Phe Leu Val Thr Glu Asp Lys Arg
            100                 105                 110

Gly Glu Arg His Pro Ile Phe Gly Asn Leu Glu Glu Val Lys Tyr
            115                 120                 125

His Glu Asn Phe Pro Thr Ile Tyr His Leu Arg Gln Tyr Leu Ala Asp
130                 135                 140

Asn Pro Glu Lys Val Asp Leu Arg Leu Val Tyr Leu Ala Leu Ala His
145                 150                 155                 160

Ile Ile Lys Phe Arg Gly His Phe Leu Ile Glu Gly Lys Phe Asp Thr
                165                 170                 175

Arg Asn Asn Asp Val Gln Arg Leu Phe Gln Glu Phe Leu Ala Val Tyr
            180                 185                 190

Asp Asn Thr Phe Glu Asn Ser Ser Leu Gln Glu Gln Asn Val Gln Val
            195                 200                 205

Glu Glu Ile Leu Thr Asp Lys Ile Ser Lys Ser Ala Lys Lys Asp Arg
210                 215                 220

Val Leu Lys Leu Phe Pro Asn Glu Lys Ser Asn Gly Arg Phe Ala Glu
225                 230                 235                 240

Phe Leu Lys Leu Ile Val Gly Asn Gln Ala Asp Phe Lys Lys His Phe
                245                 250                 255

Glu Leu Glu Glu Lys Val Pro Leu Gln Phe Ser Lys Asp Thr Tyr Glu
            260                 265                 270

Glu Glu Leu Glu Val Leu Leu Ala Gln Ile Gly Asp Asn Tyr Ala Glu
            275                 280                 285

Leu Phe Leu Ser Ala Lys Lys Leu Tyr Asp Ser Ile Leu Leu Ser Gly
290                 295                 300

Ile Leu Thr Val Thr Asp Val Gly Thr Lys Ala Pro Leu Ser Ala Ser
305                 310                 315                 320

Met Ile Gln Arg Tyr Asn Glu His Gln Met Asp Leu Ala Gln Leu Lys
                325                 330                 335

Gln Phe Ile Arg Gln Lys Leu Ser Asp Lys Tyr Asn Glu Val Phe Ser
            340                 345                 350
```

```
Asp Val Ser Lys Asp Gly Tyr Ala Gly Tyr Ile Asp Gly Lys Thr Asn
            355                 360                 365

Gln Glu Ala Phe Tyr Lys Tyr Leu Lys Gly Leu Leu Asn Lys Ile Glu
        370                 375                 380

Gly Ser Gly Tyr Phe Leu Asp Lys Ile Glu Arg Glu Asp Phe Leu Arg
385                 390                 395                 400

Lys Gln Arg Thr Phe Asp Asn Gly Ser Ile Pro His Gln Ile His Leu
                405                 410                 415

Gln Glu Met Arg Ala Ile Ile Arg Arg Gln Ala Glu Phe Tyr Pro Phe
            420                 425                 430

Leu Ala Asp Asn Gln Asp Arg Ile Glu Lys Leu Leu Thr Phe Arg Ile
        435                 440                 445

Pro Tyr Tyr Val Gly Pro Leu Ala Arg Gly Lys Ser Asp Phe Ala Trp
    450                 455                 460

Leu Ser Arg Lys Ser Ala Asp Lys Ile Thr Pro Trp Asn Phe Asp Glu
465                 470                 475                 480

Ile Val Asp Lys Glu Ser Ser Ala Glu Ala Phe Ile Asn Arg Met Thr
                485                 490                 495

Asn Tyr Asp Leu Tyr Leu Pro Asn Gln Lys Val Leu Pro Lys His Ser
            500                 505                 510

Leu Leu Tyr Glu Lys Phe Thr Val Tyr Asn Glu Leu Thr Lys Val Lys
        515                 520                 525

Tyr Lys Thr Glu Gln Gly Lys Thr Ala Phe Phe Asp Ala Asn Met Lys
    530                 535                 540

Gln Glu Ile Phe Asp Gly Val Phe Lys Val Tyr Arg Lys Val Thr Lys
545                 550                 555                 560

Asp Lys Leu Met Asp Phe Leu Glu Lys Glu Phe Asp Glu Phe Arg Ile
                565                 570                 575

Val Asp Leu Thr Gly Leu Asp Lys Glu Asn Lys Val Phe Asn Ala Ser
            580                 585                 590

Tyr Gly Thr Tyr His Asp Leu Cys Lys Ile Leu Asp Lys Asp Phe Leu
        595                 600                 605

Asp Asn Ser Lys Asn Glu Lys Ile Leu Glu Asp Ile Val Leu Thr Leu
    610                 615                 620

Thr Leu Phe Glu Asp Arg Glu Met Ile Arg Lys Arg Leu Glu Asn Tyr
625                 630                 635                 640

Ser Asp Leu Leu Thr Lys Glu Gln Val Lys Lys Leu Glu Arg Arg His
                645                 650                 655

Tyr Thr Gly Trp Gly Arg Leu Ser Glu Leu Ile His Gly Ile Arg
            660                 665                 670

Asn Lys Glu Ser Arg Lys Thr Ile Leu Asp Tyr Leu Ile Asp Asp Gly
        675                 680                 685

Asn Ser Asn Arg Asn Phe Met Gln Leu Ile Asn Asp Asp Ala Leu Ser
    690                 695                 700

Phe Lys Glu Glu Ile Ala Lys Ala Gln Val Ile Gly Glu Thr Asp Asn
705                 710                 715                 720

Leu Asn Gln Val Val Ser Asp Ile Ala Gly Ser Pro Ala Ile Lys Lys
                725                 730                 735

Gly Ile Leu Gln Ser Leu Lys Ile Val Asp Glu Leu Val Lys Ile Met
            740                 745                 750

Gly His Gln Pro Glu Asn Ile Val Val Glu Met Ala Arg Glu Asn Gln
        755                 760                 765
```

-continued

Phe Thr Asn Gln Gly Arg Arg Asn Ser Gln Gln Arg Leu Lys Gly Leu
770                 775                 780

Thr Asp Ser Ile Lys Glu Phe Gly Ser Gln Ile Leu Lys Glu His Pro
785                 790                 795                 800

Val Glu Asn Ser Gln Leu Gln Asn Asp Arg Leu Phe Leu Tyr Tyr Leu
            805                 810                 815

Gln Asn Gly Arg Asp Met Tyr Thr Gly Glu Glu Leu Asp Ile Asp Tyr
            820                 825                 830

Leu Ser Gln Tyr Asp Ile Asp His Ile Ile Pro Gln Ala Phe Ile Lys
            835                 840                 845

Asp Asn Ser Ile Asp Asn Arg Val Leu Thr Ser Ser Lys Glu Asn Arg
850                 855                 860

Gly Lys Ser Asp Asp Val Pro Ser Lys Asp Val Val Arg Lys Met Lys
865                 870                 875                 880

Ser Tyr Trp Ser Lys Leu Leu Ser Ala Lys Leu Ile Thr Gln Arg Lys
            885                 890                 895

Phe Asp Asn Leu Thr Lys Ala Glu Arg Gly Gly Leu Thr Asp Asp Asp
            900                 905                 910

Lys Ala Gly Phe Ile Lys Arg Gln Leu Val Glu Thr Arg Gln Ile Thr
            915                 920                 925

Lys His Val Ala Arg Ile Leu Asp Glu Arg Phe Asn Thr Glu Thr Asp
930                 935                 940

Glu Asn Asn Lys Lys Ile Arg Gln Val Lys Ile Val Thr Leu Lys Ser
945                 950                 955                 960

Asn Leu Val Ser Asn Phe Arg Lys Glu Phe Glu Leu Tyr Lys Val Arg
            965                 970                 975

Glu Ile Asn Asp Tyr His His Ala His Asp Ala Tyr Leu Asn Ala Val
            980                 985                 990

Ile Gly Lys Ala Leu Leu Gly Val Tyr Pro Gln Leu Glu Pro Glu Phe
            995                 1000                1005

Val Tyr Gly Asp Tyr Pro His Phe His Gly His Lys Glu Asn Lys
            1010                1015                1020

Ala Thr Ala Lys Lys Phe Phe Tyr Ser Asn Ile Met Asn Phe Phe
            1025                1030                1035

Lys Lys Asp Asp Val Arg Thr Asp Lys Asn Gly Glu Ile Ile Trp
            1040                1045                1050

Lys Lys Asp Glu His Ile Ser Asn Ile Lys Lys Val Leu Ser Tyr
            1055                1060                1065

Pro Gln Val Asn Ile Val Lys Lys Val Glu Glu Gln Thr Gly Gly
            1070                1075                1080

Phe Ser Lys Glu Ser Ile Leu Pro Lys Gly Asn Ser Asp Lys Leu
            1085                1090                1095

Ile Pro Arg Lys Thr Lys Lys Phe Tyr Trp Asp Thr Lys Lys Tyr
            1100                1105                1110

Gly Gly Phe Asp Ser Pro Ile Val Ala Tyr Ser Ile Leu Val Ile
            1115                1120                1125

Ala Asp Ile Glu Lys Gly Lys Ser Lys Lys Leu Lys Thr Val Lys
            1130                1135                1140

Ala Leu Val Gly Val Thr Ile Met Glu Lys Met Thr Phe Glu Arg
            1145                1150                1155

Asp Pro Val Ala Phe Leu Glu Arg Lys Gly Tyr Arg Asn Val Gln
            1160                1165                1170

Glu Glu Asn Ile Ile Lys Leu Pro Lys Tyr Ser Leu Phe Lys Leu

-continued

```
            1175                1180                1185
Glu Asn Gly Arg Lys Arg Leu Leu Ala Ser Ala Arg Glu Leu Gln
            1190                1195                1200
Lys Gly Asn Glu Ile Val Leu Pro Asn His Leu Gly Thr Leu Leu
            1205                1210                1215
Tyr His Ala Lys Asn Ile His Lys Val Asp Glu Pro Lys His Leu
            1220                1225                1230
Asp Tyr Val Asp Lys His Lys Asp Glu Phe Lys Glu Leu Leu Asp
            1235                1240                1245
Val Val Ser Asn Phe Ser Lys Lys Tyr Thr Leu Ala Glu Gly Asn
            1250                1255                1260
Leu Glu Lys Ile Lys Glu Leu Tyr Ala Gln Asn Asn Gly Glu Asp
            1265                1270                1275
Leu Lys Glu Leu Ala Ser Ser Phe Ile Asn Leu Leu Thr Phe Thr
            1280                1285                1290
Ala Ile Gly Ala Pro Ala Thr Phe Lys Phe Phe Asp Lys Asn Ile
            1295                1300                1305
Asp Arg Lys Arg Tyr Thr Ser Thr Thr Glu Ile Leu Asn Ala Thr
            1310                1315                1320
Leu Ile His Gln Ser Ile Thr Gly Leu Tyr Glu Thr Arg Ile Asp
            1325                1330                1335
Leu Asn Lys Leu Gly Gly Asp
            1340                1345
```

<210> SEQ ID NO 13
<211> LENGTH: 1370
<212> TYPE: PRT
<213> ORGANISM: Streptococcus agalactiae

<400> SEQUENCE: 13

```
Met Asn Lys Pro Tyr Ser Ile Gly Leu Asp Ile Gly Thr Asn Ser Val
1               5                   10                  15
Gly Trp Ser Ile Ile Thr Asp Asp Tyr Lys Val Pro Ala Lys Lys Met
            20                  25                  30
Arg Val Leu Gly Asn Thr Asp Lys Glu Tyr Ile Lys Lys Asn Leu Ile
        35                  40                  45
Gly Ala Leu Leu Phe Asp Gly Gly Asn Thr Ala Ala Asp Arg Arg Leu
    50                  55                  60
Lys Arg Thr Ala Arg Arg Arg Tyr Thr Arg Arg Arg Asn Arg Ile Leu
65                  70                  75                  80
Tyr Leu Gln Glu Ile Phe Ala Glu Glu Met Ser Lys Val Asp Asp Ser
                85                  90                  95
Phe Phe His Arg Leu Glu Asp Ser Phe Leu Val Glu Glu Asp Lys Arg
            100                 105                 110
Gly Ser Lys Tyr Pro Ile Phe Ala Thr Leu Gln Glu Glu Lys Asp Tyr
        115                 120                 125
His Glu Lys Phe Ser Thr Ile Tyr His Leu Arg Lys Glu Leu Ala Asp
    130                 135                 140
Lys Lys Glu Lys Ala Asp Leu Arg Leu Ile Tyr Ile Ala Leu Ala His
145                 150                 155                 160
Ile Ile Lys Phe Arg Gly His Phe Leu Ile Glu Asp Asp Ser Phe Asp
                165                 170                 175
Val Arg Asn Thr Asp Ile Ser Lys Gln Tyr Gln Asp Phe Leu Glu Ile
            180                 185                 190
```

```
Phe Asn Thr Thr Phe Glu Asn Asn Asp Leu Leu Ser Gln Asn Val Asp
        195                 200                 205

Val Glu Ala Ile Leu Thr Asp Lys Ile Ser Lys Ser Ala Lys Lys Asp
210                 215                 220

Arg Ile Leu Ala Gln Tyr Pro Asn Gln Lys Ser Thr Gly Ile Phe Ala
225                 230                 235                 240

Glu Phe Leu Lys Leu Ile Val Gly Asn Gln Ala Asp Phe Lys Lys Tyr
            245                 250                 255

Phe Asn Leu Glu Asp Lys Thr Pro Leu Gln Phe Ala Lys Asp Ser Tyr
        260                 265                 270

Asp Glu Asp Leu Glu Asn Leu Leu Gly Gln Ile Gly Asp Glu Phe Ala
    275                 280                 285

Asp Leu Phe Ser Ala Ala Lys Lys Leu Tyr Asp Ser Val Leu Leu Ser
290                 295                 300

Gly Ile Leu Thr Val Ile Asp Leu Ser Thr Lys Ala Pro Leu Ser Ala
305                 310                 315                 320

Ser Met Ile Gln Arg Tyr Asp Glu His Arg Glu Asp Leu Lys Gln Leu
            325                 330                 335

Lys Gln Phe Val Lys Ala Ser Leu Pro Glu Lys Tyr Gln Glu Ile Phe
        340                 345                 350

Ala Asp Ser Ser Lys Asp Gly Tyr Ala Gly Tyr Ile Glu Gly Lys Thr
    355                 360                 365

Asn Gln Glu Ala Phe Tyr Lys Tyr Leu Ser Lys Leu Leu Thr Lys Gln
370                 375                 380

Glu Asp Ser Glu Asn Phe Leu Glu Lys Ile Lys Asn Glu Asp Phe Leu
385                 390                 395                 400

Arg Lys Gln Arg Thr Phe Asp Asn Gly Ser Ile Pro His Gln Val His
            405                 410                 415

Leu Thr Glu Leu Lys Ala Ile Ile Arg Arg Gln Ser Glu Tyr Tyr Pro
        420                 425                 430

Phe Leu Lys Glu Asn Gln Asp Arg Ile Glu Lys Ile Leu Thr Phe Arg
    435                 440                 445

Ile Pro Tyr Tyr Ile Gly Pro Leu Ala Arg Glu Lys Ser Asp Phe Ala
450                 455                 460

Trp Met Thr Arg Lys Thr Asp Asp Ser Ile Arg Pro Trp Asn Phe Glu
465                 470                 475                 480

Asp Leu Val Asp Lys Glu Lys Ser Ala Glu Ala Phe Ile His Arg Met
            485                 490                 495

Thr Asn Asn Asp Phe Tyr Leu Pro Glu Glu Lys Val Leu Pro Lys His
        500                 505                 510

Ser Leu Ile Tyr Glu Lys Phe Thr Val Tyr Asn Glu Leu Thr Lys Val
    515                 520                 525

Arg Tyr Lys Asn Glu Gln Gly Glu Thr Tyr Phe Phe Asp Ser Asn Ile
530                 535                 540

Lys Gln Glu Ile Phe Asp Gly Val Phe Lys Glu His Arg Lys Val Ser
545                 550                 555                 560

Lys Lys Lys Leu Leu Asp Phe Leu Ala Lys Glu Tyr Glu Glu Phe Arg
            565                 570                 575

Ile Val Asp Val Ile Gly Leu Asp Lys Glu Asn Lys Ala Phe Asn Ala
        580                 585                 590

Ser Leu Gly Thr Tyr His Asp Leu Glu Lys Ile Leu Asp Lys Asp Phe
    595                 600                 605

Leu Asp Asn Pro Asp Asn Glu Ser Ile Leu Glu Asp Ile Val Gln Thr
```

```
                  610                 615                 620
Leu Thr Leu Phe Glu Asp Arg Glu Met Ile Lys Lys Arg Leu Glu Asn
625                 630                 635                 640

Tyr Lys Asp Leu Phe Thr Glu Ser Gln Leu Lys Lys Leu Tyr Arg Arg
                645                 650                 655

His Tyr Thr Gly Trp Gly Arg Leu Ser Ala Lys Leu Ile Asn Gly Ile
                660                 665                 670

Arg Asp Lys Glu Ser Gln Lys Thr Ile Leu Asp Tyr Leu Ile Asp Asp
                675                 680                 685

Gly Arg Ser Asn Arg Asn Phe Met Gln Leu Ile Asn Asp Asp Gly Leu
                690                 695                 700

Ser Phe Lys Ser Ile Ile Ser Lys Ala Gln Ala Gly Ser His Ser Asp
705                 710                 715                 720

Asn Leu Lys Glu Val Val Gly Glu Leu Ala Gly Ser Pro Ala Ile Lys
                725                 730                 735

Lys Gly Ile Leu Gln Ser Leu Lys Ile Val Asp Glu Leu Val Lys Val
                740                 745                 750

Met Gly Tyr Glu Pro Glu Gln Ile Val Val Glu Met Ala Arg Glu Asn
                755                 760                 765

Gln Thr Thr Asn Gln Gly Arg Arg Asn Ser Arg Gln Arg Tyr Lys Leu
                770                 775                 780

Leu Asp Asp Gly Val Lys Asn Leu Ala Ser Asp Leu Asn Gly Asn Ile
785                 790                 795                 800

Leu Lys Glu Tyr Pro Thr Asp Asn Gln Ala Leu Gln Asn Glu Arg Leu
                805                 810                 815

Phe Leu Tyr Tyr Leu Gln Asn Gly Arg Asp Met Tyr Thr Gly Glu Ala
                820                 825                 830

Leu Asp Ile Asp Asn Leu Ser Gln Tyr Asp Ile Asp His Ile Ile Pro
                835                 840                 845

Gln Ala Phe Ile Lys Asp Asp Ser Ile Asp Asn Arg Val Leu Val Ser
                850                 855                 860

Ser Ala Lys Asn Arg Gly Lys Ser Asp Asp Val Pro Ser Leu Glu Ile
865                 870                 875                 880

Val Lys Asp Cys Lys Val Phe Trp Lys Lys Leu Leu Asp Ala Lys Leu
                885                 890                 895

Met Ser Gln Arg Lys Tyr Asp Asn Leu Thr Lys Ala Glu Arg Gly Gly
                900                 905                 910

Leu Thr Ser Asp Asp Lys Ala Arg Phe Ile Gln Arg Gln Leu Val Glu
                915                 920                 925

Thr Arg Gln Ile Thr Lys His Val Ala Arg Ile Leu Asp Glu Arg Phe
                930                 935                 940

Asn Asn Glu Leu Asp Ser Lys Gly Arg Arg Ile Arg Lys Val Lys Ile
945                 950                 955                 960

Val Thr Leu Lys Ser Asn Leu Val Ser Asn Phe Arg Lys Glu Phe Gly
                965                 970                 975

Phe Tyr Lys Ile Arg Glu Val Asn Asn Tyr His His Ala His Asp Ala
                980                 985                 990

Tyr Leu Asn Ala Val Val Ala Lys Ala Ile Leu Thr Lys Tyr Pro Gln
                995                1000                1005

Leu Glu Pro Glu Phe Val Tyr Gly Asp Tyr Pro Lys Tyr Asn Ser
                1010                1015                1020

Tyr Lys Thr Arg Lys Ser Ala Thr Glu Lys Leu Phe Phe Tyr Ser
                1025                1030                1035
```

Asn Ile Met Asn Phe Phe Lys Thr Lys Val Thr Leu Ala Asp Gly
    1040                1045                1050

Thr Val Val Lys Asp Asp Ile Glu Val Asn Asn Asp Thr Gly
    1055                1060                1065

Glu Ile Val Trp Asp Lys Lys Lys His Phe Ala Thr Val Arg Lys
    1070                1075                1080

Val Leu Ser Tyr Pro Gln Asn Asn Ile Val Lys Lys Thr Glu Ile
    1085                1090                1095

Gln Thr Gly Gly Phe Ser Lys Glu Ser Ile Leu Ala His Gly Asn
    1100                1105                1110

Ser Asp Lys Leu Ile Pro Arg Lys Thr Lys Asp Ile Tyr Leu Asp
    1115                1120                1125

Pro Lys Lys Tyr Gly Gly Phe Asp Ser Pro Ile Val Ala Tyr Ser
    1130                1135                1140

Val Leu Val Val Ala Asp Ile Lys Lys Gly Lys Ala Gln Lys Leu
    1145                1150                1155

Lys Thr Val Thr Glu Leu Leu Gly Ile Thr Ile Met Glu Arg Ser
    1160                1165                1170

Arg Phe Glu Lys Asn Pro Ser Ala Phe Leu Glu Ser Lys Gly Tyr
    1175                1180                1185

Leu Asn Ile Arg Ala Asp Lys Leu Ile Ile Leu Pro Lys Tyr Ser
    1190                1195                1200

Leu Phe Glu Leu Glu Asn Gly Arg Arg Arg Leu Leu Ala Ser Ala
    1205                1210                1215

Gly Glu Leu Gln Lys Gly Asn Glu Leu Ala Leu Pro Thr Gln Phe
    1220                1225                1230

Met Lys Phe Leu Tyr Leu Ala Ser Arg Tyr Asn Glu Ser Lys Gly
    1235                1240                1245

Lys Pro Glu Glu Ile Glu Lys Lys Gln Glu Phe Val Asn Gln His
    1250                1255                1260

Val Ser Tyr Phe Asp Asp Ile Leu Gln Leu Ile Asn Asp Phe Ser
    1265                1270                1275

Lys Arg Val Ile Leu Ala Asp Ala Asn Leu Glu Lys Ile Asn Lys
    1280                1285                1290

Leu Tyr Gln Asp Asn Lys Glu Asn Ile Ser Val Asp Glu Leu Ala
    1295                1300                1305

Asn Asn Ile Ile Asn Leu Phe Thr Phe Thr Ser Leu Gly Ala Pro
    1310                1315                1320

Ala Ala Phe Lys Phe Phe Asp Lys Ile Val Asp Arg Lys Arg Tyr
    1325                1330                1335

Thr Ser Thr Lys Glu Val Leu Asn Ser Thr Leu Ile His Gln Ser
    1340                1345                1350

Ile Thr Gly Leu Tyr Glu Thr Arg Ile Asp Leu Gly Lys Leu Gly
    1355                1360                1365

Gly Asp
    1370

<210> SEQ ID NO 14
<211> LENGTH: 1368
<212> TYPE: PRT
<213> ORGANISM: Streptococcus pyogenes

<400> SEQUENCE: 14

Met Asp Lys Lys Tyr Ser Ile Gly Leu Asp Ile Gly Thr Asn Ser Val

```
1               5                   10                  15
Gly Trp Ala Val Ile Thr Asp Asp Tyr Lys Val Pro Ser Lys Lys Phe
                20                  25                  30

Lys Val Leu Gly Asn Thr Asp Arg His Ser Ile Lys Lys Asn Leu Ile
                35                  40                  45

Gly Ala Leu Leu Phe Asp Ser Gly Glu Thr Ala Glu Ala Thr Arg Leu
    50                  55                  60

Lys Arg Thr Ala Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
                100                 105                 110

His Glu Arg His Pro Ile Phe Gly Asn Ile Val Asp Glu Val Ala Tyr
                115                 120                 125

His Glu Lys Tyr Pro Thr Ile Tyr His Leu Arg Lys Lys Leu Val Asp
                130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
                180                 185                 190

Asn Gln Leu Phe Glu Glu Asn Pro Ile Asn Ala Ser Gly Val Asp Ala
                195                 200                 205

Lys Ala Ile Leu Ser Ala Arg Leu Ser Lys Ser Arg Arg Leu Glu Asn
                210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
                260                 265                 270

Asp Asp Leu Asp Asn Leu Leu Ala Gln Ile Gly Asp Gln Tyr Ala Asp
                275                 280                 285

Leu Phe Leu Ala Ala Lys Asn Leu Ser Asp Ala Ile Leu Leu Ser Asp
                290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
                340                 345                 350

Asp Gln Ser Lys Asn Gly Tyr Ala Gly Tyr Ile Asp Gly Gly Ala Ser
                355                 360                 365

Gln Glu Glu Phe Tyr Lys Phe Ile Lys Pro Ile Leu Glu Lys Met Asp
                370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
                420                 425                 430
```

```
Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
            530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
            610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
            690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
            770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
                820                 825                 830

Leu Ser Asp Tyr Asp Val Asp His Ile Val Pro Gln Ser Phe Leu Lys
            835                 840                 845
```

```
Asp Asp Ser Ile Asp Asn Lys Val Leu Thr Arg Ser Asp Lys Asn Arg
850                 855                 860

Gly Lys Ser Asp Asn Val Pro Ser Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
                915                 920                 925

Lys His Val Ala Gln Ile Leu Asp Ser Arg Met Asn Thr Lys Tyr Asp
930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
                995                 1000                1005

Val Tyr Gly Asp Tyr Lys Val Tyr Asp Val Arg Lys Met Ile Ala
1010                1015                1020

Lys Ser Glu Gln Glu Ile Gly Lys Ala Thr Ala Lys Tyr Phe Phe
1025                1030                1035

Tyr Ser Asn Ile Met Asn Phe Phe Lys Thr Glu Ile Thr Leu Ala
1040                1045                1050

Asn Gly Glu Ile Arg Lys Arg Pro Leu Ile Glu Thr Asn Gly Glu
1055                1060                1065

Thr Gly Glu Ile Val Trp Asp Lys Gly Arg Asp Phe Ala Thr Val
1070                1075                1080

Arg Lys Val Leu Ser Met Pro Gln Val Asn Ile Val Lys Lys Thr
1085                1090                1095

Glu Val Gln Thr Gly Gly Phe Ser Lys Glu Ser Ile Leu Pro Lys
1100                1105                1110

Arg Asn Ser Asp Lys Leu Ile Ala Arg Lys Lys Asp Trp Asp Pro
1115                1120                1125

Lys Lys Tyr Gly Gly Phe Asp Ser Pro Thr Val Ala Tyr Ser Val
1130                1135                1140

Leu Val Val Ala Lys Val Glu Lys Gly Lys Ser Lys Lys Leu Lys
1145                1150                1155

Ser Val Lys Glu Leu Leu Gly Ile Thr Ile Met Glu Arg Ser Ser
1160                1165                1170

Phe Glu Lys Asn Pro Ile Asp Phe Leu Glu Ala Lys Gly Tyr Lys
1175                1180                1185

Glu Val Lys Lys Asp Leu Ile Ile Lys Leu Pro Lys Tyr Ser Leu
1190                1195                1200

Phe Glu Leu Glu Asn Gly Arg Lys Arg Met Leu Ala Ser Ala Gly
1205                1210                1215

Glu Leu Gln Lys Gly Asn Glu Leu Ala Leu Pro Ser Lys Tyr Val
1220                1225                1230

Asn Phe Leu Tyr Leu Ala Ser His Tyr Glu Lys Leu Lys Gly Ser
1235                1240                1245

Pro Glu Asp Asn Glu Gln Lys Gln Leu Phe Val Glu Gln His Lys
```

```
                 1250               1255                1260

His Tyr Leu Asp Glu Ile Ile Glu Gln Ile Ser Glu Phe Ser Lys
    1265               1270                1275

Arg Val Ile Leu Ala Asp Ala Asn Leu Asp Lys Val Leu Ser Ala
    1280               1285                1290

Tyr Asn Lys His Arg Asp Lys Pro Ile Arg Glu Gln Ala Glu Asn
    1295               1300                1305

Ile Ile His Leu Phe Thr Leu Thr Asn Leu Gly Ala Pro Ala Ala
    1310               1315                1320

Phe Lys Tyr Phe Asp Thr Thr Ile Asp Arg Lys Arg Tyr Thr Ser
    1325               1330                1335

Thr Lys Glu Val Leu Asp Ala Thr Leu Ile His Gln Ser Ile Thr
    1340               1345                1350

Gly Leu Tyr Glu Thr Arg Ile Asp Leu Ser Gln Leu Gly Gly Asp
    1355               1360                1365

<210> SEQ ID NO 15
<211> LENGTH: 73
<212> TYPE: RNA
<213> ORGANISM: Artificial Sequence
<220> FEATURE:
<223> OTHER INFORMATION: synthetic polynucleotide

<400> SEQUENCE: 15
ggacagcaua gcaaguuaaa auaaggcuag uccguuauca acuugaaaaa guggcaccga      60
gucggugcuu uuu                                                        73

<210> SEQ ID NO 16
<211> LENGTH: 42
<212> TYPE: RNA
<213> ORGANISM: Artificial sequence
<220> FEATURE:
<223> OTHER INFORMATION: synthetic polynucleotide

<400> SEQUENCE: 16
gugauaagug gaaugccaug guuuuagagc uaugcuguuu ug                        42

<210> SEQ ID NO 17
<211> LENGTH: 55
<212> TYPE: DNA
<213> ORGANISM: Artificial sequence
<220> FEATURE:
<223> OTHER INFORMATION: synthetic polynucleotide

<400> SEQUENCE: 17
gagtggaagg atgccagtga taagtggaat gccatgtggg ctgtcaaaat tgagc          55

<210> SEQ ID NO 18
<211> LENGTH: 55
<212> TYPE: DNA
<213> ORGANISM: Artificial sequence
<220> FEATURE:
<223> OTHER INFORMATION: synthetic polynucleotide

<400> SEQUENCE: 18
gctcaatttt gacagcccac atggcattcc acttatcact ggcatccttc cactc          55

<210> SEQ ID NO 19
<211> LENGTH: 55
<212> TYPE: DNA
<213> ORGANISM: Artificial sequence
<220> FEATURE:
```

```
<223> OTHER INFORMATION: synthetic polynucleotide
<220> FEATURE:
<221> NAME/KEY: misc_feature
<222> LOCATION: (37)..(37)
<223> OTHER INFORMATION: where n is bromodeoxyuridine

<400> SEQUENCE: 19
gagtggaagg atgccagtga taagtggaat gccatgnggg ctgtcaaaat tgagc        55

<210> SEQ ID NO 20
<211> LENGTH: 55
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (19)..(19)
<223> OTHER INFORMATION: where n is bromodeoxyuridine

<400> SEQUENCE: 20
gctcaatttt gacagcccnc atggcattcc acttatcact ggcatccttc cactc        55

<210> SEQ ID NO 21
<211> LENGTH: 55
<212> TYPE: DNA
<213> ORGANISM: Artificial sequence
<220> FEATURE:
<223> OTHER INFORMATION: synthetic polynucleotide

<400> SEQUENCE: 21
gagtggaagg atgccagtga taagtggaat gccatgaggg ctgtcaaaat tgagc        55

<210> SEQ ID NO 22
<211> LENGTH: 55
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (40)..(40)
<223> OTHER INFORMATION: where n is bromodeoxyuridine

<400> SEQUENCE: 22
gagtggaagg atgccagtga taagtggaat gccatgtggn ctgtcaaaat tgagc        55

<210> SEQ ID NO 23
<211> LENGTH: 55
<212> TYPE: DNA
<213> ORGANISM: Artificial sequence
<220> FEATURE:
<223> OTHER INFORMATION: synthetic polynucleotide

<400> SEQUENCE: 23
gctcaatttt gacagaccac atggcattcc acttatcact ggcatccttc cactc        55

<210> SEQ ID NO 24
<211> LENGTH: 42
<212> TYPE: RNA
<213> ORGANISM: Artificial sequence
<220> FEATURE:
<223> OTHER INFORMATION: synthetic polynucleotide

<400> SEQUENCE: 24
gacgcauaaa gaugagacgc guuuuagagc uaugcuguuu ug                     42
```

```
<210> SEQ ID NO 25
<211> LENGTH: 55
<212> TYPE: DNA
<213> ORGANISM: Artificial sequence
<220> FEATURE:
<223> OTHER INFORMATION: synthetic polynucleotide

<400> SEQUENCE: 25
gctcaatttt gacagcccac atggcattcc acttatcact ggcatccttc cactc      55

<210> SEQ ID NO 26
<211> LENGTH: 1368
<212> TYPE: PRT
<213> ORGANISM: Artificial Sequence
<220> FEATURE:
<223> OTHER INFORMATION: synthetic polynucleotide

<400> SEQUENCE: 26
```

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser

```
            305                 310                 315                 320
            Met Ile Lys Arg Tyr Asp Glu His His Gln Asp Leu Thr Leu Leu Lys
                            325                 330                 335

Ala Leu Val Arg Gln Gln Leu Pro Glu Lys Tyr Lys Glu Ile Phe Phe
                            340                 345                 350

Asp Gln Ser Lys Asn Gly Tyr Ala Gly Tyr Ile Asp Gly Gly Ala Ser
                            355                 360                 365

Gln Glu Glu Phe Tyr Lys Phe Ile Lys Pro Ile Leu Glu Lys Met Asp
                            370                 375                 380

Gly Thr Glu Glu Leu Leu Val Lys Leu Asn Arg Glu Asp Leu Leu Arg
            385                 390                 395                 400

Lys Gln Arg Thr Phe Asp Asn Gly Ser Ile Pro His Gln Ile His Leu
                            405                 410                 415

Gly Glu Leu His Ala Ile Leu Arg Arg Gln Glu Asp Phe Tyr Pro Phe
                            420                 425                 430

Leu Lys Asp Asn Arg Glu Lys Ile Glu Lys Ile Leu Thr Phe Arg Ile
                            435                 440                 445

Pro Tyr Tyr Val Gly Pro Leu Ala Arg Gly Asn Ser Arg Phe Ala Trp
                            450                 455                 460

Met Thr Arg Lys Ser Glu Glu Thr Ile Thr Pro Trp Asn Phe Glu Glu
            465                 470                 475                 480

Val Val Asp Lys Gly Ala Ser Ala Gln Ser Phe Ile Glu Arg Met Thr
                            485                 490                 495

Asn Phe Asp Lys Asn Leu Pro Asn Glu Lys Val Leu Pro Lys His Ser
                            500                 505                 510

Leu Leu Tyr Glu Tyr Phe Thr Val Tyr Asn Glu Leu Thr Lys Val Lys
                            515                 520                 525

Tyr Val Thr Glu Gly Met Arg Lys Pro Ala Phe Leu Ser Gly Glu Gln
                            530                 535                 540

Lys Lys Ala Ile Val Asp Leu Leu Phe Lys Thr Asn Arg Lys Val Thr
            545                 550                 555                 560

Val Lys Gln Leu Lys Glu Asp Tyr Phe Lys Lys Ile Glu Cys Phe Asp
                            565                 570                 575

Ser Val Glu Ile Ser Gly Val Glu Asp Arg Phe Asn Ala Ser Leu Gly
                            580                 585                 590

Thr Tyr His Asp Leu Leu Lys Ile Ile Lys Asp Lys Asp Phe Leu Asp
                            595                 600                 605

Asn Glu Glu Asn Glu Asp Ile Leu Glu Asp Ile Val Leu Thr Leu Thr
            610                 615                 620

Leu Phe Glu Asp Arg Glu Met Ile Glu Glu Arg Leu Lys Thr Tyr Ala
            625                 630                 635                 640

His Leu Phe Asp Asp Lys Val Met Lys Gln Leu Lys Arg Arg Arg Tyr
                            645                 650                 655

Thr Gly Trp Gly Arg Leu Ser Arg Lys Leu Ile Asn Gly Ile Arg Asp
                            660                 665                 670

Lys Gln Ser Gly Lys Thr Ile Leu Asp Phe Leu Lys Ser Asp Gly Phe
                            675                 680                 685

Ala Asn Arg Asn Phe Met Gln Leu Ile His Asp Asp Ser Leu Thr Phe
                            690                 695                 700

Lys Glu Asp Ile Gln Lys Ala Gln Val Ser Gly Gln Gly Asp Ser Leu
            705                 710                 715                 720

His Glu His Ile Ala Asn Leu Ala Gly Ser Pro Ala Ile Lys Lys Gly
                            725                 730                 735
```

```
Ile Leu Gln Thr Val Lys Val Asp Glu Leu Val Lys Val Met Gly
            740                 745                 750

Arg His Lys Pro Glu Asn Ile Val Ile Glu Met Ala Arg Glu Asn Gln
            755                 760                 765

Thr Thr Gln Lys Gly Lys Asn Ser Arg Glu Arg Met Lys Arg Ile
770             775                 780

Glu Glu Gly Ile Lys Glu Leu Gly Ser Gln Ile Leu Lys Glu His Pro
785             790                 795                 800

Val Glu Asn Thr Gln Leu Gln Asn Glu Lys Leu Tyr Leu Tyr Tyr Leu
            805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Cys
            835                 840                 845

Asp Asp Ser Ile Asp Asn Lys Val Leu Thr Arg Ser Asp Lys Asn Arg
850             855                 860

Gly Lys Ser Asp Asn Val Pro Ser Glu Glu Val Val Lys Lys Met Lys
865             870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
            930                 935                 940

Glu Asn Asp Lys Leu Ile Arg Glu Val Lys Val Ile Thr Leu Lys Ser
945             950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
            995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140
```

-continued

```
Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

<210> SEQ ID NO 27
<211> LENGTH: 1368
<212> TYPE: PRT
<213> ORGANISM: Artificial sequence
<220> FEATURE:
<223> OTHER INFORMATION: synthetic polynucleotide

<400> SEQUENCE: 27

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125
```

-continued

```
His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
```

-continued

```
                545                 550                 555                 560
        Val Lys Gln Leu Lys Glu Asp Tyr Phe Lys Ile Glu Cys Phe Asp
                        565                 570                 575
        Ser Val Glu Ile Ser Gly Val Glu Asp Arg Phe Asn Ala Ser Leu Gly
                        580                 585                 590
        Thr Tyr His Asp Leu Leu Lys Ile Ile Lys Asp Lys Asp Phe Leu Asp
                        595                 600                 605
        Asn Glu Glu Asn Glu Asp Ile Leu Glu Asp Ile Val Leu Thr Leu Thr
                        610                 615                 620
        Leu Phe Glu Asp Arg Glu Met Ile Glu Glu Arg Leu Lys Thr Tyr Ala
        625                 630                 635                 640
        His Leu Phe Asp Asp Lys Val Met Lys Gln Leu Lys Arg Arg Arg Tyr
                        645                 650                 655
        Thr Gly Trp Gly Arg Leu Ser Arg Lys Leu Ile Asn Gly Ile Arg Asp
                        660                 665                 670
        Lys Gln Ser Gly Lys Thr Ile Leu Asp Phe Leu Lys Ser Asp Gly Phe
                        675                 680                 685
        Ala Asn Arg Asn Phe Met Gln Leu Ile His Asp Asp Ser Leu Thr Phe
                690                 695                 700
        Lys Glu Asp Ile Gln Lys Ala Gln Val Ser Gly Gln Gly Asp Ser Leu
        705                 710                 715                 720
        His Glu His Ile Ala Asn Leu Ala Gly Ser Pro Ala Ile Lys Lys Gly
                        725                 730                 735
        Ile Leu Gln Thr Val Lys Val Val Asp Glu Leu Val Lys Val Met Gly
                        740                 745                 750
        Arg His Lys Pro Glu Asn Ile Val Ile Glu Met Ala Arg Glu Asn Gln
                        755                 760                 765
        Thr Thr Gln Lys Gly Gln Lys Asn Ser Arg Glu Arg Met Lys Arg Ile
                770                 775                 780
        Glu Glu Gly Ile Lys Glu Leu Gly Ser Gln Ile Leu Lys Glu His Pro
        785                 790                 795                 800
        Val Glu Asn Thr Gln Leu Gln Asn Glu Lys Leu Tyr Leu Tyr Tyr Leu
                        805                 810                 815
        Gln Asn Gly Arg Asp Met Tyr Val Asp Gln Glu Leu Asp Ile Asn Arg
                        820                 825                 830
        Leu Ser Asp Tyr Asp Val Asp Ala Ile Val Pro Gln Ser Phe Leu Lys
                835                 840                 845
        Asp Asp Ser Ile Asp Asn Lys Val Leu Thr Arg Ser Asp Lys Asn Arg
        850                 855                 860
        Gly Lys Ser Asp Asn Val Pro Ser Glu Glu Val Val Lys Lys Met Lys
        865                 870                 875                 880
        Asn Tyr Trp Arg Gln Leu Leu Asn Ala Lys Leu Ile Thr Gln Arg Lys
                        885                 890                 895
        Phe Asp Asn Leu Thr Lys Ala Glu Arg Gly Gly Leu Ser Glu Leu Asp
                        900                 905                 910
        Lys Ala Gly Phe Ile Lys Arg Gln Leu Val Glu Thr Arg Gln Ile Thr
                        915                 920                 925
        Lys His Val Ala Gln Ile Leu Asp Ser Arg Met Asn Thr Lys Tyr Asp
                        930                 935                 940
        Glu Asn Asp Lys Leu Ile Arg Glu Val Lys Val Ile Thr Leu Lys Ser
        945                 950                 955                 960
        Lys Leu Val Ser Asp Phe Arg Lys Asp Phe Gln Phe Tyr Lys Val Arg
                        965                 970                 975
```

-continued

```
Glu Ile Asn Asn Tyr His His Ala His Asp Ala Tyr Leu Asn Ala Val
                980             985             990

Val Gly Thr Ala Leu Ile Lys Lys Tyr Pro Lys Leu Glu Ser Glu Phe
            995            1000            1005

Val Tyr Gly Asp Tyr Lys Val Tyr Asp Val Arg Lys Met Ile Ala
    1010            1015            1020

Lys Ser Glu Gln Glu Ile Gly Lys Ala Thr Ala Lys Tyr Phe Phe
    1025            1030            1035

Tyr Ser Asn Ile Met Asn Phe Phe Lys Thr Glu Ile Thr Leu Ala
    1040            1045            1050

Asn Gly Glu Ile Arg Lys Arg Pro Leu Ile Glu Thr Asn Gly Glu
    1055            1060            1065

Thr Gly Glu Ile Val Trp Asp Lys Gly Arg Asp Phe Ala Thr Val
    1070            1075            1080

Arg Lys Val Leu Ser Met Pro Gln Val Asn Ile Val Lys Lys Thr
    1085            1090            1095

Glu Val Gln Thr Gly Gly Phe Ser Lys Glu Ser Ile Leu Pro Lys
    1100            1105            1110

Arg Asn Ser Asp Lys Leu Ile Ala Arg Lys Lys Asp Trp Asp Pro
    1115            1120            1125

Lys Lys Tyr Gly Gly Phe Asp Ser Pro Thr Val Ala Tyr Ser Val
    1130            1135            1140

Leu Val Val Ala Lys Val Glu Lys Gly Lys Ser Lys Lys Leu Lys
    1145            1150            1155

Ser Val Lys Glu Leu Leu Gly Ile Thr Ile Met Glu Arg Ser Ser
    1160            1165            1170

Phe Glu Lys Asn Pro Ile Asp Phe Leu Glu Ala Lys Gly Tyr Lys
    1175            1180            1185

Glu Val Lys Lys Asp Leu Ile Ile Lys Leu Pro Lys Tyr Ser Leu
    1190            1195            1200

Phe Glu Leu Glu Asn Gly Arg Lys Arg Met Leu Ala Ser Ala Gly
    1205            1210            1215

Glu Leu Gln Lys Gly Asn Glu Leu Ala Leu Pro Ser Lys Tyr Val
    1220            1225            1230

Asn Phe Leu Tyr Leu Ala Ser His Tyr Glu Lys Leu Lys Gly Ser
    1235            1240            1245

Pro Glu Asp Asn Glu Gln Lys Gln Leu Phe Val Glu Gln His Lys
    1250            1255            1260

His Tyr Leu Asp Glu Ile Ile Glu Gln Ile Ser Glu Phe Ser Lys
    1265            1270            1275

Arg Val Ile Leu Ala Asp Ala Asn Leu Asp Lys Val Leu Ser Ala
    1280            1285            1290

Tyr Asn Lys His Arg Asp Lys Pro Ile Arg Glu Gln Ala Glu Asn
    1295            1300            1305

Ile Ile His Leu Phe Thr Leu Thr Asn Leu Gly Ala Pro Ala Ala
    1310            1315            1320

Phe Lys Tyr Phe Asp Thr Thr Ile Asp Arg Lys Arg Tyr Thr Ser
    1325            1330            1335

Thr Lys Glu Val Leu Asp Ala Thr Leu Ile His Gln Ser Ile Thr
    1340            1345            1350

Gly Leu Tyr Glu Thr Arg Ile Asp Leu Ser Gln Leu Gly Gly Asp
    1355            1360            1365
```

```
<210> SEQ ID NO 28
<211> LENGTH: 85
<212> TYPE: RNA
<213> ORGANISM: Artificial sequence
<220> FEATURE:
<223> OTHER INFORMATION: synthetic polynucleotide

<400> SEQUENCE: 28
ggacagcaua gcaaguuaaa auaaggcuag uccguuauca acuugaaaaa guggcaccga    60
gucggugcuu uuuuugcucg ugcgc                                         85

<210> SEQ ID NO 29
<211> LENGTH: 15
<212> TYPE: DNA
<213> ORGANISM: Artificial sequence
<220> FEATURE:
<223> OTHER INFORMATION: synthetic polynucleotide

<400> SEQUENCE: 29
ttgcgcacga gcaaa                                                    15

<210> SEQ ID NO 30
<211> LENGTH: 17
<212> TYPE: DNA
<213> ORGANISM: Artificial sequence
<220> FEATURE:
<223> OTHER INFORMATION: synthetic polynucleotide

<400> SEQUENCE: 30
taatacgact cactata                                                  17

<210> SEQ ID NO 31
<211> LENGTH: 90
<212> TYPE: DNA
<213> ORGANISM: Artificial sequence
<220> FEATURE:
<223> OTHER INFORMATION: synthetic polynucleotide

<400> SEQUENCE: 31
aaaaagcacc gactcggtgc cacttttca agttgataac ggactagcct tattttaact    60
tgctatgctg tcctatagtg agtcgtatta                                    90

<210> SEQ ID NO 32
<211> LENGTH: 102
<212> TYPE: DNA
<213> ORGANISM: Artificial sequence
<220> FEATURE:
<223> OTHER INFORMATION: synthetic polynucleotide

<400> SEQUENCE: 32
gcgcacgagc aaaaaaagca ccgactcggt gccacttttt caagttgata acggactagc    60
cttattttaa cttgctatgc tgtcctatag tgagtcgtat ta                      102

<210> SEQ ID NO 33
<211> LENGTH: 5292
<212> TYPE: DNA
<213> ORGANISM: Streptococcus pyogenes

<400> SEQUENCE: 33
atgcatcacc atcaccatca ccccatgaaa atcgaagaag gtaaactggt aatctggatt    60
aacggcgata aggctataa cggtctcgct gaagtcggta agaaattcga gaagatacc    120 ggaattaaag tcaccgttga gcatccggat aaactggaag agaaattccc acaggttgcg   180
```

-continued

```
gcaactggcg atggccctga cattatcttc tgggcacacg accgctttgg tggctacgct    240
caatctggcc tgttggctga aatcaccccg acaaagcgt tccaggacaa gctgtatccg     300
tttacctggg atgccgtacg ttacaacggc aagctgattg cttacccgat cgctgttgaa    360
gcgttatcgc tgatttataa caaagatctg ctgccgaacc cgccaaaaac ctgggaagag    420
atcccggcgc tggataaaga actgaaagcg aaaggtaaga gcgcgctgat gttcaacctg    480
caagaaccgt acttcacctg gccgctgatt gctgctgacg ggggttatgc gttcaagtat    540
gaaaacggca gtacgacat taagacgtg ggcgtggata acgctggcgc gaaagcgggt      600
ctgaccttcc tggttgacct gattaaaaac aaacacatga atgcagacac cgattactcc    660
atcgcagaag ctgcctttaa taaaggcgaa acagcgatga ccatcaacgg cccgtgggca    720
tggtccaaca tcgacaccag caaagtgaat tatggtgtaa cggtactgcc gaccttcaag    780
ggtcaaccat ccaaaccgtt cgttggcgtg ctgagcgcag gtattaacgc cgccagtccg    840
aacaaagagc tggcaaaaga gttcctcgaa aactatctgc tgactgatga aggtctggaa    900
gcggttaata aagacaaacc gctgggtgcc gtagcgctga agtcttacga ggaagagttg    960
gcgaaagatc cacgtattgc cgccactatg gaaaacgccc agaaaggtga atcatgccg    1020 aacatcccgc agatgtccgc tttctggtat gccgtgcgta ctgcggtgat caacgccgcc   1080
agcggtcgtc agactgtcga tgaagccctg aaagacgcgc agactaattc gagctcgaac   1140
aacaacaaca ctagtgaaaa cctgtatttc cagggagcag cctcgatgga taagaaatac   1200
tcaataggct tagatatcgg cacaaatagc gtcggatggg cggtgatcac tgatgaatat   1260
aaggttccgt ctaaaaagtt caaggttctg ggaaatacag accgccacag tatcaaaaaa   1320
aatcttatag gggctctttt atttgacagt ggagagacag cggaagcgac tcgtctcaaa   1380
cggacagctc gtagaaggta tacgtcgg aagaatcgta tttgttatct acaggagatt     1440
ttttcaaatg agatggcgaa agtagatgat agtttctttc atcgacttga agagtcttt    1500 ttggtggaag aagacaagaa gcatgaacgt catcctattt ttggaaatat agtagatgaa   1560
gttgcttatc atgagaaata tccaactatc tatcatctgc gaaaaaaatt ggtagattct   1620
actgataaag cggatttgcg cttaatctat ttggccttag cgcatatgat taagttcgt    1680 ggtcattttt tgattgaggg agatttaaat cctgataata gtgatgtgga caaactattt   1740
atccagttgg tacaaaccta caatcaatta tttgaagaaa accctattaa cgcaagtgga   1800
gtagatgcta aagcgattct ttctgcacga ttgagtaaat caagacgatt agaaaatctc   1860
attgctcagc tccccggtga aagaaaaat ggcttatttg gaatctcat tgctttgtca     1920 ttgggtttga ccctaatttt aaatcaaat tttgatttgg cagaagatgc taaattacag    1980 cttttcaaaag atacttacga tgatgattta gataatttat tggcgcaaat tggagatcaa   2040
tatgctgatt tgttttggc agctaagaat ttatcagatg ctattttact ttcagatatc    2100
ctaagagtaa atactgaaat aactaaggct cccctatcag cttcaatgat taaacgctac   2160
gatgaacatc atcaagactt gactcttta aaagctttag ttcgacaaca acttccagaa    2220
aagtataaag aaatctttt tgatcaatca aaaaacggat atgcaggtta tattgatggg   2280
ggagctagcc aagaagaatt ttataaattt atcaaaccaa ttttagaaaa atggatggt    2340 actgaggaat tattggtgaa actaaatcgt gaagatttgc tgcgcaagca acggacctt    2400 gacaacggct ctattcccca tcaaattcac ttgggtgagc tgcatgctat tttgagaaga   2460
caagaagact tttatccatt tttaaaagac aatcgtgaga agattgaaaa aatcttgact   2520
```

```
tttcgaattc cttattatgt tggtccattg gcgcgtggca atagtcgttt tgcatggatg    2580
actcggaagt ctgaagaaac aattacccca tggaattttg aagaagttgt cgataaaggt    2640
gcttcagctc aatcatttat tgaacgcatg acaaactttg ataaaaatct tccaaatgaa    2700
aaagtactac caaaacatag tttgctttat gagtatttta cggtttataa cgaattgaca    2760
aaggtcaaat atgttactga aggaatgcga aaaccagcat ttctttcagg tgaacagaag    2820
aaagccattg ttgatttact cttcaaaaca aatcgaaaag taaccgttaa gcaattaaaa    2880
gaagattatt tcaaaaaaat agaatgtttt gatagtgttg aaatttcagg agttgaagat    2940
agatttaatg cttcattagg tacctaccat gatttgctaa aaattattaa agataaagat    3000 ttttttggata atgaagaaaa tgaagatatc ttagaggata ttgttttaac attgacctta    3060
tttgaagata gggagatgat tgaggaaaga cttaaaacat atgctcacct ctttgatgat    3120
aaggtgatga acagcttaa acgtcgccgt tatactggtt ggggacgttt gtctcgaaaa    3180
ttgattaatg gtattaggga taagcaatct ggcaaaacaa tattagattt tttgaaatca    3240
gatggttttg ccaatcgcaa ttttatgcag ctgatccatg atgatagttt gacatttaaa    3300
gaagacattc aaaaagcaca agtgtctgga caaggcgata gtttacatga acatattgca    3360
aatttagctg gtagccctgc tattaaaaaa ggtatttttac agactgtaaa agttgttgat    3420
gaattggtca aagtaatggg gcggcataag ccagaaaata tcgttattga aatggcacgt    3480
gaaaatcaga caactcaaaa gggccagaaa aattcgcgag agcgtatgaa acgaatcgaa    3540
gaaggtatca agaattagg aagtcagatt cttaaagagc atcctgttga aaatactcaa    3600
ttgcaaaatg aaaagctcta tctctattat ctccaaaatg gaagagacat gtatgtggac    3660
caagaattag atattaatcg tttaagtgat tatgatgtcg atcacattgt tccacaaagt    3720
ttccttaaag acgattcaat agacaataag gtcttaacgc gttctgataa aaatcgtggt    3780
aaatcggata acgttccaag tgaagaagta gtcaaaaaga tgaaaaacta ttggagacaa    3840
cttctaaacg ccaagttaat cactcaacgt aagtttgata atttaacgaa agctgaacgt    3900
ggaggtttga gtgaacttga taaagctggt tttatcaaac gccaattggt tgaaactcgc    3960
caaatcacta agcatgtggc acaaattttg gatagtcgca tgaatactaa atacgatgaa    4020
aatgataaac ttattcgaga ggttaaagtg attaccttaa aatctaaatt agtttctgac    4080
ttccgaaaag atttccaatt ctataaagta cgtgagatta caattaccaa tcatgcccat    4140
gatgcgtatc taaatgccgt cgttggaact gctttgatta agaaatatcc aaaacttgaa    4200
tcggagtttg tctatggtga ttataaagtt tatgatgttc gtaaaatgat tgctaagtct    4260
gagcaagaaa taggcaaagc aaccgcaaaa tatttctttt actctaatat catgaacttc    4320
ttcaaaacag aaattacact tgcaaatgga gagattcgca aacgccctct aatcgaaact    4380
aatggggaaa ctggagaaat tgtctgggat aaagggcgag attttgccac agtgcgcaaa    4440
gtattgtcca tgccccaagt caatattgtc aagaaaacag aagtacagac aggcggattc    4500
tccaaggagt caattttacc aaaaagaaat tcggacaagc ttattgctcg taaaaaagac    4560
tgggatccaa aaaaatatgg tggttttgat agtccaacgg tagcttattc agtcctagtg    4620
gttgctaagg tggaaaaagg gaaatcgaag aagttaaaat ccgttaaaga gttactaggg    4680
atcacaatta tggaagaag ttcctttgaa aaaaatccga ttgacttttt agaagctaaa    4740
ggatataagg aagttaaaaa agacttaatc attaaactac ctaaatatag tctttttgag    4800
ttagaaaacg tcgtaaacg gatgctggct agtgccggaa aattacaaaa aggaaatgag    4860
ctggctctgc caagcaaata tgtgaatttt ttatatttag ctagtcatta tgaaaagttg    4920
```

```
aagggtagtc cagaagataa cgaacaaaaa caattgtttg tggagcagca taagcattat    4980
ttagatgaga ttattgagca aatcagtgaa ttttctaagc gtgttatttt agcagatgcc    5040
aatttagata aagttcttag tgcatataac aaacatagag acaaaccaat acgtgaacaa    5100
gcagaaaata ttattcattt atttacgttg acgaatcttg gagctcccgc tgcttttaaa    5160
tattttgata caacaattga tcgtaaacga tatacgtcta caaaagaagt tttagatgcc    5220
actcttatcc atcaatccat cactggtctt tatgaaacac gcattgattt gagtcagcta    5280
ggaggtgact ga                                                        5292
```